(12) United States Patent
Plummer et al.

(10) Patent No.: US 8,124,347 B2
(45) Date of Patent: Feb. 28, 2012

(54) PHOTOSYNTHETIC HYDROGEN PRODUCTION FROM THE GREEN ALGA CHLAMYDOMONAS REINHARDTH

(75) Inventors: Scott Plummer, Denver, CO (US); Mark Plummer, Greenwood Village, CO (US)

(73) Assignee: Scott Plummer, Denver, CO (US)

( * ) Notice: Subject to any disclaimer, the term of this patent is extended or adjusted under 35 U.S.C. 154(b) by 0 days.

(21) Appl. No.: 12/428,471

(22) Filed: Apr. 23, 2009

(65) Prior Publication Data

US 2010/0273149 A1  Oct. 28, 2010

(51) Int. Cl.
*C12Q 1/68* (2006.01)
*C12P 3/00* (2006.01)
*C12P 21/06* (2006.01)
*C12P 19/34* (2006.01)
*C12N 9/14* (2006.01)
*C12N 1/20* (2006.01)
*C07H 21/04* (2006.01)

(52) U.S. Cl. ........ 435/6.18; 435/6.1; 435/168; 435/195; 435/69.1; 435/91.1; 435/252.3; 536/23.1; 536/23.2

(58) Field of Classification Search ............ 435/6.18, 435/6.1, 168, 195, 69.1, 91.1, 252.3; 536/23.1, 536/23.2
See application file for complete search history.

(56) References Cited

U.S. PATENT DOCUMENTS 7,135,290 B2 * 11/2006 Dillon ........................ 435/6
2006/0228774 A1 * 10/2006 King et al. ............... 435/69.1

OTHER PUBLICATIONS

Broun et al., Catalytic plasticity of fatty acid modification enzymes underlying chemical diversity of plant lipids. Science, 1998, vol. 282: 1315-1317.*
Cohen et al., Molecular dynamics and experimental investigation of H2 and O2 in [Fe]-hydrogenase. Biochem. Soc. Trans., 2005, vol. 33 (1): 80-82.*
Entrez-Pubmed, Protein result, Algal hydrogenase search, 2 pages, Sep. 3, 2010.*
Ghirardi et al., Algal systems for hydrogen photoproduction. Hydrogen, Fuel Cells, and Infrastructure Technologies, FY 2003 Progress Report: 1-8.*
Kisselev L., Polypeptide release factors in prokaryotes and eukaryotes: same function, different structure. Structure, 2002, vol. 10: 8-9.*
Melis et al., Genomics of green lagal hydrogen research. Phtosynth. Res., 2004, vol. 82: 277-288.*
Plummer et al., Phtosynthetic hydrogen production from the green alga Chlamydomonas reinhardtii. Poster Abstract 86a, AICHE Conf. Nov. 5, 2007: 2 pages.*
Seffernick et al., Melamine deaminase and Atrazine chlorohydrolase: 98 percent identical but functionally different. J. Bacteriol.,2001, vol. 183 (8): 2405-2410.*
Vignais et al., Classification and phylogeny of hydrogenases. FEMS Microbiol. Rev., 2001: 455-501.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Stapleton, et al. A Cell-Free Microtiter Plate Screen for Improved [FeFe] Hydrogenases, PLoS (2010), ONE 5(5): e10554. doi:10. 1371/journal.pone.001055.
Nagy, et al. Application of gene-shuffling for the rapid generation of novel [FeFe]-hydrogenase libraries, Biotechnol Lett (2007) 29:421-430.

* cited by examiner

*Primary Examiner* — Ganapathirama Raghu
(74) *Attorney, Agent, or Firm* — Polsinelli Shughart PC; Tara A. Nealey

(57) ABSTRACT

The present invention relates generally to hydrogen production for use in fuel cells, foodstuffs and chemical production, and more particularly, to biologically and photosynthetically produced hydrogen. Specifically, disclosed is a method for producing bacteria and green alga that can produce hydrogen in quantities that exceed four hundred percent of the hydrogen produced by green alga in nature; thus, producing organisms which can serve as hydrogen generators for fuel cells, chemical production and numerous other applications.

12 Claims, 33 Drawing Sheets

FIG. 8
A)
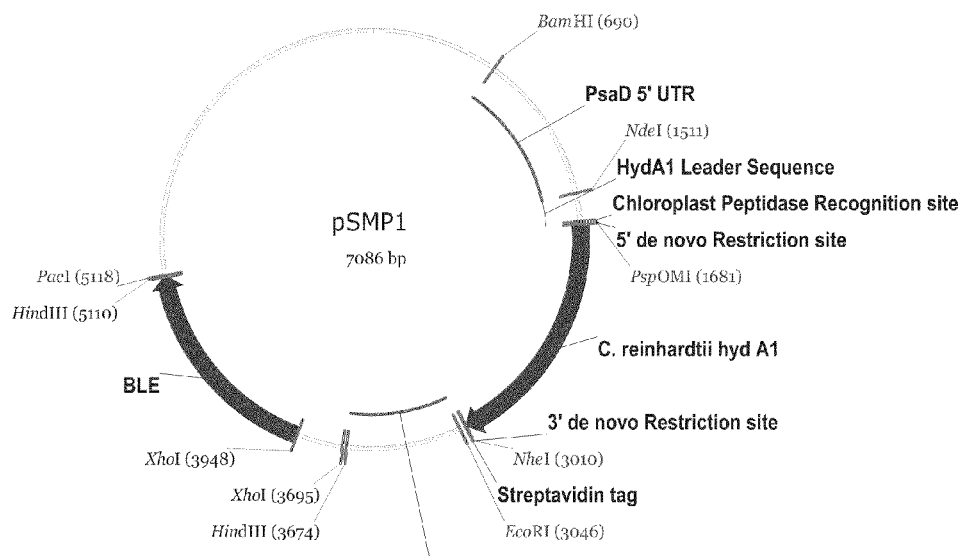
B)
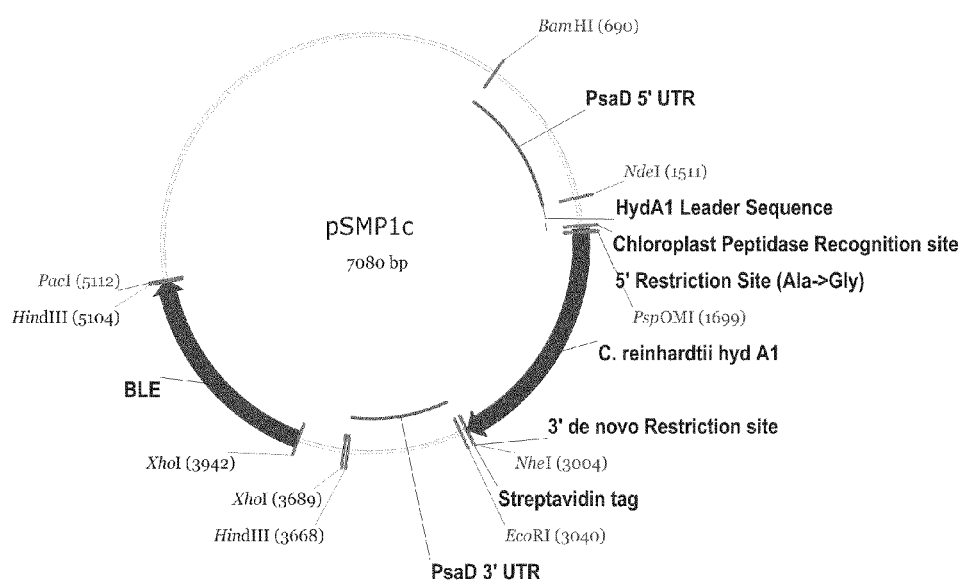

1. Strep Tag Insertion

Mutational primer:
5' GGA CGA GAA GAA GGC TAG C<u>GC CTG GAG CCA CCC GCA GTT CGA GAA GTG A</u>GA ATT CTG GC  3'
Complement primer:
5' GCC AGA ATT C<u>TC ACT TCT CGA ACT GCG GGT GGC TCC AGG C</u>GC TAG CCT TCT TCT CGT CC  3'

(a)    pSMP1

Mutational primer:
5' GCT TGC GCG GCT <u>GGG CCC</u> GCC GCA CCC G  3'
Complement primer:
5' CGG GTG CGG C<u>GG GCC C</u>AG CCG CGC AAG C  3'

(b)    pSMP1c

Mutational primer:
5' CCC GCT GCG GAG G<u>G</u>G CC<u>C</u> TTG AGT CAT GTC C  3'
Complement primer:
5' GGA CAT GAC TCA A<u>GG</u> GC<u>C</u> CCT CCG CAG CGG G  3'

(c)    pSMP2

Mutational primer:
5' CCA GCA GGC G<u>A</u>T CGC CGA GCT TGC  3'
Complement primer:
5' GCA AGC TCG GCG A<u>T</u>C GCC TGC TGG  3'

(d)    PspOMI site removal

Mutational primer:
5' CGA GGG GGG GCC <u>G</u>GG TAC CCA GC  3'
Complement primer:
5' GCT GGG TAC C<u>C</u>G GCC CCC CCT CG  3'

FIG. 17

| Chimera # | Hydrogenase Segment[1] | | | | | | | |
|---|---|---|---|---|---|---|---|---|
| | #1 | #2 | #3 | #4 | #5 | #6 | #7 | #8 |
| 1 | Aceto | Aceto | Aceto | Aceto | Saccharo | Saccharo | Saccharo | Saccharo |
| 2 | Saccharo | Saccharo | Saccharo | Saccharo | Aceto | Aceto | Aceto | Aceto |
| 18A | Aceto | Aceto | Aceto | Aceto | Saccharo | Saccharo | Aceto | Saccharo |
| 18S | Saccharo | Saccharo | Saccharo | Saccharo | Saccharo | Saccharo | Aceto | Saccharo |
| 21A | Aceto | Aceto | Aceto | Aceto | Saccharo | Saccharo | Aceto | Aceto |
| 21S | Saccharo | Saccharo | Saccharo | Saccharo | Saccharo | Saccharo | Aceto | Aceto |
| 24A | Aceto | Aceto | Aceto | Aceto | Saccharo | Aceto | Aceto | Saccharo |
| 24S | Saccharo | Saccharo | Saccharo | Saccharo | Saccharo | Aceto | Aceto | Saccharo |
| 25A | Aceto | Aceto | Aceto | Aceto | Aceto | Saccharo | Aceto | Saccharo |
| 25S | Saccharo | Saccharo | Saccharo | Saccharo | Aceto | Saccharo | Aceto | Saccharo |
| 27S | Saccharo | Saccharo | Saccharo | Saccharo | Saccharo | Aceto | Aceto | Aceto |
| 28A | Aceto | Aceto | Aceto | Aceto | Aceto | Saccharo | Aceto | Aceto |
| 28S | Saccharo | Saccharo | Saccharo | Saccharo | Aceto | Saccharo | Aceto | Aceto |
| 30A | Aceto | Aceto | Aceto | Aceto | Aceto | Aceto | Aceto | Saccharo |
| 30S | Saccharo | Saccharo | Saccharo | Saccharo | Aceto | Aceto | Aceto | Saccharo |
| 44 | Saccharo | Saccharo | Aceto | Saccharo | Aceto | Saccharo | Saccharo | Saccharo |

[1] The 1.8kb hydrogenase gene was divided into eight roughly equal segments. The segments designated as "Aceto" and "Saccharo" are from *C. acetobutylicum* and *C. saccharobutylicum*, respectively.

FIG. 19

*C. perfringens*

Upstream primer:
5' GCT ATC CAT GGC GAA TAA AAT AAT AAT CAA TGA TAA GAC 3'
Downstream primer:
5' ATA GGC GCG CCT TTT TTA TAT TTC ATG 3'

*(A) C. thermocellum*

Upstream primer:
5' GCT ATC CAT GGT AAA TGT TAC TAT AGA TAA TTG 3'
Downstream primer:
5' ATT GGC GCG CCT CAT TTA ACA GGG TAG TTT TCC 3'

Mutational primer:
5' GGC TGC TGT TGC GCA TGG TCT TGG C 3'
Complement primer:
5' GCC AAG ACC ATG CGC AAC AGC AGC C 3'

FIG. 22

HydE:
Upstream primer:
5' GCA TCG CAT ATG ACA AAC ATG ACA AAT ATG ATA AAT 3'
Downstream primer:
5' GCA TCG AGA TCT TAA TTT GGC TTT TTG CAG TCG CCT CTT G 3'

HydF:
Upstream primer:
5' GCA TCG CCA TGG GAT TGA ATG AAA CAC CAT CTG CAA ACC G 3'
Downstream primer:
5' GCA TCG GGA TCC CTA AAG AAT TTC TGC AAG TAT GTC CGG GAA G 3'

HydG:
Upstream primer:
5' GCA TCG CAT ATG GTT GAA AAA GTT GAT TTT ATA AAA G 3'
Downstream primer:
5' GCA TCG AGA TCT TTA AAA ATA AAT ATC TCT CTT TCC TTT TTC 3'

To mutate HydE in pET DLS:
Mutational primer:
5' GCG AAT TGC AAA GAC TGG CAA AGG ATC TGA ATG TAA AAG ATA TCA G 3'
Complement primer:
5' CGC TTA ACG TTT CTG ACC GTT TCC TAG ACT TAC ATT TTC TAT AGT C 3'
Additional primer:
5' CAA TAC GGG ATA ATA CCG CGC CAC ATA GCA GAA C 3'
Complement of additional primer:
5' GTT ATG CCC TAT TAT GGC GCG GTG TAT CGT CTT G 3'

To mutate HydF in pCDF:
Mutational primer:
5' GGG CAT TAA AGC CTT TTC CAT ACG CTG ATA GAA TAT TTA ATC AAT CG 3'
Complement primer:
5' CCC GTA ATT TCG GAA AAG GTA TGC GAC TAT CTT ATA AAT TAG TTA GC 3'

Additional primer:
5' CCG ACA GGA CTT AAA GAT CCC CAC CGT TTC C 3'
Complement of additional primer:
5' GGC TGT CCT GAA TTT CTA GGG GTG GCA AGG 3'

Resazurin
Blue-Purple
$A_{max}$ = 600nm

Resorufin (reduced)
Colorless

Resorufin (oxidized)
Pink
$A_{max}$ = 570nm

FIG. 26
A)
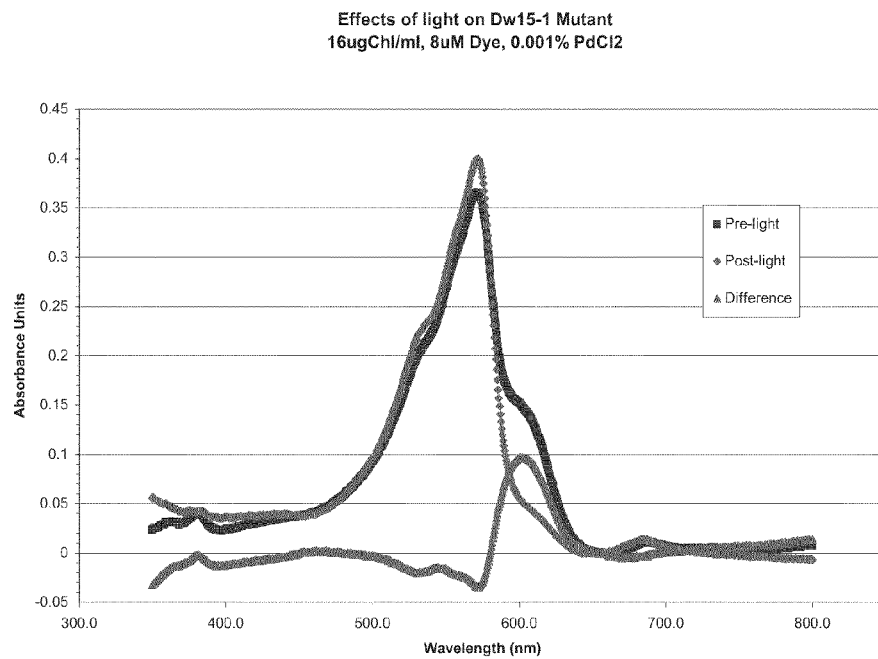
B)
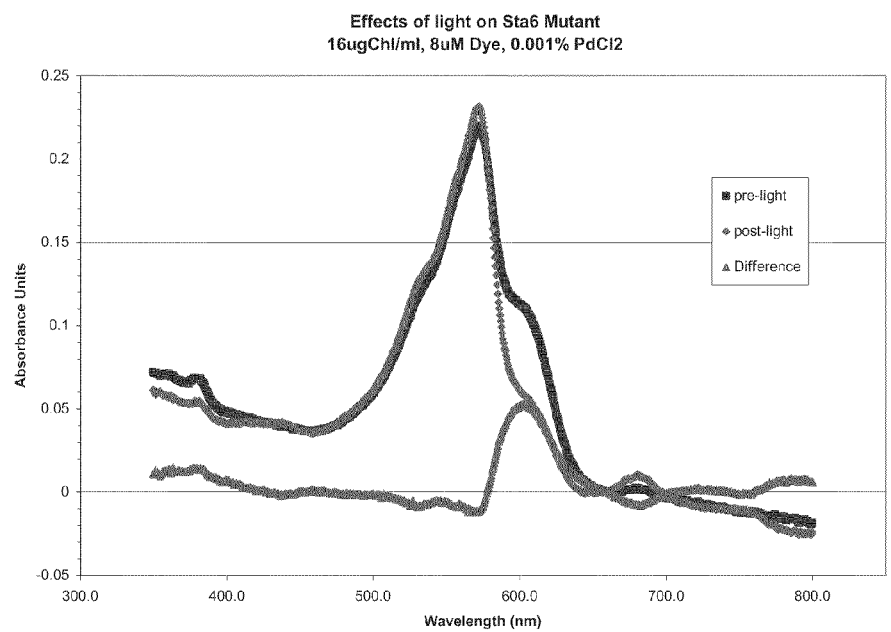

FIG. 30

Basic Fuel Cell Operation
(PEM FC example)

Anode: $2H_2 \rightarrow 4H^+ + 4e^-$

Cathode: $4e^- + 4H^+ + O_2 \rightarrow 2H_2O$

Overall: $2H_2 + O_2 \rightarrow 2H_2O$

Rated Output: 1.75 kWh per Liter of Hydrogen (note: this would cost about 20 - 22 cents at current kWh prices)

e.g.: Fuel Cell Stack weighs 180 pounds and gives continuous output of 100 kW to scale things, your home requires about 2kW of power or therefore 4.5 pounds of Hydrogen full cell stack.

PHOTOSYNTHETIC HYDROGEN PRODUCTION FROM THE GREEN ALGA CHLAMYDOMONAS REINHARDTH

CLAIM TO DOMESTIC PRIORITY

The present application claims the benefit of U.S. Provisional patent application Ser. No. 61/046,989 filed on Apr. 22, 2008, entitled "Photosynthetic Hydrogen Production from the Green Alga Chlamydomonas Reinhardth" the entire disclosure of which is incorporated herein by reference in its entirety for all purposes.

INCORPORATION OF SEQUENCE LISTING

The entire contents of a paper copy of the "Sequence Listing" and a computer readable form of the sequence listing on diskette, containing the file named Seq_Listing ST25.txt, which is 489 kilobytes in size and was created on Apr. 23, 2009 are herein incorporated by reference.

FIELD OF THE INVENTION

The present invention relates generally to hydrogen production for use in fuel cells, foodstuffs and chemical production, and more particularly, to biologically and photosynthetically produced hydrogen.

BACKGROUND OF THE INVENTION

Evidence has shown that the combustion of fossil fuels is causing a change in the composition of our atmosphere. The resulting increase in average global temperature requires an immediate and global response. A recent British climate change report suggests that we would have to decrease emissions of carbon dioxide and other greenhouse gases by 25% by the year 2050 to avoid as much as a 20% decrease in global Gross Domestic Product (GDP) caused by catastrophic drought, flooding, and disease. Ultimately, an 80% decrease in emissions would be necessary. So, if not fossil fuels, what should we use as a source of energy? If we switched to a hydrogen economy and utilized molecular hydrogen and fuel cells in all of our cars, trucks, trains, etc., a 50% reduction in the emission of carbon monoxide and nitrous oxides is likely. Of course, a decrease in emissions and a concomitant improvement in climate change is dependant on how the hydrogen is produced. Climate change would not occur if we continue to produce hydrogen by the steam reformation of natural gas and coal as this process results in localized emissions, but emissions nonetheless. However, if the hydrogen were produced biologically, perhaps by a photosynthetic organism, there would be little or no release of carbon dioxide, nitrous oxides, or methane.

Hydrogen is currently produced by steam reforming the hydrogen atoms from coal or natural gas. The reactions are: $CH_4+H_2O \rightarrow CO+3\ H_2$ (natural gas) or $C+H_2O \rightarrow CO+H_2$ (coal) and $CO+H_2O \rightarrow CO_2+H_2$. Either fuel could be the basis of a national hydrogen economy; however both fuels generate carbon dioxide, which would add greenhouse gases to our atmosphere. If future coal driven hydrogen power plants utilized carbon sequestration, pumping the carbon dioxide into a deep underground location, this problem could be eliminated. Alternatively, a carbon neutral hydrogen economy could be realized if hydrogen could be produced from the electrolysis of water where the electricity, the impetus for the reaction, is generated from a nuclear reactor, wind energy, or solar power or through photosynthetic hydrogen generation.

The study of biological hydrogen production in green algae began as a curiosity and after 75 years of research, its evolutionary origin still remains an enigma. General progress in the field has been ongoing since Hans Gaffron early 1940s discovery that the green alga *Scenedesmus obliquus* produced hydrogen; however, the last decade is marked by dramatic advances. Specifically, the hydrogenase genes for several species of green algae have been sequenced and the crystal structure determined, for two homologous bacterial hydrogenases, *C. pasteurinum* and *D. desulfuricans*. In addition, the mechanism by which a hydrogenase creates molecular hydrogen has been elucidated from extensive research on the structure, assembly, and biological properties of all hydrogenases.

Hydrogenases are iron-sulfur proteins, which have played an important role in the energy metabolism of bacteria since the earliest life on Earth. In fact, homologous non-hydrogen producing iron-sulfur proteins are common in most living cells, including humans and pathogenic bacteria. The hydrogenases, however, are different from their evolutionary cousins in that their iron sulfur clusters contain unique cyanide and carbon monoxide ligands (FIG. 1). There are two major types of hydrogenases found in a diverse array of micro-organisms. Our research focuses on the "Fe-only" hydrogenases that contain dual iron atoms in their active site complexes.

Hydrogen is produced by enzymatically combining protons with electrons from the photosynthetic electron transport chain. The protons and the electrons are generated from the first step in the photosynthetic cycle, the splitting of water into oxygen and protons. The electrons are immediately energized by a photon ($\lambda$=680 nm) in Photosystem II and passed from one compound to another, all of which compose the electron transport chain (FIG. 2). Most of the electron carriers are quinones (Q), plastiquinones (PQ), or cytochromes (Cyt). A second input of light energy ($\lambda$=700 nm) occurs during Photosystem I and the energized electrons are passed to the terminal electron carrier, ferredoxin. At this point, the electrons can participate in $CO_2$ fixation, i.e. cell growth, or be transferred to the hydrogenase to produce hydrogen.

BRIEF DESCRIPTION OF THE FIGURES

FIG. 12 shows the primers (SEQ ID NOS: 3-12) utilized to create restriction sites in the pSMP1, pSMP1c, and pSMP2 plasmids.

FIG. 17 illustrates the chimeric hydrogenases that were tested for hydrogen production.

FIG. 19 shows the primers (SEQ ID NOS: 19-22) utilized to clone the Clostridial hydrogenases into the pET DLS expression vector.

FIG. 22 shows the list of primers (SEQ ID NOS: 210-223) used for isolating the *C. thermocellum* accessory proteins from a genomic DNA preparation and for cloning the proteins into the pET DLS and pCDF plasmids.

FIG. 26 illustrates the effects of light on two algal strains.

FIG. 30 shows the reactions that occur in a PEM fuel cell.

DETAILED DESCRIPTION OF THE DISCLOSURE

Figure 1:
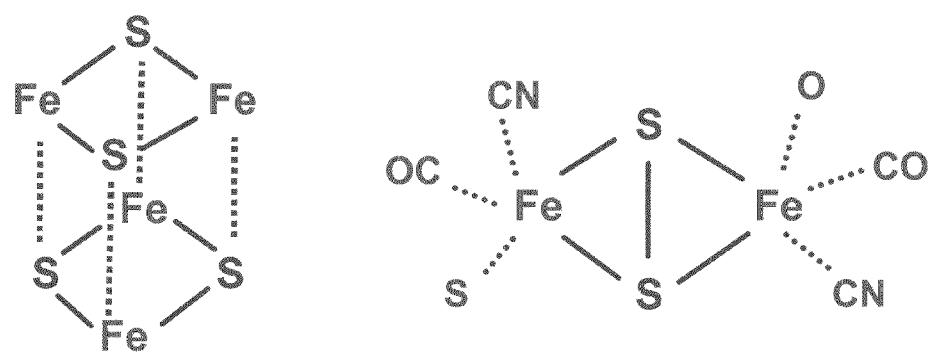
FIG. 1 is a diagram illustrating the four-iron four-sulfur (4Fe-4S) cluster and the two-iron two-sulfur (2Fe-2S) active site cluster that is present in Fe-only hydrogenases.
Figure 2:
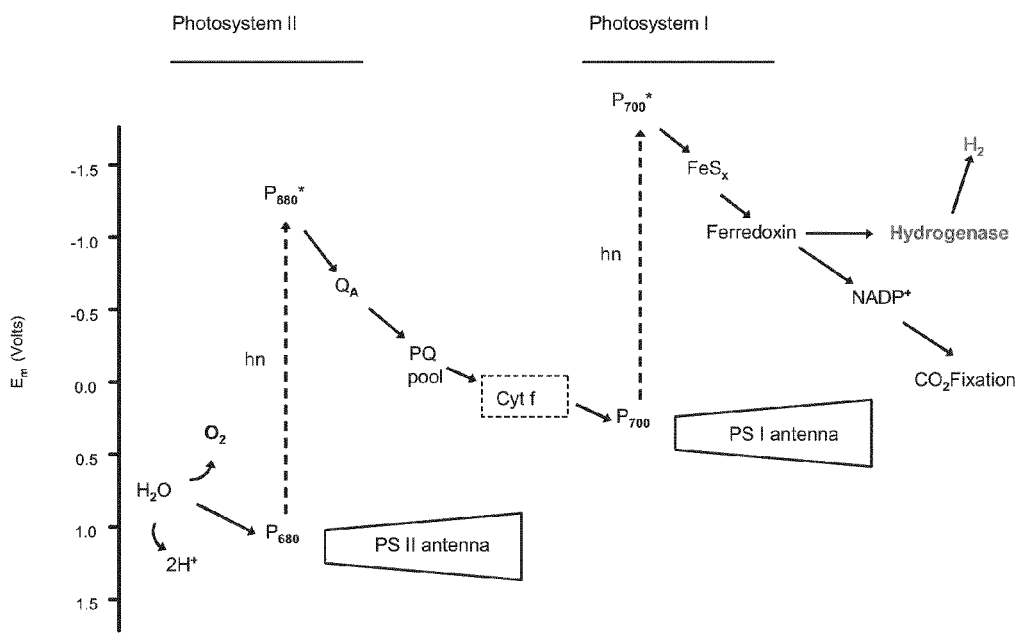
FIG. 2 illustrates the photosynthetic electron transport chain, known as the "Z-scheme."

The present invention is a method of producing photosynthetic alga capable of enhanced hydrogen production. The method is also directed toward genetically-modified bacteria that can also be used to produce hydrogen. The photosynthetic alga approach utilizes a technique known as directed evolution whereby mutations are introduced into the DNA of the native hydrogenases, the enzymes responsible for hydrogen production. Directed evolution is a technique that mimics natural evolution in that multiple mutations are created and tested for enhanced traits. Albeit on a shorter timescale, the proteins with evolved mutations are submitted to repeat cycles of evolutionary pressure.

As explained in greater detail below, the hydrogenases from a photosynthetic green algae known as *Chlamydomonas reinhardtii* were chosen. The native hydrogenases generate hydrogen by combining protons with electrons from the photosynthetic electron transport chain. Molecular hydrogen is then released into the environment. However, the creation, introduction, and expression of mutant hydrogenases in *C. reinhardtii* have not proved to be straight forward. As a result, chimeric mutant libraries were created using homologous bacterial hydrogenases, while simultaneously exploring gene expression in *C. reinhardtii*.

The bacterial hydrogenases with enhanced hydrogen production were created using degenerative oligonucleotide gene shuffling (DOGS). This technique requires that the homologous parental genes be divided into eight, roughly equal, segments. According to the present disclosure, the parental hydrogenase genes were from *Clostridium saccharobutylium* and *Clostridium acetobutylicum*. The segment boundaries were specifically chosen within regions of high homology amongst the two parental genes. Except for segments #1 and #8, the first and last segments, each segment had two unique sticky ends created by the restriction endonuclease SapI. The uniqueness of each sticky end allowed it to overlap only with its neighboring segments. For example, the downstream end of segment #2 could only overlap with the upstream end of segment #3 and the downstream end of segment #3 would overlap with only the upstream end of segment #4, thereby generating a full-length chimeric gene library with segments from both parental genes.

In addition, the expression of algal hydrogenases was achieved utilizing a specialized plasmid capable of expressing algal cDNA. This vector was obtained and modified for use with an algal hydrogenase cDNA by removing the existing PsaD gene and inserting the cDNA of the hydAI hydrogenase from *C. reinhardtii*. In addition, the hydrogenase leader sequence was inserted upstream of the hydA1 gene and a strepavidin tag was added to the downstream end. Also, de novo restriction sites were created between the leader sequence, the hydA1 gene, and the downstream tag, thus allowing for the ready removal and replacement of the hydrogenase gene.

Consequently, disclosed is a method whereby mutations can be created and tested in bacterial hydrogenases. The successful bacterial mutations are then re-created in algal hydrogenases and transformed into *C. reinhardtii* thereby creating an alga capable of enhanced hydrogen production.

Fuel cells using the disclosed hydrogen generation would efficiently generate power for numerous uses. Molecular hydrogen is the ideal fuel for use in fuel cells, if it could be produced at a cost that is competitive with current sources of energy. Commercially viable hydrogen production by photosynthesis is currently only a possibility, however, this research has shown that hydrogen-producing enzymes can be mutated to produce chimeras with equal or greater hydrogen production than was possible with the original wild-type enzyme.

The following terms and abbreviations will have the following meanings throughout this disclosure:

aa: amino acid
bp: base pair
nt: nucleotide
kD: kilodalton
PCR: polymerase chain reaction RT-PCR: reverse transcriptase polymerase chain reaction ssDNA: single stranded deoxyribonucleic acid DNase I: enzyme that degrades DNA Restriction enzymes: enzymes that cleave DNA at a specific sequence. XhoI, PacI, NdeI, NheI, EcoRI, PspOMI, AsiSI are the names of restriction enzymes that cleave unique sequences which are listed in the New England Biolabs catalog cDNA: copy DNA, the same DNA as the original gene of interest, except all the introns, or non-coding material, have been removed LB (or NZY) and TAP: nutrient broths that are used to grow bacteria and algae, respectively Vector or Plasmid: circular DNA that can be transformed (inserted) into cells to express a gene of interest from its promoter HydA1 and HydA2: hydrogenase A1 and A2 in *Chlamydomonas reinhardtii*

UTR: untranslated region (of the DNA)

Intron: an untranslated region of a gene within a translated region

GOI: gene of interest

Hydrons: hydrogen atoms with two electrons ($H^-$)

pGenD: the name of a plasmid (p) that expresses some cDNA in algae pSMP1: the name of a plasmid derived from pGenD that expresses hydrogenase cDNA and has a PspOMI restriction site immediately after the HydA1 leader sequence and before the coding sequence for the HydA1 pSMP1c: the same as pSMP1, but the PspOMI restriction site was added 20 nts downstream from the one in pSMP1.

pSMP2: the same as pSMP1, but an AsiSI restriction site instead of a PspOMI site was added 45 nts downstream of the HydA1 leader sequence.

IPTG: isopropyl-beta-D-thiogalactopyranoside, a chemical that artificially induces expression SDS-PAGE: sodium docecyl sulfate-polyacrylamide gel electrophoresis, a technique used to separate a mixture of multiple proteins Western Blot: in combination with SDS-PAGE, a technique used to identify one protein from a mixture of multiple proteins StEP: staggered extension process ITCHY: iterative truncation for the creation of hybrid enzymes RATCHITT: random chimeragenesis on transient templates DOGS: degenerative oligonucleotide gene shuffling.

Biohydrogen production from photosynthetic algae has the potential to be a viable alternative to hydrogen production from fossil fuels. It would not produce greenhouse gases ($H_2O+sunlight \rightarrow O_2+H_2$); in fact, algae, like most plants, utilizes carbon dioxide for cellular growth, so it would serve as a carbon sink. In addition, a bioreactor would not produce toxic waste, just algae and wastewater; similar to a fish tank. Also, a bioreactor would likely be about the size of an air conditioner and survive on low amounts of sunlight, so it would occupy a small amount of space and it could be located anywhere.

However, present commercial photosynthetic hydrogen production is not viable because of two major problems that prevent the hydrogenase from producing useful amounts of molecular hydrogen. First, the hydrogenase has a short half-life that prevents it from producing hydrogen for longer than a minute. Second, it is necessary that the hydrogenase be tolerant of oxygen. Since all known hydrogenases have a short half-life even in the presence of very low concentrations of oxygen, only a modified hydrogenase with increased hydrogen production and/or decreased oxygen sensitivity will allow for the commercial production of photosynthetically generated hydrogen.

Despite the evident challenge, the green alga *Chlamydomonas reinhardtii* (*C. reinhardtii*) has substantial potential. Each hydrogenase is capable of generating 6000-9000 molecules of molecular hydrogen per second. Once sustainable, a mole of hydrogenases, producing hydrogen at this rate, would generate enough hydrogen to fill the Graf Zeppelin in 10 minutes or the main tank of the space shuttle in just 2 hours. In addition, the green alga, *C. reinhardtii*, is a common lab research organism, whose genome has been sequenced; hence the potential for photosynthetic hydrogen production is apparent.

Figure 3:
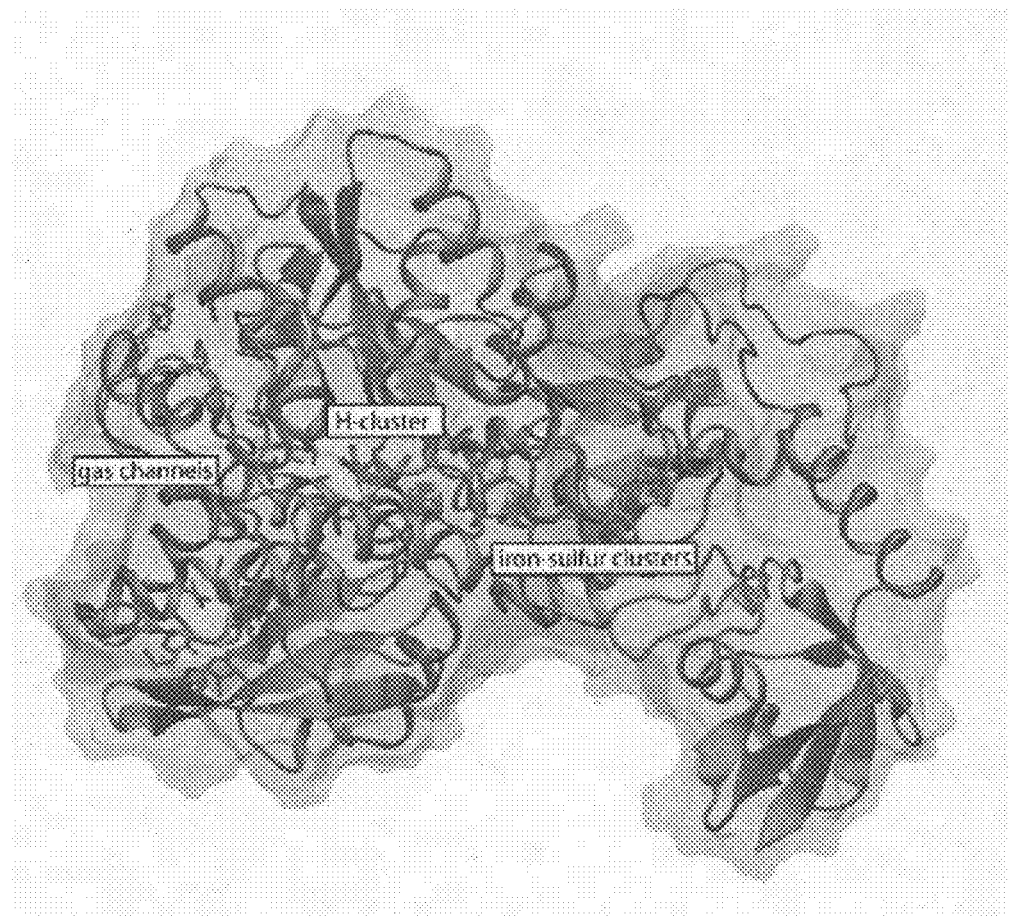
FIG. 3 shows the crystal structure of the *C. pasteurinum* bacterial hydrogenase.

Recently, the crystal structures of homologous bacterial Fe-only hydrogenases have provided insight into how oxygen irreversibly inhibits the enzyme. The active site for the production of hydrogen ($2H^++2e^- - H_2$) is protected by its location deep within the center of the mature hydrogenase (FIG. 3). Each of the reactants and the resulting hydrogen has a channel to the surface. The hydrogenase structures all have different ferredoxin binding motifs, but they all exhibit a chain of four iron, four sulfur clusters (4Fe-4S) that pass the electrons from the surface of the hydrogenase to the active site (FIG. 1 and FIG. 3). The modular 4Fe-4S clusters are separated by 1-1.5 nm intervals that allow for efficient electron transport to the active site. The protons (hydrons) pass through a putative second channel to reach the active site. This channel is lined with amino acids and protein-bound water molecules that are capable of binding the hydrons as they pass down the channel. Two putative channels exist for the release of molecular hydrogen resulting from the enzymatic reaction of the protons with the electrons at the active site (FIG. 3). Unfortunately, these channels also allow for the passage of the larger oxygen molecule, which irreversibly inhibits the hydrogenase, probably by oxidizing an iron (II) to an iron (III) in the active site cluster. However, this disclosure provides for chimeric hydrogenase with a mutation(s) that decreases the diameter of these channels, thereby restricting the larger oxygen molecules by size exclusion, while still allowing for passage of the smaller bio-hydrogen molecules.

In summary, photosynthesis generates oxygen as well as protons and energized electrons and hydrogen production is dependent upon the photosynthetic process. Hence, the enigma is how the hydrogenase enzyme could have evolved to be extremely sensitive to oxygen. Enzymatic hydrogen production is a short-term shunt to rid the cell of excess electrons. Therefore, this enzyme has probably been exposed to little if any selective pressure, which infers that its evolutionary potential is likely untapped.

Photosynthetic hydrogen production using *Chlamydomonas reinhardtii* (*C. reinhardtii*) generates no greenhouse gases. Therefore, this technique can generate clean energy. In doing so, this disclosure provides for the solution to the two major problems preventing commercialization of this technique to date: 1) the hydrogenase enzyme that produces the molecular hydrogen is sensitive to oxygen and, 2) the amount of hydrogen production needs to be increased. Since the *C. reinhardtii* hydrogenase genes have been cloned, mutation of the original parent genes is disclosed herein, as well as the method to search for a mutant algal hydrogenase with an improved phenotype. After the mutant genes are created, this disclosure further provides for a method to insert and express them in *C. reinhardtii*. Finally, a novel method of selecting or screening the mutants for enhanced traits in algae is disclosed.

Since clostridial hydrogenases share homology with their eukaryotic algal *C. reinhardtii* cousins, mutations resulting in an enhanced clostridial phenotype will result in the same enhancement when the analogous mutation is created in *C. reinhardtii*. Therefore, it is necessary to create libraries of mutated clostridial hydrogenase genes and test them for enhanced hydrogen production. These libraries serve to create that mutant hydrogenases with an improved phenotype, i.e. showing an increase in hydrogen production.

The present disclosure provides for the creation of chimeric mutants that produce more hydrogen. Gene shuffling, a technique that resembles natural evolution on a shorter time scale will be able to select for hydrogenase genes that are more oxygen tolerant and/or produce more hydrogen, thereby overcoming either of the problems of the original hydrogenase proteins. A hydrogenase protein with even a slightly improved rate of hydrogen production or tolerance for oxygen could provide insights into the types of mutations necessary to produce an enzyme that would be the basis of an economically viable biological hydrogen production system.

Figure 4:
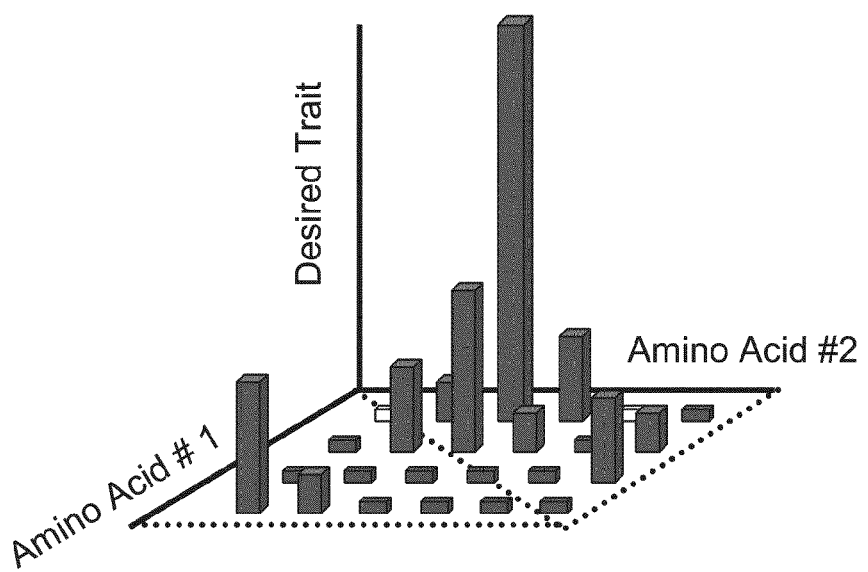
FIG. 4 is an example of sequence space; the set of all possible amino acid sequences. According to the disclosure, the protein of interest is just 2 amino acids in length.

Gene shuffling is the process of creating mutant DNA sequences which codes for a protein with an improved or a novel function. Most frequently, the DNA sequence represents a gene and the goal is to modify it by mutating it into many thousands of new genes, each mutated in a different manner, to create a new phenotype with the desired characteristics. A sizeable percentage of these genes will encode for non-functional proteins or for proteins with no improvement over the original. However, several mutant or chimeric proteins will exhibit a significantly improved functionality. The proteins with improved function can be re-shuffled, thereby amplifying the improved function. Thousands or millions of mutants can be created and all of "sequence space" can, in principle, be successfully surveyed (FIG. 4).

The sequence space ($20^n$) is the set of all possible amino acids (there are 20 common amino acids) in each position for a protein of a particular length (n). A plot of the sequence space versus the desired trait shows local maxima and minima in the desired trait. After several rounds of shuffling, it is common to find that the protein cannot be improved any further. Protein function improvements of 500×-32,000× are known to result from this method in other organisms, thereby confirming that this method can produce significant positive changes in a protein. Consequently, we can use gene shuffling to create a library of chimeric proteins. By selecting for an improved trait from that library, we can direct the evolution of the original parental protein. This technique is referred to herein as "Directed Evolution".

Figure 5:
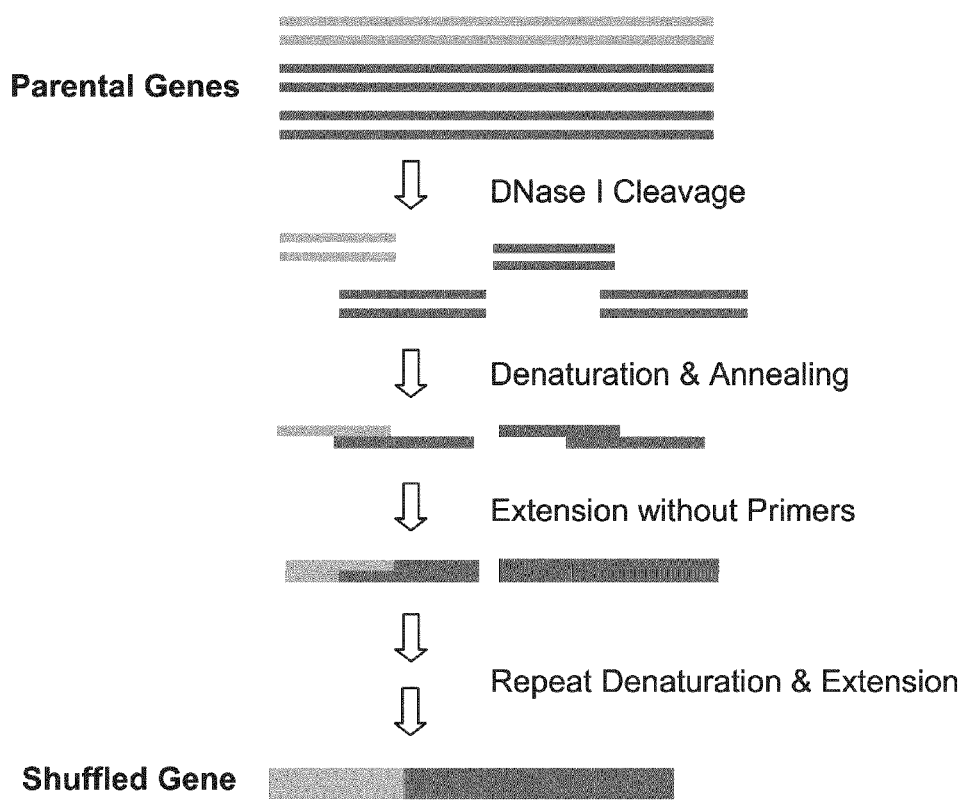
FIG. 5 is a diagram of a "Family Shuffle."

Gene shuffling using Willem Stemmer's family shuffling technique can be used to effect direct evolution. In Stemmer's protocol, multiple parent genes were digested. The fragments were recombined using multiple cycles of PCR to form chimeric progeny (FIG. 5). Other techniques soon followed, including: family shuffling with single stranded DNA (ssDNA), staggered extension process (StEP), iterative truncation for the creation of hybrid enzymes (ITCHY), random chimeragenesis on transient templates (RACHITT), and degenerative oligonucleotide gene shuffling (DOGS). Each technique generates a large number of diverse gene sequences, referred to as a library.

A selection is then performed on the chimeric proteins that are generated from the library of genes; a selection for an enhanced trait such as enzyme selectivity, stability, or activity. For algal hydrogenase research, enhanced tolerance for oxygen and/or an increased capacity for the production of hydrogen is selected for.

The disclosed directed evolution method by use of gene shuffling using a technique known as error-prone PCR can also be used. This method of creating a mutant library merely altered the conditions of standard PCR so that they were no longer optimal, thereby forcing the polymerase to make mistakes. This method, in reality, was not very random and the mutant offspring were not significantly different from the parent genes.

Figure 6:
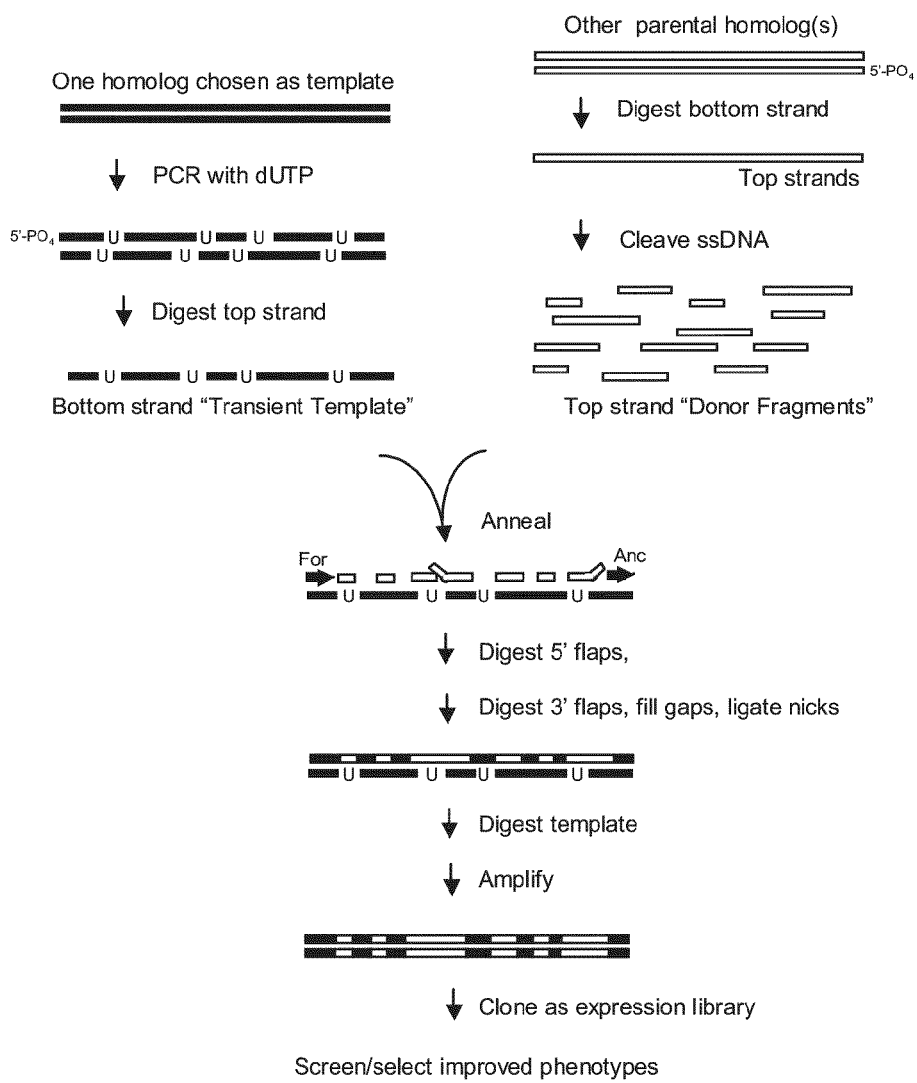
FIG. 6 is the RACHITT technique for generating a combinatorial library.

In order to find the optimal method to generate a library, several of the above shuffling methods can be used, alone or in combination. The RACHITT method generates a library containing a high percentage of diverse chimeras with little or no representation of the original parental genes (FIG. 6). It does so by choosing one of the parental genes to be a template strand, while the others are designated as donor strands. All the parental DNA is made single-stranded (ssDNA). In addition, the donor strands are digested into pieces of about 200-800 nt. The digested donor DNA oligonucleotides bind to the template strand. Once the gaps are filled in, the template strand is removed by completely digesting it down to the level of individual bases. Since all of the parental DNA was digested, a library of full-length chimeras is created. Next, the standard family shuffle (FIG. 5) was used. Error-prone PCR and the DOGS technique, as described below, are particularly useful in creating chimeric libraries.

In order to create a library of chimeras, several mutational techniques were used. The family shuffle and random chimeragenesis on transient templates (RACHITT) were used initially, but were not as effective as other methods. However, two other techniques, random mutagenesis by error-prone PCR and a variation of degenerative oligonucleotide gene shuffling (DOGS) were highly successful and led to the creation of mutational libraries disclosed herein.

Error-prone PCR is similar to standard PCR in that it uses the same primers to replicate the gene of interest (GOI). However, the polymerase has been altered so that errors in the replication process occur more often. This technique generated a mutant library with an average of 10 point mutations per gene. Although libraries of mutated genes are readily created, error-prone PCR is not the most efficient technique for the creation of a protein with improved function, as it is not known which or where a point mutation would be beneficial.

Figure 13:
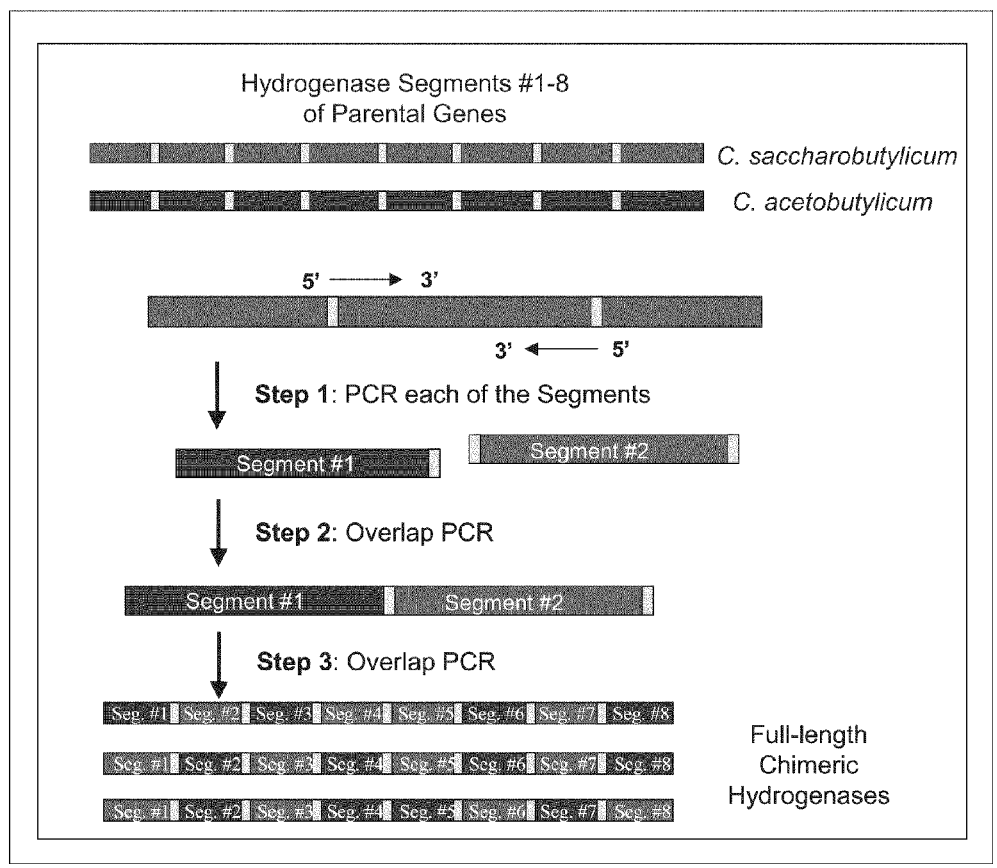
FIG. 13 illustrates the degenerative oligonucleotide gene shuffling (DOGS), the technique used to create the chimeric library.

The DOGS technique divides each parental GOI into roughly equal segments (see FIG. 13). In this study, the segment boundaries were specifically chosen within regions of high homology amongst the parent genes. Each segment of each gene was generated by an initial PCR. Forward and reverse degenerate primers were employed on both sides of the segment boundary in order to facilitate an overlap of the two segments (see FIG. 14). Each segment boundary is a unique sequence. A second PCR combined the segments in the same segment order as the original parent genes, thereby generating a full-length chimeric library.

Figure 15:
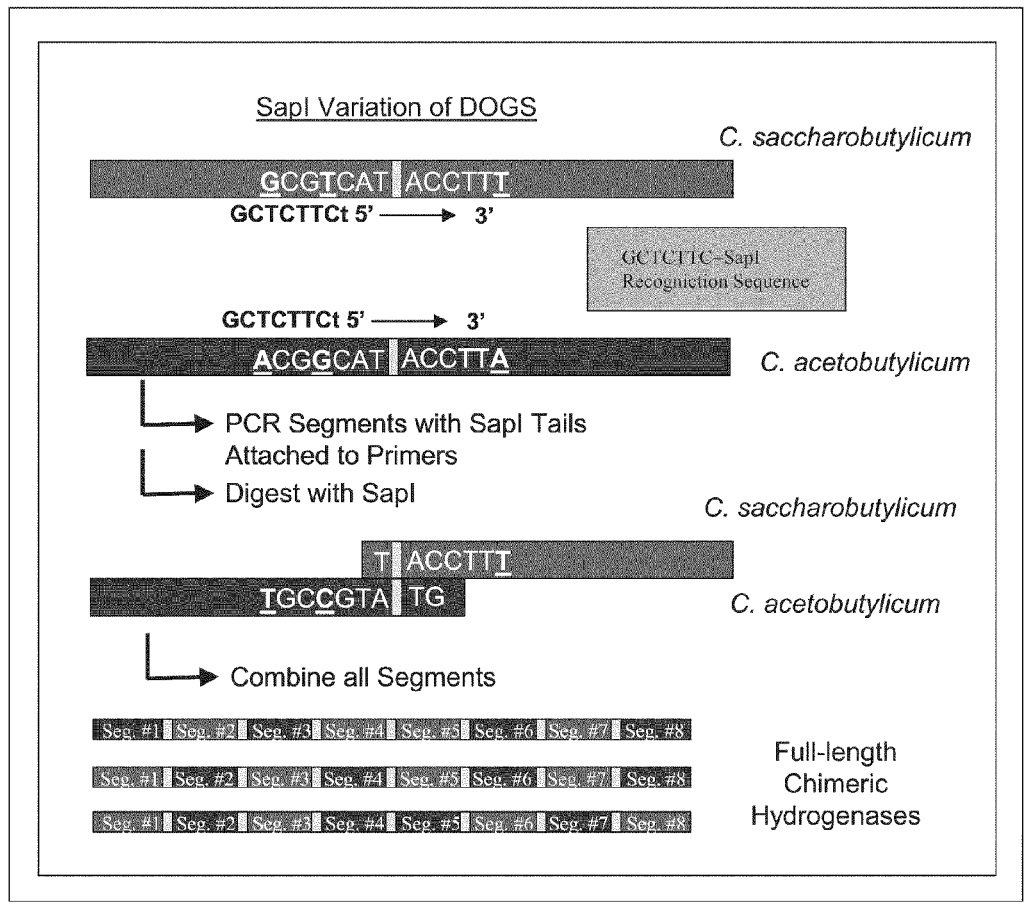
FIG. 15 illustrates the variation of the degenerative oligonucleotide gene shuffling (DOGS) technique that utilizes the exonuclease SapI.

A variation to the DOGS technique was also used; it required only three base pairs of homology as the overlap is created by a restriction enzyme (see FIG. 15). The overlap PCR steps are eliminated in favor of a simple annealing of the sticky ends generated by the enzyme.

Either variation of the DOGS method leads to a full-length chimeric gene library wherein the overlap positions occur in regions of high homology. Therefore, this shuffling technique effectively swaps segments of the parental genes by choosing the segment intersections in advance. It has the advantage of capitalizing on the evolutionary differences amongst the parent genes including the regions of high homology while maintaining the overall length of the gene.

Figure 16:
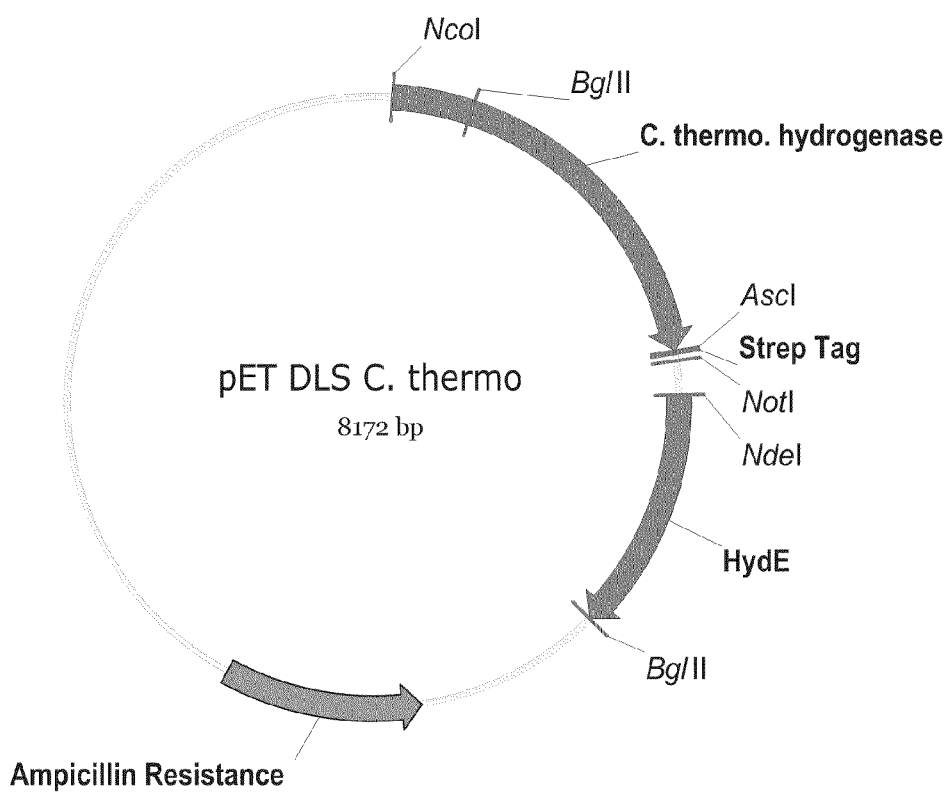
FIG. 16 is shows the pET DLS plasmid (8.2 kb) containing the *C. acetobutylicum* HydE accessory protein and the *C. thermocellum* hydrogenase (pET DLS C. thermo plasmid).

Five clostridial hydrogenases were cloned: *Clostridium saccharobutylicum* (*C. saccharobutylicum*), *Clostridium pasteurinum* (*C. pasteurinum*), *Clostridium perfringens* (*C. perfringens*), *Clostridium tetani* (*C. tetani*), and *Clostridium thermocellum* (*C. thermocellum*). All hydrogenases were cloned via restriction sites (NcoI/AscI) into the pET DLS expression vector (see FIG. 16) and tested for hydrogen production using the Methyl Viologen assay. It was necessary to use the Methyl Viologen assay, because bacteria need an artificial electron donor in place of the photosynthetic machinery that provides electrons to algal hydrogenases.

Three hydrogenases, those isolated from *C. saccharobutylicum*, *C. pasteurinum*, and *C. perfringens*, showed hydrogen production that was comparable to the values published for *C. acetobutylicum*. However, the hydrogenase isolated from *C. tetani* showed attenuated hydrogen production and the *C. thermocellum* hydrogenase showed no hydrogen production whatsoever. Since *C. thermocellum* is a thermophilic organism (55° C.) and it has the lowest homology of the five Clostridial hydrogenases that were cloned, it is possible that this hydrogenase needs its own accessory proteins in order to fold correctly.

Two chimeric libraries, by two separate methods, were created in an attempt to realize an improvement in the hydrogen production and/or oxygen tolerance over the parental Clostridial hydrogenases. First, a random mutagenesis library was created from *C. saccharobutylicum*. Utilizing the two wild-type hydrogenases that produced the most hydrogen, the hydrogenases from *C. saccharobutylicum* and *C. acetobutylicum*, a second library was created utilizing the variation on the DOGS technique (see FIGS. 13 through 15).

The random mutagenesis library was cloned via restriction sites (NcoI/AscI) into the pET DLS vector in place of the parent hydrogenase. The sequenced clones had an average of six mutations per gene (1.8 kb). There was a predominance of Adenine (A) & Thymine (T) transitions over Guanine (G) & Cytosine (C) transitions, but it was in accordance with the relative percentage of As and Ts to Gs and Cs. None of the mutations were identical. This library was not tested for hydrogen production and would benefit from a high throughput screen.

Figure 18:
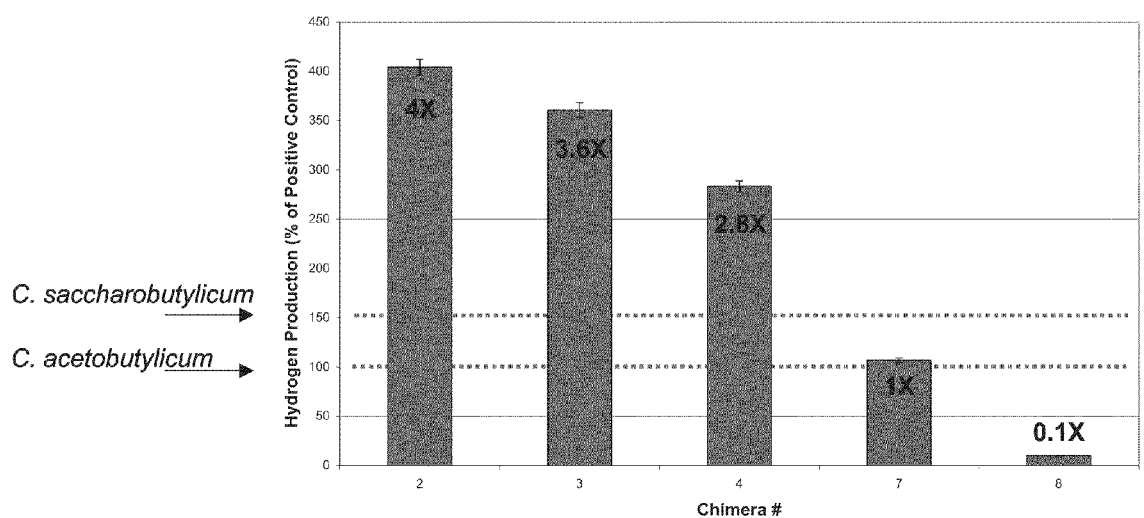
FIG. 18 shows the hydrogen production of the specified chimeric hydrogenases as a percentage of the positive control (*C. acetobutylicum*).

The library created by the DOGS method, using the SapI variation, generated 254 distinct chimeras. Sixteen chimeras, that were representative of the possible mutations in the second half of the protein, were randomly chosen and tested for hydrogen production (see FIG. 17). Several showed normalized hydrogen production at or greater than the positive control (see FIG. 18). The positive control was the non-mutated hydrogenase from *C. acetobutylicum* used in the original study by King et al. Specifically, chimera #2 (protein sequence—SEQ ID NO: 1 and DNA sequence—SEQ ID NO: 2) shows the most hydrogen production (4× the hydrogen production of the positive control). In addition to producing more hydrogen, chimera #2 also produced molecular hydrogen at a faster rate than the other mutants; the rate for chimera #2 dramatically decreased after one hour of incubation. The other chimeras produced 30-50% more hydrogen in the second hour of incubation, which likely indicates that they have a slower turnover of the hydrogenase protein. The remaining hydrogenase chimeras, #18A (protein sequence—SEQ ID NO: 85 and DNA sequence—SEQ ID NO: 153), 18S (protein sequence—SEQ ID NO: 86 and DNA sequence—SEQ ID NO: 154), and 28A (protein sequence—SEQ ID NO: 89 and DNA sequence—SEQ ID NO: 157), produced 3×, 2.8×, and 1× the amount of hydrogen of the positive control, respectively. Of the mutants tested, chimera #28S (protein sequence—SEQ ID NO: 158 and DNA sequence—SEQ ID NO: 90) was the only hydrogenase that exhibited attenuated hydrogen production, approximately 10% of the positive control.

Thus, disclosed is a method for the creation of an improved mutant such as chimeras, #2, 18A, and 18S, which showed more hydrogen production than the positive control. In fact, after one hour of incubation in the Methyl Viologen assay, these chimeras show 1-4× the amount of hydrogen production relative to the positive control. Since nearly all of the chimeras tested produced hydrogen above the level of the positive control (Chimeras #2, 18A, 18S, and 28A) or produced no hydrogen at all: Chimeras #1 (protein sequence—SEQ ID NO: 83 and DNA sequence—SEQ ID NO: 151), 21A (protein sequence—SEQ ID NO: 87 and DNA sequence—SEQ ID NO: 155), 21S (protein sequence—SEQ ID NO: 88 and DNA sequence—SEQ ID NO: 156), 30S (protein sequence—SEQ ID NO: 91 and DNA sequence—SEQ ID NO: 159), and 44 (protein sequence—SEQ ID NO: 92 and DNA sequence—SEQ ID NO: 160), this demonstrates that protein folding is critical and results in hydrogen production that is rather Boolean in nature.

Several structure/function relationships can be noted of the chimeras tested thus far. For example, chimera #1 and #18A are identical, except for segment #7 and chimeras #18A and #18S are identical to chimeras #21A and #21S, except for segment #8. Since chimeras #18A and #18S are positive for hydrogen production, whereas chimeras #1, #21A and #21S show no hydrogen production, it appears that beneficial results occur when segment #7 is derived from *C. acetobutylicum* and segment #8 be derived from *C. saccharobutylicum*. However, if both segments #5 and #8 are derived from *C. acetobutylicum* (Chimeras #28A and #28S) instead of just segment #8 (Chimeras #21A and #21S), hydrogen production is restored, although not to the levels of chimeras #18A and #18S.

Chimera #2 is a simple amalgam whose first half is derived from *C. saccharobutylicum* while its second half is derived from *C. acetobutylicum*. Again, the simple change of one segment (segment #8) is enough to decrease hydrogen production to zero (Chimera #30S), but changing segments #5 and #6 results in the hydrogen production being restored (Chimera #18S). Chimera #2 produced the most hydrogen of all the mutants tested, while its mirror image (Chimera #1) showed no discernible hydrogen production.

Five Clostridial hydrogenases were cloned (*C. perfringens* & *C. thermocellum*) or (*C. saccharobutylicum*, *C. pasteurinum*, & *C. tetani*). The original Clostridial hydrogenase, *C. acetobutylicum*, along with its accessory proteins, were cloned by King et al. into two dual expression vectors, pET Duet and pCDF (Novagen: #TB337 and #TB390). These two vectors were used as the positive control.

The Strep II tag "SAWSHPQFEK" (IBA GmbH: Göttingen, Germany) and a stop codon were cloned between the AscI and NotI restriction sites of the pET Duet vector (see FIG. 16). Thus, the Strep II tag is in frame and immediately downstream of the AscI restriction enzyme site which is just downstream of the hydrogenase gene. This plasmid, renamed "pET DLS", was designed in this manner so that both the hydrogenase and the tag were easy to insert and readily removable from the plasmid backbone. The pCDF plasmid was used without alterations.

Genomic DNA for *C. perfringens* was obtained from the American Type Culture Collection (ATCC: #13124D-5). The hydrogenase in *C. perfringens* (CpeI) was isolated by amplifying the DNA by PCR from aliquots of the genomic DNA.

The *C. thermocellum* (CthI) hydrogenase, encoded in a plasmid, was obtained from the Lee Lynd Laboratory (Dartmouth College, NH), but was found to be missing sequence on the 3' end. The missing sequence corresponded to an additional two amino acids (lysine and a stop codon), which were identified by comparison to the genomic information at the Joint Genome Institute. The missing DNA sequence was added to the end of the gene using PCR and a new downstream primer with the additional bases included (see FIG. 19 SEQ ID NOs: 17-22).

The upstream and downstream PCR primers (see FIG. 19) were designed to be homologous to the start and stop codons of the published sequences (NCBI: *C. perfringens* #AB035092 and BAA95936; *C. thermocellum* #AAD33071 and AF148212). Both primers had extra bases (tails) that corresponded to either a NcoI restriction site (upstream primer) or an AscI restriction site (downstream primer). The *C. perfringens* PCR product was digested with NcoI and AscI (New England Biolabs (NEB): #R0193S and #R0558S) and cloned into the pET DLS vector (see FIG. 16). Prior to the cloning of the *C. thermocellum* PCR product into pET DLS, it was blunt cloned into a shuttle vector (Lucigen's Clonesmart HC Kan: #40728-1) and mutated (GCC (Ala)→GCG (Ala) at 1410 bp) (Stratagene Quikchange II site directed mutagenesis kit: #200523) in order to remove an internal NcoI site (see FIG. 19). Post mutation, the *C. thermocellum* PCR product was digested, as above, and cloned into the pET DLS vector.

Two mutagenesis libraries were created. The first library was generated using a random mutagenesis kit (Stratagene GeneMorph II: #200550) according to the manufacturer's protocol. The PCR protocol that generated the highest number of mutations was followed: an initial denaturation of 2' at 95° C. followed by 30 cycles of [0.5' at 95° C., 0.5' at 59° C. 2' at 72° C.].

Figure 14:
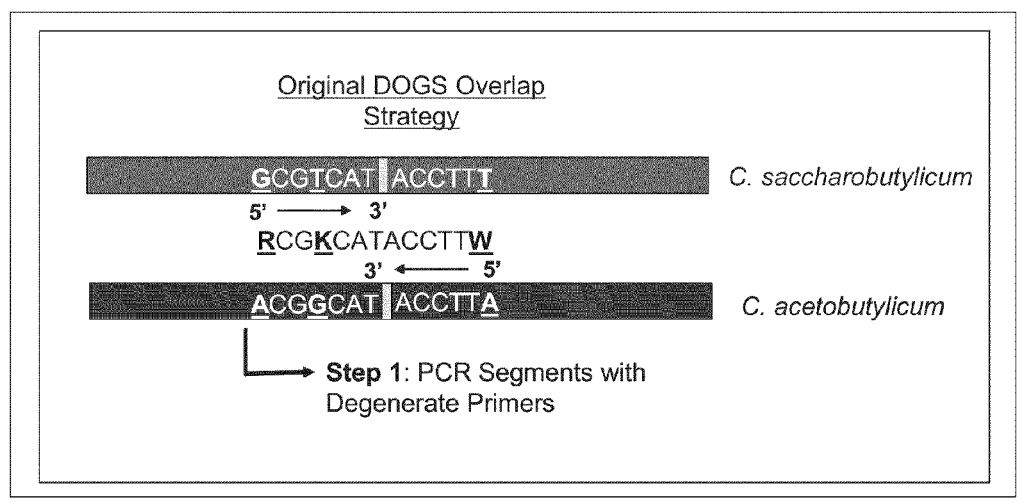
FIG. 14 illustrates the design of the primers for the original (DOGS) technique.

A second mutagenesis library was created using a variation of the original DOGS method (see FIGS. 13 through 15). The total length of the gene was first divided into eight segments of equal length. The segment lengths varied from 160bp to 290bp, as it was necessary to choose the segment boundaries within regions of homology (see Table 1 SEQ ID NOs. 23-38 (middle column); SEQ ID NOs: 39-54 (right hand column)). Each segment was individually generated by PCR using 30ng of the plasmid containing the parent hydrogenase. The PCR protocol utilized Phusion polymerase (New England Biolabs (NEB): #F530L) according to the manufacturer's protocol: an initial denaturation of 30 sec. at 98° C. followed by 35 cycles of [10sec. at 98° C., 20sec. at 57° C. Δ7° C., 20sec. at 72° C], and a final extension of 10' at 72° C. The segments were gel purified (Qiagen Qiaex II kit: #20021) and digested with SapI (NEB. #R 0569T 1

The digested segments were column purified (Qiagen Qia-Quick PCR kit: #28104) and 50-100 ng of each segment was mixed together and ligated (Lucigen T4 ligase: #30025-2). To generate the full-length hydrogenases, the ligated segments were amplified by PCR using 1-2 µl of the ligation mixture and primers that complemented the homologous regions just upstream and downstream of segment numbers one and eight, respectively.

The SapI variation of the DOGS method could generate ligations of up to four segments, so the library was ultimately created using a combination of the original DOGS method and the SapI variation. The SapI variation on the DOGS method was utilized, as above, to combine the eight individual segments, from both parental genes, into four ¼-length chimeras, each with a combination of two segments, i.e. all the possible combinations of segment 1 and segment 2 were generated as well as segment 3 with segment 4, etc. After ligating the SapI generated segments, the ¼-length chimeras were amplified by PCR using primers appropriate for the particular ligation.

The appropriate primers (see Table 1 SEQ ID NOs. 23-38 (middle column); SEQ ID NOs: 39-54 (right hand column)) had extra bases added (see Table 2 SEQ ID NOs. 55-66) that included 10-15bp of overlap with the ¼-length chimeras on either side. The quarter genes were purified (Qiagen Qiaex II kit: #20021) and then re-amplified into ½-length or full-length chimeras using a two-step program that first allowed the individual ¼-length chimeras to overlap before the outside primers generated the full-length gene: an initial denaturation of 30sec. at 98° C. followed by two cycles of [10sec. at 98° C., 30sec. at 60° C., 30sec. at 72° C], a pause at 93° C., 35 cycles of [10sec. at 98° C., 20sec. at 59° C., 40sec. at 72° C], and a final extension of 10' at 72° C.

The first two cycles allowed the segments to self-prime and extend from the overlapping regions. The outside primers were added during the pause, which lasted approximately three minutes before the full-length chimeras were generated. The resulting full-length chimeras were gel purified, digested with NcoI & AscI (NEB: #R0193S and #R0558S), column purified, and cloned into the pET DLS vector. The above procedure, of digestion with SapI followed by ligation and PCR amplification, can be repeated several times, as necessary, to obtain a full-length chimeric hydrogenase.

TABLE 1

Locations of the DOGS segment boundaries.

| Segment | Segment Length[1] | SapI Generated Overhang[2] | Overhang Location[3] | Upstream & Downstream Primers for *C. saccharobutylicum*[4] | Upstream & Downstream Primers for *C. acetobutylicum*[4] |
|---|---|---|---|---|---|
| 1 | 211 (462) | ggt | 212-214 | 5' cccacgccgaaacaag 3'<br>5' accataccttcttcaacttttg 3' | 5' cccacgccgaaacaag 3'<br>5' accattccatcttcaactttggc 3' |
| 2 | 229 | tgt | 441-443 | 5' ggtagtaaaaacaaactcag 3'<br>5' acacttagttctgtctattacaat 3' | 5' ggtaataaacacagaatccgatg 3'<br>5' acattttgatctgtcaattacaat 3' |
| 3 | 231 | cat | 672-674 | 5' tgtgtgctatgcggaaga 3'<br>5' atgcttattaggatcttctaatg 3' | 5' tgtgtactatgcggtagatg 3'<br>5' atgttttttagggctcattaagag 3' |
| 4 | 192 | aaa | 864-866 | 5' catgtaatagttgctatggc 3'<br>5' tttaactctttcaataaactctg 3' | 5' catgtcattgttgcaatggc 3'<br>5' tttaactctgcctaaaagttcagt 3' |
| 5 | 284 | aga | 1148-1150 | 5' aaaaataatggaccattccca 3' | 5' aaaaataatggcccattccctatg 3' |

TABLE 1-continued

Locations of the DOGS segment boundaries.

| Segment | Segment Length[1] | SapI Generated Overhang[2] | Overhang Location[3] | Upstream & Downstream Primers for C. saccharobutylicum[4] | Upstream & Downstream Primers for C. acetobutylicum[4] |
|---|---|---|---|---|---|
| | | | | 5' tctcttgtagtaagtactgcatc 3' | 5' tctcttgtagttaaggatgcatcaa 3' |
| 6 | 214 | ata | 1362-1364 | 5' agaattagcaaaaatgattaaagatgcaa 3' | 5' agagcttgcaaaaatgattaaagatgc 3' |
| | | | | 5' tattccttgtaatcctcttatttgtgtat 3' | 5' tatgcctttaaagcctcttacttcag 3' |
| 7 | 159 | gga | 1521-1523 | 5' ataaagaggctacagtagaaattggtgg 3' | 5' ataaaagaagcggaagttgaaattgc 3' |
| | | | | 5' tccaccatttacacatccgcc 3' | 5' tccaccatttatacatccaccag 3' |
| 8 | 205 (455) | N/A | N/A | 5' ggaggacaaccacacgta 3' | 5' ggaggtcaacctcacgtaaatg 3' |
| | | | | 5' tacgattactttctgttcgactta 3' | 5' tacgattactttctgttcgactta 3' |

[1]The first and last segments were longer to allow for nested primers. The total length of the segment is listed in parenthesis.
[2]The overhang was generated at the end of the listed segment.
[3]The location in C. Saccharobutylicum.
[4]Each of these primers had a SapI "gactgactGCTCTTCt" tail.

TABLE 2

Primers for Overlap PCR.

| Overlapping Segments[1] | Overlapping Parental Segments[2] | Forward/Reverse Degenerate Overlap Primers[3] |
|---|---|---|
| 1 & 2 with 3 & 4 | Saccharo & Saccharo | 5' gtaatagacagaactaagtgtgtgctatgcggaagatgt 3' |
| | Saccharo & Aceto | 5' gtaattgacagatcaaaatgtgtgctatgcggaagatgt 3' |
| | Aceto & Aceto | 5' gtaatagacagaactaagtgtgtactatgcggtagatgcg 3' |
| | Aceto & Saccharo | 5' gtaattgacagatcaaaatgtgtactatgcggtagatgcg 3' |
| 3 & 4 with 5 & 6 | Saccharo & Saccharo | 5' cagagtttattgaaagagttaaaaataatggaccattcccaatg 3' |
| | Saccharo & Aceto | 5' cagagtttattgaaagagttaaaaataatggcccattccctatg 3' |
| | Aceto & Aceto | 5' ctgaacttttaggcagagttaaaaataatggcccattccctatg 3' |
| | Aceto & Saccharo | 5' ctgaacttttaggcagagttaaaaataatggaccattcccaatg 3' |
| 5 & 6 with 7 & 8 | Saccharo & Saccharo | 5' aaataagaggattacaaggaataaaagaggctacagtagaaattg 3' |
| | Saccharo & Aceto | 5' aaataagaggattacaaggaataaaagaagcggaagttgaaattgc 3' |
| | Aceto & Aceto | 5' gtaagaggctttaaaggcataaaagaagcggaagttgaaattgc 3' |
| | Aceto & Saccharo | 5' gtaagaggctttaaaggcataaaagaggctacagtagaaattg 3' |

[1]The original parental genes were divided into eight segments.
[2]The parents are C. saccharobutylicum (Saccharo) and C. acetobutylicum (Aceto).
[3]The reverse primers are simply the inverse complement of the listed forward primer.

BL21 cells (Lucigen: #60300-1) were co-transformed with 30ng of pCDF and 30ng of pET DLS using an electroporator (Bio-Rad Micropulser: #165-2100) and 1 mm cuvettes (Bio-Rad: #165-2089). The pET DLS vector contains the hydrogenase to be tested and also codes for the C. acetobutylicum HydE accessory protein. The pCDF vector codes for the HydF and HydG accessory proteins, also from C. acetobutylicum. The standard settings for electroporating E-coli were used: 1800Volts, 600Ohms, and 10μF. After electroporation, the cultures were allowed to grow for one hour and plated (200μl) on standard LB plates containing Ampicillin (50μg/ml) and Streptamycin (50μg/ml).

Expression of the hydrogenases was performed using the method of Posewitz et al. Overnight cultures (10 ml) were started from a single colony and used to inoculate sterile flasks containing 125 ml of LB media supplemented with Ampicillin and Streptamycin. The flasks were shaken (300 rpm) at 37° C. until they reached an optical density of $A_{600}$=0.6-0.8 (approx. 5-6 hours). The optical density was measured on a spectrophotometer (Nanodrop Technologies: #ND-1000, Software Version 3.1.0).

In order to induce expression, IPTG was added to a final concentration of 100 mM and the flasks were transferred to a room temperature shaker (150 rpm) for one hour. The solutions were then transferred to 125 ml serum bottles (Wheaton: #223748), rubber septa (Chemglass: #CG-3022-24) were inserted, and the cultures were thoroughly degassed with Argon 5.0 (General Air: #UN 1006)) for 4-6 hours. The cultures were allowed to sit overnight at room temperature before being analyzed.

Using an argon purged gas-tight syringe (Hamilton: #81430), 1 ml of 2× Methyl Viologen (recipe in Appendix D) solution and 100 μL of a 100 mM dithionite solution (recipe in Appendix D) were added through a septum into an anaerobic 10 ml serum bottle (Wheaton: #223739). Subsequently, 1 ml of cells was transferred anaerobically to the serum bottle. The serum bttles were allowed to sit for at least 60 minutes, mixing occasionally by inversion.

The headspace of the serum bottles was tested for molecular hydrogen by gas chromatography. A 400 μl sample of the headspace gas was injected into a GC (SRI Instruments:

310C) containing a molecular sieve column (SRI Instruments: #5A 2 feet long) at a constant temperature of 40° C. The results were recorded using the PeakSimple Software (SRI Instruments version 3.29).

The error-prone PCR technique created a library of progeny genes that contained an average of 10 point mutations per hydrogenase gene. The DOGS technique created a library of 254 full-length hydrogenase genes, but each of the 254 chimeras was unique and contained sizeable amounts of shuffled genetic material.

Chlamydomonas reinhardtii (C. reinhardtii) is known to contain two hydrogenases (HydA1 and HydA2), both of which produce molecular hydrogen. However, both the transcription of the RNA and the mature hydrogenase protein are sensitive to oxygen, a by-product of photosynthesis, which results in only a brief evolution of molecular hydrogen. However, mutations engineered into the native algal hydrogenase will generate chimeric hydrogenases with an increased rate of hydrogen production and/or an increased tolerance to the presence of oxygen. Each type of chimeric hydrogenase would result in an increased amount of hydrogen production. More importantly, subsequent rounds of mutation have the potential for further improvement. In order to successfully create a mutant version of C. reinhardtii, the goal was to identify, clone, sequence, and express the hydrogenase genes that were responsible for the generation of hydrogen in algae.

C. reinhardtii contains an enzyme (hydrogenase) that produces molecular hydrogen from electrons donated by ferredoxin, an enzyme in the photosynthetic electron transport pathway, and in fact, according to the present disclosure, it was determined that C. reinhardtii actually contains two hydrogenases, HydA1 and HydA2

These hydrogenases were cloned and a vector that could express the hydrogenases in algae designed and tested. The transformation of heterogeneous DNA, via a vector, into C. reinhardtii was difficult due the distinct codon bias of the alga. Subsequent extraction of the transformed DNA was also difficult due to the alga's predilection for digesting the transformed DNA and incorporating it at random locations within the genome.

Figure 7:
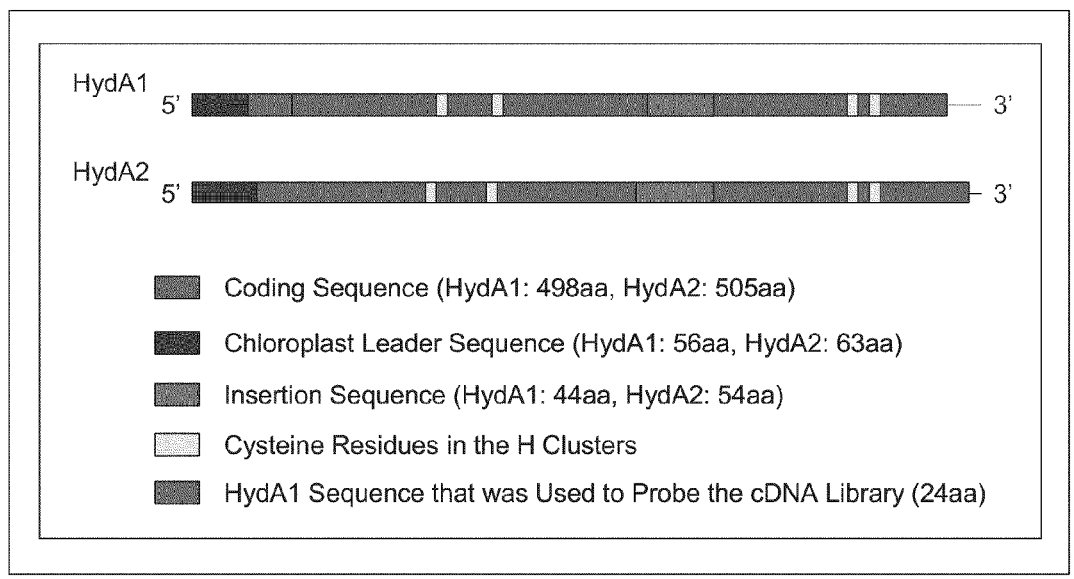
FIG. 7 is the sequence comparison of the two *C. reinhardtii* hydrogenase genes.

Probing the cDNA library successfully identified two hydrogenases, designated as HydA1 and HydA2, which were cloned and sequenced (FIG. 7). HydA1 and HydA2 are similar in that they both have the ability to produce molecular hydrogen and are sensitive to molecular oxygen. HydA2 is 68% identical and 74% similar (i.e. a related amino acid) to HydA1. Although functionally similar and approximately the same length, HydA1 (495 aa) and HydA2 (505 aa) are distinct proteins from separate genes with different promoter regions. In addition, the leader sequences in HydA1 and HydA2 are quite distinct, which indicates that they may function in different locations of the chloroplast.

First, the un-translated regions (UTR) immediately upstream (5' UTR) and downstream (3' UTR) of the gene were utilized to create a vector (pGenD) that is capable of driving the expression of cDNA in algae, including cDNA foreign to the alga.

Then apGenD vector was used to create a pGenD+Ble by inserting a Bleomycin antibiotic resistance gene (BLE) into XhoI/PacI downstream of the 3' un-translated region. Antibiotic resistance confers selectivity for the alga containing the plasmid, allowing it to grow in the presence of Bleomycin antibiotic, while repressing the growth of bacteria or algae without the plasmid.

Figure 8:
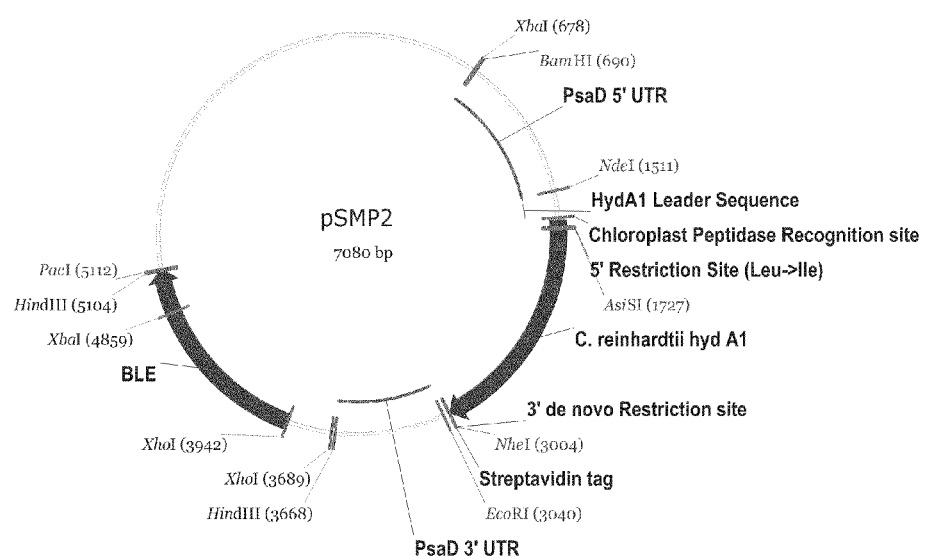
FIG. 8 is a plasmid map of the algal expression vectors: A) pSMP1, B) pSMP1c, and C) pSMP2.

Then, the pGenD+Ble vector was altered to createdthe new vector, named "pSMP", by inserting the cDNA of one of the C. reinhardtii hydrogenases (HydA1) between the NdeI and NheI restriction sites thereby replacing the original coding sequence (FIG. 8). A strepII tag was added at the 3' terminus of the HydA1 gene between the NheI and EcoRI restrictions sites (FIG. 8). The tag allows ready detection and differentiation of the HydA1 DNA, RNA, and protein from the indigenous hydrogenases. Lastly, a restriction site was created, so as to separate the HydA1 leader sequence from the DNA that codes for the mature protein.

The leader sequence contains cellular instructions for the placement of the mature protein in the correct location within the algal chloroplast. It was important to insert mutated coding sequences without changing the leader sequence. Since it was unknown whether or not an internal restriction site would impede the successful expression of the vector, three pSMP vectors (pSMP1, pSMP1c, and pSMP2) were created, each with a slightly different restriction site. In the case of pSMP1, a PspOMI restriction site was inserted, de novo, immediately downstream of the leader sequence (FIG. 8A).

As it was possible that even a small (6 bp) de novo insertion could interfere with expression, two additional pSMP vectors were created. The vector pSMP1c had a PspOMI site created from a conservative mutation about 20 nucleotides (nt) downstream of the end of the leader sequence (FIG. 8B). The vector pSMP2 had an AsiSI site created from a conservative mutation about 45 nt downstream from the end of the leader sequence (FIG. 8C). These vectors were tested for expression of HydA1 cDNA in C. reinhardtii.

Figure 9:
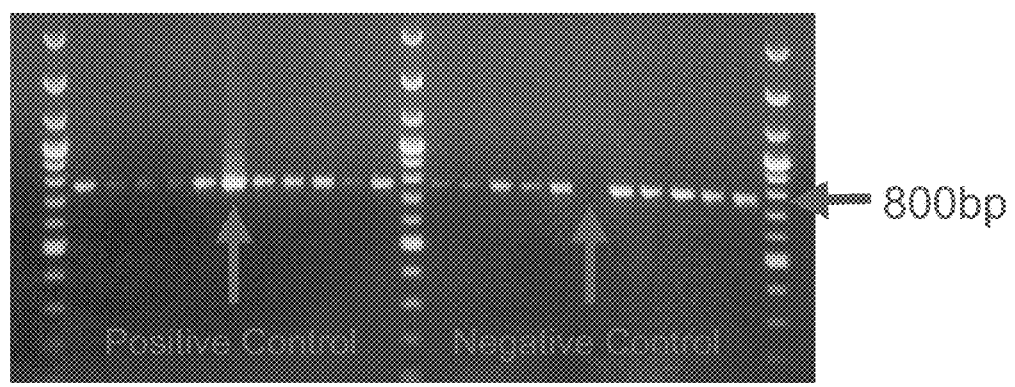
FIG. 9 is a picture of an agarose gel (1%) showing the results of PCR on the genomic DNA extracts of algal transformants.

The vectors each containing the hydrogenase, HydA1, were transformed into C. reinhardtii. Genomic DNA was extracted from 20 different transformations of the pSMP vectors. The hydrogenase DNA was amplified by polymerase chain reaction (PCR) with primers specific to the 3' end of the hydrogenase and the transformed vector. The 800 base pair (bp) band indicated that each of the 20 genomic extracts received the plasmid (FIG. 9). There was no difference in the transformation efficiency of the three vectors.

Figure 10:
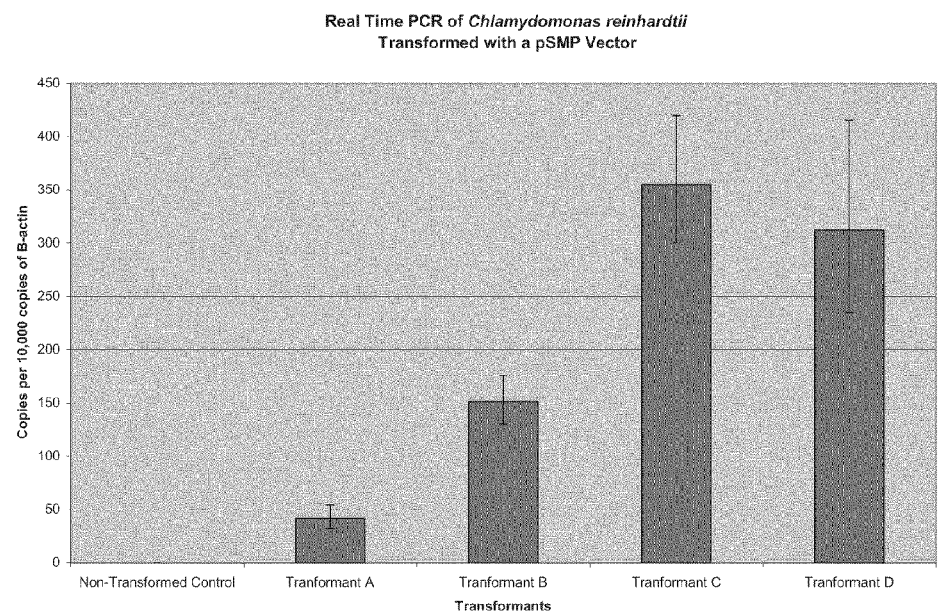
FIG. 10 shows the RNA expression levels by real time PCR of cDNA from algal transformants.

Twelve of the above transformants were tested for RNA expression using real-time reverse transcriptase PCR (RT-PCR) and four were positive for expression (FIG. 10). Five of the twelve had been transformed with pSMP1 and two (A & B in FIG. 10) of the five were positive for expression (40%). In addition, three of the twelve were transformed with pSMP1c and two (C & D in FIG. 10) of the three were positive for expression (67%). The remaining four transformants were transformed with pSMP2 and all were negative. The pSMP1 and pSMP1c vectors are therefore useful for expressing the hydrogenases in C. reinhardtii. Plasmid pSMP1c appears to be the best transformation vector given that two-thirds of the transformants were positive for expression and they had a higher level of expression than the pSMP1 transformants.

Figure 11:
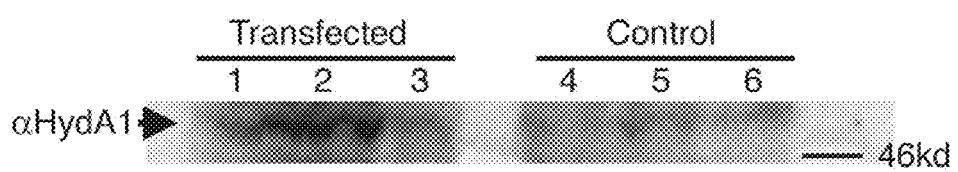
FIG. 11 shows the western blot of one of the transformants and a non-transformed control.

A transformant containing pSMP1 was tested for protein expression by Western blot (FIG. 11). Two proteins, at approximately 49 kiloDaltons (kD) and 97 kD, were present in the transformed sample and not present in the non-transformed control. The 49 kD band is the correct molecular weight of the HydA1 protein and the faint band at 97 kD (data not shown) is likely a dimer.

The results show that pSMP1 and pSMP1c vectors are useful for expressing the hydrogenases in C. reinhardtii. Plasmid pSMP1c appears to be the best transformation vector given that two-thirds of the transformants were positive for expression and they both had a higher level of expression than the pSMP1 transformants. Because the RT-PCR and Western blot were positive for expression insertion and expression of the wild-type hydrogenase (cDNA) in C. reinhardtii was accomplished.

In order to isolate the HydA1 and HydA2, a cDNA library was obtained (John Davies, Exelixis Inc.: San Francisco, Calif.), which had been created under anaerobic conditions and believed to contain the hydrogenases. The library consisted of viral particles, known as phage, which contained the cDNA of *C. reinhardtii*. In order to detect cDNA that contained a hydrogenase, the phage library was allowed to infect XL-1 Blue bacteria (Stratagene: #211204 and #211203). The infected cells were then mixed with top agarose and plated on LB-agar plates at a density of 5000 plaques per plate. The phage-infected bacteria formed a lawn punctuated with plaques, clear spots where the cDNA containing phage have infected and lysed all the bacteria surrounding the initial infection. The pattern of clear spots on the plates were copied by overlaying the plate with a membrane (ISC BioExpress: #F-3193-82) for three minutes. Afterwards, the plate was sealed with Para film and saved at 4° C. until it could be determined whether any of the plaques contained a hydrogenase. The membrane was treated and washed three times (Promega Technical Bulletin #72) before the DNA was cross-linked to the membrane via exposure to UV light ($\lambda$=365 nm).

The membrane, which now contains a copy of the plaques on the LB plate, was pre-hybridized (Sigma Perfect-Hyb: #H-3032) for 30 minutes at 68° C. to block non-specific binding sites, before it was hybridized to a chemiluminescent probe for 3 hours at 68° C. The chemiluminescent probe was created by binding a reporter molecule, digoxigenin, to the oligonucleotide of putative hydrogenase DNA mentioned above. First though, the oligonucleotide was purified and concentrated before it was labeled with digoxigenin-dUTP (Roche: #1-573-152) using a random labeling kit (MBI Fermentas: #K0621). The suspected hydrogenase portion of the probe binds homologous cDNA on the membrane, presumably hydrogenase containing cDNA. After the probe bound to the cDNA on the membrane, it was washed, blocked, and treated with an anti-digoxigenin antibody, which is bound to alkaline phosphatase (Roche: #1-093-274). Detection of the bound antibody was accomplished by providing two substrates to the alkaline phosphatase, which results in a purple color wherever the probe is bound to the membrane. (Roche: #1-175-041).

The purple spots on the treated membrane corresponded to plaques on the LB plate that contained cDNA, which bound the probe. The bound cDNA were possible hydrogenases, so the designated plaques were removed from the agar with a wide bore pipette tip. Phage were purified from the agar by incubating the plaques in 1 ml of phage buffer while shaking for three hours at room temperature. The purified phage were diluted and allowed to re-infect fresh XL-1 Blue bacteria. Afterwards, they were re-plated at an approximate density of 100 plaques per plate. The purification process was repeated, as above, by copying the new plates with membranes, treating the membranes with the chemiluminescent probe, and isolating the positive plaques. The initial positive plaques were considered "plaque purified" after performing three rounds of plating and purifying.

The cDNA were extracted from the purified phage by infecting XPORT bacteria (Stratagene: #211204) and plating with NZY top agarose on NZY plates. The plates were incubated overnight at 37° C. The phage was collected by overlaying the plate with 3 ml of SM buffer (recipe in Appendix D) for 30 minutes, centrifuging, and resuspending in 100 µl of SM Buffer. The concentrated cells were used to infect XLOLR cells (Stratagene: #211204) before plating on LB plates. As a result, cDNA was now contained as a plasmid within the XLOLR bacteria.

The *C. reinhardtii* hydrogenase HydA1 gene was amplified by PCR from the cDNA described above. Restriction sites (NdeI and NheI) were added to the primers to facilitate cloning into the vector. The pSMP1, pSMP1c, and pSMP2 plasmids were created by replacing the original gene (PsaD) with the HydA1 DNA. Both the pGenD+Ble plasmid and the HydA1 gene were digested with NdeI and NheI (New England Biolabs (NEB): NdeI: #R0111S and NheI: #R0131S), purified (Qiagen Qiaex II kit: #20021), and ligated (Lucigen T4 ligase: #30025-2). The strepII tag (IBA GmbH: Gottingen, Germany) was inserted, by PCR mutagenesis, at the 3' terminus of the HydA1 gene between the NheI and EcoRI (NEB: #R0101 S) restriction sites. The mutagenesis (Stratagene QuikChange Site-Directed Mutagenesis kit: #200519) was performed according to the manufacturer's protocol, except the extension time was increased to 2-3 minutes/kb in order to accommodate the large insertion (30bp) (FIG. 12). The PspOMI (NEB: #V0215S) restriction sites in pSMP1 and pSMP1c and the AsiSI (NEB: #R0630S) restriction site in pSMP2 were created by site directed mutation (Stratagene Quik-change Multi site directed mutagenesis kit: #200515) after an existing PspOMI site was removed from a different location. The PCR protocol and the mutational primers were designed according to the manufacturer's protocol (FIG. 12, SEQ ID NOS. 3-12).

All of the algal strains, including the pSMP1 transformants, were grown under oxygenic conditions in 50 ml of sterile TAP media utilizing 250 ml Erlenmeyer flasks. The flasks were shaken at 100-150 rpm and exposed to 100 µE (1 µE=1 µEinstein=1 µmoles photons/$m^2$·sec=500 foot candles) of light from standard fluorescent fixtures.

Each of the three pSMP vectors were transformed into the dw15-1 (courtesy of Barb Sears: Michigan State Univ.), a fast growing variant of the common *C. reinhardtii* cc425 strain, using a BTX ECM 630 electroporator with the following settings: 750 Volts, 25 µF, and 1575 ohms. Immediately after electroporation, the algae were mixed with 3 ml of cornstarch suspended in TAP+60 µM sucrose and plated on Tris-Acetate-Phosphate (TAP) plates containing 10 µg/ml of the antibiotic Zeocin (140). The resulting transformants were grown, as above, for one week before they were transferred to standard TAP plates containing no antibiotics. The transformants were transferred to plates without antibiotics as Zeocin is a presumed mutagen and antibiotics are not necessary to maintain the transformants, since the plasmid DNA is incorporated into the alga's genome.

Algal transformants containing the pSMP1, pSMP1c, or pSMP2 vectors, were inoculated from plates into liquid culture. The cultures were harvested at chlorophyll (Chl) concentrations between 15-18µg Chl/ml (exponential growth phase) and all 50ml was centrifuged at 4000g for 5 minutes. The genomic DNA was isolated (Qiagen DNAeasy Plant kit: #69104) and PCR was performed on the genomic preparations from each of the three different pSMP transformations. The primers were specific to the 3' end of the hydrogenase cDNA. The PCR conditions were: 1' initial denaturation at 95° C., 35 cycles of [30sec. at 95° C., 30sec at 60° C., and 2' at 72° C], and 10' final extension 72° C. The upstream primer (5' CCAGCTGCTGCCAGAATTC 3', SEQ ID NO. 13) and the downstream primer (5' CCAGCTGCTGCCAGAATTC 3', SEQ ID NO. 14) amplify the last 800 bases at the 3' end of the HydA1 hydrogenase.

Cells were harvested at chlorophyll (Chl) concentrations between 18-25 µg Chl/ml by centrifuging 10ml of algal culture at 2000g for 1 minute. RNA was obtained (Qiagen RNAeasy kit: #74104) and treated with a DNaseI (Ambion Turbo DNA-free kit: #1907) to remove the residual plasmid DNA. The cDNA was generated from the purified RNA (Qiagen Quantitect Reverse Transcription kit: #205311). Real-Time RT-PCR was performed on all of the samples using an upstream primer (5' GACGAGAAGAAG-GCTAGCGC 3', SEQ ID NO. 15) specific to the 3' end of the hydrogenase and a downstream primer (5' CCAGCTGCT-GCCAGAATTC 3', SEQ ID NO. 16) that was specific to the strepll tag (IBA GmbH: Germany). DyNAmo SYBR Green (Applied Biosystems: #4367660) on an Applied Biosystems 7300 Real Time PCR system was used. The real time RTPCR program was: an initial dissociation of 10 minutes at 95° C. followed by 40 cycles of 95° C. for 15 seconds and 60° C. for one minute, and lastly, a dissociation stage of 95° C. for 15 seconds, 60° C. for 30 seconds, and 95° C. for 15 seconds.

Cells were harvested at chlorophyll (Chl) concentrations between 16-20 μg Chl/ml by centrifuging 10 ml of algal culture at 2000 g for one minute. The pellet was resuspended in lysis buffer (6% SDS in 1×PBS) plus 10 μl/ml each of Phosphatase Inhibitor Cocktails 1 & 2 (Sigma: #P5726-5 ml and #P2850-5 ml). The samples were vortexed, mixed with loading buffer, and separated by SDS-PAGE under reducing conditions (1% β-mercaptoethanol) using an 8-16% Tris-Glycine gel (Invitrogen: #EC6048BOX).

Since SDS interferes with the Bradford total protein assay, the chlorophyll concentration of each of the samples was determined by the method of Harris (76) and equal amounts of chlorophyll (and thereby of protein) were loaded onto the gel. The gel was subjected to 125 Volts for approximately 2 hours, or until the dye front reached the bottom of the gel. The proteins were transferred to a PVDF Hybond-P membrane (Amersham: #RPN303F) for 1.5 hours at 25 Volts. Proof of equal loading of the gel lanes was obtained by staining the gel (for total protein) overnight in Coomasie (Pierce: #24590) (not shown). The stained gel was dried and sealed in cellophane (Invitrogen: #NC2380).

The membrane was blocked in 1×PBS containing 0.5% Tween-20, 3% BSA, and 1/1000Biotin Blocking Buffer (IBA GmbH: #2-0501-002) following the IBA protocol for all washes. The membrane was probed with an anti strepll tag mouse antibody (IBA GmbH: #2-1507-001) at 4° C. overnight at a concentration of 1000 ng/ml (1/200dilution of the stock concentration). The secondary antibody (donkey anti-mouse conjugated to horse radish peroxidase (HRP)) (Jackson Labs: #715-035-151) was allowed to incubate for one hour at room temperature at a concentration of 67 ng/ml (1:3000 dilution of the stock). Protein was detected using ECL-plus developing solutions (Amersham: #RPN2132) and visualized using a Kodak DS Image Station 440CF using 1D Image Analysis Software.

Bacterial hydrogenases were cloned and the best two were used as the parent genes in a combinatorial shuffle that resulted in a library of chimeric hydrogenases. Several chimeric hydrogenases showed hydrogen production, including three chimeras that produced hydrogen at levels three to four times higher than the parent hydrogenases.

Since several chimeras produced hydrogen, despite significant differences in their amino acid sequences, several mutational pathways may result in mutants with improved hydrogen production. The remainder of the mutant library can be tested for hydrogen production. The chimeric proteins with an improved hydrogen production can be sequenced and computationally modeled, both of which are capable of identifying the mutations that result in the improved chimeric proteins. Such modeling has been initiated and is described below. When such a comparison is made of the diversity of successful chimeras, it is possible that a combination of the individual mutations will result in a chimera with a dramatically increased level of hydrogen production. Shuffles with additional parent genes or successive shuffles of the improved chimeric hydrogenases from the first shuffle may also result in a highly evolved hydrogenase. Thus, also disclosed is a method for mutating bacterial hydrogenases to produce increased amounts of hydrogen after just one round of a combinatorial shuffle.

Exogenous DNA of hydrogenases can be successfully re-introduced into the genome of *Chlamydomonas reinhardtii* (*C. reinhardtii*). Once transformed, the plasmid containing the hydrogenase gene was successfully expressed at both the RNA and protein levels thus, illustrating that mutated *C. reinhardtii* hydrogenase genes can also be inserted and expressed. Therefore, the present disclosure provides for expression of chimeric hydrogenases in *C. reinhardtii*, and expression of chimeric algal hydrogenases containing mutations with improved function. Further disclosed then is a method for using these chimeric algal hydrogenases, when expressed in *C. reinhardtii* for photosynthetic hydrogen production and eventually, renewable energy via hydrogen powered fuel cells.

Additionally, disclosed is a model system by which different mutations can readily be created and tested. Further analysis of the hydrogen production of the remainder of the existing mutant library in conjunction with molecular modeling determines what characteristics are shared between the mutants with improved hydrogen production. Considerable improvement frequently results from the comparison and combination of mutations isolated in the first round of shuffling. In addition, future rounds of directed evolution might benefit by the inclusion of the other four Clostridial parent sequences.

In order to link the photosynthetic transport chain with an improved hydrogenase, the mutations that result in the most improved bacterial mutant will need to be re-created in the algal hydrogenase. Since the algal hydrogenase has a disparate codon bias and is merely homologous, not identical, to the bacterial hydrogenase, mutations in the algal enzyme will need to be created and tested to determine if the same improvement is realized. Ultimately, an improved chimeric algal hydrogenase, transformed into *C. reinhardtii*, is the basis for an economically viable method of hydrogen production.

Six chimeric hydrogenase proteins and a wild type hydrogenase from *Clostridium acetobutylicum* were used to develop a prediction model for other protein mutants that were not tested for hydrogen production. The hydrogenase mutants yielded hydrogen productions from zero to 4 times that produced by the wild type control.

In the first step, amino acid compositions were used to construct alpha-helix structures. These structures were then energy minimized using OPLS molecular mechanics technology. Next, the positive and negative electrostatic potential energy surfaces were calculated for each protein mutant. The computations up to this point were performed with the Hyper-Chem 7.5 computational chemistry program.

In the next step, positive to negative electrostatic surface area ratios were plotted versus experimental hydrogen production for the six protein mutants and the wild type control. The plot was then regressed with several mathematical functions using the Microcal Origin 4.1 program. The function that fit the plot with the least error was Log Normal Gaussian. Hence, this function was chosen as the prediction model. The Log Normal Gaussian function has been successfully used in several other studies relating molecular performance with molecular structure.

The selected prediction model suggests that the ratio of positive to negative surface area is a measure of how a given protein mutant will fold into its tertiary state and how the final tertiary state affects hydrogen production. The results also show that a surface area ratio in the range of 15 to 115 is required to achieve hydrogen production greater than that obtained with the wild type control (please reference the accompanying FIG.). The maximum hydrogen production is achieved with a positive to negative electrostatic surface area ratio of 42.

In the final step, fifteen hydrogenase mutants, for which hydrogen productions were not experimentally obtained, were analyzed using the above described procedure. Five mutants exhibited positive to negative electrostatic surface area ratios that were within the above-mentioned range. These proteins are predicted to produce hydrogen at 39.7×, 32.6×, 31.8×, 27.0×, & 26.8× that produced by the wild type protein. These mutants were named C26S (protein sequence—SEQ ID NO: 207 and DNA sequence—SEQ ID NO: 144), C4S (protein sequence—SEQ ID NO: 187 and DNA sequence—SEQ ID NO: 122), C22S (protein sequence—SEQ ID NO: 203 and DNA sequence—SEQ ID NO: 140), C24S (protein sequence—SEQ ID NO: 205 and DNA sequence—SEQ ID NO: 142), and C25S (protein sequence—SEQ ID NO: 206 and DNA sequence—SEQ ID NO: 143), respectively. Whereas the remaining ten mutants, C6S (protein sequence—SEQ ID NO: 189 and DNA sequence—SEQ ID NO: 124), C9S (protein sequence—SEQ ID NO: 192 and DNA sequence—SEQ ID NO: 127), C11S (protein sequence—SEQ ID NO: 194 and DNA sequence—SEQ ID NO: 129), C13S (protein sequence—SEQ ID NO: 196 and DNA sequence—SEQ ID NO: 131), C14S (protein sequence—SEQ ID NO: 197 and DNA sequence—SEQ ID NO: 132), C15S (protein sequence—SEQ ID NO: 198 and DNA sequence—SEQ ID NO: 133), C19S (protein sequence—SEQ ID NO: 201 and DNA sequence—SEQ ID NO: 137), C23S (protein sequence—SEQ ID NO: 204 and DNA sequence—SEQ ID NO: 141) and C29S (protein sequence—SEQ ID NO: 209 and DNA sequence—SEQ ID NO: 147) are predicted to yield no significant hydrogen productions since their surface area ratios were much greater than 115.

The genome of *C. thermocellum* has been sequenced, so its accessory proteins (HydE, HydF, and HydG) were found by electronically searching the published genome for comparable sequences to the known accessory protein sequences of *Clostridium acetobutylicum* (*C. acetobutylicum*). *C. thermocellum* HydE, HydF, and HydG were designated as gene 2382 on contig 245, gene 3099 on contig 253, and gene 1213 on contig 221, respectively.

All three *C. thermocellum* accessory proteins were cloned into the same locations within the same vectors as their corresponding genes from *C. acetobutylicum*. The new pET DLS (FIG. 20) and pCDF plasmids (FIG. 21), with the substituted *C. thermocellum* accessory proteins, were tested for hydrogen production using the Methyl Viologen assay described in Chapter Three. A second new pCDF plasmid was also created wherein the *C. thermocellum* HydG replaced the *C. acetobutylicum* version, but the *C. acetobutylicum* HydF was still intact. This hybrid vector, along with the first pCDF plasmid was constructed to determine if all three of the *C. thermocellum* accessory proteins are necessary for expression or if some combination of *C. thermocellum* and *C. acetobutylicum* proteins is needed.

Along with a positive and negative control, the above mentioned plasmids were tested for hydrogen expression. Five different combinations (see Table 3) of plasmids were tested and all were negative. These plasmids were also given to Matthew Posewitz (NREL: Golden, Colo.) and his lab obtained negative results as well. Hence, it seems that the hydrogenase from *C. thermocellum* requires a higher temperature or something yet to be determined, in order to produce molecular hydrogen.

TABLE 3

Various combinations of the three pDLS and pCDF plasmids that contain the *C. thermocellum* accessory proteins.

| pDLS plasmid | pCDF plasmid | Result |
| --- | --- | --- |
| Positive Control | Standard pCDF | Positive H2 production |
| Standard pDLS | Standard pCDF | No $H_2$ production |
| Plasmid #1 | Standard pCDF | No $H_2$ production |
| Plasmid #1 | Plasmid #2 | No $H_2$ production |
| Plasmid #1 | Plasmid #3 | No $H_2$ production |
| Standard pDLS | Plasmid #2 | No $H_2$ production |
| Standard pDLS | Plasmid #3 | No $H_2$ production |

Using primers that were designed for these putative sequences (FIG. 22, SEQ ID NOS. 210-223) and genomic DNA from *C. thermocellum* (American Type Culture Collection: #27405D), the genes for all three accessory proteins were obtained by PCR. KOD polymerase (VWR: #80511-384) was utilized with the following PCR conditions: 2' initial denaturation at 94° C., 35 cycles of [15sec. at 94° C., 30sec. at 55-60° C. gradient, and 1.5' at 72° C], and a 10' final extension at 72° C.

Figure 20:
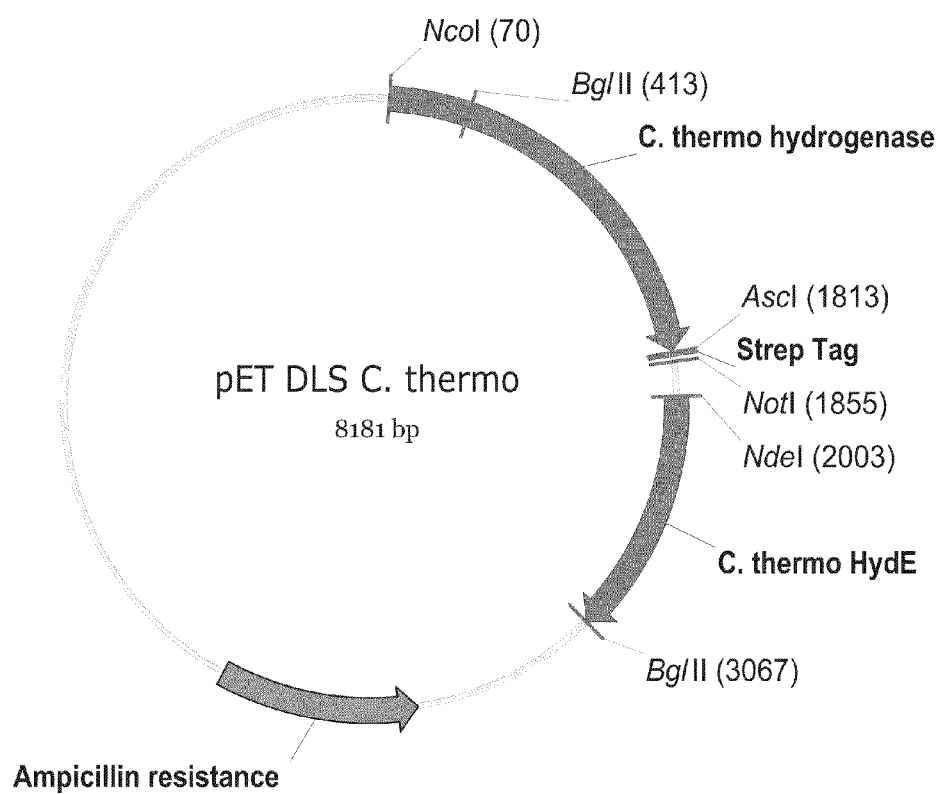
FIG. 20 shows the pET DLS Plasmid (8.2 kb) which contains the *C. thermocellum* hydrogenase and the HydE accessory protein.

The *C. thermocellum* HydE gene was cloned into the *C. thermocellum* pET DLS vector, replacing the *C. acetobutylicum* HydE gene (FIG. 20). However, the first step was to silently mutate the BglII site found within the *C. thermocellum* hydrogenase, so that the *C. acetobutylicum* HydE protein could be ligated only into the NdeI/BglII site (FIG. 22, SEQ ID NOS. 210-223). The Quikchange Multi site directed mutagenesis kit (Stratagene: #200515-5) was employed with the following PCR conditions: 1' initial denaturation at 95° C., 30 cycles of [1' at 95° C., 1' at 55° C., and 16.5' at 65° C]. Since a silent mutation was made in the *C. thermocellum* hydrogenase, it needed to be re-inserted in the NcoI/AscI site, once the *C. thermocellum* HydE gene was successfully ligated. The resulting plasmid was sequenced and compared to the expected sequence in the published genome.

Figure 21:
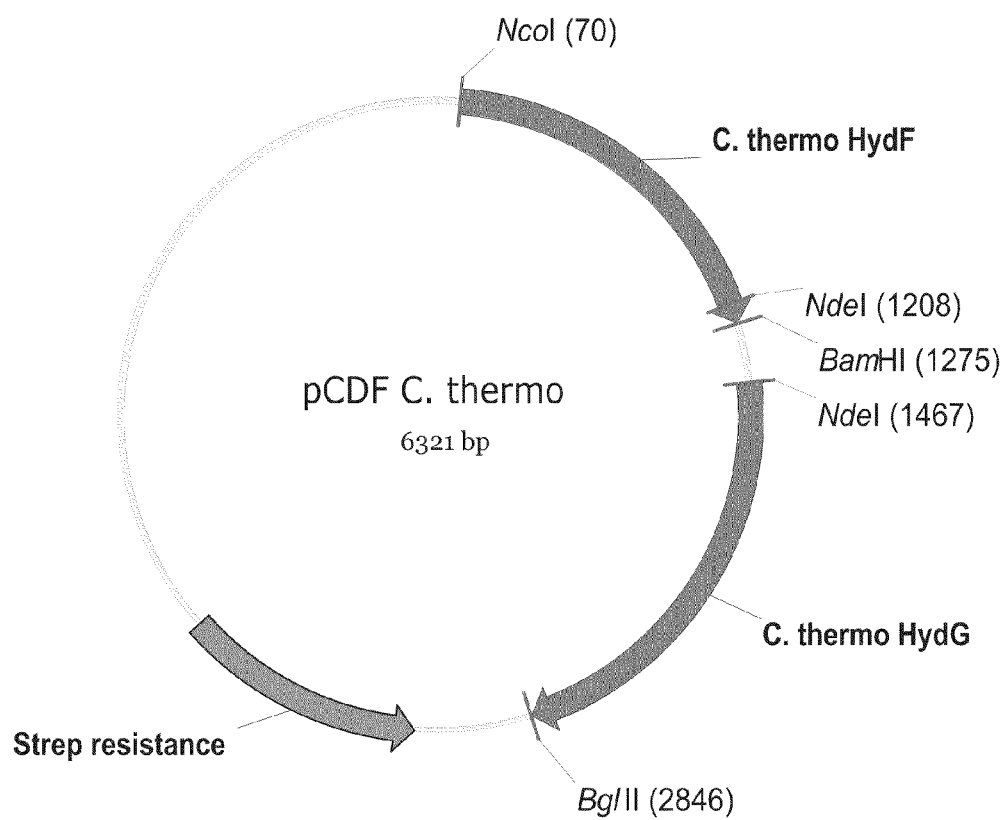
FIG. 21 shows the pCDF Plasmid (6.3 kb) which contains the *C. thermocellum* HydF and HydG accessory proteins.

The *C. thermocellum* HydF and HydG genes were cloned into pCDF, also in place of the corresponding *C. acetobutylicum* genes (FIG. 21). As was done for the pET DLS plasmid, a silent mutation was introduced into the *C. acetobutylicum* HydF to remove an internal NdeI site (FIG. 22). Again, the Quikchange Multi site directed mutagenesis kit (Stratagene: #200515-5) was utilized under similar PCR conditions: 1' initial denaturation at 95° C., 30 cycles of [1' at 95° C., 1' at 55° C., and 13' at 65° C.]. This mutation allowed us to replace the *C. acetobutylicum* HydG gene with the *C. thermocellum* version into the NdeI/BglII site without disrupting the HydF gene. The new *C. thermocellum* HydF was then cloned into the NcoI/BamHI sites, thereby replacing the mutated *C. acetobutylicum* HydF gene. The pCDF plasmid with the *C. acetobutylicum* HydF gene and the *C. thermocellum* HydG gene was kept, so it could be determined if all or just one of the *C. thermocellum* accessory proteins were necessary for successful expression.

Two sets of primers were used to create each of the silent mutations in the *C. thermocellum* pET DLS and pCDF vectors. The second set of complementary primers was non-mutational and hybridized, approximately half way around the plasmid from the engineered point mutation. The second set of primers was designed to eliminate any problems due to the processivity of the polymerase, so that it could successfully copy these large plasmids (FIG. 22).

Figure 23:
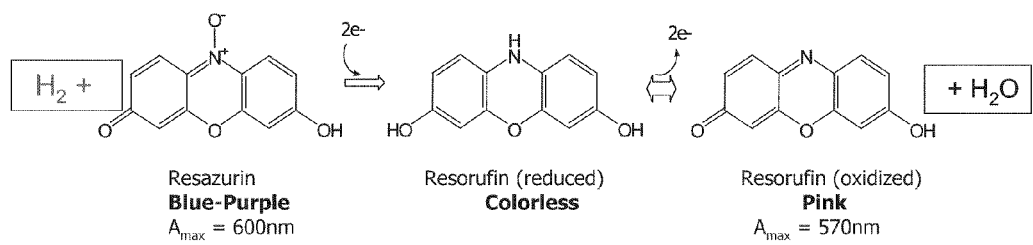
FIG. 23 illustrates the reaction mechanism for the reaction of molecular hydrogen withthe redox dye, resazurin.

The resazurin assay was designed to measure the evolution of molecular hydrogen from *C. reinhardtii* cells. Resazurin is a redox dye that reacts with molecular hydrogen (FIG. 23). However, resazurin has two oxidized forms rather than just one so its reaction kinetics is not as simple as phenolphthalein. Molecular hydrogen reacts irreversibly with resazurin (blue, $A_{max}$ of 600 nm) to form reduced resorufin (colorless). The oxidized form of resorufin (pink, $A_{max}$ of 580 nm) is in a fast equilibrium with the reduced form. In theory, the reaction between molecular hydrogen and resazurin could be measured by the decrease in absorbance of resazurin or the increase in absorption of the oxidized form of resorufin.

Wild type strains of *Chlamydomonas reinhardtii*, dw15-1 (Barb Sears, MSU) and cc425 were grown in tris-acetate-phosphate (TAP), pH=7.2, or TAP plus arginine (cc425) in sterile 250 ml Erlenmeyer flasks on a shaker rotating at 150 rpm in a 25° C. constant temperature room and continuously illuminated with white fluorescent light at 100 µE (1 µE=1 µEinstein=1 µmoles photons/m$^2$·sec=500 foot candles). Hydrogen production mutant strains of *Chlamydomonas reinhardtii*, 103-9, sta6 and sta7 amongst others (obtained from Dr. Posewitz of the National Renewable Energy Laboratory, Golden Colo.) were also grown in TAP. Cells were harvested at chlorophyll (Chl) concentrations between 10-18 µg Chl/ml (exponential growth phase), centrifuged at 4000 g for 5 minutes, and resuspended at 16 µg Chl/ml in anaerobic induction buffer (AIB) plus 0.001% (wt) $PdCl_2$ and 8 uM Resazurin. AIB consists of 40 mM $K_2HPO_4$, 10 mM $KH_2PO_4$, and 3mM $MgCl_2$ and was prepared according to Ghirardi et al. A stock suspension of 0.05% (wt) $PdCl_2$ was made by mixing water and powdered $PdCl_2$ (Pressure Chemical: #1735) in a serum bottle, which was capped, flushed with nitrogen gas (General Air: purity 4.8) for 15 min, and then autoclaved. A working solution of 0.01% (wt) Resazurin (Research Chemicals Ltd: #21187) in AIB was created by diluting a 0.1% (wt) stock solution.

Using sterile technique, 2.5 ml of the algal suspensions were added to a sterile anaerobic cuvette, made to order by Allen Scientific Glass (Boulder, Colo.) by fusing the top 2 cm of a serum bottle to about 4 cm of square glass tubing. Each cuvette contained a stir bar (VWR #58949-030) and was capped with a butyl rubber stopper (VWR #80062-438). The cuvettes were wrapped in aluminum foil to inhibit photosynthetic oxygen generation and purged with Argon (General Air: purity 5.0) for 15 minutes to remove the oxygen using 25G7/8 needles (VWR #BD305124). The purged cuvettes were incubated at room temperature, in the dark, for four hours in order to induce production of oxygen sensitive hydrogenases.

After induction, cuvettes were placed on a stir plate and exposed to blue light (Dolan-Jenner #BG2820) filtered by a solution of 1% $CUSO_4$. The cuvettes were exposed for 6 minutes at 5001 µE (approx. 2500 ft. candles). Following illumination, the cuvettes were immediately placed in 50 ml Falcon tubes and centrifuged for 5 min at 5000 g. Spectra (350-800 nm) of the cell-free supernatants were obtained using a Varian CARY 5E UV/Vis/NIR spectrophotometer.

Hydrogen gas in the headspace of each cuvette was quantified using a HP 5890 series II gas chromatograph equipped with a molecular sieve column (Supelco 5A 60/80) and a thermal conductivity (TCD) detector. A simple constant temperature (60° C.) program is sufficient to separate $H_2$ from $O_2$ and $N_2$.

Figure 24:
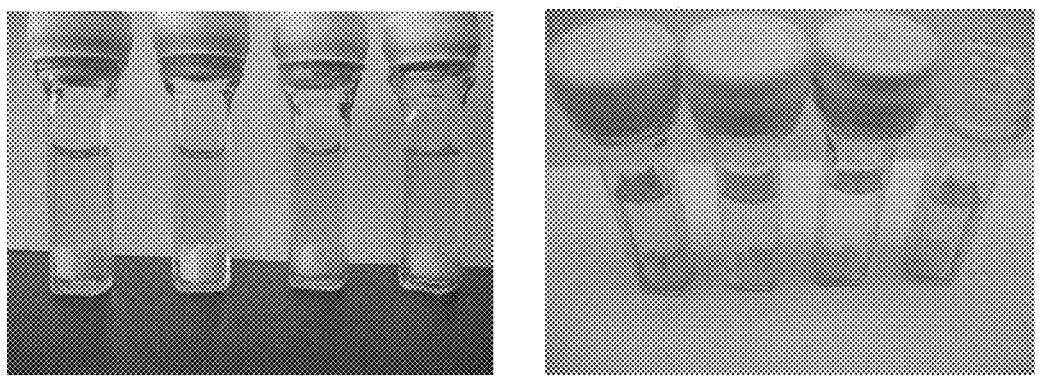
FIG. 24 are before and after pictures of four cuvettes containing resazurin.
Figure 25:
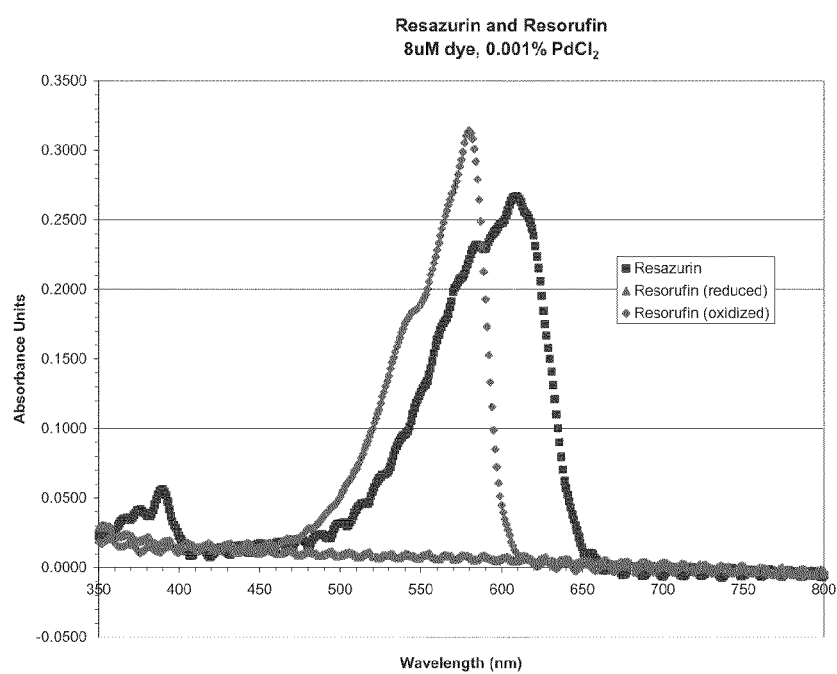
FIG. 25 shows the spectra of the various forms of resazurin and resorufin.

With no algae present, resazurin successfully reacted with 10% molecular hydrogen (Balance Nitrogen, General Air) in anaerobic cuvettes (Allen Scientific Glass: Boulder, Colo.) (FIG. 24). Hydrogen gas (100 µl of 10% $H_2$) was injected into cuvette #2 (the second cuvette from the left), which was enough hydrogen to turn the solution slightly pink. Cuvettes #3 and #4 both had an excess of hydrogen injected, which forced the equilibrium into the reduced and colorless form of resorufin. Afterwards, cuvette #4 was opened to the air and thereby completely converted into the oxidized form of resorufin. The resulting UV/Vis spectra were overlapping but distinguishable from each other (FIG. 25).

Alternatively, if the alga transformants were exposed to oxygen before they were tested for molecular hydrogen production this assay could also be used to select for alga that contained mutant hydrogenases that are less sensitive to oxygen. If the alga were exposed to a concentration of oxygen at or slightly above their tolerance level, the hydrogenase chimeras that survived and produced hydrogen would have a higher oxygen tolerance. Finally, the enhanced hydrogenase chimeras from both of these selection techniques are sequenced and their individual mutations combined to create a mutant that exhibits both enhancements.

As indicated by the reduced size of the 600 nm peak in FIG. 26, a yet to be determined compound(s) in the algae is responsible for reducing the resazurin before it could be reduced by hydrogen generated from the algae. This reduced spectra occurred, regardless of when the resazurin/$PdCl_2$ mixture was added to the cells. Furthermore, this technique is not recommended because the spectrum of hydrogen producing algae (dw15-1, FIG. 26A) was not significantly different from the spectrum of non-hydrogen producing algae (sta6 mutant, FIG. 26B). A difference of approximately 0.07 absorbance units, at λ=610 nm, between these two strains was common. Duplicate samples produced spectra that were similar but whose absorbencies, at λ=610 nm, deviated slightly from each other. In addition to sta6, several other mutants with retarded hydrogen production were tested. Thus, the present disclosure provides that while spectra similar to sta6 were evident, there is no evident relationship between hydrogen production and the absorbance differences ($A_{610}$ of dw15-1 minus the $A_{610}$ of a mutant). However, molecular hydrogen definitely reacts with resazurin and the difference is significant. Yet, when algae generated the molecular hydrogen the resulting spectra showed a reaction with molecular hydrogen or a reaction with some unknown compound(s) within the algae.

Figure 27:
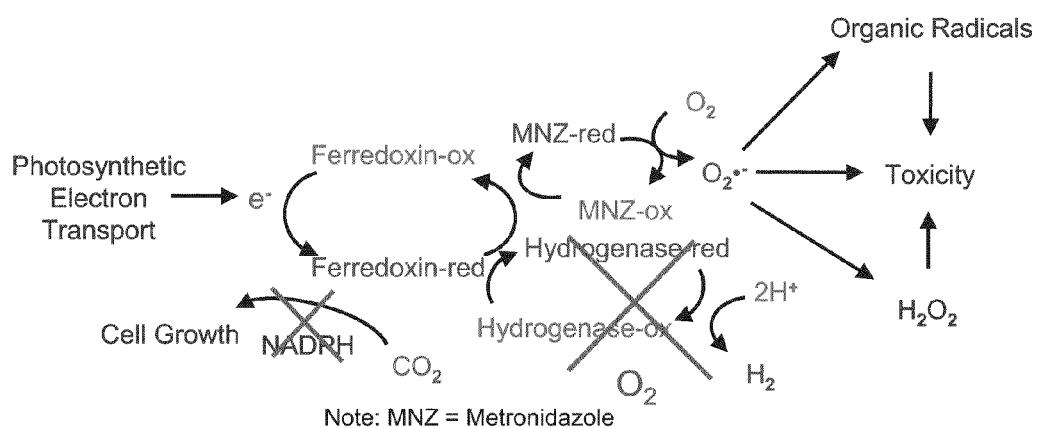
FIG. 27 is a diagram of the metronidazole method of selection for algae with an enhanced hydrogenase.
Figure 28:
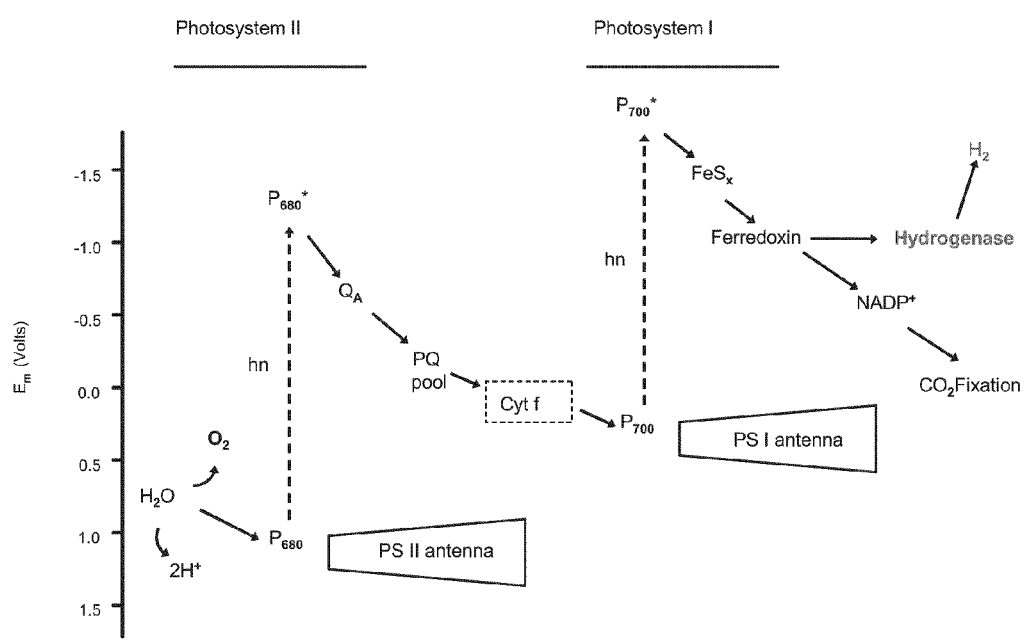
FIG. 28 illustrates the photosynthetic electron transport chain, known as the "Z-scheme"

Alternatively, selection of algal mutants can be accomplished using the metronidazole assay. The electrons created by the hydrolysis of water are ultimately transported to ferredoxin (FIG. 27). Ferredoxin is a common compound that is involved in many electron transport pathways. In *C. reinhardtii*, as in most plants, ferredoxin normally transfers electrons to the Calvin cycle, the pathway that is responsible for cell growth by converting carbon dioxide from the atmosphere into glucose. In *C. reinhardtii*, ferredoxin can also transfer electrons to a hydrogenase when the algae experiences dark and anaerobic conditions.

The photo-hydrogen group at the National Renewable Energy Lab (NREL: Golden, Colo.) developed a chemical method to select for oxygen tolerant mutants. The *C. reinhardtii* cells were induced to produce hydrogenases and then treated with Metronidazole (MNZ), a toxic substance that non-specifically kills cells by creating oxygen free radicals known as superoxide radicals (FIG. 27). Superoxide radicals spawn organic radicals and hydrogen peroxide, all of which are quite toxic to *C. reinhardtii* cells. When the algal cells are induced to produce hydrogenases, cell growth ceases and a brief period of hydrogen production ensues when the cells are exposed to light.

If, however, sufficient concentrations of metronidazole and oxygen are added before the cells are exposed to the light, the hydrogenase is irreversibly inhibited by the oxygen, ferredoxin transfers all of its electrons to MNZ, and the algal cells die. It was theorized that, if little or no oxygen were added, a proportion of the electrons would be transferred to the surviving hydrogenases; hydrogenases that likely have a higher tolerance to oxygen. Given a constant number of available electrons, the algal cells containing hydrogenases with a higher tolerance to oxygen would then see more electrons transferred to the hydrogenase and fewer electrons transferred to MNZ; a lower concentration of toxic radicals and enhanced cell viability would result. The *C. reinhardtii* cells containing enhanced hydrogenases could then be isolated and analyzed.

Wild type strains of *Chlamydomonas reinhardtii*, dw15-1 (Barb Sears, MSU) and cc425 were grown in tris-acetate-phosphate (TAP), pH=7.2, or TAP plus 50-200 µg/ml arginine (cc425) in sterile 250 ml Erlenmeyer flasks on a shaker rotating at 150 rpm in a 25° C. constant temperature room and constantly illuminated with 100 µE of white fluorescent light (1 µE=1 µEinstein=1 µmoles photons/m$^2$·sec=500 foot candles). Cells were harvested when they reached a concentration of $2.4 \times 10^6$ cells/ml, centrifuged at 2-3000 g for 5 minutes at 22° C., and resuspended to a final concentration of $1 \times 10^7$ cells/ml in sterile induction buffer (AIB) plus 20 µl of sterile 0.5M sodium acetate (10 mM final concentration) per ml of cells. AIB consists of 40 mM $K_2HPO_4$, 10 mM $KH_2PO_4$, and 3 mM $MgCl_2$ and was prepared according to Ghirardi et al.

Using sterile technique, 1 ml of the resuspended algae was transferred to a 12 ml serum vial with a flea sized stir bar and sealed with a sterile septum (VWR #80062-438) using sterilized forceps. The serum vials were wrapped in aluminum foil to inhibit photosynthetic oxygen generation and gently purged with Argon (General Air: purity 5.0) for 2 hours using 25G7/8 needles (VWR #BD305124). A manifold was used to flush multiple samples simultaneously. The purged serum vials were incubated at room temperature, in the dark, an additional 2 hours in order to induce production of oxygen sensitive hydrogenases. Metronidazole treatment was started immediately or the samples were refrigerated overnight to minimize the loss of hydrogenase activity. If refrigerated overnight, the vials were allowed to warm to room temperature, approximately 15-30 minutes, and flushed with argon for 15 minutes before the metronidazole selection.

During this procedure, the septa were frequently wiped with ethanol to insure sterility. A maximum of 45 ml of fresh Metronidazole stock solution (50 mM Metronidazole & 1.25 mM $NaN_3$) was added to 70 ml serum vials wrapped in aluminum foil. The metronidazole containing vials were sealed with a septum and gently flushed with argon for 30 minutes, as described above. Add 4 ml of the anaerobic MNZ stock, using a 5 ml syringe and a 20 gauge needle. The MNZ-cell mixture was placed on a stir plate until the solution was well mixed. After mixing, an initial 100 µl sample of cells was removed using a 1 ml syringe and a 23 gauge needle in a dark sterile hood in a very dark lab. The cells were dispensed into an eppendorf tube and stored at room temperature in the dark. An aliquot of 100% oxygen (2.2 ml of 100% oxygen results in an approximate final headspace oxygen concentration of 25% given 9 ml of headspace in a 15 ml serum vial) was added to the headspace of the MNZ-cell mixture. The vial was shaken vigorously, by hand, for 5-10 seconds and then allowed to mix vigorously on a stir plate for 4 minutes. Afterwards, the aluminum foil was removed and the serum vial was exposed to 320 µE (approx. 2200 ft. candles) of light using a source (Dolan-Jenner #BG2820) filtered by a solution of 1% $CuSO_4$. The cells were exposed to the light for 6 minutes and then a second 100 µl sample of cells was removed to a second eppendorf tube and store, as above. The serum vials were re-wrapped in aluminum foil and also stored in the dark at room temperature.

In a dark laminar flow hood, the time point samples were washed and resuspended in TAP before making the following dilutions: 1/100, 1/1000 and 1/10,000. For each of the dilutions, 100 µl was plated using 1-2 ml of cornstarch solution (25% cornstarch in TAP+60 mM sucrose). In order to obtain all of the surviving algae, the serum vials were washed several times in TAP and inoculated in 50 ml of TAP and grown, as above.

MNZ is quite toxic, so gloves were always used when it was handled. The excess MNZ solutions, as well as the MNZ/cell mixtures, were disposed into a waste bottle and submitted to the Environmental Health and Safety department.

However, the metronidazole failed to kill more than 90% of the wild type *C. reinhardtii* cells, regardless of the amount of oxygen that was injected into the serum vials. In fact, the cell death rate did not increase even when the cells were bubbled with 100% oxygen. Therefore, the technique was abandoned. Several brands of MNZ were tried with identical outcomes, so possibilities for why this technique didn't work include that the MNZ was unable to enter the algal cell or that the MNZ entered the cytoplasm, only to be destroyed. Since very little remained of the original NREL MNZ technique and the originally published algal selected mutants contained hydrogenases that were only slightly enhanced over the wild-type, it remains unknown as whether this technique was responsible for the published mutants.

More recently, hydrogen has been used in the "hydrotreating" or purification of fuel oil, the hydrogenation of oils to form margarine, in the production of ammonia-based fertilizers, in rocket fuel, and in fuel cells. The chemical reactions forming the basis of the fuel cell were first realized by William Nicholson, Anthony Carlisle, Christian Schoenbein, and William Grove; Swiss and English scientists in the early 1800s who were the first to combine oxygen and hydrogen gases in order to produce water. The term "fuel cell" was coined in 1889 when the very first fuel cell was created by Ludwig Mond and Charles Langer. Francis Bacon invented the first practical fuel cell in 1959. Since his invention, fuel cells have been used to power a diverse range of vehicles from a simple farm tractor to the Apollo mission and the space shuttles. It wasn't until the year 2000 that practical fuel cells for cars were unveiled by Ballard Power Systems. Perhaps someday soon, John Bockris' 1970 prediction of a "hydrogen economy" will become a reality and a national network of hydrogen energy will become the norm. In order to have a national network, reliable method of producing molecular hydrogen is needed. Hydrogen is currently produced by steam reforming the hydrogen atoms from coal or natural gas. However, the present disclosure providing for biohydrogen production from photosynthetic algae has the potential to be a viable alternative to hydrogen production from fossil fuels. It would not produce greenhouse gases ($H_2O$+sunlight→$O_2$+$H_2$); in fact, algae like most plants, utilizes carbon dioxide for cellular growth, so it would serve as a carbon sink. In addition, a bioreactor would not produce toxic waste, just algae and wastewater; similar to a fish tank. Also, a bioreactor would likely be about the size of an air conditioner and survive on low amounts of sunlight, so it would occupy a small amount of space and it could be located anywhere in the country.

Hydrogen could be generated locally by on-site electrolyzers or more likely by a centralized power plant. If molecular hydrogen is generated in a central location, it could eventually be piped to on site compressors and storage tanks or in the near-term, it could be simply delivered in trucks, just as gasoline is today. Often hydrogen is safer than gasoline in that it is non-toxic and non-poisonous. In addition and unlike gasoline, hydrogen will not contribute to groundwater pollution when it leaks from an underground storage tank.

Molecular hydrogen could be used to power cars directly as well as truck and trains, personal residences, and the workplace. In fact, the first area of significant usage of hydrogen power is via stationary fuel cells in industrial applications. Stationary and modular fuel cells already provide the benefit of highly reliable power with a consistent voltage, which is ideal for modern industries, which depend on computers. Fuel cells are also available for portable uses such as remote construction/military sites, laptop computers, and cell phones. To date, fuel cells have also been installed and demonstrated in 50 different types of mobile vehicles from "buses to bicycles." Lastly, home usage of fuel cells is possible as modular fuel cells, about the size of a common refrigerator, can provide enough power for a residence.

Figure 29:
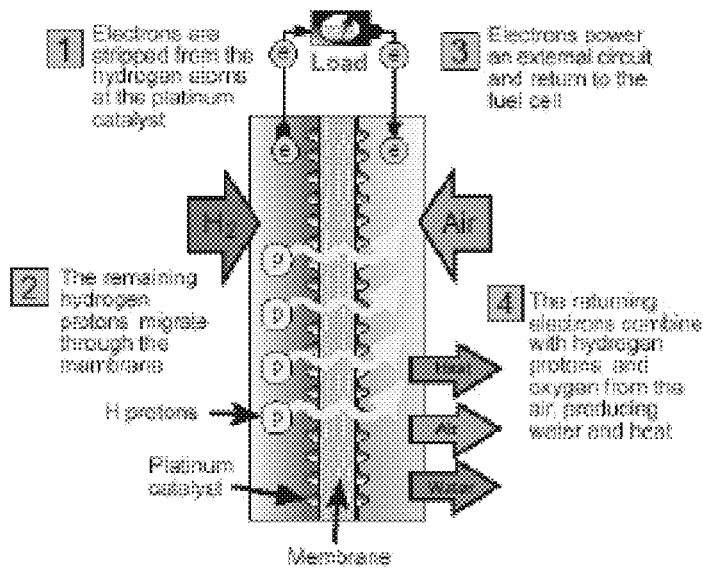
FIG. 29 shows the proton exchange membrane fuel cell (PEM FC).
Figure 31:
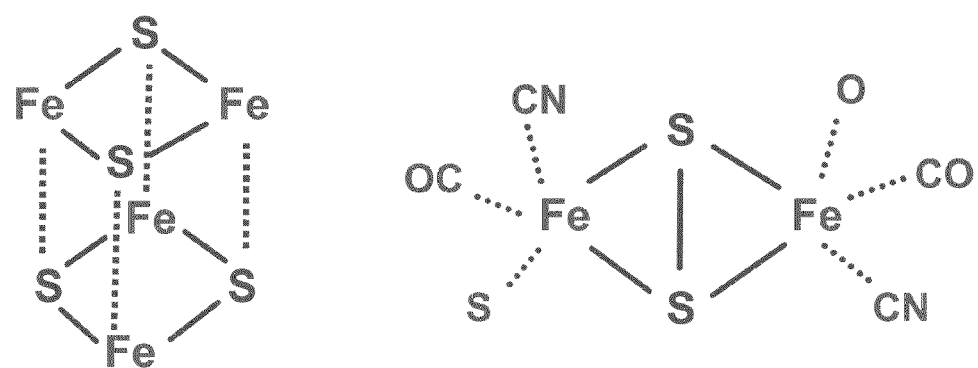
FIG. 31 is a diagram of the four-iron four-sulfur (4Fe-4S) cluster and the two-iron two sulfur (2Fe-2S) active site cluster that is present in Fe-only hydrogenases.
Figure 32:
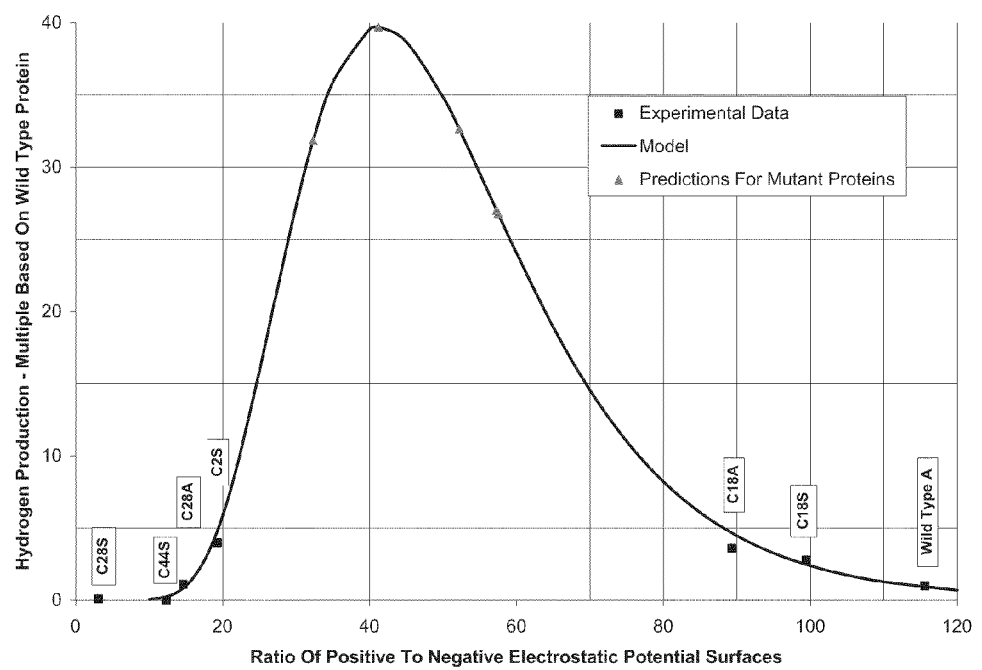
FIG. 32 shows the ratio of positive to negative surface area as a measure of how a given protein mutant will fold into its tertiary state and how the final tertiary state affects hydrogen production.

There are a myriad of different types of fuel cells, however the proton exchange membrane (PEM) fuel cell is the most common (FIG. 29) and hydrogen is the ultimate fuel for a fuel cell. In principle, fuel cells operate by chemically combining hydrogen with oxygen to form water, electricity, and heat. In fact, a fuel cell operates similarly to a battery that doesn't require recharging. Specifically, hydrogen gas flows into the anode side of a PEM fuel cell where a platinum catalyst removes the protons of hydrogen from the electrons. The electrons form a current, i.e. electricity, while the protons pass through the membrane that divides the anode from the cathode. Meanwhile, oxygen or air enters the cathode where it is combined with the protons and the electrons in order to form water (FIG. 30). Hydrogen fuel cells perform the reverse electrolysis reaction.

Fuel cell technology is a promising and newly affordable technology for the stationary and portable generation of heat and electricity in both the public and private sectors. Thus, fuel cell technology will likely blossom and initiate a hydrogen economy whereby environmental concerns are lessened. Consequently, a biological, non-polluting, method of generating molecular hydrogen, the fuel for a fuel cell, has increased potential. Such potential may lead to the abandonment of societal and political disputes concerning fossil fuels.

The invention claimed is:

1. A method of producing algae capable of enhanced hydrogen production, said method comprising:
    making and testing one or more mutated algal hydrogenases for amount of hydrogen production;
    identifying one or more of said mutated algal hydrogenases as capable of causing enhanced hydrogen production in algae, wherein an amount of hydrogen production higher than that of a wild type hydrogenase is indicative of the ability to cause enhanced hydrogen production in algae;
    expressing in an algae a DNA sequence coding for at least one mutated algal hydrogenase identified as capable of increased hydrogen production;
    selecting an algae expressing said mutated algal hydrogenase identified as capable of increased hydrogen production, wherein said mutated algal hydrogenase has a positive to negative electrostatic potential energy surface area (EPSA) ratio in the range of 15 to 115, which is indicative that said algae is capable of enhanced hydrogen production.

2. The method of claim 1 wherein making one or more mutated algal hydrogenases comprises:
    identifying two or more hydrogenase parent proteins;
    obtaining cDNAs coding for said parent hydrogenases;
    producing multiple DNA fragments corresponding to segments of each of said cDNA coding for said parent hydrogenases; and
    reconstructing full-length chimeric hydrogenase cDNAs by putting segments from cDNAs coding for different parent hydrogenases together in the same order as they occur in the parent hydrogenase coding sequences.

3. The method of claim 2 wherein said segments are between about 100 and 350 base pairs.

4. The method of claim 2 wherein the full-length chimeric hydrogenase cDNAs encoding mutated algal hydrogenases are tested in a bacterial system or an algal system to identify mutations capable of enhanced hydrogen production.

5. The method of claim 4 wherein the full-length chimeric hydrogenase cDNAs encoding mutated algal hydrogenases are analyzed to identify specific mutations that lead to enhanced hydrogen production.

6. The method of claim 2, further comprising the step of expressing one or more mutated algal hydrogenases by transforming algae using a plasmid comprising the full-length chimeric hydrogenase cDNAs.

7. The method of claim 1, further comprising the step of computing the positive EPSA, the negative EPSA, and the ratio of the positive EPSA to the negative EPSA.

8. The method of claim 1, wherein the positive EPSA to negative EPSA ratio is in the range of 15 to 42.

9. The method of claim 1, wherein making and testing one or more mutated hydrogenases comprises making a mutated hydrogenase comprising an amino acid sequence having ninety percent or greater homology to SEQID 198 and testing the mutant hydrogenase for amount of hydrogen production.

10. The method of claim 9, wherein the mutated hydrogenase produces an amount of hydrogen more than 4 times that of a wild type hydrogenase.

11. The method of claim 6, wherein the plasmid is pSMP.

12. The method of claim 11, wherein pSMP is a plasmid comprised of a previous plasmid known to the art, pGenD+Ble, and modified by removing the existing PsaD gene and inserting the chimeric hydrogenase cDNA, a leader sequence, a downstream tag, and restriction sites that separate them.

* * * * *

UNITED STATES PATENT AND TRADEMARK OFFICE
CERTIFICATE OF CORRECTION

| | | |
|---|---|---|
| PATENT NO. | : 8,124,347 B2 | |
| APPLICATION NO. | : 12/428471 | |
| DATED | : February 28, 2012 | |
| INVENTOR(S) | : Scott Plummer et al. | |

It is certified that error appears in the above-identified patent and that said Letters Patent is hereby corrected as shown below:

On the title page item (54) and col. 1, line 1, in the title: "PHOTOSYNTHETIC HYDROGEN PRODUCTION FROM THE GREEN ALGA CHLAMYDOMONAS REINHARDTH" should read --PHOTOSYNTHETIC HYDROGEN PRODUCTION FROM THE GREEN ALGA CHLAMYDOMONAS REINHARDTII--

Signed and Sealed this
Fourteenth Day of August, 2012

David J. Kappos
*Director of the United States Patent and Trademark Office*

SEQUENCE LISTING

<160> NUMBER OF SEQ ID NOS: 223

<210> SEQ ID NO 1
<211> LENGTH: 584
<212> TYPE: PRT
<213> ORGANISM: Chlamydomonas reinhardtii

<400> SEQUENCE: 1

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190
```

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Glu Val Glu Ile Ala Gly
450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 2
<211> LENGTH: 1752
<212> TYPE: DNA
<213> ORGANISM: Chlamydomonas reinhardtii

<400> SEQUENCE: 2

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggcccat tccctatgtt tacatcttgc     900
tgtcctgcat gggtaagatt agctcaaaat tatcatcctg aattattaga taatctttca     960
tcagcaaaat caccacaaca aatatttggt actgcatcaa aaacttacta tccttcaatt    1020
tcaggaatag ctccagaaga tgtttataca gttactatca tgccttgtaa tgataaaaaa    1080
tatgaagcag atattccttt catggaaact aacagcttaa gagatattga tgcatccttc    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
tcaaaacatg aa                                                        1752
```

<210> SEQ ID NO 3
<211> LENGTH: 59
<212> TYPE: DNA
<213> ORGANISM: Chlamydomonas reinhardtii

<400> SEQUENCE: 3

```
ggacgagaag aaggctagcg cctggagcca cccgcagttc gagaagtgag aattctggc      59
```

<210> SEQ ID NO 4
<211> LENGTH: 59
<212> TYPE: DNA
<213> ORGANISM: Chlamydomonas reinhardtii

<400> SEQUENCE: 4

-continued

```
gccagaattc tcacttctcg aactgcgggt ggctccaggc gctagccttc ttctcgtcc    59
```

<210> SEQ ID NO 5
<211> LENGTH: 28
<212> TYPE: DNA
<213> ORGANISM: Chlamydomonas reinhardtii

<400> SEQUENCE: 5

```
gcttgcgcgg ctgggcccgc cgcacccg                                      28
```

<210> SEQ ID NO 6
<211> LENGTH: 28
<212> TYPE: DNA
<213> ORGANISM: Chlamydomonas reinhardtii

<400> SEQUENCE: 6

```
cgggtgcggc gggcccagcc gcgcaagc                                      28
```

<210> SEQ ID NO 7
<211> LENGTH: 31
<212> TYPE: DNA
<213> ORGANISM: Chlamydomonas reinhardtii

<400> SEQUENCE: 7

```
cccgctgcgg aggggccctt gagtcatgtc c                                  31
```

<210> SEQ ID NO 8
<211> LENGTH: 31
<212> TYPE: DNA
<213> ORGANISM: Chlamydomonas reinhardtii

<400> SEQUENCE: 8

```
ggacatgact caagggcccc tccgcagcgg g                                  31
```

<210> SEQ ID NO 9
<211> LENGTH: 24
<212> TYPE: DNA
<213> ORGANISM: Chlamydomonas reinhardtii

<400> SEQUENCE: 9

```
ccagcaggcg atcgccgagc ttgc                                          24
```

<210> SEQ ID NO 10
<211> LENGTH: 23
<212> TYPE: DNA
<213> ORGANISM: Chlamydomonas reinhardtii

<400> SEQUENCE: 10

```
gctgggtacc cggccccccc tcg                                           23
```

<210> SEQ ID NO 11
<211> LENGTH: 23
<212> TYPE: DNA
<213> ORGANISM: Chlamydomonas reinhardtii

<400> SEQUENCE: 11

```
cgagggggggg ccgggtaccc agc                                          23
```

<210> SEQ ID NO 12
<211> LENGTH: 23
<212> TYPE: DNA
<213> ORGANISM: Chlamydomonas reinhardtii

<400> SEQUENCE: 12

```
gctgggtacc cggcccccc tcg                                              23

<210> SEQ ID NO 13
<211> LENGTH: 19
<212> TYPE: DNA
<213> ORGANISM: Chlamydomonas reinhardtii

<400> SEQUENCE: 13
ccagctgctg ccagaattc                                                  19

<210> SEQ ID NO 14
<211> LENGTH: 19
<212> TYPE: DNA
<213> ORGANISM: Chlamydomonas reinhardtii

<400> SEQUENCE: 14
ccagctgctg ccagaattc                                                  19

<210> SEQ ID NO 15
<211> LENGTH: 20
<212> TYPE: DNA
<213> ORGANISM: Chlamydomonas reinhardtii

<400> SEQUENCE: 15
gacgagaaga aggctagcgc                                                 20

<210> SEQ ID NO 16
<211> LENGTH: 19
<212> TYPE: DNA
<213> ORGANISM: Chlamydomonas reinhardtii

<400> SEQUENCE: 16
ccagctgctg ccagaattc                                                  19

<210> SEQ ID NO 17
<211> LENGTH: 39
<212> TYPE: DNA
<213> ORGANISM: Chlamydomonas reinhardtii

<400> SEQUENCE: 17
gctatccatg gcgaataaaa taataatcaa tgataagac                            39

<210> SEQ ID NO 18
<211> LENGTH: 27
<212> TYPE: DNA
<213> ORGANISM: Chlamydomonas reinhardtii

<400> SEQUENCE: 18
ataggcgcgc cttttttata tttcatg                                         27

<210> SEQ ID NO 19
<211> LENGTH: 33
<212> TYPE: DNA
<213> ORGANISM: Chlamydomonas reinhardtii

<400> SEQUENCE: 19
gctatccatg gtaaatgtta ctatagataa ttg                                  33

<210> SEQ ID NO 20
<211> LENGTH: 33
<212> TYPE: DNA
<213> ORGANISM: Chlamydomonas reinhardtii

<400> SEQUENCE: 20
```

```
attggcgcgc tcatttaac agggtagttt tcc                                   33

<210> SEQ ID NO 21
<211> LENGTH: 25
<212> TYPE: DNA
<213> ORGANISM: Chlamydomonas reinhardtii

<400> SEQUENCE: 21
ggctgctgtt gcgcatggtc ttggc                                           25

<210> SEQ ID NO 22
<211> LENGTH: 25
<212> TYPE: DNA
<213> ORGANISM: Chlamydomonas reinhardtii

<400> SEQUENCE: 22
gccaagacca tgcgcaacag cagcc                                           25

<210> SEQ ID NO 23
<211> LENGTH: 16
<212> TYPE: DNA
<213> ORGANISM: Chlamydomonas reinhardtii

<400> SEQUENCE: 23
cccacgccga aacaag                                                     16

<210> SEQ ID NO 24
<211> LENGTH: 22
<212> TYPE: DNA
<213> ORGANISM: Chlamydomonas reinhardtii

<400> SEQUENCE: 24
accatacctt cttcaacttt tg                                              22

<210> SEQ ID NO 25
<211> LENGTH: 20
<212> TYPE: DNA
<213> ORGANISM: Chlamydomonas reinhardtii

<400> SEQUENCE: 25
ggtagtaaaa acaaactcag                                                 20

<210> SEQ ID NO 26
<211> LENGTH: 24
<212> TYPE: DNA
<213> ORGANISM: Chlamydomonas reinhardtii

<400> SEQUENCE: 26
acacttagtt ctgtctatta caat                                            24

<210> SEQ ID NO 27
<211> LENGTH: 18
<212> TYPE: DNA
<213> ORGANISM: Chlamydomonas reinhardtii

<400> SEQUENCE: 27
tgtgtgctat gcggaaga                                                   18

<210> SEQ ID NO 28
<211> LENGTH: 23
<212> TYPE: DNA
<213> ORGANISM: Chlamydomonas reinhardtii

<400> SEQUENCE: 28
```

```
atgcttatta ggatcttcta atg                                    23

<210> SEQ ID NO 29
<211> LENGTH: 20
<212> TYPE: DNA
<213> ORGANISM: Chlamydomonas reinhardtii

<400> SEQUENCE: 29
catgtaatag ttgctatggc                                        20

<210> SEQ ID NO 30
<211> LENGTH: 23
<212> TYPE: DNA
<213> ORGANISM: Chlamydomonas reinhardtii

<400> SEQUENCE: 30
tttaactctt tcaataaact ctg                                    23

<210> SEQ ID NO 31
<211> LENGTH: 21
<212> TYPE: DNA
<213> ORGANISM: Chlamydomonas reinhardtii

<400> SEQUENCE: 31
aaaaataatg gaccattccc a                                      21

<210> SEQ ID NO 32
<211> LENGTH: 23
<212> TYPE: DNA
<213> ORGANISM: Chlamydomonas reinhardtii

<400> SEQUENCE: 32
tctcttgtag taagtactgc atc                                    23

<210> SEQ ID NO 33
<211> LENGTH: 29
<212> TYPE: DNA
<213> ORGANISM: Chlamydomonas reinhardtii

<400> SEQUENCE: 33
agaattagca aaaatgatta aagatgcaa                              29

<210> SEQ ID NO 34
<211> LENGTH: 29
<212> TYPE: DNA
<213> ORGANISM: Chlamydomonas reinhardtii

<400> SEQUENCE: 34
tattccttgt aatcctctta tttgtgtat                              29

<210> SEQ ID NO 35
<211> LENGTH: 29
<212> TYPE: DNA
<213> ORGANISM: Chlamydomonas reinhardtii

<400> SEQUENCE: 35
ataaaagagg ctacagtaga aattggtgg                              29

<210> SEQ ID NO 36
<211> LENGTH: 21
<212> TYPE: DNA
<213> ORGANISM: Chlamydomonas reinhardtii

<400> SEQUENCE: 36
```

```
tccaccattt acacatccgc c                                              21

<210> SEQ ID NO 37
<211> LENGTH: 18
<212> TYPE: DNA
<213> ORGANISM: Chlamydomonas reinhardtii

<400> SEQUENCE: 37
ggaggacaac cacacgta                                                  18

<210> SEQ ID NO 38
<211> LENGTH: 24
<212> TYPE: DNA
<213> ORGANISM: Chlamydomonas reinhardtii

<400> SEQUENCE: 38
tacgattact ttctgttcga ctta                                           24

<210> SEQ ID NO 39
<211> LENGTH: 16
<212> TYPE: DNA
<213> ORGANISM: Chlamydomonas reinhardtii

<400> SEQUENCE: 39
cccacgccga aacaag                                                    16

<210> SEQ ID NO 40
<211> LENGTH: 23
<212> TYPE: DNA
<213> ORGANISM: Chlamydomonas reinhardtii

<400> SEQUENCE: 40
accattccat cttcaactttt ggc                                           23

<210> SEQ ID NO 41
<211> LENGTH: 23
<212> TYPE: DNA
<213> ORGANISM: Chlamydomonas reinhardtii

<400> SEQUENCE: 41
ggtaataaac acagaatccg atg                                            23

<210> SEQ ID NO 42
<211> LENGTH: 24
<212> TYPE: DNA
<213> ORGANISM: Chlamydomonas reinhardtii

<400> SEQUENCE: 42
acattttgat ctgtcaatta caat                                           24

<210> SEQ ID NO 43
<211> LENGTH: 20
<212> TYPE: DNA
<213> ORGANISM: Chlamydomonas reinhardtii

<400> SEQUENCE: 43
tgtgtactat gcggtagatg                                                20

<210> SEQ ID NO 44
<211> LENGTH: 23
<212> TYPE: DNA
<213> ORGANISM: Chlamydomonas reinhardtii

<400> SEQUENCE: 44
```

-continued atgtttttta gggtcattaa gag          23

<210> SEQ ID NO 45
<211> LENGTH: 20
<212> TYPE: DNA
<213> ORGANISM: Chlamydomonas reinhardtii

<400> SEQUENCE: 45
catgtcattg ttgcaatggc          20

<210> SEQ ID NO 46
<211> LENGTH: 24
<212> TYPE: DNA
<213> ORGANISM: Chlamydomonas reinhardtii

<400> SEQUENCE: 46
tttaactctg cctaaaagtt cagt          24

<210> SEQ ID NO 47
<211> LENGTH: 24
<212> TYPE: DNA
<213> ORGANISM: Chlamydomonas reinhardtii

<400> SEQUENCE: 47
aaaaataatg gcccattccc tatg          24

<210> SEQ ID NO 48
<211> LENGTH: 25
<212> TYPE: DNA
<213> ORGANISM: Chlamydomonas reinhardtii

<400> SEQUENCE: 48
tctcttgtag ttaaggatgc atcaa          25

<210> SEQ ID NO 49
<211> LENGTH: 27
<212> TYPE: DNA
<213> ORGANISM: Chlamydomonas reinhardtii

<400> SEQUENCE: 49
agagcttgca aaaatgatta aagatgc          27

<210> SEQ ID NO 50
<211> LENGTH: 26
<212> TYPE: DNA
<213> ORGANISM: Chlamydomonas reinhardtii

<400> SEQUENCE: 50
tatgccttta aagcctctta cttcag          26

<210> SEQ ID NO 51
<211> LENGTH: 26
<212> TYPE: DNA
<213> ORGANISM: Chlamydomonas reinhardtii

<400> SEQUENCE: 51
ataaaagaag cggaagttga aattgc          26

<210> SEQ ID NO 52
<211> LENGTH: 23
<212> TYPE: DNA
<213> ORGANISM: Chlamydomonas reinhardtii

<400> SEQUENCE: 52
tccaccattt atacatccac cag                                              23

<210> SEQ ID NO 53
<211> LENGTH: 22
<212> TYPE: DNA
<213> ORGANISM: Chlamydomonas reinhardtii

<400> SEQUENCE: 53
ggaggtcaac ctcacgtaaa tg                                               22

<210> SEQ ID NO 54
<211> LENGTH: 24
<212> TYPE: DNA
<213> ORGANISM: Chlamydomonas reinhardtii

<400> SEQUENCE: 54
tacgattact ttctgttcga ctta                                             24

<210> SEQ ID NO 55
<211> LENGTH: 39
<212> TYPE: DNA
<213> ORGANISM: Chlamydomonas reinhardtii

<400> SEQUENCE: 55
gtaatagaca gaactaagtg tgtgctatgc ggaagatgt                             39

<210> SEQ ID NO 56
<211> LENGTH: 39
<212> TYPE: DNA
<213> ORGANISM: Chlamydomonas reinhardtii

<400> SEQUENCE: 56
gtaattgaca gatcaaaatg tgtgctatgc ggaagatgt                             39

<210> SEQ ID NO 57
<211> LENGTH: 40
<212> TYPE: DNA
<213> ORGANISM: Chlamydomonas reinhardtii

<400> SEQUENCE: 57
gtaatagaca gaactaagtg tgtactatgc ggtagatgcg                            40

<210> SEQ ID NO 58
<211> LENGTH: 40
<212> TYPE: DNA
<213> ORGANISM: Chlamydomonas reinhardtii

<400> SEQUENCE: 58
gtaattgaca gatcaaaatg tgtactatgc ggtagatgcg                            40

<210> SEQ ID NO 59
<211> LENGTH: 44
<212> TYPE: DNA
<213> ORGANISM: Chlamydomonas reinhardtii

<400> SEQUENCE: 59
cagagtttat tgaaagagtt aaaaataatg gaccattccc aatg                       44

<210> SEQ ID NO 60
<211> LENGTH: 44
<212> TYPE: DNA
<213> ORGANISM: Chlamydomonas reinhardtii

<400> SEQUENCE: 60
cagagtttat tgaaagagtt aaaaataatg gcccattccc tatg                44

<210> SEQ ID NO 61
<211> LENGTH: 44
<212> TYPE: DNA
<213> ORGANISM: Chlamydomonas reinhardtii

<400> SEQUENCE: 61
ctgaactttt aggcagagtt aaaaataatg gcccattccc tatg                44

<210> SEQ ID NO 62
<211> LENGTH: 44
<212> TYPE: DNA
<213> ORGANISM: Chlamydomonas reinhardtii

<400> SEQUENCE: 62
ctgaactttt aggcagagtt aaaaataatg gaccattccc aatg                44

<210> SEQ ID NO 63
<211> LENGTH: 45
<212> TYPE: DNA
<213> ORGANISM: Chlamydomonas reinhardtii

<400> SEQUENCE: 63
aaataagagg attacaagga ataaaagagg ctacagtaga aattg               45

<210> SEQ ID NO 64
<211> LENGTH: 46
<212> TYPE: DNA
<213> ORGANISM: Chlamydomonas reinhardtii

<400> SEQUENCE: 64
aaataagagg attacaagga ataaaagaag cggaagttga aattgc              46

<210> SEQ ID NO 65
<211> LENGTH: 44
<212> TYPE: DNA
<213> ORGANISM: Chlamydomonas reinhardtii

<400> SEQUENCE: 65
gtaagaggct ttaaaggcat aaaagaagcg gaagttgaaa ttgc                44

<210> SEQ ID NO 66
<211> LENGTH: 43
<212> TYPE: DNA
<213> ORGANISM: Chlamydomonas reinhardtii

<400> SEQUENCE: 66
gtaagaggct ttaaaggcat aaaagaggct acagtagaaa ttg                 43

<210> SEQ ID NO 67
<211> LENGTH: 212
<212> TYPE: DNA
<213> ORGANISM: Chlamydomonas reinhardtii

<400> SEQUENCE: 67
atggccaaaa caataatctt aaatggcaat gaagtgcata cagataaaga tattactatc    60
cttgagctag caagagaaaa taatgtagat atcccaacac tctgctttt aaaggattgt    120 ggcaattttg gaaaatgcgg agtctgtatg gtagaggtag aaggcaaggg ctttagagct    180
gcttgtgttg ccaaagttga agatggaatg gt                                 212

```
<210> SEQ ID NO 68
<211> LENGTH: 229
<212> TYPE: DNA
<213> ORGANISM: Chlamydomonas reinhardtii

<400> SEQUENCE: 68
aataaacaca gaatccgatg aagtaaaaga acgaatcaaa aaaagagttt caatgcttct      60
tgataagcat gaatttaaat gtggacaatg ttctagaaga gaaaattgtg aattccttaa     120
acttgtaata aagacaaaag caaaagcttc aaaaccattt ttaccagaag ataaggatgc     180
tctagttgat aatagaagta aggctattgt aattgacaga tcaaaatgt                 229

<210> SEQ ID NO 69
<211> LENGTH: 231
<212> TYPE: DNA
<213> ORGANISM: Chlamydomonas reinhardtii

<400> SEQUENCE: 69
gtactatgcg gtagatgcgt agctgcatgt aaacagcaca caagcacttg ctcaattcaa      60
tttattaaaa aagatggaca aagggctgtt ggaactgttg atgatgtttg tcttgatgac     120
tcaacatgct tattatgcgg tcagtgtgta atcgcttgtc ctgttgctgc tttaaaagaa     180
aaatcccata tagaaaaagt tcaagaagct cttaatgacc ctaaaaaaca t              231

<210> SEQ ID NO 70
<211> LENGTH: 192
<212> TYPE: DNA
<213> ORGANISM: Chlamydomonas reinhardtii

<400> SEQUENCE: 70
gtcattgttg caatggctcc atcagtaaga actgctatgg gcgaattatt caaaatggga      60
tatggaaaag atgtaacagg aaaactatat actgcactta gaatgttagg ctttgataaa     120
gtatttgata taaactttgg tgcagatatg actataatgg aagaagctac tgaactttta     180
ggcagagtta aa                                                         192

<210> SEQ ID NO 71
<211> LENGTH: 284
<212> TYPE: DNA
<213> ORGANISM: Chlamydomonas reinhardtii

<400> SEQUENCE: 71
aataatggcc cattccctat gtttacatct tgctgtcctg catgggtaag attagctcaa      60
aattatcatc ctgaattatt agataatctt tcatcagcaa aatcaccaca acaaatattt     120
ggtactgcat caaaaactta ctatccttca atttcaggaa tagctccaga agatgtttat     180
acagttacta tcatgccttg taatgataaa aaatatgaag cagatattcc tttcatggaa     240
actaacagct aagagatat tgatgcatcc ttaactacaa gaga                       284

<210> SEQ ID NO 72
<211> LENGTH: 214
<212> TYPE: DNA
<213> ORGANISM: Chlamydomonas reinhardtii

<400> SEQUENCE: 72
gcttgcaaaa atgattaaag atgcaaaaat taaatttgca gatcttgaag atggtgaagt      60
tgatcctgct atgggtactt acagtggtgc tggagctatc tttggtgcaa ccggtggcgt     120
tatggaagct gcaataagat cagctaaaga ctttgctgaa aataaagaac ttgaaaatgt     180
tgattacact gaagtaagag gctttaaagg cata                                 214
```

```
<210> SEQ ID NO 73
<211> LENGTH: 159
<212> TYPE: DNA
<213> ORGANISM: Chlamydomonas reinhardtii

<400> SEQUENCE: 73
aaagaagcgg aagttgaaat tgctggaaat aaactaaacg ttgctgttat aaatggtgct      60
tctaacttct tcgagtttat gaaatctgga aaaatgaacg aaaaacaata tcactttata     120
gaagtaatgg cttgccctgg tggatgtata aatggtgga                            159

<210> SEQ ID NO 74
<211> LENGTH: 228
<212> TYPE: DNA
<213> ORGANISM: Chlamydomonas reinhardtii

<400> SEQUENCE: 74
ggtcaacctc acgtaaatgc tcttgataga gaaaatgttg attacagaaa actaagagca      60
tcagtattat acaaccaaga taaaaatgtt ctttcaaaga gaaagtcaca tgataatcca     120
gctattatta aatgtatga tagctacttt ggaaaaccag gtgaaggact tgctcacaaa     180
ttactacacg taaaatacac aaaagataaa aatgtttcaa aacatgaa                 228

<210> SEQ ID NO 75
<211> LENGTH: 215
<212> TYPE: DNA
<213> ORGANISM: Chlamydomonas reinhardtii

<400> SEQUENCE: 75
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggt                                215

<210> SEQ ID NO 76
<211> LENGTH: 229
<212> TYPE: DNA
<213> ORGANISM: Chlamydomonas reinhardtii

<400> SEQUENCE: 76
agtaaaaaca aactcagaaa aagtacaaga aagagttaaa atgagagttg ctactttgct      60
tgataagcat gaatttaaat gtggaccttg tccaagaaga gaaaattgcg aattttttaaa    120 gttagttata aaaacaaaag ctaaggctaa caagccttttt gtggttgaag acaaatcaca    180
atacatagat attagaagta aatcaattgt aatagacaga actaagtgt                229

<210> SEQ ID NO 77
<211> LENGTH: 231
<212> TYPE: DNA
<213> ORGANISM: Chlamydomonas reinhardtii

<400> SEQUENCE: 77
gtgctatgcg gaagatgtga agcagcatgt aaaacaaaga caggtacagg agctatttca      60
atttgtaaga gtgaatcagg aagaatagtg caagcaacag gcggaaagtg ctttgatgat     120
acaaattgtt tattatgtgg acaatgcgtt gcagcatgtc cagtaggagc tttaactgaa     180
aaaacacacg ttgatagagt taagaagca ttagaagatc ctaataagca t               231
```

```
<210> SEQ ID NO 78
<211> LENGTH: 192
<212> TYPE: DNA
<213> ORGANISM: Chlamydomonas reinhardtii

<400> SEQUENCE: 78
gtaatagttg ctatggcacc atcaatcaga acttctatgg gagagttatt taaattaggc    60
tatggggttg atgtaactgg aaaattatat gcttcaatga gagcattagg atttgataag   120
gtatttgata ttaactttgg ggctgatatg acaataatgg aagaagcaac agagtttatt   180
gaaagagtta aa                                                       192

<210> SEQ ID NO 79
<211> LENGTH: 284
<212> TYPE: DNA
<213> ORGANISM: Chlamydomonas reinhardtii

<400> SEQUENCE: 79
aataatggac cattcccaat gtttacttca tgttgtccgg catgggttag acaagtggaa    60
aattattacc cagaattttt agaaaactta tcatcagcta aatcaccaca acaaatattt   120
ggtgcagcaa gcaaaacata ctatcctcaa atatcaggta agtgctaa agatgtattt    180 actgttacaa taatgccttg tacagcaaag aaatttgagg ctgatagaga agaaatgtat   240
aatgagggaa ttaaaaatat agatgcagta cttactacaa gaga                   284

<210> SEQ ID NO 80
<211> LENGTH: 214
<212> TYPE: DNA
<213> ORGANISM: Chlamydomonas reinhardtii

<400> SEQUENCE: 80
attagcaaaa atgattaaag atgcaaagat taatttttgct aatttagaag acgaacaagc   60
tgatccagca atgggagaat acactgggggc tggagttata ttcggagcta caggtggagt  120
tatggaagca gcacttagaa ctgctaagga tttcgttgaa gataaagatt taactgatat  180
agaatataca caaataagag gattacaagg aata                              214

<210> SEQ ID NO 81
<211> LENGTH: 159
<212> TYPE: DNA
<213> ORGANISM: Chlamydomonas reinhardtii

<400> SEQUENCE: 81
aaagaggcta cagtagaaat tggtggagaa aattataacg tagctgtaat taatggtgca    60
gcaaacttag ctgaattcat gaatagcggt aaaatccttg aaaagaacta tcattttatt   120
gaagtaatgg cttgcccagg cggatgtgta aatggtgga                         159

<210> SEQ ID NO 82
<211> LENGTH: 201
<212> TYPE: DNA
<213> ORGANISM: Chlamydomonas reinhardtii

<400> SEQUENCE: 82
ggacaaccac acgtaagtgc aaaggaaaga gaaaaagtag atgttagaac tgtaagagca    60 tctgtttttat ataaccaaga taaaaattta gagaagagaa aatcacataa aaatacagca  120 ttattaaaata tgtactatga ttatatggga gctccaggac aaggaaaagc tcatgaatta  180
ttacacttaa aatacaataa a                                            201
```

-continued

```
<210> SEQ ID NO 83
<211> LENGTH: 1722
<212> TYPE: DNA
<213> ORGANISM: Chlamydomonas reinhardtii

<400> SEQUENCE: 83
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaagagt tcaatgctt cttgataagc atgaatttaa atgtggacaa       300
tgttctagaa gagaaaattg tgaattcctt aaacttgtaa taaagacaaa agcaaaagct     360
tcaaaaccat ttttaccaga agataaggat gctctagttg ataatagaag taaggctatt     420
gtaattgaca gatcaaaatg tgtactatgc ggtagatgcg tagctgcatg taaacagcac     480
acaagcactt gctcaattca atttattaaa aaagatggca aaagggctgt tggaactgtt     540
gatgatgttt gtcttgatga ctcaacatgc ttattatgcg gtcagtgtgt aatcgcttgt     600
cctgttgctg ctttaaaaga aaatcccat atagaaaaag ttcaagaagc tcttaatgac      660
cctaaaaaac atgtcattgt tgcaatggct ccatcagtaa gaactgctat gggcgaatta     720
ttcaaaatgg gatatggaaa agatgtaaca ggaaaactat atactgcact agaatgtta     780 ggctttgata agtatttga tataaacttt ggtgcagata tgactataat ggaagaagct     840
actgaacttt taggcagagt taaaaataat ggaccattcc caatgtttac ttcatgttgt    900
ccggcatggg ttagacaagt ggaaaattat acccagaat ttttagaaaa cttatcatca      960
gctaaatcac cacaacaaat atttggtgca gcaagcaaaa catactatcc tcaaatatca    1020
ggtataagtg ctaaagatgt atttactgtt acaataatgc cttgtacagc aaagaaattt    1080
gaggctgata gagaagaaat gtataatgag ggaattaaaa atatagatgc agtacttact    1140
acaagagaat tagcaaaaat gattaaagat gcaaagatta attttgctaa tttagaagac    1200
gaacaagctg atccagcaat gggagaatac actggggctg gagttatatt cggagctaca    1260
ggtggagtta tggaagcagc acttagaact gctaaggatt tcgttgaaga taaagattta    1320
actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggacaacca cacgtaagtg caaggaaag agaaaaagta     1560 gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                        1722

<210> SEQ ID NO 84
<211> LENGTH: 1752
<212> TYPE: DNA
<213> ORGANISM: Chlamydomonas reinhardtii

<400> SEQUENCE: 84
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
```

```
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc ttttgtggt tgaagacaaa tcacaataca tagatattag aagtaaatca     420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag agctttaac tgaaaaaaca cacgttgata gagttaaaga agcattagaa     660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag cataaaaga agcggaagtt    1380 gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752

<210> SEQ ID NO 85
<211> LENGTH: 1722
<212> TYPE: DNA
<213> ORGANISM: Chlamydomonas reinhardtii

<400> SEQUENCE: 85
atggccaaaa caataatctt aaatggcaat gaagtgcata cagataaaga tattactatc     60
cttgagctag caagagaaaa taatgtagat atcccaacac tctgcttttt aaaggattgt    120 ggcaatttttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taagacaaa agcaaaagct    360 tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
```

```
cctgttgctg ctttaaaaga aaaatcccat atagaaaaag ttcaagaagc tcttaatgac      660
cctaaaaaac atgtcattgt tgcaatggct ccatcagtaa gaactgctat gggcgaatta      720
ttcaaaatgg gatatggaaa agatgtaaca ggaaaactat atactgcact agaatgtta       780 ggctttgata aagtatttga tataaacttt ggtgcagata tgactataat ggaagaagct      840
actgaacttt taggcagagt taaaaataat ggaccattcc caatgtttac ttcatgttgt      900
ccggcatggg ttagacaagt ggaaaattat tacccagaat ttttagaaaa cttatcatca      960
gctaaatcac cacaacaaat atttggtgca gcaagcaaaa catactatcc tcaaatatca     1020
ggtataagtg ctaaagatgt atttactgtt acaataatgc cttgtacagc aaagaaattt     1080
gaggctgata gaagaaat gtataatgag ggaattaaaa atatagatgc agtacttact       1140
acaagagaat tagcaaaaat gattaaagat gcaaagatta attttgctaa tttagaagac     1200
gaacaagctg atccagcaat gggagaatac actggggctg gagttatatt cggagctaca     1260
ggtggagtta tggaagcagc acttagaact gctaaggatt tcgttgaaga taagatttta    1320
actgatatag aatatacaca aataagagga ttacaaggaa taaaagaagc ggaagttgaa     1380
attgctggaa ataaactaaa cgttgctgtt ataaatggtg cttctaactt cttcgagttt     1440
atgaaatctg gaaaaatgaa cgaaaaacaa tatcacttta tagaagtaat ggcttgccct     1500
ggtggatgta taaatggtgg aggacaacca cacgtaagtg caaggaaag agaaaaagta     1560 gatgttagaa ctgtaagagc atctgtttta tataaccaag ataaaaattt agagaagaga     1620
aaatcacata aaaatacagc attattaaat atgtactatg attatatggg agctccagga     1680
caaggaaaag ctcatgaatt attacactta aaatacaata aa                       1722

<210> SEQ ID NO 86
<211> LENGTH: 1725
<212> TYPE: DNA
<213> ORGANISM: Chlamydomonas reinhardtii

<400> SEQUENCE: 86
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag agctttaac tgaaaaaaca cacgttgata gagttaaaga agcattagaa       660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggaccat tcccaatgtt tacttcatgt     900
tgtccggcat gggttagaca agtggaaaat tattacccag aatttttaga aaacttatca     960
tcagctaaat caccacaaca aatatttggt gcagcaagca aacatacta tcctcaaata    1020
```

| | |
|---|---:|
| tcaggtataa gtgctaaaga tgtatttact gttacaataa tgccttgtac agcaaagaaa | 1080 |
| tttgaggctg atagagaaga aatgtataat gagggaatta aaaatataga tgcagtactt | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga gcggaagtt | 1380 |
| gaaattgctg gaaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggacaa ccacacgtaa gtgcaaagga agagaaaaa | 1560 |
| gtagatgtta gaactgtaag agcatctgtt ttatataacc aagataaaaa tttagagaag | 1620 |
| agaaaatcac ataaaaatac agcattatta aatatgtact atgattatat gggagctcca | 1680 |
| ggacaaggaa aagctcatga attattacac ttaaaataca ataaa | 1725 |

<210> SEQ ID NO 87
<211> LENGTH: 1749
<212> TYPE: DNA
<213> ORGANISM: Chlamydomonas reinhardtii

<400> SEQUENCE: 87

| | |
|---|---:|
| atggccaaaa caataatctt aaatggcaat gaagtgcata cagataaaga tattactatc | 60 |
| cttgagctag caagagaaaa taatgtagat atcccaacac tctgcttttt aaaggattgt | 120 |
| ggcaattttg gaaaatgcgg agtctgtatg gtagaggtag aaggcaaggg ctttagagct | 180 |
| gcttgtgttg ccaaagttga agatggaatg gtaataaaca cagaatccga tgaagtaaaa | 240 |
| gaacgaatca aaaaagagt ttcaatgctt cttgataagc atgaatttaa atgtggacaa | 300 |
| tgttctagaa gagaaaattg tgaattcctt aaacttgtaa taaagacaaa agcaaaagct | 360 |
| tcaaaaccat ttttaccaga agataaggat gctctagttg ataatagaag taaggctatt | 420 |
| gtaattgaca gatcaaaatg tgtactatgc ggtagatgcg tagctgcatg taaacagcac | 480 |
| acaagcactt gctcaattca atttattaaa aaagatggac aaagggctgt tggaactgtt | 540 |
| gatgatgttt gtcttgatga ctcaacatgc ttattatgcg gtcagtgtgt aatcgcttgt | 600 |
| cctgttgctg ctttaaaaga aaaatcccat atagaaaaag ttcaagaagc tcttaatgac | 660 |
| cctaaaaaac atgtcattgt tgcaatggct ccatcagtaa gaactgctat gggcgaatta | 720 |
| ttcaaaatgg gatatggaaa agatgtaaca ggaaaactat atactgcact tagaatgtta | 780 |
| ggctttgata agtatttga tataaacttt ggtgcagata tgactataat ggaagaagct | 840 |
| actgaacttt taggcagagt taaaaataat ggaccattcc caatgtttac ttcatgttgt | 900 |
| ccggcatggg ttagacaagt tggaaaattat taccccagaa ttttagaaaa cttatcatca | 960 |
| gctaaatcac cacaacaaat atttggtgca gcaagcaaaa catactatcc tcaaatatca | 1020 |
| ggtataagtg ctaaagatgt atttactgtt acaataatgc cttgtacagc aaagaaattt | 1080 |
| gaggctgata gagaagaaat gtataatgag ggaattaaaa atatagatgc agtacttact | 1140 |
| acaagagaat tagcaaaaat gattaaagat gcaagatta ttttgctaa tttagaagac | 1200 |
| gaacaagctg atccagcaat gggagaatac actggggctg agttatatt cggagctaca | 1260 |
| ggtggagtta tggaagcagc acttagaact gctaaggatt tcgttgaaga taaagattta | 1320 |
| actgatatag aatatacaca aataaggagga ttacaaggaa taaaagaagc ggaagttgaa | 1380 |
| attgctggaa ataaactaaa cgttgctgtt ataaatggtg cttctaactt cttcgagttt | 1440 |

```
atgaaatctg gaaaaatgaa cgaaaaacaa tatcacttta tagaagtaat ggcttgccct    1500
ggtggatgta taaatggtgg aggtcaacct cacgtaaatg ctcttgatag agaaaatgtt    1560
gattacagaa aactaagagc atcagtatta taaccaag ataaaaatgt tctttcaaag      1620
agaaagtcac atgataatcc agctattatt aaaatgtatg atagctactt tggaaaacca    1680
ggtgaaggac ttgctcacaa attactacac gtaaaataca caaagataa aaatgtttca     1740 aaacatgaa                                                             1749
```

<210> SEQ ID NO 88
<211> LENGTH: 1752
<212> TYPE: DNA
<213> ORGANISM: Chlamydomonas reinhardtii

<400> SEQUENCE: 88

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca     180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc ttttgtggt tgaagacaaa tcacaataca tagatattag aagtaaatca     420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca gtggaaaaat tattacccag aatttttaga aaacttatca    960
tcagctaaat caccacaaca aatatttggt gcagcaagca aacatactaa tcctcaaata   1020
tcaggtataa gtgctaaaga tgtatttact gttacaataa tgccttgtac agcaaagaaa   1080
tttgaggctg atagagaaga aatgtataat gagggaatta aaaatataga tgcagtactt   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag aataaaaga agcggaagtt     1380 gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttataacc aagataaaaa tgttctttca      1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                         1752
```

<210> SEQ ID NO 89
<211> LENGTH: 1749
<212> TYPE: DNA
<213> ORGANISM: Chlamydomonas reinhardtii

<400> SEQUENCE: 89

| | | | | | | |
|---|---|---|---|---|---|---|
| atggccaaaa | caataatctt | aaatggcaat | gaagtgcata | cagataaaga | tattactatc | 60 |
| cttgagctag | caagagaaaa | taatgtagat | atcccaacac | tctgcttttt | aaaggattgt | 120 |
| ggcaattttg | gaaaatgcgg | agtctgtatg | gtagaggtag | aaggcaaggg | ctttagagct | 180 |
| gcttgtgttg | ccaaagttga | agatggaatg | gtaataaaca | cagaatccga | tgaagtaaaa | 240 |
| gaacgaatca | aaaaaagagt | ttcaatgctt | cttgataagc | atgaatttaa | atgtggacaa | 300 |
| tgttctagaa | gagaaaattg | tgaattcctt | aaacttgtaa | taaagacaaa | agcaaaagct | 360 |
| tcaaaaccat | ttttaccaga | agataaggat | gctctagttg | ataatagaag | taaggctatt | 420 |
| gtaattgaca | gatcaaaatg | tgtactatgc | ggtagatgcg | tagctgcatg | taaacagcac | 480 |
| acaagcactt | gctcaattca | atttattaaa | aaagatggac | aaagggctgt | tggaactgtt | 540 |
| gatgatgttt | gtcttgatga | ctcaacatgc | ttattatgcg | gtcagtgtgt | aatcgcttgt | 600 |
| cctgttgctg | ctttaaaaga | aaaatcccat | atagaaaaag | ttcaagaagc | tcttaatgac | 660 |
| cctaaaaaac | atgtcattgt | tgcaatggct | ccatcagtaa | gaactgctat | gggcgaatta | 720 |
| ttcaaaatgg | gatatggaaa | agatgtaaca | ggaaaactat | atactgcact | tagaatgtta | 780 |
| ggctttgata | agtatttga | tataaacttt | ggtgcagata | tgactataat | ggaagaagct | 840 |
| actgaacttt | taggcagagt | taaaaataat | ggcccattcc | ctatgtttac | atcttgctgt | 900 |
| cctgcatggg | taagattagc | tcaaaattat | catcctgaat | tattagataa | tctttcatca | 960 |
| gcaaaatcac | cacaacaaat | atttggtact | gcatcaaaaa | cttactatcc | ttcaatttca | 1020 |
| ggaatagctc | cagaagatgt | ttatacagtt | actatcatgc | cttgtaatga | taaaaaatat | 1080 |
| gaagcagata | ttcctttcat | ggaaactaac | agcttaagag | atattgatgc | atccttaact | 1140 |
| acaagagaat | tagcaaaaat | gattaaagat | gcaaagatta | atttttgctaa | tttagaagac | 1200 |
| gaacaagctg | atccagcaat | gggagaatac | actggggctg | gagttatatt | cggagctaca | 1260 |
| ggtggagtta | tggaagcagc | acttagaact | gctaaggatt | tcgttgaaga | taaagattta | 1320 |
| actgatatag | aatatacaca | aataagagga | ttacaaggaa | taaagaagc | ggaagttgaa | 1380 |
| attgctggaa | ataaactaaa | cgttgctgtt | ataaatggtg | cttctaactt | cttcgagttt | 1440 |
| atgaaatctg | gaaaatgaa | cgaaaaacaa | tatcacttta | tagaagtaat | ggcttgccct | 1500 |
| ggtggatgta | taaatggtgg | aggtcaacct | cacgtaaatg | ctcttgatag | agaaaatgtt | 1560 |
| gattacagaa | aactaagagc | atcagtatta | tacaaccaag | ataaaaatgt | tctttcaaag | 1620 |
| agaaagtcac | atgataatcc | agctattatt | aaaatgtatg | atagctactt | tggaaaacca | 1680 |
| ggtgaaggac | ttgctcacaa | attactacac | gtaaaataca | caaagataa | aaatgtttca | 1740 |
| aaacatgaa | | | | | | 1749 |

<210> SEQ ID NO 90
<211> LENGTH: 1752
<212> TYPE: DNA
<213> ORGANISM: Chlamydomonas reinhardtii

<400> SEQUENCE: 90

| | | | | | | |
|---|---|---|---|---|---|---|
| atggcaataa | acatagtaat | tgatgaaaaa | actattcaag | tacaggaaaa | tactacagtt | 60 |
| atacaagctg | ccctagcaaa | tgggatagat | ataccaagtt | tatgctatct | taatgagtgt | 120 |

```
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca   960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa    1752

<210> SEQ ID NO 91
<211> LENGTH: 1725
<212> TYPE: DNA
<213> ORGANISM: Chlamydomonas reinhardtii

<400> SEQUENCE: 91
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
```

```
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tccctatgtt tacatcttgc      900
tgtcctgcat gggtaagatt agctcaaaat tatcatcctg aattattaga taatctttca      960
tcagcaaaat caccacaaca aatatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag agcttgcaaa aatgattaaa gatgcaaaaa ttaaatttgc agatcttgaa     1200
gatggtgaag ttgatcctgc tatgggtact tacagtggtg ctggagctat ctttggtgca     1260
accggtggcg ttatggaagc tgcaataaga tcagctaaag actttgctga aaataaagaa     1320
cttgaaaatg ttgattacac tgaagtaaga ggctttaaag catcaaaaga agcggaagtt     1380
gaaattgctg gaaataaact aaacgttgct gttataaatg gtgcttctaa cttcttcgag     1440
tttatgaaat ctggaaaaat gaacgaaaaa caatatcact ttatagaagt aatggcttgc     1500
cctggtggat gtataaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725

<210> SEQ ID NO 92
<211> LENGTH: 1725
<212> TYPE: DNA
<213> ORGANISM: Chlamydomonas reinhardtii

<400> SEQUENCE: 92
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaaataca tagatattag aagtaaatca      420
attgtaatag acagaactaa gtgtgtacta tgcggtagat gcgtagctgc atgtaaacag      480
cacacaagca cttgctcaat tcaatttatt aaaaaagatg acaaagggc tgttggaact      540 gttgatgatg tttgtcttga tgactcaaca tgcttattat gcggtcagtg tgtaatcgct      600
tgtcctgttg ctgctttaaa agaaaaatcc catatagaaa aagttcaaga agctcttaat      660 gacccttaaaa acatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggcccat tccctatgtt tacatcttgc      900
```

```
tgtcctgcat gggtaagatt agctcaaaat tatcatcctg aattattaga taatctttca      960
tcagcaaaat caccacaaca aatatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag aattagcaaa aatgattaaa gatgcaaaga ttaattttgc taatttagaa     1200
gacgaacaag ctgatccagc aatgggagaa tacactgggg ctggagttat attcggagct     1260
acaggtggag ttatggaagc agcacttaga actgctaagg atttcgttga agataaagat     1320
ttaactgata tagaatatac acaaataaga ggattacaag aataaaaga ggctacagta      1380
gaaattggtg agaaaatta taacgtagct gtaattaatg gtgcagcaaa cttagctgaa      1440
ttcatgaata gcggtaaaat ccttgaaaag aactatcatt ttattgaagt aatggcttgc     1500
ccaggcggat gtgtaaatgg tggaggacaa ccacacgtaa gtgcaaagga aagagaaaaa     1560
gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                    1725

<210> SEQ ID NO 93
<211> LENGTH: 1752
<212> TYPE: DNA
<213> ORGANISM: Chlamydomonas reinhardtii

<400> SEQUENCE: 93
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata gcatgaatt aaatgtgga       300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag agctttaac tgaaaaaaca cacgttgata gagttaaaga agcattagaa      660
gatcctaata agcatgtcat tgttgcaatg gctccatcag taagaactgc tatgggcgaa     720
ttattcaaaa tgggatatgg aaaagatgta acaggaaaaac tatatactgc acttagaatg    780
ttaggctttg ataaagtatt tgatataaac tttggtgcag atatgactat aatggaagaa    840
gctactgaac tttttaggcag agttaaaaat aatggcccat tccctatgtt tacatcttgc     900
tgtcctgcat gggtaagatt agctcaaaat tatcatcctg aattattaga taatctttca     960
tcagcaaaat caccacaaca aatatttggt actgcatcaa aaacttacta tccttcaatt    1020
tcaggaatag ctccagaaga tgtttataca gttactatca tgccttgtaa tgataaaaaa    1080
tatgaagcag atattccttt catggaaact aacagcttaa gagatattga tgcatcctta    1140
actacaagag agcttgcaaa aatgattaaa gatgcaaaaa ttaaattgc agatcttgaa      1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
```

```
cttgaaaatg ttgattacac tgaagtaaga ggctttaaag gcataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
tcaaaacatg aa                                                       1752
```

<210> SEQ ID NO 94
<211> LENGTH: 1752
<212> TYPE: DNA
<213> ORGANISM: Chlamydomonas reinhardtii

<400> SEQUENCE: 94

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtacta tgcggtagat gcgtagctgc atgtaaacag    480
cacacaagca cttgctcaat tcaatttatt aaaaaagatg gacaaagggc tgttggaact    540
gttgatgatg tttgtcttga tgactcaaca tgcttattat gcggtcagtg tgtaatcgct    600
tgtcctgttg ctgcttttaaa agaaaaatcc catatagaaa aagttcaaga agctcttaat    660
gaccctaaaa aacatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag gcataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
```

```
ccaggtgaag gacttgctca caaattacta cacgtaaaat acacaaaaga taaaaatgtt      1740
tcaaaacatg aa                                                         1752

<210> SEQ ID NO 95
<211> LENGTH: 1752
<212> TYPE: DNA
<213> ORGANISM: Chlamydomonas reinhardtii

<400> SEQUENCE: 95
atggcaataa acatagtaat tgatgaaaaa actattcaag tacaggaaaa tactacagtt        60
atacaagctg ccctagcaaa tgggatagat ataccaagtt tatgctatct taatgagtgt       120
ggtaatgttg aaagtgtgg agtgtgtgca gtagaaatag aaggaaaaaa taacttagca        180
cttgcatgta taacaaaagt tgaagaaggt atggtaataa acacagaatc cgatgaagta       240
aaagaacgaa tcaaaaaaag agtttcaatg cttcttgata agcatgaatt taaatgtgga       300
caatgttcta agagagaaaa ttgtgaattc cttaaacttg taataaagac aaaagcaaaa       360
gcttcaaaac cattttttacc agaagataag gatgctctag ttgataatag aagtaaggct       420
attgtaattg acagatcaaa atgtgtgcta tgcggaagat gtgaagcagc atgtaaaaca       480
aagacaggta caggagctat ttcaatttgt aagagtgaat caggaagaat agtgcaagca       540
acaggcggaa agtgctttga tgatacaaat tgtttattat gtggacaatg cgttgcagca       600
tgtccagtag gagctttaac tgaaaaaaca cacgttgata gagttaaaga agcattagaa       660
gatcctaata agcatgtaat agttgctatg gcaccatcaa tcagaacttc tatgggagag       720
ttatttaaat taggctatgg ggttgatgta actggaaaat tatatgcttc aatgagagca       780
ttaggatttg ataaggtatt tgatattaac tttggggctg atatgacaat aatgaagaa       840 gcaacagagt ttattgaaag agttaaaaat aatggcccat tccctatgtt tacatcttgc       900
tgtcctgcat gggtaagatt agctcaaaat tatcatcctg aattattaga taatctttca       960
tcagcaaaat caccacaaca aatatttggt actgcatcaa aaacttacta tccttcaatt      1020
tcaggaatag ctccagaaga tgtttataca gttactatca tgccttgtaa tgataaaaaa      1080
tatgaagcag atattccttt catggaaact aacagcttaa gagatattga tgcatcctta      1140
actacaagag agcttgcaaa aatgattaaa gatgcaaaaa ttaaatttgc agatcttgaa      1200
gatggtgaag ttgatcctgc tatgggtact tacagtggtg ctggagctat ctttggtgca      1260
accggtggcg ttatggaagc tgcaataaga tcagctaaag actttgctga aaataaagaa      1320
cttgaaaatg ttgattacac tgaagtaaga ggctttaaag gcataaaaga agcggaagtt      1380
gaaattgctg gaaataaact aaacgttgct gttataaatg gtgcttctaa cttcttcgag      1440
tttatgaaat ctggaaaaat gaacgaaaaa caatatcact ttatagaagt aatggcttgc      1500
cctggtggat gtataaatgg tggaggtcaa cctcacgtaa atgctcttga tagagaaaat      1560
gttgattaca gaaaactaag agcatcagta ttatacaacc aagataaaaa tgttctttca      1620
aagagaaagt cacatgataa tccagctatt attaaaatgt atgatagcta ctttggaaaa      1680
ccaggtgaag gacttgctca caaattacta cacgtaaaat acacaaaaga taaaaatgtt      1740
tcaaaacatg aa                                                         1752

<210> SEQ ID NO 96
<211> LENGTH: 1749
<212> TYPE: DNA
<213> ORGANISM: Chlamydomonas reinhardtii

<400> SEQUENCE: 96
```

```
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg aaaatgcgg agtctgtatg gtagaggtag aaggcaaggg ctttagagct   180
gcttgtgttg ccaaagttga agatggaatg gtagtaaaaa caaactcaga aaaagtacaa   240
gaaagagtta aaatgagagt tgctactttg cttgataagc atgaatttaa atgtggacct   300
tgtccaagaa gagaaaattg cgaattttta agttagttaa taaaaacaaa agctaaggct   360
aacaagcctt ttgtggttga agacaaatca caatacatag atattagaag taaatcaatt   420
gtaatagaca gaactaagtg tgtgctatgc ggaagatgtg aagcagcatg taaaacaaag   480
acaggtacag gagctatttc aatttgtaag agtgaatcag gaagaatagt gcaagcaaca   540
ggcggaaagt gctttgatga tacaaattgt ttattatgtg gacaatgcgt tgcagcatgt   600
ccagtaggag ctttaactga aaaaacacac gttgatagag ttaaagaagc attagaagat   660
cctaataagc atgtaatagt tgctatggca ccatcaatca gaacttctat gggagagtta   720
tttaaattag ctatggggt tgatgtaact ggaaaattat atgcttcaat gagagcatta   780
ggatttgata aggtatttga tattaacttt ggggctgata tgacaataat ggaagaagca   840
acagagttta ttgaaagagt taaaaataat ggcccattcc ctatgtttac atcttgctgt   900
cctgcatggg taagattagc tcaaaattat catcctgaat tattagataa tctttcatca   960
gcaaaatcac cacaacaaat atttggtact gcatcaaaaa cttactatcc ttcaatttca  1020
ggaatagctc cagaagatgt ttatacagtt actatcatgc cttgtaatga taaaaaatat  1080
gaagcagata ttcctttcat ggaaactaac agcttaagag atattgatgc atccttaact  1140
acaagagagc ttgcaaaaat gattaaagat gcaaaaatta aatttgcaga tcttgaagat  1200
ggtgaagttg atcctgctat gggtacttac agtggtgctg gagctatctt tggtgcaacc  1260
ggtggcgtta tggaagctgc aataagatca gctaaagact ttgctgaaaa taagaaactt  1320
gaaaatgttg attacactga gtaagaggc tttaaaggca taaaagaagc ggaagttgaa  1380
attgctggaa ataaactaaa cgttgctgtt ataaatggtg cttctaactt cttcgagttt  1440
atgaaatctg gaaaaatgaa cgaaaaacaa tatcactttta tagaagtaat ggcttgccct  1500
ggtggatgta taaatggtgg aggtcaacct cacgtaaatg ctcttgatag agaaaatgtt  1560
gattacagaa aactaagagc atcagtatta tacaaccaag ataaaaatgt tctttcaaag  1620
agaaagtcac atgataatcc agctattatt aaaatgtatg atagctactt tggaaaacca  1680
ggtgaaggac ttgctcacaa attactacac gtaaaataca caaaagataa aaatgtttca  1740
aaacatgaa                                                          1749
```

<210> SEQ ID NO 97
<211> LENGTH: 1752
<212> TYPE: DNA
<213> ORGANISM: Chlamydomonas reinhardtii

<400> SEQUENCE: 97

```
atggcaataa acatagtaat tgatgaaaaa actattcaag tacaggaaaa tactacagtt    60
atacaagctg ccctagcaaa tgggatagat ataccaagtt tatgctatct taatgagtgt   120
ggtaatgttg aaagtgtgg agtgtgtgca gtagaaatag aaggaaaaaa taacttagca   180
cttgcatgta taacaaaagt tgaagaaggt atggtagtaa aaacaaactc agaaaaagta   240
caagaaagag ttaaaatgag agttgctact ttgcttgata gcatgaatt taaatgtgga   300
ccttgtccaa gaagagaaaa ttgcgaattt ttaaagttag ttataaaaac aaaagctaag   360
```

```
gctaacaagc cttttgtggt tgaagacaaa tcacaataca tagatattag aagtaaatca    420
attgtaatag acagaactaa gtgtgtacta tgcggtagat gcgtagctgc atgtaaacag    480
cacacaagca cttgctcaat tcaatttatt aaaaaagatg acaaagggc tgttggaact    540 gttgatgatg tttgtcttga tgactcaaca tgcttattat gcggtcagtg tgtaatcgct    600
tgtcctgttg ctgcttttaaa agaaaaatcc catatagaaa aagttcaaga agctcttaat    660
gaccctaaaa aacatgtcat tgttgcaatg gctccatcag taagaactgc tatgggcgaa    720
ttattcaaaa tgggatatgg aaaagatgta acaggaaaac tatatactgc acttagaatg    780
ttaggctttg ataaagtatt tgatataaac tttggtgcag atatgactat aatggaagaa    840
gctactgaac ttttaggcag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaaa actttgctga aaataaagaa   1320
cttgaaaatg ttgattacac tgaagtaaga ggctttaaag cataaaaga agcggaagtt   1380 gaaattgctg aaataaaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caattactacc cacgtaaaat acacaaaaga taaaaatgtt   1740
tcaaaacatg aa                                                       1752
```

<210> SEQ ID NO 98
<211> LENGTH: 1752
<212> TYPE: DNA
<213> ORGANISM: Chlamydomonas reinhardtii

<400> SEQUENCE: 98

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtaataa acacagaatc cgatgaagta    240
aaagaacgaa tcaaaaaaag agtttcaatg cttcttgata agcatgaatt taaatgtgga    300
caatgttcta gaagagaaaa ttgtgaattc cttaaacttg taataaagac aaaagcaaaa    360
gcttcaaaac catttttacc agaagataag gatgctctag ttgataatag aagtaaggct    420
attgtaattg acagatcaaa atgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtcat tgttgcaatg gctccatcag taagaactgc tatgggcgaa    720
```

```
ttattcaaaa tgggatatgg aaaagatgta acaggaaaac tatatactgc acttagaatg    780
ttaggctttg ataaagtatt tgatataaac tttggtgcag atatgactat aatggaagaa    840
gctactgaac ttttaggcag agttaaaaat aatggcccat tccctatgtt tacatcttgc    900
tgtcctgcat gggtaagatt agctcaaaat tatcatcctg aattattaga taatctttca    960
tcagcaaaat caccacaaca atatttggt actgcatcaa aaacttacta tccttcaatt    1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact acagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag cataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752

<210> SEQ ID NO 99
<211> LENGTH: 1749
<212> TYPE: DNA
<213> ORGANISM: Chlamydomonas reinhardtii

<400> SEQUENCE: 99
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtagtaaaaa caaactcaga aaagtacaa    240
gaaagagtta aaatgagagt tgctactttg cttgataagc atgaatttaa atgtggacct    300
tgtccaagaa gagaaaattg cgaatttta aagttagtta taaaaacaaa agctaaggct    360
aacaagcctt tgtggttga agacaaatca caatacatag atattagaag taaatcaatt    420
gtaatagaca gaactaagtg tgtgctatgc ggaagatgtg aagcagcatg taaaacaaag    480
acaggtacag gagctatttc aatttgtaag agtgaatcag gaagaatagt gcaagcaaca    540
ggcggaaagt gctttgatga tacaaattgt ttattatgtg gacaatgcgt tgcagcatgt    600
ccagtaggag ctttaactga aaaaacacac gttgatagag ttaaagaagc attagaagat    660
cctaataagc atgtcattgt tgcaatggct ccatcagtaa gaactgctat gggcgaatta    720
ttcaaaatgg gatatggaaa agatgtaaca ggaaaactat atactgcact agaatgttta   780
ggctttgata agtatttga tataaacttt ggtgcagata tgactataat ggaagaagct    840
actgaacttt taggcagagt taaaaataat ggcccattcc ctatgttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
```

```
gaagcagata ttcctttcat ggaaactaac agcttaagag atattgatgc atccttaact    1140
acaagagagc ttgcaaaaat gattaaagat gcaaaaatta aatttgcaga tcttgaagat    1200
ggtgaagttg atcctgctat gggtacttac agtggtgctg agctatctt tggtgcaacc     1260 ggtggcgtta tggaagctgc aataagatca gctaaagact ttgctgaaaa taagaacttt   1320
gaaaatgttg attacactga agtaagaggc tttaaaggca taaaagaagc ggaagttgaa    1380
attgctggaa ataaactaaa cgttgctgtt ataaatggtg cttctaactt cttcgagttt    1440
atgaaatctg gaaaaatgaa cgaaaaacaa tatcactttta tagaagtaat ggcttgccct   1500
ggtggatgta taaatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaaagataa aaatgtttca   1740
aaacatgaa                                                           1749

<210> SEQ ID NO 100
<211> LENGTH: 1752
<212> TYPE: DNA
<213> ORGANISM: Chlamydomonas reinhardtii

<400> SEQUENCE: 100
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaa taacttagca      180 cttgcatgta taacaaaagt tgaagaaggt atggtaataa acacagaatc cgatgaagta     240
aaagaacgaa tcaaaaaaag agtttcaatg cttcttgata agcatgaatt taaatgtgga   300
caatgttcta agagagaaaa ttgtgaattc cttaaacttg taataaagac aaaagcaaaa   360
gcttcaaaac cattttttacc agaagataag gatgctctag ttgataatag aagtaaggct   420
attgtaattg acagatcaaa atgtgtacta tgcggtagat gcgtagctgc atgtaaacag   480
cacacaagca cttgctcaat tcaatttatt aaaaaagatg gacaaagggc tgttggaact   540
gttgatgatg tttgtcttga tgactcaaca tgcttattat gcggtcagtg tgtaatcgct   600
tgtcctgttg ctgcttttaa agaaaaatcc catatagaaa aagttcaaga agctcttaat   660 gacccctaaaa aacatgtaat agttgctatg gcaccatcaa tcagaacttc tatgggagag   720
ttatttaaat taggctatgg ggttgatgta actggaaaat tatatgcttc aatgagagca   780
ttaggatttg ataaggtatt tgatattaac tttggggctg atatgacaat aatggaagaa   840
gcaacagagt ttattgaaag agttaaaaat aatggcccat tccctatgtt tacatcttgc   900
tgtcctgcat gggtaagatt agctcaaaat tatcatcctg aattattaga taatctttca   960
tcagcaaaat caccacaaca atatttggt actgcatcaa aaacttacta tccttcaatt   1020
tcaggaatag ctccagaaga tgttttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataagaa   1320 cttgaaaatg ttgattacac tgaagtaaga ggctttaaag gcataaaaga agcggaagtt   1380
gaaattgctg gaaataaact aaacgttgct gttataaatg gtgcttctaa cttcttcgag   1440
```

```
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
tcaaaacatg aa                                                        1752

<210> SEQ ID NO 101
<211> LENGTH: 1749
<212> TYPE: DNA
<213> ORGANISM: Chlamydomonas reinhardtii

<400> SEQUENCE: 101
atggccaaaa caataatctt aaatggcaat gaagtgcata cagataaaga tattactatc     60
cttgagctag caagagaaaa taatgtagat atcccaacac tctgcttttt aaaggattgt    120 ggcaatttg gaaaatgcgg agtctgtatg gtagaggtag aaggcaaggg ctttagagct    180
gcttgtgttg ccaagttga agatggaatg gtagtaaaaa caaactcaga aaagtacaa     240 gaaagagtta aatgagagt tgctactttg cttgataagc atgaatttaa atgtggacct    300
tgtccaagaa gagaaaattg cgaattttta agttagttta aaaaacaaa agctaaggct    360 aacaagcctt ttgtggttga agacaaatca caatacatag atattagaag taaatcaatt    420
gtaatagaca gaactaagtg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtaatagt tgctatggca ccatcaatca gaacttctat gggagagtta    720
tttaaattag gctatggggt tgatgtaact ggaaaattat atgcttcaat gagagcatta    780
ggatttgata ggtatttga tattaacttt ggggctgata tgacaataat ggaagaagca    840
acagagttta ttgaaagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaatat   1080 gaagcagata ttcctttcat ggaaactaac agcttaagag atattgatgc atccttaact   1140
acaagagagc ttgcaaaaat gattaaagat gcaaaatta aatttgcaga tcttgaagat   1200
ggtgaagttg atcctgctat gggtacttac agtggtgctg gagctatctt tggtgcaacc   1260
ggtggcgtta tggaagctgc aataagatca gctaaagact ttgctgaaaa taagaaactt   1320
gaaaatgttg attacactga gtaagaggc tttaaggca taaagaagc ggaagttgaa    1380 attgctggaa ataaactaaa cgttgctgtt ataaatggtg cttctaactt cttcgagttt   1440
atgaaatctg gaaaaatgaa cgaaaaacaa tatcacttta tagaagtaat ggcttgccct   1500
ggtggatgta taatggtgg aggtcaacct cacgtaaatg ctcttgatag agaaaatgtt   1560
gattacagaa aactaagagc atcagtatta taccaagata aaaatgtt tctttcaaag    1620 agaaagtcac atgataatcc agctattatt aaaatgtatg atagctactt tggaaaacca   1680
ggtgaaggac ttgctcacaa attactacac gtaaaataca caaagataa aaatgtttca   1740 aaacatgaa                                                          1749
```

<210> SEQ ID NO 102
<211> LENGTH: 1749
<212> TYPE: DNA
<213> ORGANISM: Chlamydomonas reinhardtii

<400> SEQUENCE: 102

| | | | | | |
|---|---|---|---|---|---|
| atggccaaaa | caataatctt | aaatggcaat | gaagtgcata | cagataaaga | tattactatc | 60 |
| cttgagctag | caagagaaaa | taatgtagat | atcccaacac | tctgcttttt | aaaggattgt | 120 |
| ggcaattttg | gaaaatgcgg | agtctgtatg | gtagaggtag | aaggcaaggg | ctttagagct | 180 |
| gcttgtgttg | ccaaagttga | agatggaatg | gtaataaaca | cagaatccga | tgaagtaaaa | 240 |
| gaacgaatca | aaaaaagagt | ttcaatgctt | cttgataagc | atgaatttaa | atgtggacaa | 300 |
| tgttctagaa | gagaaaattg | tgaattcctt | aaacttgtaa | taaagacaaa | agcaaaagct | 360 |
| tcaaaaccat | ttttaccaga | agataaggat | gctctagttg | ataatagaag | taaggctatt | 420 |
| gtaattgaca | gatcaaaatg | tgtgctatgc | ggaagatgtg | aagcagcatg | taaaacaaag | 480 |
| acaggtacag | gagctatttc | aatttgtaag | agtgaatcag | gaagaatagt | gcaagcaaca | 540 |
| ggcggaaagt | gctttgatga | tacaaattgt | ttattatgtg | gacaatgcgt | tgcagcatgt | 600 |
| ccagtaggag | ctttaactga | aaaaacacac | gttgatagag | ttaaagaagc | attagaagat | 660 |
| cctaataagc | atgtaatagt | tgctatggca | ccatcaatca | gaacttctat | gggagagtta | 720 |
| tttaaattag | gctatggggt | tgatgtaact | ggaaaattat | atgcttcaat | gagagcatta | 780 |
| ggatttgata | aggtatttga | tattaacttt | ggggctgata | tgacaataat | ggaagaagca | 840 |
| acagagttta | ttgaaagagt | taaaaataat | ggcccattcc | ctatgtttac | atcttgctgt | 900 |
| cctgcatggg | taagattagc | tcaaaattat | catcctgaat | tattagataa | tctttcatca | 960 |
| gcaaaatcac | cacaacaaat | atttggtact | gcatcaaaaa | cttactatcc | ttcaatttca | 1020 |
| ggaatagctc | cagaagatgt | ttatacagtt | actatcatgc | cttgtaatga | taaaaaatat | 1080 |
| gaagcagata | ttcctttcat | ggaaactaac | agcttaagag | atattgatgc | atccttaact | 1140 |
| acaagagagc | ttgcaaaaat | gattaaagat | gcaaaaatta | aatttgcaga | tcttgaagat | 1200 |
| ggtgaagttg | atcctgctat | gggtacttac | agtggtgctg | gagctatctt | tggtgcaacc | 1260 |
| ggtggcgtta | tggaagctgc | aataagatca | gctaaagact | ttgctgaaaa | taagaacttt | 1320 |
| gaaaatgttg | attacactga | agtaagaggc | tttaaaggca | taaagaaagc | ggaagttgaa | 1380 |
| attgctggaa | ataaactaaa | cgttgctgtt | ataaatggtg | cttctaactt | cttcgagttt | 1440 |
| atgaaatctg | gaaaatgaa | cgaaaaacaa | tatcacttta | tagaagtaat | ggcttgccct | 1500 |
| ggtggatgta | taaatggtgg | aggtcaacct | cacgtaaatg | ctcttgatag | agaaaatgtt | 1560 |
| gattacagaa | aactaagagc | atcagtatta | tacaaccaag | ataaaaatgt | tctttcaaag | 1620 |
| agaaagtcac | atgataatcc | agctattatt | aaaatgtatg | atagctactt | tggaaaacca | 1680 |
| ggtgaaggac | ttgctcacaa | attactacac | gtaaaataca | caaagataa | aaatgtttca | 1740 |
| aaacatgaa | | | | | 1749 |

<210> SEQ ID NO 103
<211> LENGTH: 1752
<212> TYPE: DNA
<213> ORGANISM: Chlamydomonas reinhardtii

<400> SEQUENCE: 103

| | | | | | |
|---|---|---|---|---|---|
| atggcaataa | acatagtaat | tgatgaaaaa | actattcaag | tacaggaaaa | tactacagtt | 60 |
| atacaagctg | ccctagcaaa | tgggatagat | ataccaagtt | tatgctatct | taatgagtgt | 120 |

```
ggtaatgttg gaaagtgtgg agtgtgtgca gtagaaatag aaggaaaaaa taacttagca    180
cttgcatgta taacaaaagt tgaagaaggt atggtaataa acacagaatc cgatgaagta    240
aaagaacgaa tcaaaaaaag agtttcaatg cttcttgata agcatgaatt taaatgtgga    300
caatgttcta gaagagaaaa ttgtgaattc cttaaacttg taataaagac aaaagcaaaa    360
gcttcaaaac cattttttacc agaagataag gatgctctag ttgataatag aagtaaggct    420
attgtaattg acagatcaaa atgtgtacta tgcggtagat gcgtagctgc atgtaaacag    480
cacacaagca cttgctcaat tcaatttatt aaaaaagatg gacaaggggc tgttggaact    540
gttgatgatg tttgtcttga tgactcaaca tgcttattat gcggtcagtg tgtaatcgct    600
tgtcctgttg ctgctttaaa agaaaaatcc catatagaaa aagttcaaga agctcttaat    660
gaccctaaaa aacatgtcat tgttgcaatg gctccatcag taagaactgc tatgggcgaa    720
ttattcaaaa tgggatatgg aaaagatgta acaggaaaac tatatactgc acttagaatg    780
ttaggctttg ataaagtatt tgatataaac tttggtgcag atatgactat aatggaagaa    840
gctactgaac ttttaggcag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgttttataca gttactatca tgccttgtaa tgataaaaaa   1080
tatgaagcag atattccttt catggaaact aacagcttaa gagatattga tgcatcctta   1140
actacaaagg agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag cataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752
```

<210> SEQ ID NO 104
<211> LENGTH: 1749
<212> TYPE: DNA
<213> ORGANISM: Chlamydomonas reinhardtii

<400> SEQUENCE: 104

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtagtaaaaa caaactcaga aaaagtacaa    240
gaaagagtta aaatgagagt tgctactttg cttgataagc atgaatttaa atgtggacct    300
tgtccaagaa gagaaaattg cgaattttta aagttagtta taaaaacaaa agctaaggct    360
aacaagccctt ttgtggttga agacaaatca caatacatag atattagaag taatcaattc    420
gtaatagaca gaactaagtg tgtactatgc ggtagatgcg tagctgcatg taaacagcac    480
```

```
acaagcactt gctcaattca atttattaaa aaagatggac aaagggctgt tggaactgtt      540
gatgatgttt gtcttgatga ctcaacatgc ttattatgcg gtcagtgtgt aatcgcttgt      600
cctgttgctg ctttaaaaga aaaatcccat atagaaaaag ttcaagaagc tcttaatgac      660
cctaaaaaac atgtcattgt tgcaatggct ccatcagtaa aactgctat gggcgaatta      720 ttcaaaatgg gatatggaaa agatgtaaca ggaaaactat atactgcact tagaatgtta      780
ggctttgata agtatttga tataaacttt ggtgcagata tgactataat ggaagaagct      840
actgaacttt taggcagagt taaaaataat ggcccattcc ctatgtttac atcttgctgt      900
cctgcatggg taagattagc tcaaaattat catcctgaat tattagataa tctttcatca      960
gcaaaatcac cacaacaaat atttggtact gcatcaaaaa cttactatcc ttcaatttca     1020
ggaatagctc cagaagatgt ttatacagtt actatcatgc cttgtaatga taaaaatat     1080 gaagcagata ttcctttcat ggaaactaac agcttaagag atattgatgc atccttaact     1140
acaagagagc ttgcaaaaat gattaaagat gcaaaaatta aatttgcaga tcttgaagat     1200
ggtgaagttg atcctgctat gggtacttac agtggtgctg gagctatctt tggtgcaacc     1260
ggtggcgtta tggaagctgc aataagatca gctaaagact ttgctgaaaa taagaaactt     1320
gaaaatgttg attacactga gtaagaggc tttaaaggca taaagaagc ggaagttgaa      1380 attgctggaa ataaactaaa cgttgctgtt ataaatggtg cttctaactt cttcgagttt     1440
atgaaatctg gaaaatgaa cgaaaaacaa tatcacttta tagaagtaat ggcttgccct     1500
ggtggatgta taaatggtgg aggtcaacct cacgtaaatg ctcttgatag agaaaatgtt     1560
gattacagaa aactaagagc atcagtatta tacaaccaag ataaaaatgt tctttcaaag     1620
agaaagtcac atgataatcc agctattatt aaaatgtatg atagctactt tggaaaacca     1680
ggtgaaggac ttgctcacaa attactacac gtaaaataca caaagataa aaatgtttca     1740 aaacatgaa                                                            1749

<210> SEQ ID NO 105
<211> LENGTH: 1749
<212> TYPE: DNA
<213> ORGANISM: Chlamydomonas reinhardtii

<400> SEQUENCE: 105
atggccaaaa caataatctt aaatggcaat gaagtgcata cagataaaga tattactatc       60
cttgagctag caagagaaaa taatgtagat atcccaacac tctgcttttt aaaggattgt      120
ggcaattttg gaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaagagt ttcaatgctt cttgataagc atgaattaa atgtggacaa      300 tgttctagaa gagaaaattg tgaattcctt aaacttgtaa taagacaaa agcaaaagct      360 tcaaaaccat ttttaccaga agataaggat gctctagttg ataatagaag taaggctatt      420
gtaattgaca gatcaaaatg tgtgctatgc ggaagatgtg aagcagcatg taaaacaaag      480
acaggtacag gagctatttc aatttgtaag agtgaatcag gaagaatagt gcaagcaaca      540
ggcggaaagt gctttgatga tacaaattgt ttattatgtg acaatgcgt tgcagcatgt      600 ccagtaggag ctttaactga aaaaacacac gttgatagag ttaagaagc attagaagat      660 cctaataagc atgtcattgt tgcaatggct ccatcagtaa aactgctat gggcgaatta      720 ttcaaaatgg gatatggaaa agatgtaaca ggaaaactat atactgcact tagaatgtta      780
ggctttgata agtatttga tataaacttt ggtgcagata tgactataat ggaagaagct      840
```

```
actgaactttt taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagagc ttgcaaaaat gattaaagat gcaaaaatta aatttgcaga tcttgaagat   1200
ggtgaagttg atcctgctat gggtacttac agtggtgctg agctatcttt ggtgcaacc    1260 ggtggcgtta tggaagctgc aataagatca gctaaagact ttgctgaaaa taagaacttt   1320
gaaaatgttg attacactga agtaagaggc tttaaaggca taaagaagc ggaagttgaa    1380 attgctggaa ataaactaaa cgttgctgtt ataaatggtg cttctaactt cttcgagttt   1440
atgaaatctg gaaaatgaa cgaaaaacaa tatcacttta tagaagtaat ggcttgccct    1500
ggtggatgta taatggtgg aggtcaacct cacgtaaatg ctcttgatag agaaaatgtt    1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaaagataa aaatgtttca   1740
aaacatgaa                                                           1749

<210> SEQ ID NO 106
<211> LENGTH: 1749
<212> TYPE: DNA
<213> ORGANISM: Chlamydomonas reinhardtii

<400> SEQUENCE: 106
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtaatagt tgctatggca ccatcaatca gaacttctat gggagagtta    720
tttaaattag gctatggggt tgatgtaact ggaaaattat atgcttcaat gagagcatta    780
ggatttgata aggtatttga tattaacttt ggggctgata tgacaataat ggaagaagca    840 acagagtttta ttgaaagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagagc ttgcaaaaat gattaaagat gcaaaaatta aatttgcaga tcttgaagat   1200
```

```
ggtgaagttg atcctgctat gggtacttac agtggtgctg agctatctt tggtgcaacc     1260 ggtggcgtta tggaagctgc aataagatca gctaaagact ttgctgaaaa taagaactt     1320 gaaaatgttg attacactga agtaagaggc tttaaaggca taaagaagc ggaagttgaa     1380 attgctggaa ataaactaaa cgttgctgtt ataaatggtg cttctaactt cttcgagttt    1440
atgaaatctg gaaaaatgaa cgaaaaacaa tatcacttta tagaagtaat ggcttgccct    1500
ggtggatgta taaatggtgg aggtcaacct cacgtaaatg ctcttgatag agaaaatgtt    1560
gattacagaa aactaagagc atcagtatta acaaccaag ataaaaatgt tctttcaaag     1620
agaaagtcac atgataatcc agctattatt aaaatgtatg atagctactt tggaaaacca    1680
ggtgaaggac ttgctcacaa attactacac gtaaaataca caaagataa aatgttttca     1740 aaacatgaa                                                           1749

<210> SEQ ID NO 107
<211> LENGTH: 1749
<212> TYPE: DNA
<213> ORGANISM: Chlamydomonas reinhardtii

<400> SEQUENCE: 107
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaagttga agatggaatg gtaataaaca cagaatccga tgaagtaaaa     240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga gataaggat gctctagttg ataatagaag taaggctatt     420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca    1020
ggtataagtg ctaaagatgt atttactgtt acaataatgc cttgtacagc aaagaaattt    1080
gaggctgata gagaagaaat gtaaatgag ggaattaaaa atatagatgc agtacttact     1140
acaagagaat tagcaaaaat gattaaagat gcaagatta atttgctaa tttagaagac    1200 gaacaagctg atccagcaat gggagaatac actggggctg agttatatt cggagctaca    1260 ggtggagtta tggaagcagc acttagaact gctaaggatt tcgttgaaga taagattta     1320 actgatatag aatatacaca aataagagga ttacaaggaa taaagaggc tacagtagaa    1380 attggtggag aaaattataa cgtagctgta attaatggtg cagcaaactt agctgaattc    1440
atgaatagcg gtaaaatcct tgaaagaaac tatcatttta ttgaagtaat ggcttgccca    1500
ggcggatgtg taaatggtgg aggtcaacct cacgtaaatg ctcttgatag agaaaatgtt    1560
```

```
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataaa aatgtttca    1740 aaacatgaa                                                           1749
```

<210> SEQ ID NO 108
<211> LENGTH: 1722
<212> TYPE: DNA
<213> ORGANISM: Chlamydomonas reinhardtii

<400> SEQUENCE: 108

```
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg aaaatgcgg agtctgtatg gtagaggtag aaggcaaggg ctttagagct    180
gcttgtgttg ccaaagttga agatggaatg gtaataaaca cagaatccga tgaagtaaaa   240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct   360
tcaaaaccat ttttaccaga agataaggat gctctagttg ataatagaag taaggctatt   420
gtaattgaca gatcaaaatg tgtactatgc ggtagatgcg tagctgcatg taaacagcac   480
acaagcactt gctcaattca atttattaaa aaagatggac aaagggctgt tggaactgtt   540
gatgatgttt gtcttgatga ctcaacatgc ttattatgcg gtcagtgtgt aatcgcttgt   600
cctgttgctg cttttaaaga aaaatcccat atagaaaaag ttcaagaagc tcttaatgac   660
cctaaaaaac atgtcattgt tgcaatggct ccatcagtaa gaactgctat gggcgaatta   720
ttcaaaatgg gatatggaaa agatgtaaca ggaaaactat atactgcact tagaatgtta   780
ggctttgata agtatttga tataaactt ggtgcagata tgactataat ggaagaagct    840
actgaacttt taggcagagt taaaaataat ggaccattcc caatgtttac ttcatgttgt   900
ccggcatggg ttagacaagt ggaaaattat tacccagaat ttttagaaaa cttatcatca   960
gctaaatcac cacaacaaat atttggtgca gcaagcaaaa catactatcc tcaaatatca  1020
ggtataagtg ctaagatgt atttactgtt acaataatgc cttgtacagc aaagaaattt  1080
gaggctgata gagaagaaat gtataatgag ggaattaaaa atatagatgc agtacttact  1140
acaagagaat tagcaaaaat gattaaagat gcaagagatta ttttgctaa tttagaagac  1200 gaacaagctg atccagcaat gggagaatac actggggctg gagttatatt cggagctaca  1260
ggtggagtta tggaagcagc acttagaact gctaaggatt tcgttgaaga taaagattta  1320
actgatatag aatatacaca aataagagga ttacaaggaa taaaagaagc ggaagttgaa  1380
attgctggaa ataaactaaa cgttgctgtt ataaatggtg cttctaactt cttcgagttt  1440
atgaaatctg gaaaatgaa cgaaaaacaa tatcactta tagaagtaat ggcttgccct   1500
ggtggatgta taatggtgg aggacaacca cacgtaagtg caaaggaaag agaaaaagta  1560 gatgttgaa ctgtaagagc atctgtttta tataaccaag ataaaaattt agagaagaga   1620
aaatcacata aaaatacagc attattaaat atgtactatg attatatggg agctccagga  1680
caaggaaaag ctcatgaatt attacactta aaatacaata aa                     1722
```

<210> SEQ ID NO 109
<211> LENGTH: 1722
<212> TYPE: DNA
<213> ORGANISM: Chlamydomonas reinhardtii

<400> SEQUENCE: 109

```
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg aaaatgcgg agtctgtatg gtagaggtag aaggcaaggg ctttagagct    180
gcttgtgttg ccaagttga agatggaatg gtaataaaca cagaatccga tgaagtaaaa    240
gaacgaatca aaaaaagagt ttcaatgctt cttgataagc atgaatttaa atgtggacaa   300
tgttctagaa gagaaaattg tgaattcctt aaacttgtaa taaagacaaa agcaaaagct   360
tcaaaaccat ttttaccaga agataaggat gctctagttg ataatagaag taaggctatt   420
gtaattgaca gatcaaaatg tgtactatgc ggtagatgcg tagctgcatg taaacagcac   480
acaagcactt gctcaattca atttattaaa aaagatggac aaagggctgt tggaactgtt   540
gatgatgttt gtcttgatga ctcaacatgc ttattatgcg gtcagtgtgt aatcgcttgt   600
cctgttgctg ctttaaaaga aaaatcccat atagaaaaag ttcaagaagc tcttaatgac   660
cctaaaaaac atgtcattgt tgcaatggct ccatcagtaa gaactgctat gggcgaatta   720
ttcaaaatgg gatatggaaa agatgtaaca ggaaaactat atactgcact tagaatgtta   780
ggctttgata aagtatttga tataaacttt ggtgcagata tgactataat ggaagaagct   840
actgaacttt taggcagagt taaaaataat ggaccattcc caatgtttac ttcatgttgt   900
ccggcatggg ttagacaagt ggaaaattat tacccagaat ttttagaaaa cttatcatca   960
gctaaatcac cacaacaaat atttggtgca gcaagcaaaa catactatcc tcaaatatca  1020
ggtataagtg ctaaagatgt atttactgtt acaataatgc cttgtacagc aaagaaattt  1080
gaggctgata gaagagaaat gtataatgag ggaattaaaa atatagatgc agtacttact  1140
acaagagagc ttgcaaaaat gattaaagat gcaaaaatta aatttgcaga tcttgaagat  1200
ggtgaagtta tcctgctat gggtacttac agtggtgctg gagctatctt tggtgcaacc  1260
ggtggcgtta tggaagctgc aataagatca gctaaagact ttgctgaaaa taagaacttt  1320
gaaaatgttg attacactga gtaagaggc tttaaaggca taaagaggc tacagtagaa   1380
attggtggag aaaattataa cgtagctgta attaatggtg cagcaaactt agctgaattc  1440
atgaatagcg gtaaaatcct tgaaaagaac tatcatttta ttgaagtaat ggcttgccca  1500
ggcggatgtg taaatggtgg aggacaacca cacgtaagtg caaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga  1680
caaggaaaag ctcatgaatt attacactta aaatacaata aa                     1722
```

<210> SEQ ID NO 110
<211> LENGTH: 1722
<212> TYPE: DNA
<213> ORGANISM: Chlamydomonas reinhardtii

<400> SEQUENCE: 110

```
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg aaaatgcgg agtctgtatg gtagaggtag aaggcaaggg ctttagagct    180
gcttgtgttg ccaagttga agatggaatg gtaataaaca cagaatccga tgaagtaaaa    240
gaacgaatca aaaaaagagt ttcaatgctt cttgataagc atgaatttaa atgtggacaa   300
tgttctagaa gagaaaattg tgaattcctt aaacttgtaa taaagacaaa agcaaaagct   360
```

-continued

```
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata aagtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtaatgag ggaattaaaa atatagatgc agtacttact   1140
acaagagaat tagcaaaaat gattaaagat gcaaagatta atttttgctaa tttagaagac   1200 gaacaagctg atccagcaat gggagaatac actggggctg gagttatatt cggagctaca   1260 ggtgagtta tggaagcagc acttagaact gctaaggatt tcgttgaaga taagattta   1320 actgatatag aatatacaca aataagagga ttacaaggaa taaaagaggc tacagtagaa   1380
attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggacaacca cacgtaagtg caaggaaag agaaaaagta   1560 gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722
```

<210> SEQ ID NO 111
<211> LENGTH: 1749
<212> TYPE: DNA
<213> ORGANISM: Chlamydomonas reinhardtii

<400> SEQUENCE: 111

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
```

```
ggctttgata aagtatttga tataaacttt ggtgcagata tgactataat ggaagaagct    840
actgaacttt taggcagagt taaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaagagatta attttgctaa tttagaagac   1200
gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaaagaagc ggaagttgaa   1380
attgctggaa ataaactaaa cgttgctgtt ataaatggtg cttctaactt cttcgagttt   1440
atgaaatctg gaaaaatgaa cgaaaaacaa tatcacttta tagaagtaat ggcttgccct   1500
ggtggatgta taaatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataa aaatgtttca   1740 aaacatgaa                                                           1749

<210> SEQ ID NO 112
<211> LENGTH: 1749
<212> TYPE: DNA
<213> ORGANISM: Chlamydomonas reinhardtii

<400> SEQUENCE: 112
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taagagacaaa agcaaaagct    360 tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata aagtatttga tataaacttt ggtgcagata tgactataat ggaagaagct    840
actgaacttt taggcagagt taaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
```

```
acaagagagc ttgcaaaaat gattaaagat gcaaaaatta aatttgcaga tcttgaagat    1200
ggtgaagttg atcctgctat gggtacttac agtggtgctg gagctatctt tggtgcaacc    1260
ggtggcgtta tggaagctgc aataagatca gctaaagact ttgctgaaaa taaagaactt    1320
gaaaatgttg attacactga agtaagaggc tttaaaggca taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggtcaacct cacgtaaatg ctcttgatag agaaaatgtt    1560
gattacagaa aactaagagc atcagtatta tacaaccaag ataaaaatgt tctttcaaag    1620
agaaagtcac atgataatcc agctattatt aaaatgtatg atagctactt tggaaaacca    1680
ggtgaaggac ttgctcacaa attactacac gtaaaataca caaagataaa aatgtttca    1740 aaacatgaa                                                           1749

<210> SEQ ID NO 113
<211> LENGTH: 1749
<212> TYPE: DNA
<213> ORGANISM: Chlamydomonas reinhardtii

<400> SEQUENCE: 113
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaagagt ttcaatgctt cttgataagc atgaatttaa atgtggacaa     300
tgttctagaa gagaaaattg tgaattcctt aaacttgtaa taaagacaaa agcaaaagct     360
tcaaaaccat ttttaccaga agataaggat gctctagttg ataatagaag taaggctatt     420
gtaattgaca gatcaaaatg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg ctttaaaaga aaaatcccat atagaaaaag ttcaagaagc tcttaatgac     660
cctaaaaaac atgtcattgt tgcaatggct ccatcagtaa gaactgctat gggcgaatta     720
ttcaaaatgg gatatggaaa agatgtaaca ggaaaactat atactgcact agaatgttta     780
ggctttgata agtatttga tataaacttt ggtgcagata tgactataat ggaagaagct     840
actgaacttt taggcagagt taaaaataat ggcccattcc ctatgtttac atcttgctgt     900
cctgcatggg taagattagc tcaaaattat catcctgaat tattagataa tctttcatca     960 gcaaatcac cacaacaaat atttggtact gcatcaaaaa cttactatcc ttcaatttca    1020
ggaatagctc cagaagatgt ttatacagtt actatcatgc cttgtaatga taaaaaatat    1080
gaagcagata ttccttttcat ggaaactaac agcttaagag atattgatgc atccttaact    1140
acaagagaat tagcaaaaat gattaaagat gcaaagatta attttgctaa tttgaagac     1200 gaacaagctg atccagcaat gggagaatac actggggctg gagttatatt cggagctaca    1260
ggtggagtta tggaagcagc acttagaact gctaaggatt cgttgaaga taaagattta    1320 actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
```

-continued

```
ggcggatgtg taaatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataaa aatgtttca    1740 aaacatgaa                                                           1749

<210> SEQ ID NO 114
<211> LENGTH: 1722
<212> TYPE: DNA
<213> ORGANISM: Chlamydomonas reinhardtii

<400> SEQUENCE: 114
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaagttgga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taagacaaa agcaaaagct    360 tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aagatggac aaagggctgt tggaactgtt    540
gatgatgttt gtcttgatga ctcaacatgc ttattatgcg gtcagtgtgt aatcgcttgt    600
cctgttgctg ctttaaaaga aaaatcccat atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact agaatgtta    780 ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagagc ttgcaaaaat gattaaagat gcaaaaatta aatttgcaga tcttgaagat   1200
ggtgaagttg atcctgctat gggtacttac agtggtgctg gagctatctt tggtgcaacc   1260
ggtggcgtta tggaagctgc aataagatca gctaaagact ttgctgaaaa taagaacctt   1320
gaaaatgttg attacactga agtaagaggc tttaaaggca taaaagaagc ggaagttgaa   1380
attgctggaa ataaactaaa cgttgctgtt ataaatggtg cttctaactt cttcgagttt   1440
atgaaatctg gaaaaatgaa cgaaaaacaa tatcactttta tagaagtaat ggcttgccct   1500
ggtggatgta taatggtgg aggacaacca cacgtaagtg caaggaaag agaaaaagta   1560 gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                       1722

<210> SEQ ID NO 115
<211> LENGTH: 1722
```

```
<212> TYPE: DNA
<213> ORGANISM: Chlamydomonas reinhardtii

<400> SEQUENCE: 115
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaaagagt ttcaatgctt cttgataagc atgaatttaa atgtggacaa     300
tgttctagaa gagaaaattg tgaattcctt aaacttgtaa taaagacaaa agcaaaagct     360
tcaaaaccat ttttaccaga agataaggat gctctagttg ataatagaag taaggctatt     420
gtaattgaca gatcaaaatg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg cttttaaaga aaaatcccat atagaaaaag ttcaagaagc tcttaatgac     660
cctaaaaaac atgtcattgt tgcaatggct ccatcagtaa gaactgctat gggcgaatta     720
ttcaaaatgg gatatggaaa agatgtaaca ggaaaactat atactgcact tagaatgtta     780
ggctttgata agtatttga tataaacttt ggtgcagata tgactataat ggaagaagct     840
actgaacttt taggcagagt taaaaataat ggcccattcc ctatgtttac atcttgctgt     900
cctgcatggg taagattagc tcaaaattat catcctgaat tattagataa tctttcatca     960
gcaaaatcac cacaacaaat atttggtact gcatcaaaaa cttactatcc ttcaatttca    1020
ggaatagctc cagaagatgt ttatacagtt actatcatgc cttgtaatga taaaaaatat    1080
gaagcagata ttcctttcat ggaaactaac agcttaagag atattgatgc atccttaact    1140
acaagagaat tagcaaaaat gattaaagat gcaagatta attttgctaa tttagaagac    1200
gaacaagctg atccagcaat gggagaatac actggggctg gagttatatt cggagctaca    1260
ggtggagtta tggaagcagc acttagaact gctaaggatt tcgttgaaga taaagattta    1320
actgatatag aatatacaca aataagagga ttacaaggaa taaaagaagc ggaagttgaa    1380
attgctggaa ataaactaaa cgttgctgtt ataaatggtg cttctaactt cttcgagttt    1440
atgaaatctg gaaaatgaa cgaaaaacaa tatcacttta tagaagtaat ggcttgccct    1500
ggtggatgta taaatggtgg aggacaacca cacgtaagtg caaaggaaag agaaaaagta    1560
gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                      1722

<210> SEQ ID NO 116
<211> LENGTH: 1722
<212> TYPE: DNA
<213> ORGANISM: Chlamydomonas reinhardtii

<400> SEQUENCE: 116
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtaataaaca cagaatccga tgaagtaaaa     240
gaacgaatca aaaaaagagt ttcaatgctt cttgataagc atgaatttaa atgtggacaa     300
```

```
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat ggcgaatta    720 ttcaaaatgg gatatggaaa agatgtaaca ggaaaactat atactgcact tagaatgtta    780
ggctttgata agtatttga tataaacttt ggtgcagata tgactataat ggaagaagct    840
actgaacttt taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
gaagcagata ttcctttcat ggaaactaac agcttaagag atattgatgc atccttaact   1140
acaagagagc ttgcaaaaat gattaaagat gcaaaaatta aatttgcaga tcttgaagat   1200
ggtgaagtta tcctgctat gggtacttac agtggtgctg gagctatctt tggtgcaacc   1260
ggtggcgtta tggaagctgc aataagatca gctaaagact ttgctgaaaa taagaacttt   1320
gaaaatgttg attacactga agtaagaggc tttaaaggca taaagaggc tacagtagaa   1380 attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggacaacca cacgtaagtg caaaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                     1722
```

<210> SEQ ID NO 117
<211> LENGTH: 1749
<212> TYPE: DNA
<213> ORGANISM: Chlamydomonas reinhardtii

<400> SEQUENCE: 117

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg cttttaaaga aaaatcccat atagaaaaag ttcaagaagc tcttaatgac    660
cctaaaaaac atgtcattgt tgcaatggct ccatcagtaa gaactgctat ggcgaatta    720
```

```
ttcaaaatgg gatatggaaa agatgtaaca ggaaaactat atactgcact tagaatgtta    780
ggctttgata aagtatttga tataaacttt ggtgcagata tgactataat ggaagaagct    840
actgaactt  taggcagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagagc ttgcaaaaat gattaaagat gcaaaaatta aatttgcaga tcttgaagat   1200
ggtgaagttg atcctgctat gggtacttac agtggtgctg gagctatctt tggtgcaacc   1260
ggtggcgtta tggaagctgc aataagatca gctaaagact ttgctgaaaa taagaacttt   1320
gaaaatgttg attacactga agtaagaggc tttaaaggca taaaagaagc ggaagttgaa   1380
attgctggaa ataaactaaa cgttgctgtt ataaatggtg cttctaactt cttcgagttt   1440
atgaaatctg gaaaaatgaa cgaaaaacaa tatcacttta tagaagtaat ggcttgccct   1500
ggtggatgta taaatggtgg aggtcaacct cacgtaaatg ctcttgatag agaaaatgtt   1560
gattacagaa aactaagagc atcagtatta tacaaccaag ataaaaatgt tctttcaaag   1620
agaaagtcac atgataatcc agctattatt aaaatgtatg atagctactt tggaaaacca   1680
ggtgaaggac ttgctcacaa attactacac gtaaaataca caaagataaa aatgtttca    1740
aaacatgaa                                                           1749

<210> SEQ ID NO 118
<211> LENGTH: 1749
<212> TYPE: DNA
<213> ORGANISM: Chlamydomonas reinhardtii

<400> SEQUENCE: 118
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt  tcaatgctt  cttgataagc atgaatttaa atgtggacaa    300
tgttctagaa gagaaaattg tgaattcctt aaacttgtaa taagacaaa  agcaaaagct    360
tcaaaaccat ttttaccaga agataaggat gctctagttg ataatagaag taaggctatt    420
gtaattgaca gatcaaaatg tgtactatgc ggtagatgcg tagctgcatg taaacagcac    480
acaagcactt gctcaattca atttattaaa aaagatggac aaagggctgt tggaactgtt    540
gatgatgttt gtcttgatga ctcaacatgc ttattatgcg gtcagtgtgt aatcgcttgt    600
cctgttgctg ctttaaaaga aaatcccat  atagaaaaag ttcaagaagc tcttaatgac    660
cctaaaaaac atgtcattgt tgcaatggct ccatcagtaa gaactgctat gggcgaatta    720
ttcaaaatgg gatatggaaa agatgtaaca ggaaaactat atactgcact tagaatgtta    780
ggctttgata aagtatttga tataaacttt ggtgcagata tgactataat ggaagaagct    840
actgaactt  taggcagagt taaaaataat ggcccattcc ctatgtttac atcttgctgt    900
cctgcatggg taagattagc tcaaaattat catcctgaat tattagataa tctttcatca    960
gcaaaatcac cacaacaaat atttggtact gcatcaaaaa cttactatcc ttcaatttca   1020
ggaatagctc cagaagatgt ttatacagtt actatcatgc cttgtaatga taaaaaatat   1080
```

```
gaagcagata ttcctttcat ggaaactaac agcttaagag atattgatgc atccttaact   1140
acaagagaat tagcaaaaat gattaaagat gcaaagatta attttgctaa tttagaagac   1200
gaacaagctg atccagcaat gggagaatac actggggctg agttatatt cggagctaca    1260 ggtggagtta tggaagcagc acttagaact gctaaggatt tcgttgaaga taaagattta   1320
actgatatag aatatacaca ataagagga ttacaaggaa taaaagaagc ggaagttgaa    1380
attgctggaa ataaactaaa cgttgctgtt ataaatggtg cttctaactt cttcgagttt   1440
atgaaatctg gaaaatgaa cgaaaaacaa tatcacttta tagaagtaat ggcttgccct    1500
ggtggatgta taaatggtgg aggtcaacct cacgtaaatg ctcttgatag agaaaatgtt   1560
gattacagaa aactaagagc atcagtatta taaaccaag ataaaaatgt tctttcaaag    1620
agaaagtcac atgataatcc agctattatt aaaatgtatg atagctactt tggaaaacca   1680
ggtgaaggac ttgctcacaa attactacac gtaaaataca caaaagataa aaatgtttca   1740
aaacatgaa                                                            1749

<210> SEQ ID NO 119
<211> LENGTH: 1749
<212> TYPE: DNA
<213> ORGANISM: Chlamydomonas reinhardtii

<400> SEQUENCE: 119
atggccaaaa caataatctt aaatggcaat gaagtgcata cagataaaga tattactatc    60
cttgagctag caagagaaaa taatgtagat atcccaacac tctgcttttt aaaggattgt   120
ggcaattttg gaaatgcgg agtctgtatg gtagaggtag aaggcaaggg ctttagagct    180
gcttgtgttg ccaaagttga agatggaatg gtaataaaca cagaatccga tgaagtaaaa   240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct   360
tcaaaaccat ttttaccaga gataaggat gctctagttg ataatagaag taaggctatt    420
gtaattgaca gatcaaaatg tgtactatgc ggtagatgcg tagctgcatg taaacagcac   480
acaagcactt gctcaattca atttattaaa aaagatggac aaagggctgt tggaactgtt   540
gatgatgttt gtcttgatga ctcaacatgc ttattatgcg gtcagtgtgt aatcgcttgt   600
cctgttgctg ctttaaaaga aaaatcccat atagaaaaag ttcaagaagc tcttaatgac   660
cctaaaaaac atgtcattgt tgcaatggct ccatcagtaa gaactgctat gggcgaatta   720
ttcaaaatgg gatatggaaa agatgtaaca ggaaaactat atactgcact tagaatgtta   780
ggctttgata agtatttga tataaacttt ggtgcagata tgactataat ggaagaagct    840
actgaacttt taggcagagt taaaaataat ggcccattcc ctatgtttac atcttgctgt   900
cctgcatggg taagattagc tcaaaattat catcctgaat tattagataa tctttcatca   960
gcaaaatcac cacaacaaat atttggtact gcatcaaaaa cttactatcc ttcaatttca  1020
ggaatagctc cagaagatgt ttatacagtt actatcatgc cttgtaatga taaaaaatat  1080
gaagcagata ttcctttcat ggaaactaac agcttaagag atattgatgc atccttaact  1140
acaagagagc ttgcaaaaat gattaaagat gcaaaaatta aatttgcaga tcttgaagat  1200
ggtgaagttg atcctgctat gggtacttac agtggtgctg agctatctt tggtgcaacc   1260 ggtggcgtta tggaagctgc aataagatca gctaaagact ttgctgaaaa taaagaactt  1320
gaaaatgttg attacactga agtaagaggc tttaaaggca taaagaggc tacagtagaa   1380 attggtggag aaaattataa cgtagctgta attaatggtg cagcaaactt agctgaattc  1440
```

```
atgaatagcg gtaaaatcct tgaaaagaac tatcatttta ttgaagtaat ggcttgccca      1500
ggcggatgtg taaatggtgg aggtcaacct cacgtaaatg ctcttgatag agaaaatgtt      1560
gattacagaa aactaagagc atcagtatta tacaaccaag ataaaaatgt tctttcaaag      1620
agaaagtcac atgataatcc agctattatt aaaatgtatg atagctactt tggaaaacca      1680
ggtgaaggac ttgctcacaa attactacac gtaaaataca caaaagataa aaatgtttca      1740
aaacatgaa                                                              1749

<210> SEQ ID NO 120
<211> LENGTH: 1722
<212> TYPE: DNA
<213> ORGANISM: Chlamydomonas reinhardtii

<400> SEQUENCE: 120
atggccaaaa caataatctt aaatggcaat gaagtgcata cagataaaga tattactatc        60
cttgagctag caagagaaaa taatgtagat atcccaacac tctgcttttt aaaggattgt       120
ggcaattttg gaaatgcgg agtctgtatg gtagaggtag aaggcaaggg ctttagagct        180
gcttgtgttg ccaaagttga agatggaatg gtaataaaca cagaatccga tgaagtaaaa       240
gaacgaatca aaaaagagt ttcaatgctt cttgataagc atgaatttaa atgtggacaa        300
tgttctagaa gagaaaattg tgaattcctt aaacttgtaa taagacaaa agcaaaagct       360 tcaaaaccat ttttaccaga agataaggat gctctagttg ataatagaag taaggctatt       420
gtaattgaca gatcaaaatg tgtactatgc ggtagatgcg tagctgcatg taaacagcac       480
acaagcactt gctcaattca atttattaaa aaagatggac aaagggctgt tggaactgtt       540
gatgatgttt gtcttgatga ctcaacatgc ttattatgcg gtcagtgtgt aatcgcttgt       600
cctgttgctg ctttaaaaga aaaatcccat atagaaaaag ttcaagaagc tcttaatgac       660
cctaaaaaac atgtcattgt tgcaatggct ccatcagtaa gaactgctat gggcgaatta       720
ttcaaaatgg gatatggaaa agatgtaaca ggaaaactat atactgcact tagaatgtta       780
ggctttgata agtatttga tataaacttt ggtgcagata tgactataat ggaagaagct       840
actgaacttt taggcagagt taaaaataat ggcccattcc ctatgtttac atcttgctgt       900
cctgcatggg taagattagc tcaaaattat catcctgaat tattagataa tctttcatca       960
gcaaaatcac cacaacaaat atttggtact gcatcaaaaa cttactatcc ttcaatttca      1020
ggaatagctc cagaagatgt ttatacagtt actatcatgc cttgtaatga taaaaaatat      1080
gaagcagata ttcctttcat ggaaactaac agcttaagag atattgatgc atccttaact      1140
acaagagagc ttgcaaaaat gattaaagat gcaaaaatta aatttgcaga tcttgaagat      1200
ggtgaagttg atcctgctat gggtacttac agtggtgctg gagctatctt tggtgcaacc      1260
ggtggcgtta tggaagctgc aataagatca gctaaagact ttgctgaaaa taagaaactt      1320
gaaaatgttg attacactga agtaagaggc tttaaaggca taaagaagc ggaagttgaa       1380 attgctggaa ataaactaaa cgttgctgtt ataaatggtg cttctaactt cttcgagttt      1440
atgaaatctg gaaaaatgaa cgaaaaacaa tatcactttta tagaagtaat ggcttgccct      1500
ggtggatgta taatggtgg aggacaacca cacgtaagtg caaggaaag agaaaaagta        1560 gatgttagaa ctgtaagagc atctgtttta tataaccaag ataaaaattt agagaagaga      1620
aaatcacata aaaatacagc attattaaat atgtactatg attatatggg agctccagga      1680
caaggaaaag ctcatgaatt attacactta aaatacaata aa                         1722
```

<210> SEQ ID NO 121
<211> LENGTH: 1725
<212> TYPE: DNA
<213> ORGANISM: Chlamydomonas reinhardtii

<400> SEQUENCE: 121

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg  agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata gcatgtcat  tgttgcaatg gctccatcag taagaactgc tatgggcgaa     720
ttattcaaaa tgggatatgg aaaagatgta acaggaaaac tatatactgc acttagaatg     780
ttaggctttg ataaagtatt tgatataaac tttggtgcag atatgactat aatggaagaa     840
gctactgaac ttttaggcag agttaaaaat aatggaccat tcccaatgtt tacttcatgt     900
tgtccggcat gggttagaca agtggaaaat tattacccag aatttttaga aaacttatca     960
tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagaagaa  aatgtataat gagggaatta aaaatataga tgcagtactt    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag aataaaaga  ggctacagta    1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725
```

<210> SEQ ID NO 122
<211> LENGTH: 1725
<212> TYPE: DNA
<213> ORGANISM: Chlamydomonas reinhardtii

<400> SEQUENCE: 122

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg  agtgtgtgca gtagaaatag aaggaaaaaa taacttagca     180
cttgcatgta taacaaaagt tgaagaaggt atggtagtaa aaacaaactc agaaaaagta     240
```

```
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtacta tgcggtagat gcgtagctgc atgtaaacag    480
cacacaagca cttgctcaat tcaatttatt aaaaagatg gacaaagggc tgttggaact     540
gttgatgatg tttgtcttga tgactcaaca tgcttattat gcggtcagtg tgtaatcgct    600
tgtcctgttg ctgctttaaa agaaaaatcc catatagaaa aagttcaaga agctcttaat    660
gaccctaaaa aacatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aattttttaga aaacttatca   960 tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagaagaa aatgtataat gagggaatta aaatataga tgcagtactt     1140 actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatgaagc agcacttaga actgctaagg atttcgttga agataaagat    1320
ttaactgata tagaatatac acaaataaga ggattacaag aataaaaga ggctacagta    1380 gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga agagaaaaa    1560 gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                   1725
```

<210> SEQ ID NO 123
<211> LENGTH: 1725
<212> TYPE: DNA
<213> ORGANISM: Chlamydomonas reinhardtii

<400> SEQUENCE: 123

```
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtaataa acacagaatc cgatgaagta    240
aaagaacgaa tcaaaaaaag agtttcaatg cttcttgata agcatgaatt taaatgtgga    300
caatgttcta gaagagaaaa ttgtgaattc cttaaacttg taataaagac aaaagcaaaa    360
gcttcaaaac cattttttacc agaagataag gatgctctag ttgataatag aagtaaggct    420
attgtaattg acagatcaaa atgtgtgcta tgcggaagat gtgaagcagc atgtaaaaca   480
aagacaggta caggagctat ttcaatttgt aagagtgaat caggaagaat agtgcaagca   540
acaggcggaa agtgctttga tgatacaaat tgtttattat gtggacaatg cgttgcagca   600
tgtccagtag gagctttaac tgaaaaaaca cacgttgata gagttaaaga agcattagaa   660
```

```
gatcctaata agcatgtaat agttgctatg gcaccatcaa tcagaacttc tatgggagag      720
ttatttaaat taggctatgg ggttgatgta actggaaaat tatatgcttc aatgagagca      780 ttaggattg ataaggtatt tgatattaac tttggggctg atatgacaat aatgaagaa        840 gcaacagagt ttattgaaag agttaaaaat aatggaccat tcccaatgtt tacttcatgt      900
tgtccggcat gggttagaca gtggaaaat tattacccag aattttaga aaacttatca        960 tcagctaaat caccacaaca aatatttggt gcagcaagca aaacatacta tcctcaaata     1020
tcaggtataa gtgctaaaga tgtatttact gttacaataa tgccttgtac agcaaagaaa     1080
tttgaggctg atagagaaga aatgtataat gagggaatta aaaatataga tgcagtactt     1140
actacaagag aattagcaaa aatgattaaa gatgcaaaga ttaattttgc taatttagaa     1200
gacgaacaag ctgatccagc aatgggagaa tacactgggg ctggagttat attcggagct     1260
acaggtggag ttatggaagc agcacttaga actgctaagg atttcgttga agataaagat     1320
ttaactgata tagaatatac acaaataaga ggattacaag gaataaaaga ggctacagta     1380
gaaattggtg agaaaattta aacgtagct gtaattaatg gtgcagcaaa cttagctgaa      1440
ttcatgaata gcggtaaaat ccttgaaaag aactatcatt ttattgaagt aatggcttgc     1500
ccaggcggat gtgtaaatgg tggaggacaa ccacacgtaa gtgcaaagga agagaaaaa      1560 gtagatgtta gaactgtaag agcatctgtt ttatataacc aagataaaaa tttagagaag     1620
agaaaatcac ataaaaatac agcattatta aatatgtact atgattatat gggagctcca     1680
ggacaaggaa aagctcatga attattacac ttaaaataca ataaa                     1725

<210> SEQ ID NO 124
<211> LENGTH: 1722
<212> TYPE: DNA
<213> ORGANISM: Chlamydomonas reinhardtii

<400> SEQUENCE: 124
atggccaaaa caataatctt aaatggcaat gaagtgcata cagataaaga tattactatc       60
cttgagctag caagagaaaa taatgtagat atcccaacac tctgcttttt aaaggattgt      120
ggcaattttg gaaaatgcgg agtctgtatg gtagaggtag aaggcaaggg ctttagagct      180
gcttgtgttg ccaaagttga agatggaatg gtagtaaaaa caaactcaga aaaagtacaa      240
gaaagagtta aaatgagagt tgctactttg cttgataagc atgaatttaa atgtggacct      300
tgtccaagaa gagaaaattg cgaattttta aagttagtta taaaaacaaa agctaaggct      360
aacaagcctt ttgtggttga agacaaatca caatacatag atattagaag taaatcaatt      420
gtaatagaca gaactaagtg tgtgctatgc ggaagatgtg aagcagcatg taaaacaaag      480
acaggtacag gagctatttc aatttgtaag agtgaatcag gaagaatagt gcaagcaaca      540
ggcggaaagt gctttgatga tacaaattgt ttattatgtg gacaatgcgt tgcagcatgt      600
ccagtaggag ctttaactga aaaaacacac gttgatagag ttaaagaagc attagaagat      660
cctaataagc atgtaatagt tgctatggca ccatcaatca gaacttctat gggagagtta      720
tttaaattag gctatggggt tgatgtaact ggaaaattat atgcttcaat gagagcatta      780
ggatttgata aggtatttga tattaacttt ggggctgata tgacaataat ggaagaagca      840
acagagttta ttgaaagagt taaaataat ggaccattcc caatgtttac ttcatgttgt      900
ccggcatggg ttagacaagt ggaaaattat acccagaat tttagaaaa cttatcatca       960 gctaaatcac cacaacaaat atttggtgca gcaagcaaaa catactatcc tcaaatatca     1020
ggtataagtg ctaaagatgt atttactgtt acaataatgc cttgtacagc aaagaaattt     1080
```

| gaggctgata gagaagaaat gtataatgag ggaattaaaa atatagatgc agtacttact | 1140 |
| acaagagaat tagcaaaaat gattaaagat gcaaagatta attttgctaa tttagaagac | 1200 |
| gaacaagctg atccagcaat gggagaatac actggggctg agttatatt cggagctaca | 1260 |
| ggtggagtta tggaagcagc acttagaact gctaaggatt tcgttgaaga taaagattta | 1320 |
| actgatatag aatatacaca ataagagga ttacaaggaa taaaagaggc tacagtagaa | 1380 |
| attggtggag aaaattataa cgtagctgta attaatggtg cagcaaactt agctgaattc | 1440 |
| atgaatagcg gtaaaatcct tgaaaagaac tatcatttta ttgaagtaat ggcttgccca | 1500 |
| ggcggatgtg taaatggtgg aggacaacca cacgtaagtg caaggaaag agaaaaagta | 1560 |
| gatgttagaa ctgtaagagc atctgtttta taaccaag ataaaaattt agagaagaga | 1620 |
| aaatcacata aaaatacagc attattaaat atgtactatg attatatggg agctccagga | 1680 |
| caaggaaaag ctcatgaatt attacactta aaatacaata aa | 1722 |

<210> SEQ ID NO 125
<211> LENGTH: 1725
<212> TYPE: DNA
<213> ORGANISM: Chlamydomonas reinhardtii

<400> SEQUENCE: 125

| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaaagt tgaagaaggt atggtagtaa aacaaactc agaaaaagta | 240 |
| caagaaaagag ttaaaatgag agttgctact ttgcttgata agcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtacta tgcggtagat gcgtagctgc atgtaaacag | 480 |
| cacacaagca cttgctcaat tcaatttatt aaaaaagatg gacaaagggc tgttggaact | 540 |
| gttgatgatg tttgtcttga tgactcaaca tgcttattat gcggtcagtg tgtaatcgct | 600 |
| tgtcctgttg ctgctttaaa agaaaaatcc catatagaaa aagttcaaga agctcttaat | 660 |
| gacccctaaaa aacatgtcat tgttgcaatg gctccatcag taagaactgc tatgggcgaa | 720 |
| ttattcaaaa tgggatatgg aaaagatgta acaggaaaac tatatactgc acttagaatg | 780 |
| ttaggctttg ataaagtatt tgatataaac tttggtgcag atatgactat aatggaagaa | 840 |
| gctactgaac ttttaggcag agttaaaaat aatggaccat tcccaatgtt tacttcatgt | 900 |
| tgtccggcat gggttagaca gtggaaaat tattacccag aatttttaga aaacttatca | 960 |
| tcagctaaat caccacaaca aatatttggt gcagcaagca aaacatacta tcctcaaata | 1020 |
| tcaggtataa gtgctaaaga tgtatttact gttacaataa tgccttgtac agcaaagaaa | 1080 |
| tttgaggctg atagaagaa aatgtataat gagggaatta aaatataga tgcagtactt | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga ggctacagta | 1380 |
| gaaattggtg gagaaaatta taacgtagct gtaattaatg gtgcagcaaa cttagctgaa | 1440 |
| ttcatgaata gcggtaaaat ccttgaaaag aactatcatt ttattgaagt aatggcttgc | 1500 |

-continued

| | |
|---|---|
| ccaggcggat gtgtaaatgg tggaggacaa ccacacgtaa gtgcaaagga aagagaaaaa | 1560 |
| gtagatgtta gaactgtaag agcatctgtt ttatataacc aagataaaaa tttagagaag | 1620 |
| agaaaatcac ataaaaatac agcattatta aatatgtact atgattatat gggagctcca | 1680 |
| ggacaaggaa aagctcatga attattacac ttaaaataca ataaa | 1725 |

<210> SEQ ID NO 126
<211> LENGTH: 1725
<212> TYPE: DNA
<213> ORGANISM: Chlamydomonas reinhardtii

<400> SEQUENCE: 126

| | |
|---|---|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaaagt tgaagaaggt atggtaataa acacagaatc cgatgaagta | 240 |
| aaagaacgaa tcaaaaaaag agtttcaatg cttcttgata agcatgaatt taaatgtgga | 300 |
| caatgttcta gaagagaaaa ttgtgaattc cttaaacttg taataaagac aaaagcaaaa | 360 |
| gcttcaaaac cattttttacc agaagataag gatgctctag ttgataatag aagtaaggct | 420 |
| attgtaattg acagatcaaa atgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag gagctttaac tgaaaaaaca cacgttgata gagttaaaga agcattagaa | 660 |
| gatcctaata agcatgtcat tgttgcaatg gctccatcag taagaactgc tatgggcgaa | 720 |
| ttattcaaaa tgggatatgg aaaagatgta acaggaaaac tatatactgc acttagaatg | 780 |
| ttaggctttg ataaagtatt tgatataaac tttggtgcag atatgactat aatgaaagaa | 840 |
| gctactgaac ttttaggcag agttaaaaat aatggaccat tcccaatgtt tacttcatgt | 900 |
| tgtccggcat gggttagaca agtggaaaat tattacccag aattttttaga aaacttatca | 960 |
| tcagctaaat caccacaaca atatttggt gcagcaagca aaacatacta tcctcaaata | 1020 |
| tcaggtataa gtgctaaaga tgtatttact gttacaataa tgccttgtac agcaaagaaa | 1080 |
| tttgaggctg atagagaaga aatgtataat gagggaatta aaaatataga tgcagtactt | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga ggctacagta | 1380 |
| gaaattggtg gagaaaatta taacgtagct gtaattaatg gtgcagcaaa cttagctgaa | 1440 |
| ttcatgaata gcggtaaaat ccttgaaaag aactatcatt ttattgaagt aatggcttgc | 1500 |
| ccaggcggat gtgtaaatgg tggaggacaa ccacacgtaa gtgcaaagga aagagaaaaa | 1560 |
| gtagatgtta gaactgtaag agcatctgtt ttatataacc aagataaaaa tttagagaag | 1620 |
| agaaaatcac ataaaaatac agcattatta aatatgtact atgattatat gggagctcca | 1680 |
| ggacaaggaa aagctcatga attattacac ttaaaataca ataaa | 1725 |

<210> SEQ ID NO 127
<211> LENGTH: 1722
<212> TYPE: DNA
<213> ORGANISM: Chlamydomonas reinhardtii

<400> SEQUENCE: 127

```
atggccaaaa caataatctt aaatggcaat gaagtgcata cagataaaga tattactatc    60
cttgagctag caagagaaaa taatgtagat atcccaacac tctgctttt aaaggattgt    120
ggcaattttg gaaaatgcgg agtctgtatg gtagaggtag aaggcaaggg ctttagagct    180
gcttgtgttg ccaagttga agatggaatg gtagtaaaaa caaactcaga aaaagtacaa    240
gaaagagtta aatgagagt tgctactttg cttgataagc atgaatttaa atgtggacct    300
tgtccaagaa gagaaaattg cgaattttta agttagtta taaaaacaaa agctaaggct    360
aacaagcctt ttgtggttga agacaaatca caatacatag atattagaag taaatcaatt    420
gtaatagaca gaactaagtg tgtgctatgc ggaagatgtg aagcagcatg taaaacaaag    480
acaggtacag gagctatttc aatttgtaag agtgaatcag aagaatagt gcaagcaaca    540
ggcggaaagt gctttgatga tacaaattgt ttattatgtg acaatgcgt tgcagcatgt    600
ccagtaggag ctttaactga aaaaacacac gttgatagag ttaaagaagc attagaagat    660
cctaataagc atgtcattgt tgcaatggct ccatcagtaa aactgctat gggcgaatta    720
ttcaaaatgg gatatggaaa agatgtaaca ggaaaactat atactgcact agaatgtta    780
ggctttgata agtatttga tataaacttt ggtgcagata tgactataat ggaagaagct    840
actgaacttt taggcagagt taaaaataat ggaccattcc caatgtttac ttcatgttgt    900
ccggcatggg ttagacaagt ggaaaattat acccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gaagaaat gtataatgag ggaattaaaa atatagatgc agtacttact   1140
acaagagaat tagcaaaaat gattaaagat gcaaagatta attttgctaa tttagaagac   1200
gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaaagaggc tacagtagaa   1380
attggtggag aaaattataa cgtagctgta attaatggtg cagcaaactt agctgaattc   1440
atgaatagcg gtaaaatcct tgaaaagaac tatcattta ttgaagtaat ggcttgccca   1500
ggcggatgtg taaatggtgg aggacaacca cacgtaagtg caaaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722
```

<210> SEQ ID NO 128
<211> LENGTH: 1725
<212> TYPE: DNA
<213> ORGANISM: Chlamydomonas reinhardtii

<400> SEQUENCE: 128

```
atggcaataa acatagtaat tgatgaaaaa actattcaag tacaggaaaa tactacagtt    60
atacaagctg ccctagcaaa tgggatagat ataccaagtt tatgctatct taatgagtgt   120
ggtaatgttg aaagtgtgg agtgtgtgca gtagaaatag aaggaaaaaa taacttagca   180
cttgcatgta taacaaagt tgaagaaggt atggtaataa acacagaatc cgatgaagta   240
aaagaacgaa tcaaaaaaag agtttcaatg cttcttgata gcatgaatt taaatgtgga   300
caatgttcta aagagaaaa ttgtgaattc cttaaacttg taataaagac aaaagcaaaa   360
```

```
gcttcaaaac cattttacc agaagataag gatgctctag ttgataatag aagtaaggct        420
attgtaattg acagatcaaa atgtgtacta tgcggtagat gcgtagctgc atgtaaacag        480
cacacaagca cttgctcaat tcaatttatt aaaaaagatg acaaaggggc tgttggaact        540
gttgatgatg tttgtcttga tgactcaaca tgcttattat gcggtcagtg tgtaatcgct        600
tgtcctgttg ctgctttaaa agaaaaatcc catatagaaa aagttcaaga agctcttaat        660
gaccctaaaa aacatgtaat agttgctatg gcaccatcaa tcagaacttc tatgggagag        720
ttatttaaat taggctatgg ggttgatgta actggaaaat tatatgcttc aatgagagca        780
ttaggatttg ataaggtatt tgatattaac tttggggctg atatgacaat aatggaagaa        840
gcaacagagt ttattgaaag agttaaaaat aatggaccat tcccaatgtt tacttcatgt        900
tgtccggcat gggttagaca agtggaaaat tattacccag aattttaga aaacttatca        960 tcagctaaat caccacaaca aatatttggt gcagcaagca aaacatacta tcctcaaata       1020
tcaggtataa gtgctaaaga tgtatttact gttacaataa tgccttgtac agcaaagaaa       1080
tttgaggctg atagaagaa atgtataat gagggaatta aaatataga tgcagtactt       1140 actacaagag aattagcaaa aatgattaaa gatgcaaaga ttaattttgc taatttagaa       1200
gacgaacaag ctgatccagc aatgggagaa tacactgggg ctggagttat attcggagct       1260
acaggtggag ttatggaagc agcacttaga actgctaagg atttcgttga agataaagat       1320
ttaactgata tagaatatac acaaataaga ggattacaag gaataaaaga ggctacagta       1380
gaaattggtg gagaaaatta taacgtagct gtaattaatg gtgcagcaaa cttagctgaa       1440
ttcatgaata gcggtaaaat ccttgaaaag aactatcatt ttattgaagt aatggcttgc       1500
ccaggcggat gtgtaaatgg tggaggacaa ccacacgtaa gtgcaaagga agagaaaaa       1560 gtagatgtta gaactgtaag agcatctgtt ttatataacc aagataaaaa tttagagaag       1620
agaaaatcac ataaaaatac agcattatta aatatgtact atgattatat gggagctcca       1680
ggacaaggaa aagctcatga attattacac ttaaaataca ataaa                     1725
```

<210> SEQ ID NO 129
<211> LENGTH: 1722
<212> TYPE: DNA
<213> ORGANISM: Chlamydomonas reinhardtii

<400> SEQUENCE: 129

```
atggccaaaa caataatctt aaatggcaat gaagtgcata cagataaaga tattactatc         60
cttgagctag caagagaaaa taatgtagat atcccaacac tctgcttttt aaaggattgt        120 ggcaatttg gaaatgcgg agtctgtatg gtagaggtag aaggcaaggg ctttagagct        180
gcttgtgttg ccaaagttga agatggaatg gtagtaaaaa caaactcaga aaaagtacaa        240
gaaagagtta aaatgagagt tgctactttg cttgataagc atgaatttaa atgtggacct        300
tgtccaagaa gagaaaattg cgaattttta aagttagtta taaaaacaaa agctaaggct        360
aacaagcctt ttgtggttga agacaaatca caatacatag atattagaag taaatcaatt        420
gtaatagaca gaactaagtg tgtactatgc ggtagatgcg tagctgcatg taaacagcac        480
acaagcactt gctcaattca atttattaaa aaagatggac aaagggctgt tggaactgtt        540
gatgatgttt gtcttgatga ctcaacatgc ttattatgcg gtcagtgtgt aatcgcttgt        600
cctgttgctg ctttaaaaga aaaatcccat atagaaaaag ttcaagaagc tcttaatgac        660
cctaaaaaac atgtaatagt tgctatggca ccatcaatca gaacttctat gggagagtta        720
tttaaattag gctatggggt tgatgtaact ggaaaattat atgcttcaat gagagcatta        780
```

```
ggatttgata aggtatttga tattaactttt ggggctgata tgacaataat ggaagaagca    840
acagagttta ttgaaagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaaagatta attttgctaa tttagaagac   1200
gaacaagctg atccagcaat gggagaatac actggggctg gagttatatt cggagctaca   1260
ggtggagtta tggaagcagc acttagaact gctaaggatt tcgttgaaga taaagattta   1320
actgatatag aatatacaca aataagagga ttacaaggaa taaaagaggc tacagtagaa   1380
attggtggag aaaattataa cgtagctgta attaatggtg cagcaaactt agctgaattc   1440
atgaatagcg gtaaaatcct tgaaaagaac tatcatttta ttgaagtaat ggcttgccca   1500
ggcggatgtg taaatggtgg aggacaacca cacgtaagtg caaaggaaag agaaaaagta   1560
gatgttagaa ctgtaagagc atctgtttta tataaccaag ataaaaattt agagaagaga   1620
aaatcacata aaaatacagc attattaaat atgtactatg attatatggg agctccagga   1680
caaggaaaag ctcatgaatt attacactta aaatacaata aa                      1722
```

<210> SEQ ID NO 130
<211> LENGTH: 1722
<212> TYPE: DNA
<213> ORGANISM: Chlamydomonas reinhardtii

<400> SEQUENCE: 130

```
atggccaaaa caataatctt aaatggcaat gaagtgcata cagataaaga tattactatc     60
cttgagctag caagagaaaa taatgtagat atcccaacac tctgcttttt aaaggattgt    120
ggcaattttg gaaaatgcgg agtctgtatg gtagaggtag aaggcaaggg ctttagagct    180
gcttgtgttg ccaaagttga agatggaatg gtaataaaca cagaatccga tgaagtaaaa    240
gaacgaatca aaaaagagt ttcaatgctt cttgataagc atgaatttaa atgtggacaa    300
tgttctagaa gagaaaattg tgaattcctt aaacttgtaa taaagacaaa agcaaaagct    360
tcaaaaccat ttttaccaga agataaggat gctctagttg ataatagaag taaggctatt    420
gtaattgaca gatcaaaatg tgtgctatgc ggaagatgtg aagcagcatg taaaacaaag    480
acaggtacag gagctatttc aatttgtaag agtgaatcag gaagaatagt gcaagcaaca    540
ggcggaaagt gctttgatga tacaaattgt ttattatgtg acaatgcgt tgcagcatgt    600 ccagtaggag ctttaactga aaaacacac gttgatagag ttaaagaagc attagaagat    660
cctaataagc atgtaatagt tgctatggca ccatcaatca gaacttctat gggagagtta    720
tttaaattag gctatggggt tgatgtaact ggaaaattat atgcttcaat gagagcatta    780
ggatttgata aggtatttga tattaactttt ggggctgata tgacaataat ggaagaagca    840
acagagttta ttgaaagagt taaaaataat ggaccattcc caatgtttac ttcatgttgt    900
ccggcatggg ttagacaagt ggaaaattat tacccagaat ttttagaaaa cttatcatca    960
gctaaatcac cacaacaaat atttggtgca gcaagcaaaa catactatcc tcaaatatca   1020
ggtataagtg ctaaagatgt atttactgtt acaataatgc cttgtacagc aaagaaattt   1080
gaggctgata gagaagaaat gtataatgag ggaattaaaa atatagatgc agtacttact   1140
acaagagaat tagcaaaaat gattaaagat gcaaagatta attttgctaa tttagaagac   1200
```

```
gaacaagctg atccagcaat gggagaatac actggggctg agttatatt cggagctaca    1260 ggtggagtta tggaagcagc acttagaact gctaaggatt tcgttgaaga taaagattta    1320
actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggacaacca cacgtaagtg caaggaaag agaaaaagta    1560 gatgttagaa ctgtaagagc atctgtttta tataaccaag ataaaaattt agagaagaga    1620
aaatcacata aaaatacagc attattaaat atgtactatg attatatggg agctccagga    1680
caaggaaaag ctcatgaatt attacactta aaatacaata aa                       1722
```

<210> SEQ ID NO 131
<211> LENGTH: 1725
<212> TYPE: DNA
<213> ORGANISM: Chlamydomonas reinhardtii

<400> SEQUENCE: 131

```
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaaata aggaaaaaaa taacttagca     180
cttgcatgta taacaaaagt tgaagaaggt atggtaataa acacagaatc cgatgaagta     240
aaagaacgaa tcaaaaaaag agtttcaatg cttcttgata agcatgaatt taaatgtgga     300
caatgttcta aagagaaaaa ttgtgaattc cttaaacttg taataaagac aaaagcaaaa     360
gcttcaaaac cattttttacc agaagataag gatgctctag ttgataatag aagtaaggct     420
attgtaattg acagatcaaa atgtgtacta tgcggtagat gcgtagctgc atgtaaacag     480
cacacaagca cttgctcaat tcaatttatt aaaaaagatg acaaaggggc tgttggaact     540
gttgatgatg tttgtcttga tgactcaaca tgcttattat gcggtcagtg tgtaatcgct     600
tgtcctgttg ctgctttaaa agaaaaatcc catatagaaa aagttcaaga agctcttaat     660 gacccctaaaa aacatgtcat tgttgcaatg gctccatcag taagaactgc tatgggcgaa     720
ttattcaaaa tgggatatgg aaaagatgta acaggaaaac tatatactgc acttagaatg     780
ttaggctttg ataaagtatt tgatataaac tttggtgcag atatgactat aatggaagaa     840
gctactgaac ttttaggcag agttaaaaat aatggaccat tcccaatgtt tacttcatgt     900
tgtccggcat gggttagaca gtggaaaaat tattacccag aattttaga aaacttatca     960 tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagaagaa atgtataat gagggaatta aaaatataga tgcagtactt    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag gaataaaaga ggctacagta    1380
gaaattggtg gagaaaatta aacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga agagaaaaa    1560 gtagatgtta gaactgtaag agcatctgtt ttatataacc aagataaaaa tttagagaag    1620
```

```
agaaaatcac ataaaaatac agcattatta aatatgtact atgattatat gggagctcca    1680
ggacaaggaa aagctcatga attattacac ttaaaataca ataaa                    1725

<210> SEQ ID NO 132
<211> LENGTH: 1722
<212> TYPE: DNA
<213> ORGANISM: Chlamydomonas reinhardtii

<400> SEQUENCE: 132
atggccaaaa caataatctt aaatggcaat gaagtgcata cagataaaga tattactatc      60
cttgagctag caagagaaaa taatgtagat atcccaacac tctgcttttt aaaggattgt     120
ggcaattttg gaaaatgcgg agtctgtatg gtagaggtag aaggcaaggg ctttagagct     180
gcttgtgttg ccaaagttga agatggaatg gtagtaaaaa caaactcaga aaaagtacaa     240
gaaagagtta aaatgagagt tgctactttg cttgataagc atgaatttaa atgtggacct     300
tgtccaagaa gagaaaattg cgaatttttt aagttagtta taaaaacaaa agctaaggct     360
aacaagcctt ttgtggttga agacaaatca caatacatag atattagaag taaatcaatt     420
gtaatagaca gaactaagtg tgtactatgc ggtagatgcg tagctgcatg taaacagcac     480
acaagcactt gctcaattca atttattaaa aaagatggac aaagggctgt tggaactgtt     540
gatgatgttt gtcttgatga ctcaacatgc ttattatgcg gtcagtgtgt aatcgcttgt     600
cctgttgctg cttttaaaga aaaatcccat atagaaaaag ttcaagaagc tcttaatgac     660
cctaaaaaac atgtcattgt tgcaatggct ccatcagtaa gaactgctat gggcgaatta     720
ttcaaaatgg gatatggaaa agatgtaaca ggaaaactat atactgcact tagaatgtta     780
ggctttgata agtatttga tataaacttt ggtgcagata tgactataat ggaagaagct     840
actgaacttt taggcagagt taaaaataat ggaccattcc caatgtttac ttcatgttgt     900
ccggcatggg ttagacaagt ggaaaattat tacccagaat ttttagaaaa cttatcatca     960
gctaaatcac cacaacaaat atttggtgca gcaagcaaaa catactatcc tcaaatatca    1020
ggtataagtg ctaagatgt atttactgtt acaataatgc cttgtacagc aaagaaattt    1080
gaggctgata gagaagaaat gtataatgag ggaattaaaa atatagatgc agtacttact    1140
acaagagaat tagcaaaaat gattaaagat gcaagatta attttgctaa tttagaagac    1200
gaacaagctg atccagcaat gggagaatac actggggctg gagttatatt cggagctaca    1260
ggtggagtta tggaagcagc acttagaact gctaaggatt tcgttgaaga taaagattta    1320
actgatatag aatatacaca aataagagga ttacaaggaa taaaagaggc tacagtagaa    1380
attggtggag aaaattataa cgtagctgta attaatggtg cagcaaactt agctgaattc    1440
atgaatagcg gtaaaatcct tgaaaagaac tatcatttta ttgaagtaat ggcttgccca    1500
ggcggatgtg taaatggtgg aggacaacca cacgtaagtg caaaggaaag agaaaaagta    1560
gatgttagaa ctgtaagagc atctgtttta taaccaag ataaaaattt agagaagaga    1620
aaatcacata aaaatacagc attattaaat atgtactatg attatatggg agctccagga    1680
caaggaaaag ctcatgaatt attacactta aaatacaata aa                       1722

<210> SEQ ID NO 133
<211> LENGTH: 1722
<212> TYPE: DNA
<213> ORGANISM: Chlamydomonas reinhardtii

<400> SEQUENCE: 133
atggccaaaa caataatctt aaatggcaat gaagtgcata cagataaaga tattactatc      60
```

```
cttgagctag caagagaaaa taatgtagat atcccaacac tctgctttt aaaggattgt      120 ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaagagt tcaatgctt cttgataagc atgaatttaa atgtggacaa       300
tgttctagaa gagaaaattg tgaattcctt aaacttgtaa taagacaaa agcaaaagct       360 tcaaaaccat ttttaccaga agataaggat gctctagttg ataatagaag taaggctatt      420
gtaattgaca gatcaaaatg tgtgctatgc ggaagatgtg aagcagcatg taaaacaaag      480
acaggtacag gagctatttc aatttgtaag agtgaatcag aagaatagt gcaagcaaca       540 ggcggaaagt gctttgatga tacaaattgt ttattatgtg gacaatgcgt tgcagcatgt      600
ccagtaggag ctttaactga aaaaacacac gttgatagag ttaaagaagc attagaagat      660
cctaataagc atgtcattgt tgcaatggct ccatcagtaa gaactgctat gggcgaatta      720
ttcaaaatgg gatatggaaa agatgtaaca ggaaaactat atactgcact agaatgtta      780 ggctttgata agtatttga tataaacttt ggtgcagata tgactataat ggaagaagct      840
actgaacttt taggcagagt taaaaataat ggaccattcc caatgttac ttcatgttgt      900 ccggcatggg ttagacaagt ggaaaattat tacccagaat ttttagaaaa cttatcatca      960
gctaaatcac cacaacaaat atttggtgca gcaagcaaaa catactatcc tcaaatatca     1020
ggtataagtg ctaaagatgt atttactgtt acaataatgc cttgtacagc aaagaaattt     1080
gaggctgata gagaagaaat gtataatgag ggaattaaaa atatagatgc agtacttact     1140
acaagagaat tagcaaaaat gattaaagat gcaaagatta attttgctaa tttagaagac     1200
gaacaagctg atccagcaat gggagaatac actgggcctg gagttatatt cggagctaca     1260
ggtggagtta tggaagcagc acttagaact gctaaggatt tcgttgaaga taaagattta     1320
actgatatag aatatacaca aataagagga ttacaaggaa taaaagaggc tacagtagaa     1380
attggtggag aaaattataa cgtagctgta attaatggtg cagcaaactt agctgaattc     1440
atgaatagcg gtaaaatcct tgaaaagaac tatcatttta ttgaagtaat ggcttgccca     1500
ggcggatgtg taaatggtgg aggacaacca cacgtaagtg caaaggaaag agaaaaagta     1560
gatgttagaa ctgtaagagc atctgtttta tataaccaag ataaaaattt agagaagaga     1620
aaatcacata aaaatacagc attattaaat atgtactatg attatatggg agctccagga     1680
caaggaaaag ctcatgaatt attacactta aaatacaata aa                         1722

<210> SEQ ID NO 134
<211> LENGTH: 1722
<212> TYPE: DNA
<213> ORGANISM: Chlamydomonas reinhardtii

<400> SEQUENCE: 134
atggccaaaa caataatctt aaatggcaat gaagtgcata cagataaaga tattactatc        60
cttgagctag caagagaaaa taatgtagat atcccaacac tctgctttt aaaggattgt      120 ggcaattttg gaaaatgcgg agtctgtatg gtagaggtag aaggcaaggg ctttagagct      180
gcttgtgttg ccaaagttga agatggaatg gtaataaaca cagaatccga tgaagtaaaa      240
gaacgaatca aaaaagagt tcaatgctt cttgataagc atgaatttaa atgtggacaa       300
tgttctagaa gagaaaattg tgaattcctt aaacttgtaa taagacaaa agcaaaagct       360 tcaaaaccat ttttaccaga agataaggat gctctagttg ataatagaag taaggctatt      420
gtaattgaca gatcaaaatg tgtactatgc ggtagatgcg tagctgcatg taaacagcac      480
```

```
acaagcactt gctcaattca atttattaaa aaagatggac aaagggctgt tggaactgtt       540
gatgatgttt gtcttgatga ctcaacatgc ttattatgcg gtcagtgtgt aatcgcttgt       600
cctgttgctg ctttaaaaga aaaatcccat atagaaaaag ttcaagaagc tcttaatgac       660
cctaaaaaac atgtaatagt tgctatggca ccatcaatca gaacttctat gggagagtta       720
tttaaattag ctatggggt tgatgtaact ggaaaattat atgcttcaat gagagcatta        780
ggatttgata aggtatttga tattaacttt ggggctgata tgacaataat ggaagaagca       840
acagagttta ttgaaagagt taaaaataat ggaccattcc caatgtttac ttcatgttgt       900
ccggcatggg ttagacaagt ggaaaattat tacccagaat ttttagaaaa cttatcatca       960
gctaaatcac cacaacaaat atttggtgca gcaagcaaaa catactatcc tcaaatatca      1020
ggtataagtg ctaaagatgt atttactgtt acaataatgc cttgtacagc aaagaaattt      1080
gaggctgata gagaagaaat gtataatgag ggaattaaaa atatagatgc agtacttact      1140
acaagagaat tagcaaaaat gattaaagat gcaaagatta ttttgctaa tttagaagac       1200 gaacaagctg atccagcaat gggagaatac actggggctg gagttatatt cggagctaca      1260
ggtggagtta tggaagcagc acttagaact gctaaggatt tcgttgaaga taaagattta      1320
actgatatag aatatacaca aataagagga ttacaaggaa taaaagaggc tacagtagaa      1380
attggtggag aaaattataa cgtagctgta attaatggtg cagcaaactt agctgaattc      1440
atgaatagcg gtaaaatcct tgaaaagaac tatcatttta ttgaagtaat ggcttgccca      1500
ggcggatgtg taaatggtgg aggacaacca cacgtaagtg caaggaaag agaaaaagta       1560 gatgttagaa ctgtaagagc atctgtttta tataaccaag ataaaaattt agagaagaga      1620
aaatcacata aaaatacagc attattaaat atgtactatg attatatggg agctccagga      1680
caaggaaaag ctcatgaatt attacactta aaatacaata aa                         1722

<210> SEQ ID NO 135
<211> LENGTH: 1752
<212> TYPE: DNA
<213> ORGANISM: Chlamydomonas reinhardtii

<400> SEQUENCE: 135
atggcaataa acatagtaat tgatgaaaaa actattcaag tacaggaaaa tactacagtt        60
atacaagctg ccctagcaaa tgggatagat ataccaagtt tatgctatct taatgagtgt       120
ggtaatgttg aaagtgtgg agtgtgtgca gtagaaatag aaggaaaaaa taacttagca       180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggaccat tcccaatgtt tacttcatgt      900
```

```
tgtccggcat gggttagaca agtggaaaat tattacccag aattttttaga aaacttatca    960
tcagctaaat caccacaaca atatttggt gcagcaagca aaacatacta tcctcaaata     1020
tcaggtataa gtgctaaaga tgtatttact gttacaataa tgccttgtac agcaaagaaa    1080
tttgaggctg atagagaaga aatgtataat gagggaatta aaaatataga tgcagtactt    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
acaggtggag ttatggaagc agcacttaga actgctaagg atttcgttga agataaagat    1320
ttaactgata tagaatatac acaaataaga ggattacaag gaataaaaga ggctacagta    1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat cacaaaaga taaaaatgtt    1740
tcaaaacatg aa                                                        1752

<210> SEQ ID NO 136
<211> LENGTH: 1725
<212> TYPE: DNA
<213> ORGANISM: Chlamydomonas reinhardtii

<400> SEQUENCE: 136
atggcaataa acatagtaat tgatgaaaaa actattcaag tacaggaaaa tactacagtt    60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata gcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag agctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aattttttaga aaacttatca    960
tcagctaaat caccacaaca atatttggt gcagcaagca aaacatacta tcctcaaata     1020
tcaggtataa gtgctaaaga tgtatttact gttacaataa tgccttgtac agcaaagaaa    1080
tttgaggctg atagagaaga aatgtataat gagggaatta aaaatataga tgcagtactt    1140
actacaagag aattagcaaa aatgattaaa gatgcaaaga ttaattttgc taatttagaa    1200
gacgaacaag ctgatccagc aatgggagaa tacactgggg ctggagttat attcggagct    1260
```

```
acaggtggag ttatggaagc agcacttaga actgctaagg atttcgttga agataaagat    1320
ttaactgata tagaatatac acaaataaga ggattacaag gaataaaaga agcggaagtt    1380
gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725

<210> SEQ ID NO 137
<211> LENGTH: 1725
<212> TYPE: DNA
<213> ORGANISM: Chlamydomonas reinhardtii

<400> SEQUENCE: 137
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780 ttaggattttg ataaggtatt tgatattaac tttggggctg atatgacaat aatggaagaa     840
gcaacagagt ttattgaaag agttaaaaat aatggaccat tcccaatgtt tacttcatgt     900
tgtccggcat gggttagaca agtggaaaat tattacccag aattttttaga aaacttatca     960 tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagagaaga aatgtataat gagggaatta aaaatataga tgcagtactt    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag gcataaaaga ggctacagta    1380
gaaattggtg gagaaaatta taacgtagct gtaattaatg gtgcagcaaa cttagctgaa    1440
ttcatgaata gcggtaaaat ccttgaaaag aactatcatt ttattgaagt aatggcttgc    1500
ccaggcggat gtgtaaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
```
ggacaaggaa aagctcatga attattacac ttaaaataca ataaa 1725

<210> SEQ ID NO 138
<211> LENGTH: 1725
<212> TYPE: DNA
<213> ORGANISM: Chlamydomonas reinhardtii

<400> SEQUENCE: 138

| | | | | | |
|---|---|---|---|---|---|
| atggcaataa | acatagtaat | tgatgaaaaa | actattcaag | tacaggaaaa | tactacagtt | 60 |
| atacaagctg | ccctagcaaa | tgggatagat | ataccaagtt | tatgctatct | taatgagtgt | 120 |
| ggtaatgttg | gaaagtgtgg | agtgtgtgca | gtagaaatag | aaggaaaaaa | taacttagca | 180 |
| cttgcatgta | taacaaaagt | tgaagaaggt | atggtagtaa | aaacaaactc | agaaaaagta | 240 |
| caagaaagag | ttaaaatgag | agttgctact | ttgcttgata | agcatgaatt | taaatgtgga | 300 |
| ccttgtccaa | gaagagaaaa | ttgcgaattt | ttaaagttag | ttataaaaac | aaaagctaag | 360 |
| gctaacaagc | cttttgtggt | tgaagacaaa | tcacaataca | tagatattag | aagtaaatca | 420 |
| attgtaatag | acagaactaa | gtgtgtgcta | tgcggaagat | gtgaagcagc | atgtaaaaca | 480 |
| aagacaggta | caggagctat | ttcaatttgt | aagagtgaat | caggaagaat | agtgcaagca | 540 |
| acaggcggaa | agtgctttga | tgatacaaat | tgtttattat | gtggacaatg | cgttgcagca | 600 |
| tgtccagtag | gagctttaac | tgaaaaaaca | cacgttgata | gagttaaaga | agcattagaa | 660 |
| gatcctaata | agcatgtaat | agttgctatg | gcaccatcaa | tcagaacttc | tatgggagag | 720 |
| ttatttaaat | taggctatgg | ggttgatgta | actggaaaat | tatatgcttc | aatgagagca | 780 |
| ttaggatttg | ataaggtatt | tgatattaac | tttggggctg | atatgacaat | aatggaagaa | 840 |
| gcaacagagt | ttattgaaag | agttaaaaat | aatggcccat | tccctatgtt | tacatcttgc | 900 |
| tgtcctgcat | gggtaagatt | agctcaaaat | tatcatcctg | aattattaga | taatctttca | 960 |
| tcagcaaaat | caccacaaca | aatatttggt | actgcatcaa | aaacttacta | tccttcaatt | 1020 |
| tcaggaatag | ctccagaaga | tgtttataca | gttactatca | tgccttgtaa | tgataaaaaa | 1080 |
| tatgaagcag | atattccttt | catggaaact | aacagcttaa | gagatattga | tgcatcctta | 1140 |
| actacaagag | aattagcaaa | aatgattaaa | gatgcaaaga | ttaattttgc | taatttagaa | 1200 |
| gacgaacaag | ctgatccagc | aatgggagaa | tacactgggg | ctggagttat | attcggagct | 1260 |
| acaggtggag | ttatggaagc | agcacttaga | actgctaagg | atttcgttga | agataaagat | 1320 |
| ttaactgata | tagaatatac | acaaataaga | ggattacaag | gaataaaaga | ggctacagta | 1380 |
| gaaattggtg | gagaaaatta | taacgtagct | gtaattaatg | gtgcagcaaa | cttagctgaa | 1440 |
| ttcatgaata | gcggtaaaat | ccttgaaaag | aactatcatt | ttattgaagt | aatggcttgc | 1500 |
| ccaggcggat | gtgtaaatgg | tggaggacaa | ccacacgtaa | gtgcaaagga | aagagaaaaa | 1560 |
| gtagatgtta | gaactgtaag | agcatctgtt | ttatataacc | aagataaaaa | tttagagaag | 1620 |
| agaaaatcac | ataaaaatac | agcattatta | aatatgtact | atgattatat | gggagctcca | 1680 |
| ggacaaggaa | aagctcatga | attattacac | ttaaaataca | ataaa | | 1725 |

<210> SEQ ID NO 139
<211> LENGTH: 1752
<212> TYPE: DNA
<213> ORGANISM: Chlamydomonas reinhardtii

<400> SEQUENCE: 139

| | | | | | |
|---|---|---|---|---|---|
| atggcaataa | acatagtaat | tgatgaaaaa | actattcaag | tacaggaaaa | tactacagtt | 60 |
| atacaagctg | ccctagcaaa | tgggatagat | ataccaagtt | tatgctatct | taatgagtgt | 120 |

```
ggtaatgttg aaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc ttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aattttaga aaacttatca    960
tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagagaaga aatgtataat gagggaatta aaaatataga tgcagtactt   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag aataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752

<210> SEQ ID NO 140
<211> LENGTH: 1752
<212> TYPE: DNA
<213> ORGANISM: Chlamydomonas reinhardtii

<400> SEQUENCE: 140
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg aaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc ttttgtggt tgaagacaaa tcacaataca tagatattag aagtaaatca    420
attgtaatag acagaactaa gtgtgtgcta tgcggaagat gtgaagcagc atgtaaaaca    480
```

```
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggaccat tcccaatgtt tacttcatgt    900
tgtccggcat gggttagaca agtggaaaat tattacccag aattttttaga aaacttatca    960 tcagctaaat caccacaaca aatatttggt gcagcaagca aaacatacta tcctcaaata   1020
tcaggtataa gtgctaaaga tgtatttact gttacaataa tgccttgtac agcaaagaaa   1080
tttgaggctg atagaagaa aatgtataat gagggaatta aaaatataga tgcagtactt    1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatgaagc tgcaataaga tcagctaaag actttgctga aaataaagaa   1320
cttgaaaatg ttgattacac tgaagtaaga ggctttaaag cataaaaga ggctacagta    1380 gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                       1752

<210> SEQ ID NO 141
<211> LENGTH: 1752
<212> TYPE: DNA
<213> ORGANISM: Chlamydomonas reinhardtii

<400> SEQUENCE: 141
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata gcatgaatt taaatgtgga    300 ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatggaagaa    840
```

```
gcaacagagt ttattgaaag agttaaaaat aatggcccat tccctatgtt tacatcttgc      900
tgtcctgcat gggtaagatt agctcaaaat tatcatcctg aattattaga taatctttca      960
tcagcaaaat caccacaaca aatatttggt actgcatcaa aaacttacta tccttcaatt     1020
tcaggaatag ctccagaaga tgtttataca gttactatca tgccttgtaa tgataaaaaa     1080
tatgaagcag atattccttt catggaaact aacagcttaa gagatattga tgcatcctta     1140
actacaagag aattagcaaa aatgattaaa gatgcaaaga ttaattttgc taatttagaa     1200
gacgaacaag ctgatccagc aatgggagaa tacactgggg ctggagttat attcggagct     1260
acaggtggag ttatggaagc agcacttaga actgctaagg atttcgttga agataaagat     1320
ttaactgata tagaatatac acaaataaga ggattacaag gaataaaaga ggctacagta     1380
gaaattggtg gagaaaatta taacgtagct gtaattaatg gtgcagcaaa cttagctgaa     1440
ttcatgaata gcggtaaaat ccttgaaaag aactatcatt ttattgaagt aatggccttgc    1500 ccaggcggat gtgtaaatgg tggaggtcaa cctcacgtaa atgctcttga tagagaaaat     1560
gttgattaca gaaaactaag agcatcagta ttatacaacc aagataaaaa tgttctttca     1620
aagagaaagt cacatgataa tccagctatt attaaaatgt atgatagcta ctttggaaaa     1680
ccaggtgaag gacttgctca caattacta cacgtaaaat acacaaaaga taaaaatgtt      1740
tcaaaacatg aa                                                        1752

<210> SEQ ID NO 142
<211> LENGTH: 1725
<212> TYPE: DNA
<213> ORGANISM: Chlamydomonas reinhardtii

<400> SEQUENCE: 142
atggcaataa acatagtaat tgatgaaaaa actattcaag tacaggaaaa tactacagtt       60
atacaagctg ccctagcaaa tgggatagat ataccaagtt tatgctatct taatgagtgt      120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta      240
caagaaagag ttaaaatgag agttgctact ttgcttgata agcatgaatt taaatgtgga      300
ccttgtccaa gaagagaaaa ttgcgaattt ttaaagttag ttataaaaac aaaagctaag      360
gctaacaagc cttttgtggt tgaagacaaa tcacaataca tagatattag aagtaaatca      420
attgtaatag acagaactaa gtgtgtgcta tgcggaagat gtgaagcagc atgtaaaaca      480
aagacaggta caggagctat ttcaatttgt aagagtgaat caggaagaat agtgcaagca      540
acaggcggaa agtgctttga tgatacaaat tgtttattat gtggacaatg cgttgcagca      600
tgtccagtag gagctttaac tgaaaaaaca cacgttgata gagttaaaga agcattagaa      660
gatcctaata agcatgtaat agttgctatg gcaccatcaa tcagaacttc tatgggagag      720
ttatttaaat taggctatgg ggttgatgta actggaaaat tatatgcttc aatgagagca      780
ttaggatttg ataaggtatt tgatattaac tttggggctg atatgacaat aatggaagaa      840
gcaacagagt ttattgaaag agttaaaaat aatggaccat tcccaatgtt tacttcatgt      900
tgtccggcat gggttagaca agtggaaaat tattacccag aatttttaga aaacttatca      960
tcagctaaat caccacaaca aatatttggt gcagcaagca aacatactta tcctcaaata     1020
tcaggtataa gtgctaaaga tgtatttact gttacaataa tgccttgtac agcaaagaaa     1080
tttgaggctg atagaagaa aatgtataat gagggaatta aaaatataga tgcagtactt     1140
actacaagag agcttgcaaa aatgattaaa gatgcaaaaa ttaaatttgc agatcttgaa     1200
```

| | |
|---|---|
| gatggtgaag ttgatcctgc tatgggtact tacagtggtg ctggagctat ctttggtgca | 1260 |
| accggtggcg ttatggaagc tgcaataaga tcagctaaag actttgctga aaataaagaa | 1320 |
| cttgaaaatg ttgattacac tgaagtaaga ggctttaaag cataaaaga agcggaagtt | 1380 |
| gaaattgctg aaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggacaa ccacacgtaa gtgcaaagga aagagaaaaa | 1560 |
| gtagatgtta gaactgtaag agcatctgtt ttatataacc aagataaaaa tttagagaag | 1620 |
| agaaaatcac ataaaaatac agcattatta aatatgtact atgattatat gggagctcca | 1680 |
| ggacaaggaa aagctcatga attattacac ttaaaataca ataaa | 1725 |

<210> SEQ ID NO 143
<211> LENGTH: 1725
<212> TYPE: DNA
<213> ORGANISM: Chlamydomonas reinhardtii

<400> SEQUENCE: 143

| | |
|---|---|
| atggcaataa acatagtaat tgatgaaaaa actattcaag tacaggaaaa tactacagtt | 60 |
| atacaagctg ccctagcaaa tgggatagat ataccaagtt tatgctatct taatgagtgt | 120 |
| ggtaatgttg aaagtgtgg agtgtgtgca gtagaaatag aaggaaaaaa taacttagca | 180 |
| cttgcatgta taacaaagt tgaagaaggt atggtagtaa aaacaaactc agaaaaagta | 240 |
| caagaaagag ttaaaatgag agttgctact ttgcttgata gcatgaatt taaatgtgga | 300 |
| ccttgtccaa gaagagaaaa ttgcgaattt ttaaagttag ttataaaaac aaaagctaag | 360 |
| gctaacaagc cttttgtggt tgaagacaaa tcacaataca tagatattag aagtaaatca | 420 |
| attgtaatag acagaactaa gtgtgtgcta tgcggaagat gtgaagcagc atgtaaaaca | 480 |
| aagacaggta caggagctat ttcaatttgt aagagtgaat caggaagaat agtgcaagca | 540 |
| acaggcggaa agtgctttga tgatacaaat tgtttattat gtggacaatg cgttgcagca | 600 |
| tgtccagtag agctttaac tgaaaaaaca cacgttgata gagttaaaga agcattagaa | 660 |
| gatcctaata agcatgtaat agttgctatg gcaccatcaa tcagaacttc tatgggagag | 720 |
| ttatttaaat taggctatgg ggttgatgta actggaaaat tatatgcttc aatgagagca | 780 |
| ttaggatttg ataaggtatt tgatattaac tttggggctg atatgacaat aatggaagaa | 840 |
| gcaacagagt ttattgaaag agttaaaaat aatggcccat tccctatgtt tacatcttgc | 900 |
| tgtcctgcat gggtaagatt agctcaaaat tatcatcctg aattattaga taatcttca | 960 |
| tcagcaaaat caccacaaca aatatttggt actgcatcaa aaacttacta tccttcaatt | 1020 |
| tcaggaatag ctccagaaga tgtttataca gttactatca tgccttgtaa tgataaaaaa | 1080 |
| tatgaagcag atattccttt catggaaact aacagcttaa gagatattga tgcatcctta | 1140 |
| actacaagag aattagcaaa aatgattaaa gatgcaaaga ttaattttgc taatttagaa | 1200 |
| gacgaacaag ctgatccagc aatgggagaa tacactgggg ctggagttat attcggagct | 1260 |
| acaggtggag ttatggaagc agcacttaga actgctaagg atttcgttga agataaagat | 1320 |
| ttaactgata tagaatatac acaaataaga ggattacaag gaataaaaga agcggaagtt | 1380 |
| gaaattgctg aaataaact aaacgttgct gttataaatg gtgcttctaa cttcttcgag | 1440 |
| tttatgaaat ctggaaaaat gaacgaaaaa caatatcact ttatagaagt aatggcttgc | 1500 |
| cctggtggat gtataaatgg tggaggacaa ccacacgtaa gtgcaaagga aagagaaaaa | 1560 |
| gtagatgtta gaactgtaag agcatctgtt ttatataacc aagataaaaa tttagagaag | 1620 |

```
agaaaatcac ataaaaatac agcattatta aatatgtact atgattatat gggagctcca    1680
ggacaaggaa aagctcatga attattacac ttaaaataca ataaa                    1725

<210> SEQ ID NO 144
<211> LENGTH: 1725
<212> TYPE: DNA
<213> ORGANISM: Chlamydomonas reinhardtii

<400> SEQUENCE: 144
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg aaagtgtgg agtgtgtgca gtagaaatag aaggaaaaaa taacttagca      180
cttgcatgta taacaaaagt tgaagaaggt atggtagtaa aaacaaactc agaaaaagta     240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatgggaagaa   840 gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatggaagc tgcaataaga tcagctaaag actttgctga aaataaagaa   1320
cttgaaaatg ttgattacac tgaagtaaga ggctttaaag gcataaaaga ggctacagta   1380
gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggacaa ccacacgtaa gtgcaaagga aagagaaaaa   1560
gtagatgtta gaactgtaag agcatctgtt ttatataacc aagataaaaa tttagagaag   1620
agaaaatcac ataaaaatac agcattatta aatatgtact atgattatat gggagctcca   1680
ggacaaggaa aagctcatga attattacac ttaaaataca ataaa                    1725

<210> SEQ ID NO 145
<211> LENGTH: 1752
<212> TYPE: DNA
<213> ORGANISM: Chlamydomonas reinhardtii

<400> SEQUENCE: 145
atggcaataa acatagtaat tgatgaaaaa actattcaag tacaggaaaa tactacagtt      60
```

```
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
attgtaatag acagaactaa gtgtgtgcta tgcggaagat gtgaagcagc atgtaaaaca     480
aagacaggta caggagctat ttcaatttgt aagagtgaat caggaagaat agtgcaagca     540
acaggcggaa agtgctttga tgatacaaat tgtttattat gtggacaatg cgttgcagca     600
tgtccagtag gagctttaac tgaaaaaaca cacgttgata gagttaaaga agcattagaa     660
gatcctaata agcatgtaat agttgctatg gcaccatcaa tcagaacttc tatgggagag     720
ttatttaaat taggctatgg ggttgatgta actggaaaat tatatgcttc aatgagagca     780
ttaggatttg ataaggtatt tgatattaac tttggggctg atatgacaat aatggaagaa     840
gcaacagagt ttattgaaag agttaaaaat aatggaccat tcccaatgtt tacttcatgt     900
tgtccggcat gggttagaca agtggaaaat tattacccag aattttttaga aaacttatca     960 tcagctaaat caccacaaca aatatttggt gcagcaagca aaacatacta tcctcaaata    1020
tcaggtataa gtgctaaaga tgtatttact gttacaataa tgccttgtac agcaaagaaa    1080
tttgaggctg atagaagaa atgtataat gagggaatta aaaatataga tgcagtactt    1140
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcggaagtt    1380 gaaattgctg gaaataaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggtcaa cctcacgtaa atgctcttga tagagaaaat    1560
gttgattaca gaaaactaag agcatcagta ttatacaacc aagataaaaa tgttctttca    1620
aagagaaagt cacatgataa tccagctatt attaaaatgt atgatagcta ctttggaaaa    1680
ccaggtgaag gacttgctca caaattacta cacgtaaaat acacaaaaga taaaaatgtt    1740
tcaaaacatg aa                                                        1752

<210> SEQ ID NO 146
<211> LENGTH: 1752
<212> TYPE: DNA
<213> ORGANISM: Chlamydomonas reinhardtii

<400> SEQUENCE: 146
atggcaataa acatagtaat tgatgaaaaa actattcaag tacaggaaaa tactacagtt      60
atacaagctg ccctagcaaa tgggatagat ataccaagtt tatgctatct taatgagtgt     120
ggtaatgttg gaaagtgtgg agtgtgtgca gtagaaatag aaggaaaaaa taacttagca     180
cttgcatgta taacaaaagt tgaagaaggt atggtagtaa aaacaaactc agaaaaagta     240
caagaaagag ttaaaatgag agttgctact ttgcttgata agcatgaatt taaatgtgga     300
ccttgtccaa gaagagaaaa ttgcgaattt ttaaagttag ttataaaaac aaaagctaag     360
gctaacaagc cttttgtggt tgaagacaaa tcacaataca tagatattag aagtaaatca     420
```

```
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
ttaggatttg ataaggtatt tgatattaac tttggggctg atatgacaat aatgaaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag aattagcaaa aatgattaaa gatgcaaaga ttaattttgc taatttagaa   1200
gacgaacaag ctgatccagc aatgggagaa tacactgggg ctggagttat attcggagct   1260
acaggtggag ttatggaagc agcacttaga actgctaagg atttcgttga agataaagat   1320
ttaactgata tagaatatac acaaataaga ggattacaag gaataaaaga agcggaagtt   1380
gaaattgctg gaaataaact aaacgttgct gttataaatg gtgcttctaa cttcttcgag   1440
tttatgaaat ctggaaaaat gaacgaaaaa caatatcact ttatagaagt aatggcttgc   1500
cctggtggat gtataaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat cacaaaaaga taaaaatgtt   1740
tcaaaacatg aa                                                       1752

<210> SEQ ID NO 147
<211> LENGTH: 1752
<212> TYPE: DNA
<213> ORGANISM: Chlamydomonas reinhardtii

<400> SEQUENCE: 147
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg gaaagtgtgg agtgtgtgca gtagaaatag aaggaaaaaa taacttagca    180
cttgcatgta taacaaagt tgaagaaggt atggtagtaa aaacaaactc agaaaaagta    240
caagaaagag ttaaaatgag agttgctact ttgcttgata agcatgaatt taaatgtgga    300
ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag gagctttaac tgaaaaaaca cacgttgata gagttaaaga agcattagaa    660
gatcctaata agcatgtaat agttgctatg gcaccatcaa tcagaacttc tatgggagag    720
ttatttaaat taggctatgg ggttgatgta actggaaaat tatatgcttc aatgagagca    780
```

```
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
actacaagag agcttgcaaa aatgattaaa gatgcaaaaa ttaaatttgc agatcttgaa   1200
gatggtgaag ttgatcctgc tatgggtact tacagtggtg ctggagctat ctttggtgca   1260
accggtggcg ttatgaaagc tgcaataaga tcagctaaag actttgctga aaataaagaa   1320
cttgaaaatg ttgattacac tgaagtaaga ggctttaaag cataaaagaa ggctacagta   1380
gaaattggtg gagaaaatta taacgtagct gtaattaatg gtgcagcaaa cttagctgaa   1440
ttcatgaata gcggtaaaat ccttgaaaag aactatcatt ttattgaagt aatggcttgc   1500
ccaggcggat gtgtaaatgg tggaggtcaa cctcacgtaa atgctcttga tagagaaaat   1560
gttgattaca gaaaactaag agcatcagta ttatacaacc aagataaaaa tgttctttca   1620
aagagaaagt cacatgataa tccagctatt attaaaatgt atgatagcta ctttggaaaa   1680
ccaggtgaag gacttgctca caaattacta cacgtaaaat acacaaaaga taaaaatgtt   1740
tcaaaacatg aa                                                        1752

<210> SEQ ID NO 148
<211> LENGTH: 1725
<212> TYPE: DNA
<213> ORGANISM: Chlamydomonas reinhardtii

<400> SEQUENCE: 148
atggcaataa acatagtaat tgatgaaaaa actattcaag tacaggaaaa tactacagtt     60
atacaagctg ccctagcaaa tgggatagat ataccaagtt tatgctatct taatgagtgt    120
ggtaatgttg aaagtgtgg agtgtgtgca gtagaaatag aaggaaaaaa taacttagca    180
cttgcatgta taacaaaagt tgaagaaggt atggtagtaa aaacaaactc agaaaaagta    240
caagaaagag ttaaaatgag agttgctact ttgcttgata gcatgaatt taaatgtgga    300 ccttgtccaa gaagagaaaa ttgcgaattt ttaaagttag ttataaaaac aaaagctaag    360
gctaacaagc cttttgtggt tgaagacaaa tcacaataca tagatattag aagtaaatca    420
attgtaatag acagaactaa gtgtgtgcta tgcggaagat gtgaagcagc atgtaaaaca    480
aagacaggta caggagctat ttcaatttgt aagagtgaat caggaagaat agtgcaagca    540
acaggcggaa agtgctttga tgatacaaat tgtttattat gtggacaatg cgttgcagca    600
tgtccagtag agctttaac tgaaaaaaca cacgttgata gagttaaaga agcattagaa    660
gatcctaata gcatgtaat agttgctatg gcaccatcaa tcagaacttc tatgggagag    720 ttattaaat taggctatgg ggttgatgta actggaaaat tatatgcttc aatgagagca    780
ttaggatttg ataaggtatt tgatattaac tttggggctg atatgacaat aatggaagaa    840
gcaacagagt ttattgaaag agttaaaaat aatggcccat tccctatgtt tacatcttgc    900
tgtcctgcat gggtaagatt agctcaaaat tatcatcctg aattattaga taatctttca    960
tcagcaaaat caccacaaca aatatttggt actgcatcaa aaacttacta tccttcaatt   1020
tcaggaatag ctccagaaga tgtttataca gttactatca tgccttgtaa tgataaaaaa   1080
tatgaagcag atattccttt catggaaact aacagcttaa gagatattga tgcatcctta   1140
```

```
actacaagag agcttgcaaa aatgattaaa gatgcaaaaa ttaaatttgc agatcttgaa    1200
gatggtgaag ttgatcctgc tatgggtact tacagtggtg ctggagctat ctttggtgca    1260
accggtggcg ttatggaagc tgcaataaga tcagctaaag actttgctga aaataaagaa    1320
cttgaaaatg ttgattacac tgaagtaaga ggctttaaag cataaaaga agcggaagtt    1380 gaaattgctg aaataaaact aaacgttgct gttataaatg gtgcttctaa cttcttcgag    1440
tttatgaaat ctggaaaaat gaacgaaaaa caatatcact ttatagaagt aatggcttgc    1500
cctggtggat gtataaatgg tggaggacaa ccacacgtaa gtgcaaagga aagagaaaaa    1560
gtagatgtta gaactgtaag agcatctgtt ttatataacc aagataaaaa tttagagaag    1620
agaaaatcac ataaaaatac agcattatta aatatgtact atgattatat gggagctcca    1680
ggacaaggaa aagctcatga attattacac ttaaaataca ataaa                    1725
```

<210> SEQ ID NO 149
<211> LENGTH: 575
<212> TYPE: PRT
<213> ORGANISM: Chlamydomonas reinhardtii

<400> SEQUENCE: 149

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270
```

```
Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 150
<211> LENGTH: 583
<212> TYPE: PRT
<213> ORGANISM: Chlamydomonas reinhardtii

<400> SEQUENCE: 150

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80
```

-continued

Glu Arg Ile Lys Lys Arg Val Ser Met Leu Leu Asp Lys His Glu Phe
            85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
        130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
        210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
                260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
        370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
        450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

```
Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
        530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 151
<211> LENGTH: 574
<212> TYPE: PRT
<213> ORGANISM: Chlamydomonas reinhardtii

<400> SEQUENCE: 151

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300
```

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
            370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 152
<211> LENGTH: 584
<212> TYPE: PRT
<213> ORGANISM: Chlamydomonas reinhardtii

<400> SEQUENCE: 152

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
            50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
            85                  90                  95

Phe Lys Cys Gly Pro Cys Pro Arg Arg Glu Asn Cys Glu Phe Leu Lys
            100                 105                 110

```
Leu Val Ile Lys Thr Lys Ala Lys Ala Asn Lys Pro Phe Val Val Glu
            115                 120                 125
Asp Lys Ser Gln Tyr Ile Asp Ile Arg Ser Lys Ser Ile Val Ile Asp
        130                 135                 140
Arg Thr Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
                165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
        195                 200                 205
Lys Thr His Val Asp Arg Val Lys Glu Ala Leu Glu Asp Pro Asn Lys
210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
        275                 280                 285
Lys Asn Asn Gly Pro Phe Pro Met Phe Thr Ser Cys Cys Pro Ala Trp
290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
                325                 330                 335
Tyr Pro Ser Ile Ser Gly Ile Ala Pro Glu Asp Val Tyr Thr Val Thr
            340                 345                 350
Ile Met Pro Cys Asn Asp Lys Lys Tyr Glu Ala Asp Ile Pro Phe Met
        355                 360                 365
Glu Thr Asn Ser Leu Arg Asp Ile Asp Ala Ser Leu Thr Thr Arg Glu
        370                 375                 380
Leu Ala Lys Met Ile Lys Asp Ala Lys Ile Lys Phe Ala Asp Leu Glu
385                 390                 395                 400
Asp Gly Glu Val Asp Pro Ala Met Gly Thr Tyr Ser Gly Ala Gly Ala
                405                 410                 415
Ile Phe Gly Ala Thr Gly Gly Val Met Glu Ala Ala Ile Arg Ser Ala
            420                 425                 430
Lys Asp Phe Ala Glu Asn Lys Glu Leu Glu Asn Val Asp Tyr Thr Glu
        435                 440                 445
Val Arg Gly Phe Lys Gly Ile Lys Glu Ala Glu Val Glu Ile Ala Gly
        450                 455                 460
Asn Lys Leu Asn Val Ala Val Ile Asn Gly Ala Ser Asn Phe Phe Glu
465                 470                 475                 480
Phe Met Lys Ser Gly Lys Met Asn Glu Lys Gln Tyr His Phe Ile Glu
                485                 490                 495
Val Met Ala Cys Pro Gly Gly Cys Ile Asn Gly Gly Gln Pro His
            500                 505                 510
Val Asn Ala Leu Asp Arg Glu Asn Val Asp Tyr Arg Lys Leu Arg Ala
        515                 520                 525
Ser Val Leu Tyr Asn Gln Asp Lys Asn Val Leu Ser Lys Arg Lys Ser
```

```
                        530                 535                 540
His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 153
<211> LENGTH: 574
<212> TYPE: PRT
<213> ORGANISM: Chlamydomonas reinhardtii

<400> SEQUENCE: 153

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
```

```
                    325                 330                 335
Pro Gln Ile Ser Gly Ile Ser Ala Lys Asp Val Phe Thr Val Thr Ile
                340                 345                 350
Met Pro Cys Thr Ala Lys Lys Phe Glu Ala Asp Arg Glu Glu Met Tyr
                355                 360                 365
Asn Glu Gly Ile Lys Asn Ile Asp Ala Val Leu Thr Thr Arg Glu Leu
                370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
                420                 425                 430
Asp Phe Val Glu Asp Lys Asp Leu Thr Asp Ile Glu Tyr Thr Gln Ile
                435                 440                 445
Arg Gly Leu Gln Gly Ile Lys Glu Ala Glu Val Glu Ile Ala Gly Asn
                450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
Met Ala Cys Pro Gly Gly Cys Ile Asn Gly Gly Gly Gln Pro His Val
                500                 505                 510
Ser Ala Lys Glu Arg Glu Lys Val Asp Val Arg Thr Val Arg Ala Ser
                515                 520                 525
Val Leu Tyr Asn Gln Asp Lys Asn Leu Glu Lys Arg Lys Ser His Lys
                530                 535                 540
Asn Thr Ala Leu Leu Asn Met Tyr Tyr Asp Tyr Met Gly Ala Pro Gly
545                 550                 555                 560
Gln Gly Lys Ala His Glu Leu Leu His Leu Lys Tyr Asn Lys
                565                 570

<210> SEQ ID NO 154
<211> LENGTH: 575
<212> TYPE: PRT
<213> ORGANISM: Chlamydomonas reinhardtii

<400> SEQUENCE: 154

Met Ala Ile Asn Ile Val Ile Asp Glu Lys Thr Ile Gln Val Gln Glu
1               5                   10                  15
Asn Thr Thr Val Ile Gln Ala Ala Leu Ala Asn Gly Ile Asp Ile Pro
                20                  25                  30
Ser Leu Cys Tyr Leu Asn Glu Cys Gly Asn Val Gly Lys Cys Gly Val
                35                  40                  45
Cys Ala Val Glu Ile Glu Gly Lys Asn Asn Leu Ala Leu Ala Cys Ile
                50                  55                  60
Thr Lys Val Glu Glu Gly Met Val Val Lys Thr Asn Ser Glu Lys Val
65                  70                  75                  80
Gln Glu Arg Val Lys Met Arg Val Ala Thr Leu Leu Asp Lys His Glu
                85                  90                  95
Phe Lys Cys Gly Pro Cys Pro Arg Arg Glu Asn Cys Glu Phe Leu Lys
                100                 105                 110
Leu Val Ile Lys Thr Lys Ala Lys Ala Asn Lys Pro Phe Val Val Glu
                115                 120                 125
Asp Lys Ser Gln Tyr Ile Asp Ile Arg Ser Lys Ser Ile Val Ile Asp
```

-continued

```
            130                 135                 140
Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                    165                 170                 175

Ile Val Gln Ala Thr Gly Gly Lys Cys Phe Asp Asp Thr Asn Cys Leu
                    180                 185                 190

Leu Cys Gly Gln Cys Val Ala Ala Cys Pro Val Gly Ala Leu Thr Glu
                    195                 200                 205

Lys Thr His Val Asp Arg Val Lys Glu Ala Leu Glu Asp Pro Asn Lys
                    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                    245                 250                 255

Ser Met Arg Ala Leu Gly Phe Asp Lys Val Phe Asp Ile Asn Phe Gly
                    260                 265                 270

Ala Asp Met Thr Ile Met Glu Glu Ala Thr Glu Phe Ile Glu Arg Val
                    275                 280                 285

Lys Asn Asn Gly Pro Phe Pro Met Phe Thr Ser Cys Cys Pro Ala Trp
                    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                    325                 330                 335

Tyr Pro Gln Ile Ser Gly Ile Ser Ala Lys Asp Val Phe Thr Val Thr
                    340                 345                 350

Ile Met Pro Cys Thr Ala Lys Lys Phe Glu Ala Asp Arg Glu Glu Met
                    355                 360                 365

Tyr Asn Glu Gly Ile Lys Asn Ile Asp Ala Val Leu Thr Thr Arg Glu
                    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                    405                 410                 415

Ile Phe Gly Ala Thr Gly Gly Val Met Glu Ala Ala Leu Arg Thr Ala
                    420                 425                 430

Lys Asp Phe Val Glu Asp Lys Asp Leu Thr Asp Ile Glu Tyr Thr Gln
                    435                 440                 445

Ile Arg Gly Leu Gln Gly Ile Lys Glu Ala Glu Val Glu Ile Ala Gly
                    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                    485                 490                 495

Val Met Ala Cys Pro Gly Gly Cys Ile Asn Gly Gly Gly Gln Pro His
                    500                 505                 510

Val Ser Ala Lys Glu Arg Glu Lys Val Asp Val Arg Thr Val Arg Ala
                    515                 520                 525

Ser Val Leu Tyr Asn Gln Asp Lys Asn Leu Glu Lys Arg Lys Ser His
                    530                 535                 540

Lys Asn Thr Ala Leu Leu Asn Met Tyr Tyr Asp Tyr Met Gly Ala Pro
545                 550                 555                 560
```

```
Gly Gln Gly Lys Ala His Glu Leu Leu His Leu Lys Tyr Asn Lys
            565                 570                 575

<210> SEQ ID NO 155
<211> LENGTH: 583
<212> TYPE: PRT
<213> ORGANISM: Chlamydomonas reinhardtii

<400> SEQUENCE: 155

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365
```

-continued

Asn Glu Gly Ile Lys Asn Ile Asp Ala Val Leu Thr Thr Arg Glu Leu
            370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
                500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 156
<211> LENGTH: 584
<212> TYPE: PRT
<213> ORGANISM: Chlamydomonas reinhardtii

<400> SEQUENCE: 156

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
            130                 135                 140

Arg Thr Lys Cys Val Leu Cys Gly Arg Cys Glu Ala Ala Cys Lys Thr
145                 150                 155                 160

-continued

Lys Thr Gly Thr Gly Ala Ile Ser Ile Cys Lys Ser Glu Ser Gly Arg
             165                 170                 175

Ile Val Gln Ala Thr Gly Gly Lys Cys Phe Asp Thr Asn Cys Leu
         180                 185                 190

Leu Cys Gly Gln Cys Val Ala Ala Cys Pro Val Gly Ala Leu Thr Glu
         195                 200                 205

Lys Thr His Val Asp Arg Val Lys Glu Ala Leu Glu Asp Pro Asn Lys
         210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
             245                 250                 255

Ser Met Arg Ala Leu Gly Phe Asp Lys Val Phe Asp Ile Asn Phe Gly
         260                 265                 270

Ala Asp Met Thr Ile Met Glu Glu Ala Thr Glu Phe Ile Glu Arg Val
         275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
             325                 330                 335

Tyr Pro Gln Ile Ser Gly Ile Ser Ala Lys Asp Val Phe Thr Val Thr
         340                 345                 350

Ile Met Pro Cys Thr Ala Lys Lys Phe Glu Ala Asp Arg Glu Glu Met
         355                 360                 365

Tyr Asn Glu Gly Ile Lys Asn Ile Asp Ala Val Leu Thr Thr Arg Glu
         370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
             405                 410                 415

Ile Phe Gly Ala Thr Gly Gly Val Met Glu Ala Ala Leu Arg Thr Ala
         420                 425                 430

Lys Asp Phe Val Glu Asp Lys Asp Leu Thr Asp Ile Glu Tyr Thr Gln
         435                 440                 445

Ile Arg Gly Leu Gln Gly Ile Lys Glu Ala Glu Val Glu Ile Ala Gly
         450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
             485                 490                 495

Val Met Ala Cys Pro Gly Gly Cys Ile Asn Gly Gly Gly Gln Pro His
         500                 505                 510

Val Asn Ala Leu Asp Arg Glu Asn Val Asp Tyr Arg Lys Leu Arg Ala
         515                 520                 525

Ser Val Leu Tyr Asn Gln Asp Lys Asn Val Leu Ser Arg Lys Ser
         530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
             565                 570                 575

Asp Lys Asn Val Ser Lys His Glu
             580

-continued

```
<210> SEQ ID NO 157
<211> LENGTH: 583
<212> TYPE: PRT
<213> ORGANISM: Chlamydomonas reinhardtii

<400> SEQUENCE: 157

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
    370                 375                 380
```

```
Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
            405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
            565                 570                 575

Lys Asn Val Ser Lys His Glu
            580

<210> SEQ ID NO 158
<211> LENGTH: 584
<212> TYPE: PRT
<213> ORGANISM: Chlamydomonas reinhardtii

<400> SEQUENCE: 158

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
            85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
            130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
            165                 170                 175
```

```
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
            195                 200                 205
Lys Thr His Val Asp Arg Val Lys Glu Ala Leu Glu Asp Pro Asn Lys
            210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
            245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
            275                 280                 285
Lys Asn Asn Gly Pro Phe Pro Met Phe Thr Ser Cys Cys Pro Ala Trp
            290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
            325                 330                 335
Tyr Pro Ser Ile Ser Gly Ile Ala Pro Glu Asp Val Tyr Thr Val Thr
            340                 345                 350
Ile Met Pro Cys Asn Asp Lys Lys Tyr Glu Ala Asp Ile Pro Phe Met
            355                 360                 365
Glu Thr Asn Ser Leu Arg Asp Ile Asp Ala Ser Leu Thr Thr Arg Glu
            370                 375                 380
Leu Ala Lys Met Ile Lys Asp Ala Lys Ile Asn Phe Ala Asn Leu Glu
385                 390                 395                 400
Asp Glu Gln Ala Asp Pro Ala Met Gly Glu Tyr Thr Gly Ala Gly Val
            405                 410                 415
Ile Phe Gly Ala Thr Gly Gly Val Met Glu Ala Ala Leu Arg Thr Ala
            420                 425                 430
Lys Asp Phe Val Glu Asp Lys Asp Leu Thr Asp Ile Glu Tyr Thr Gln
            435                 440                 445
Ile Arg Gly Leu Gln Gly Ile Lys Glu Ala Glu Val Glu Ile Ala Gly
            450                 455                 460
Asn Lys Leu Asn Val Ala Val Ile Asn Gly Ala Ser Asn Phe Phe Glu
465                 470                 475                 480
Phe Met Lys Ser Gly Lys Met Asn Glu Lys Gln Tyr His Phe Ile Glu
            485                 490                 495
Val Met Ala Cys Pro Gly Gly Cys Ile Asn Gly Gly Gly Gln Pro His
            500                 505                 510
Val Asn Ala Leu Asp Arg Glu Asn Val Asp Tyr Arg Lys Leu Arg Ala
            515                 520                 525
Ser Val Leu Tyr Asn Gln Asp Lys Asn Val Leu Ser Lys Arg Lys Ser
            530                 535                 540
His Asp Asn Pro Ala Ile Ile Lys Met Tyr Asp Ser Tyr Phe Gly Lys
545                 550                 555                 560
Pro Gly Glu Gly Leu Ala His Lys Leu Leu His Val Lys Tyr Thr Lys
            565                 570                 575
Asp Lys Asn Val Ser Lys His Glu
            580
```

<210> SEQ ID NO 159
<211> LENGTH: 575
<212> TYPE: PRT
<213> ORGANISM: Chlamydomonas reinhardtii

<400> SEQUENCE: 159

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
```

```
                385                 390                 395                 400
Asp Gly Glu Val Asp Pro Ala Met Gly Thr Tyr Ser Gly Ala Gly Ala
                    405                 410                 415

Ile Phe Gly Ala Thr Gly Gly Val Met Glu Ala Ala Ile Arg Ser Ala
                420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Val Glu Ile Ala Gly
        450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
        530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 160
<211> LENGTH: 575
<212> TYPE: PRT
<213> ORGANISM: Chlamydomonas reinhardtii

<400> SEQUENCE: 160

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
```

```
            195                 200                 205
Lys Ser His Ile Glu Lys Val Gln Glu Ala Leu Asn Asp Pro Lys Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 161
<211> LENGTH: 584
<212> TYPE: PRT
<213> ORGANISM: Chlamydomonas reinhardtii

<400> SEQUENCE: 161

Met Ala Ile Asn Ile Val Ile Asp Glu Lys Thr Ile Gln Val Gln Glu
```

-continued

```
1               5               10              15
Asn Thr Thr Val Ile Gln Ala Ala Leu Ala Asn Gly Ile Asp Ile Pro
                20              25              30

Ser Leu Cys Tyr Leu Asn Glu Cys Gly Asn Val Gly Lys Cys Gly Val
                35              40              45

Cys Ala Val Glu Ile Glu Gly Lys Asn Asn Leu Ala Leu Ala Cys Ile
50              55              60

Thr Lys Val Glu Glu Gly Met Val Val Lys Thr Asn Ser Glu Lys Val
65              70              75              80

Gln Glu Arg Val Lys Met Arg Val Ala Thr Leu Leu Asp Lys His Glu
                85              90              95

Phe Lys Cys Gly Pro Cys Pro Arg Arg Glu Asn Cys Glu Phe Leu Lys
                100             105             110

Leu Val Ile Lys Thr Lys Ala Lys Ala Asn Lys Pro Phe Val Val Glu
                115             120             125

Asp Lys Ser Gln Tyr Ile Asp Ile Arg Ser Lys Ser Ile Val Ile Asp
                130             135             140

Arg Thr Lys Cys Val Leu Cys Gly Arg Cys Glu Ala Ala Cys Lys Thr
145             150             155             160

Lys Thr Gly Thr Gly Ala Ile Ser Ile Cys Lys Ser Glu Ser Gly Arg
                165             170             175

Ile Val Gln Ala Thr Gly Gly Lys Cys Phe Asp Asp Thr Asn Cys Leu
                180             185             190

Leu Cys Gly Gln Cys Val Ala Ala Cys Pro Val Gly Ala Leu Thr Glu
                195             200             205

Lys Thr His Val Asp Arg Val Lys Glu Ala Leu Glu Asp Pro Asn Lys
                210             215             220

His Val Ile Val Ala Met Ala Pro Ser Val Arg Thr Ala Met Gly Glu
225             230             235             240

Leu Phe Lys Met Gly Tyr Gly Lys Asp Val Thr Gly Lys Leu Tyr Thr
                245             250             255

Ala Leu Arg Met Leu Gly Phe Asp Lys Val Phe Asp Ile Asn Phe Gly
                260             265             270

Ala Asp Met Thr Ile Met Glu Glu Ala Thr Glu Leu Leu Gly Arg Val
                275             280             285

Lys Asn Asn Gly Pro Phe Pro Met Phe Thr Ser Cys Cys Pro Ala Trp
                290             295             300

Val Arg Leu Ala Gln Asn Tyr His Pro Glu Leu Leu Asp Asn Leu Ser
305             310             315             320

Ser Ala Lys Ser Pro Gln Gln Ile Phe Gly Thr Ala Ser Lys Thr Tyr
                325             330             335

Tyr Pro Ser Ile Ser Gly Ile Ala Pro Glu Asp Val Tyr Thr Val Thr
                340             345             350

Ile Met Pro Cys Asn Asp Lys Lys Tyr Glu Ala Asp Ile Pro Phe Met
                355             360             365

Glu Thr Asn Ser Leu Arg Asp Ile Asp Ala Ser Leu Thr Thr Arg Glu
                370             375             380

Leu Ala Lys Met Ile Lys Asp Ala Lys Ile Lys Phe Ala Asp Leu Glu
385             390             395             400

Asp Gly Glu Val Asp Pro Ala Met Gly Thr Tyr Ser Gly Ala Gly Ala
                405             410             415

Ile Phe Gly Ala Thr Gly Gly Val Met Glu Ala Ala Ile Arg Ser Ala
                420             425             430
```

```
Lys Asp Phe Ala Glu Asn Lys Glu Leu Glu Asn Val Asp Tyr Thr Glu
        435                 440                 445

Val Arg Gly Phe Lys Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580
```

<210> SEQ ID NO 162
<211> LENGTH: 584
<212> TYPE: PRT
<213> ORGANISM: Chlamydomonas reinhardtii

<400> SEQUENCE: 162

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220
```

```
His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
            245                 250                 255

Ser Met Arg Ala Leu Gly Phe Asp Lys Val Phe Asp Ile Asn Phe Gly
        260                 265                 270

Ala Asp Met Thr Ile Met Glu Glu Ala Thr Glu Phe Ile Glu Arg Val
    275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
        340                 345                 350

Ile Met Pro Cys Asn Asp Lys Lys Tyr Glu Ala Asp Ile Pro Phe Met
    355                 360                 365

Glu Thr Asn Ser Leu Arg Asp Ile Asp Ala Ser Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
            405                 410                 415

Ile Phe Gly Ala Thr Gly Gly Val Met Glu Ala Ala Ile Arg Ser Ala
        420                 425                 430

Lys Asp Phe Ala Glu Asn Lys Glu Leu Glu Asn Val Asp Tyr Thr Glu
    435                 440                 445

Val Arg Gly Phe Lys Gly Ile Lys Glu Ala Glu Val Glu Ile Ala Gly
450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
            485                 490                 495

Val Met Ala Cys Pro Gly Gly Cys Ile Asn Gly Gly Gly Gln Pro His
        500                 505                 510

Val Asn Ala Leu Asp Arg Glu Asn Val Asp Tyr Arg Lys Leu Arg Ala
    515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 163
<211> LENGTH: 584
<212> TYPE: PRT
<213> ORGANISM: Chlamydomonas reinhardtii

<400> SEQUENCE: 163

Met Ala Ile Asn Ile Val Ile Asp Glu Lys Thr Ile Gln Val Gln Glu
1               5                   10                  15
```

```
Asn Thr Thr Val Ile Gln Ala Leu Ala Asn Gly Ile Asp Ile Pro
            20                  25                  30
Ser Leu Cys Tyr Leu Asn Glu Cys Gly Asn Val Gly Lys Cys Gly Val
            35                  40                  45
Cys Ala Val Glu Ile Glu Gly Lys Asn Asn Leu Ala Leu Ala Cys Ile
50                  55                  60
Thr Lys Val Glu Glu Gly Met Val Ile Asn Thr Glu Ser Asp Glu Val
65                  70                  75                  80
Lys Glu Arg Ile Lys Lys Arg Val Ser Met Leu Leu Asp Lys His Glu
                85                  90                  95
Phe Lys Cys Gly Gln Cys Ser Arg Arg Glu Asn Cys Glu Phe Leu Lys
            100                 105                 110
Leu Val Ile Lys Thr Lys Ala Lys Ala Ser Lys Pro Phe Leu Pro Glu
            115                 120                 125
Asp Lys Asp Ala Leu Val Asp Asn Arg Ser Lys Ala Ile Val Ile Asp
130                 135                 140
Arg Ser Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
            165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
            195                 200                 205
Lys Thr His Val Asp Arg Val Lys Glu Ala Leu Glu Asp Pro Asn Lys
            210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
            245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
            275                 280                 285
Lys Asn Asn Gly Pro Phe Pro Met Phe Thr Ser Cys Cys Pro Ala Trp
290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
            325                 330                 335
Tyr Pro Ser Ile Ser Gly Ile Ala Pro Glu Asp Val Tyr Thr Val Thr
            340                 345                 350
Ile Met Pro Cys Asn Asp Lys Lys Tyr Glu Ala Asp Ile Pro Phe Met
            355                 360                 365
Glu Thr Asn Ser Leu Arg Asp Ile Asp Ala Ser Leu Thr Thr Arg Glu
            370                 375                 380
Leu Ala Lys Met Ile Lys Asp Ala Lys Ile Lys Phe Ala Asp Leu Glu
385                 390                 395                 400
Asp Gly Glu Val Asp Pro Ala Met Gly Thr Tyr Ser Gly Ala Gly Ala
                405                 410                 415
Ile Phe Gly Ala Thr Gly Gly Val Met Glu Ala Ala Ile Arg Ser Ala
            420                 425                 430
Lys Asp Phe Ala Glu Asn Lys Glu Leu Glu Asn Val Asp Tyr Thr Glu
            435                 440                 445
```

Val Arg Gly Phe Lys Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 164
<211> LENGTH: 583
<212> TYPE: PRT
<213> ORGANISM: Chlamydomonas reinhardtii

<400> SEQUENCE: 164

Met Ala Lys Thr Ile Ile Leu Asn Gly Asn Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
    50                  55                  60

Lys Val Glu Asp Gly Met Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Arg Glu Asn Cys Glu Phe Leu Lys Leu
            100                 105                 110

Val Ile Lys Thr Lys Ala Lys Ala Asn Lys Pro Phe Val Val Glu Asp
        115                 120                 125

Lys Ser Gln Tyr Ile Asp Ile Arg Ser Lys Ser Ile Val Ile Asp Arg
130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
            245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
            275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 165
<211> LENGTH: 584
<212> TYPE: PRT
<213> ORGANISM: Chlamydomonas reinhardtii

<400> SEQUENCE: 165

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

```
Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
            195                 200                 205

Lys Ser His Ile Glu Lys Val Gln Glu Ala Leu Asn Asp Pro Lys Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
            275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Glu Val Glu Ile Ala Gly
```

```
                   450                 455                 460
Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
            530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 166
<211> LENGTH: 584
<212> TYPE: PRT
<213> ORGANISM: Chlamydomonas reinhardtii

<400> SEQUENCE: 166

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
```

```
                         245                 250                 255
Ala Leu Arg Met Leu Gly Phe Asp Lys Val Phe Asp Ile Asn Phe Gly
                 260                 265                 270

Ala Asp Met Thr Ile Met Glu Glu Ala Thr Glu Leu Leu Gly Arg Val
             275                 280                 285

Lys Asn Asn Gly Pro Phe Pro Met Phe Thr Ser Cys Cys Pro Ala Trp
         290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                 325                 330                 335

Tyr Pro Ser Ile Ser Gly Ile Ala Pro Glu Asp Val Tyr Thr Val Thr
             340                 345                 350

Ile Met Pro Cys Asn Asp Lys Lys Tyr Glu Ala Asp Ile Pro Phe Met
         355                 360                 365

Glu Thr Asn Ser Leu Arg Asp Ile Asp Ala Ser Leu Thr Thr Arg Glu
     370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                 405                 410                 415

Ile Phe Gly Ala Thr Gly Gly Val Met Glu Ala Ala Ile Arg Ser Ala
             420                 425                 430

Lys Asp Phe Ala Glu Asn Lys Glu Leu Glu Asn Val Asp Tyr Thr Glu
         435                 440                 445

Val Arg Gly Phe Lys Gly Ile Lys Glu Ala Glu Val Glu Ile Ala Gly
     450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                 485                 490                 495

Val Met Ala Cys Pro Gly Gly Cys Ile Asn Gly Gly Gly Gln Pro His
             500                 505                 510

Val Asn Ala Leu Asp Arg Glu Asn Val Asp Tyr Arg Lys Leu Arg Ala
         515                 520                 525

Ser Val Leu Tyr Asn Gln Asp Lys Asn Val Leu Ser Lys Arg Lys Ser
     530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                 565                 570                 575

Asp Lys Asn Val Ser Lys His Glu
             580

<210> SEQ ID NO 167
<211> LENGTH: 583
<212> TYPE: PRT
<213> ORGANISM: Chlamydomonas reinhardtii

<400> SEQUENCE: 167

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
```

-continued

```
                35                  40                  45
Cys Met Val Glu Val Glu Gly Lys Gly Phe Arg Ala Ala Cys Val Ala
 50                  55                  60
Lys Val Glu Asp Gly Met Val Val Lys Thr Asn Ser Glu Lys Val Gln
 65                  70                  75                  80
Glu Arg Val Lys Met Arg Val Ala Thr Leu Leu Asp Lys His Glu Phe
                 85                  90                  95
Lys Cys Gly Pro Cys Pro Arg Arg Glu Asn Cys Glu Phe Leu Lys Leu
                100                 105                 110
Val Ile Lys Thr Lys Ala Lys Ala Asn Lys Pro Phe Val Val Glu Asp
                115                 120                 125
Lys Ser Gln Tyr Ile Asp Ile Arg Ser Lys Ser Ile Val Ile Asp Arg
130                 135                 140
Thr Lys Cys Val Leu Cys Gly Arg Cys Glu Ala Ala Cys Lys Thr Lys
145                 150                 155                 160
Thr Gly Thr Gly Ala Ile Ser Ile Cys Lys Ser Glu Ser Gly Arg Ile
                165                 170                 175
Val Gln Ala Thr Gly Gly Lys Cys Phe Asp Asp Thr Asn Cys Leu Leu
                180                 185                 190
Cys Gly Gln Cys Val Ala Cys Pro Val Gly Ala Leu Thr Glu Lys
                195                 200                 205
Thr His Val Asp Arg Val Lys Glu Ala Leu Glu Asp Pro Asn Lys His
                210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
                260                 265                 270
Asp Met Thr Ile Met Glu Glu Ala Thr Glu Leu Leu Gly Arg Val Lys
                275                 280                 285
Asn Asn Gly Pro Phe Pro Met Phe Thr Ser Cys Cys Pro Ala Trp Val
290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Ile Ala Pro Glu Asp Val Tyr Thr Val Thr Ile
                340                 345                 350
Met Pro Cys Asn Asp Lys Lys Tyr Glu Ala Asp Ile Pro Phe Met Glu
                355                 360                 365
Thr Asn Ser Leu Arg Asp Ile Asp Ala Ser Leu Thr Thr Arg Glu Leu
                370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
                420                 425                 430
Asp Phe Ala Glu Asn Lys Glu Leu Glu Asn Val Asp Tyr Thr Glu Val
                435                 440                 445
Arg Gly Phe Lys Gly Ile Lys Glu Ala Glu Val Glu Ile Ala Gly Asn
450                 455                 460
```

```
Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gln Pro His Val
            500                 505                 510

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 168
<211> LENGTH: 584
<212> TYPE: PRT
<213> ORGANISM: Chlamydomonas reinhardtii

<400> SEQUENCE: 168

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
            115                 120                 125

Asp Lys Asp Ala Leu Val Asp Asn Arg Ser Lys Ala Ile Val Ile Asp
        130                 135                 140

Arg Ser Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255
```

-continued

```
Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
            580

<210> SEQ ID NO 169
<211> LENGTH: 583
<212> TYPE: PRT
<213> ORGANISM: Chlamydomonas reinhardtii

<400> SEQUENCE: 169

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45
```

-continued

```
Cys Met Val Glu Val Glu Gly Lys Gly Phe Arg Ala Ala Cys Val Ala
 50                  55                  60

Lys Val Glu Asp Gly Met Val Val Lys Thr Asn Ser Glu Lys Val Gln
 65                      70                  75                  80

Glu Arg Val Lys Met Arg Val Ala Thr Leu Leu Asp Lys His Glu Phe
                     85                  90                  95

Lys Cys Gly Pro Cys Pro Arg Arg Glu Asn Cys Glu Phe Leu Lys Leu
                100                 105                 110

Val Ile Lys Thr Lys Ala Lys Ala Asn Lys Pro Phe Val Val Glu Asp
            115                 120                 125

Lys Ser Gln Tyr Ile Asp Ile Arg Ser Lys Ser Ile Val Ile Asp Arg
130                 135                 140

Thr Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
                180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
                260                 265                 270

Asp Met Thr Ile Met Glu Glu Ala Thr Glu Phe Ile Glu Arg Val Lys
            275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
                340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
450                 455                 460

Lys Leu Asn Val Ala Val Ile Asn Gly Ala Ser Asn Phe Phe Glu Phe
465                 470                 475                 480
```

-continued

```
Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 170
<211> LENGTH: 583
<212> TYPE: PRT
<213> ORGANISM: Chlamydomonas reinhardtii

<400> SEQUENCE: 170

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Gln Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270
```

Asp Met Thr Ile Met Glu Glu Ala Thr Glu Phe Ile Glu Arg Val Lys
            275                 280                 285

Asn Asn Gly Pro Phe Pro Met Phe Thr Ser Cys Cys Pro Ala Trp Val
        290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
        370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
        530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 171
<211> LENGTH: 584
<212> TYPE: PRT
<213> ORGANISM: Chlamydomonas reinhardtii

<400> SEQUENCE: 171

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

```
Thr Lys Val Glu Glu Gly Met Val Ile Asn Thr Glu Ser Asp Glu Val
 65                  70                  75                  80

Lys Glu Arg Ile Lys Lys Arg Val Ser Met Leu Leu Asp Lys His Glu
                 85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
```

```
                        485                 490                 495
Val Met Ala Cys Pro Gly Gly Cys Ile Asn Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
            530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 172
<211> LENGTH: 583
<212> TYPE: PRT
<213> ORGANISM: Chlamydomonas reinhardtii

<400> SEQUENCE: 172

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Glu Asn Cys Glu Phe Leu Lys Leu
            100                 105                 110

Val Ile Lys Thr Lys Ala Lys Ala Asn Lys Pro Phe Val Val Glu Asp
        115                 120                 125

Lys Ser Gln Tyr Ile Asp Ile Arg Ser Lys Ser Ile Val Ile Asp Arg
130                 135                 140

Thr Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
```

```
                275                 280                 285
Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 173
<211> LENGTH: 583
<212> TYPE: PRT
<213> ORGANISM: Chlamydomonas reinhardtii

<400> SEQUENCE: 173

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
```

```
             65                  70                  75                  80
Glu Arg Ile Lys Lys Arg Val Ser Met Leu Leu Asp Lys His Glu Phe
                     85                  90                  95
Lys Cys Gly Gln Cys Ser Arg Arg Glu Asn Cys Glu Phe Leu Lys Leu
                100                 105                 110
Val Ile Lys Thr Lys Ala Lys Ala Ser Lys Pro Phe Leu Pro Glu Asp
            115                 120                 125
Lys Asp Ala Leu Val Asp Asn Arg Ser Lys Ala Ile Val Ile Asp Arg
130                 135                 140
Ser Lys Cys Val Leu Cys Gly Arg Cys Glu Ala Ala Cys Lys Thr Lys
145                 150                 155                 160
Thr Gly Thr Gly Ala Ile Ser Ile Cys Lys Ser Glu Ser Gly Arg Ile
                165                 170                 175
Val Gln Ala Thr Gly Gly Lys Cys Phe Asp Asp Thr Asn Cys Leu Leu
            180                 185                 190
Cys Gly Gln Cys Val Ala Ala Cys Pro Val Gly Ala Leu Thr Glu Lys
            195                 200                 205
Thr His Val Asp Arg Val Lys Glu Ala Leu Glu Asp Pro Asn Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
                260                 265                 270
Asp Met Thr Ile Met Glu Glu Ala Thr Glu Leu Leu Gly Arg Val Lys
            275                 280                 285
Asn Asn Gly Pro Phe Pro Met Phe Thr Ser Cys Cys Pro Ala Trp Val
            290                 295                 300
Arg Leu Ala Gln Asn Tyr His Pro Glu Leu Leu Asp Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Ile Ala Pro Glu Asp Val Tyr Thr Val Thr Ile
                340                 345                 350
Met Pro Cys Asn Asp Lys Lys Tyr Glu Ala Asp Ile Pro Phe Met Glu
            355                 360                 365
Thr Asn Ser Leu Arg Asp Ile Asp Ala Ser Leu Thr Thr Arg Glu Leu
    370                 375                 380
Ala Lys Met Ile Lys Asp Ala Lys Ile Lys Phe Ala Asp Leu Glu Asp
385                 390                 395                 400
Gly Glu Val Asp Pro Ala Met Gly Thr Tyr Ser Gly Ala Gly Ala Ile
                405                 410                 415
Phe Gly Ala Thr Gly Gly Val Met Glu Ala Ala Ile Arg Ser Ala Lys
                420                 425                 430
Asp Phe Ala Glu Asn Lys Glu Leu Glu Asn Val Asp Tyr Thr Glu Val
            435                 440                 445
Arg Gly Phe Lys Gly Ile Lys Glu Ala Glu Val Glu Ile Ala Gly Asn
    450                 455                 460
Lys Leu Asn Val Ala Val Ile Asn Gly Ala Ser Asn Phe Phe Glu Phe
465                 470                 475                 480
Met Lys Ser Gly Lys Met Asn Glu Lys Gln Tyr His Phe Ile Glu Val
                485                 490                 495
```

```
Met Ala Cys Pro Gly Gly Cys Ile Asn Gly Gly Gln Pro His Val
            500             505             510

Asn Ala Leu Asp Arg Glu Asn Val Asp Tyr Arg Lys Leu Arg Ala Ser
            515             520             525

Val Leu Tyr Asn Gln Asp Lys Asn Val Leu Ser Lys Arg Lys Ser His
    530             535             540

Asp Asn Pro Ala Ile Ile Lys Met Tyr Asp Ser Tyr Phe Gly Lys Pro
545             550             555             560

Gly Glu Gly Leu Ala His Lys Leu Leu His Val Lys Tyr Thr Lys Asp
                565             570             575

Lys Asn Val Ser Lys His Glu
            580

<210> SEQ ID NO 174
<211> LENGTH: 583
<212> TYPE: PRT
<213> ORGANISM: Chlamydomonas reinhardtii

<400> SEQUENCE: 174

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
        210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285
```

```
Asn Asn Gly Pro Phe Pro Met Phe Thr Ser Cys Cys Pro Ala Trp Val
            290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
                340                 345                 350

Met Pro Cys Asn Asp Lys Lys Tyr Glu Ala Asp Ile Pro Phe Met Glu
                355                 360                 365

Thr Asn Ser Leu Arg Asp Ile Asp Ala Ser Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
                435                 440                 445

Arg Gly Phe Lys Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
                500                 505                 510

Asn Ala Leu Asp Arg Glu Asn Val Asp Tyr Arg Lys Leu Arg Ala Ser
                515                 520                 525

Val Leu Tyr Asn Gln Asp Lys Asn Val Leu Ser Lys Arg Lys Ser His
            530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580
```

<210> SEQ ID NO 175
<211> LENGTH: 583
<212> TYPE: PRT
<213> ORGANISM: Chlamydomonas reinhardtii

<400> SEQUENCE: 175

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
            50                  55                  60

Lys Val Glu Asp Gly Met Val Ile Asn Thr Glu Ser Asp Glu Val Lys
65                  70                  75                  80
```

-continued

```
Glu Arg Ile Lys Lys Arg Val Ser Met Leu Leu Asp Lys His Glu Phe
             85                  90                  95
Lys Cys Gly Gln Cys Ser Arg Arg Glu Asn Cys Glu Phe Leu Lys Leu
            100                 105                 110
Val Ile Lys Thr Lys Ala Lys Ala Ser Lys Pro Phe Leu Pro Glu Asp
            115                 120                 125
Lys Asp Ala Leu Val Asp Asn Arg Ser Lys Ala Ile Val Ile Asp Arg
    130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
            165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
            195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
            245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
            275                 280                 285
Asn Asn Gly Pro Phe Pro Met Phe Thr Ser Cys Cys Pro Ala Trp Val
    290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
            325                 330                 335
Pro Gln Ile Ser Gly Ile Ser Ala Lys Asp Val Phe Thr Val Thr Ile
            340                 345                 350
Met Pro Cys Thr Ala Lys Lys Phe Glu Ala Asp Arg Glu Glu Met Tyr
            355                 360                 365
Asn Glu Gly Ile Lys Asn Ile Asp Ala Val Leu Thr Thr Arg Glu Leu
    370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
            405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
            435                 440                 445
Arg Gly Leu Gln Gly Ile Lys Glu Ala Thr Val Glu Ile Gly Gly Glu
    450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
            485                 490                 495
Met Ala Cys Pro Gly Gly Cys Val Asn Gly Gly Gly Gln Pro His Val
            500                 505                 510
```

-continued

Asn Ala Leu Asp Arg Glu Asn Val Asp Tyr Arg Lys Leu Arg Ala Ser
            515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 176
<211> LENGTH: 574
<212> TYPE: PRT
<213> ORGANISM: Chlamydomonas reinhardtii

<400> SEQUENCE: 176

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
            370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 177
<211> LENGTH: 574
<212> TYPE: PRT
<213> ORGANISM: Chlamydomonas reinhardtii

<400> SEQUENCE: 177

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
            85                  90                  95

Lys Cys Gly Gln Cys Ser Arg Arg Glu Asn Cys Glu Phe Leu Lys Leu
            100                 105                 110

```
Val Ile Lys Thr Lys Ala Lys Ala Ser Lys Pro Phe Leu Pro Glu Asp
            115                 120                 125
Lys Asp Ala Leu Val Asp Asn Arg Ser Lys Ala Ile Val Ile Asp Arg
        130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
    290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
            340                 345                 350
Met Pro Cys Thr Ala Lys Lys Phe Glu Ala Asp Arg Glu Glu Met Tyr
        355                 360                 365
Asn Glu Gly Ile Lys Asn Ile Asp Ala Val Leu Thr Thr Arg Glu Leu
    370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
        435                 440                 445
Arg Gly Leu Gln Gly Ile Lys Glu Ala Thr Val Glu Ile Gly Gly Glu
    450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
                485                 490                 495
Met Ala Cys Pro Gly Gly Cys Val Asn Gly Gly Gly Gln Pro His Val
            500                 505                 510
Ser Ala Lys Glu Arg Glu Lys Val Asp Val Arg Thr Val Arg Ala Ser
        515                 520                 525
Val Leu Tyr Asn Gln Asp Lys Asn Leu Glu Lys Arg Lys Ser His Lys
```

```
                    530                 535                 540
Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 178
<211> LENGTH: 583
<212> TYPE: PRT
<213> ORGANISM: Chlamydomonas reinhardtii

<400> SEQUENCE: 178

Met Ala Lys Thr Ile Ile Leu Asn Gly Asn Glu Val His Thr Asp Lys
1               5                  10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
```

```
                         340                 345                 350
Met Pro Cys Thr Ala Lys Lys Phe Glu Ala Asp Arg Glu Glu Met Tyr
                355                 360                 365

Asn Glu Gly Ile Lys Asn Ile Asp Ala Val Leu Thr Thr Arg Glu Leu
        370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
                435                 440                 445

Arg Gly Phe Lys Gly Ile Lys Glu Ala Thr Val Glu Ile Gly Gly Glu
                450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gly Gln Pro His Val
                500                 505                 510

Asn Ala Leu Asp Arg Glu Asn Val Asp Tyr Arg Lys Leu Arg Ala Ser
                515                 520                 525

Val Leu Tyr Asn Gln Asp Lys Asn Val Leu Ser Lys Arg Lys Ser His
                530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
                580

<210> SEQ ID NO 179
<211> LENGTH: 583
<212> TYPE: PRT
<213> ORGANISM: Chlamydomonas reinhardtii

<400> SEQUENCE: 179

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
                50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
                100                 105                 110

Val Ile Lys Thr Lys Ala Lys Ala Ser Lys Pro Phe Leu Pro Glu Asp
                115                 120                 125

Lys Asp Ala Leu Val Asp Asn Arg Ser Lys Ala Ile Val Ile Asp Arg
```

-continued

```
            130                 135                 140
Ser Lys Cys Val Leu Cys Gly Arg Cys Val Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
                180                 185                 190

Cys Gly Gln Cys Val Ile Ala Cys Pro Val Ala Ala Leu Lys Glu Lys
                195                 200                 205

Ser His Ile Glu Lys Val Gln Glu Ala Leu Asn Asp Pro Lys Lys His
210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
                260                 265                 270

Asp Met Thr Ile Met Glu Glu Ala Thr Glu Leu Leu Gly Arg Val Lys
                275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
                340                 345                 350

Met Pro Cys Asn Asp Lys Lys Tyr Glu Ala Asp Ile Pro Phe Met Glu
                355                 360                 365

Thr Asn Ser Leu Arg Asp Ile Asp Ala Ser Leu Thr Thr Arg Glu Leu
                370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
                435                 440                 445

Arg Gly Leu Gln Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gly Gln Pro His Val
                500                 505                 510

Asn Ala Leu Asp Arg Glu Asn Val Asp Tyr Arg Lys Leu Arg Ala Ser
                515                 520                 525

Val Leu Tyr Asn Gln Asp Lys Asn Val Leu Ser Lys Arg Lys Ser His
                530                 535                 540

Asp Asn Pro Ala Ile Ile Lys Met Tyr Asp Ser Tyr Phe Gly Lys Pro
545                 550                 555                 560
```

```
Gly Glu Gly Leu Ala His Lys Leu Leu His Val Lys Tyr Thr Lys Asp
            565                 570                 575
Lys Asn Val Ser Lys His Glu
            580
```

<210> SEQ ID NO 180
<211> LENGTH: 574
<212> TYPE: PRT
<213> ORGANISM: Chlamydomonas reinhardtii

<400> SEQUENCE: 180

```
Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
                20                  25                  30
Thr Leu Cys Phe Leu Lys Asp Cys Gly Asn Phe Gly Lys Cys Gly Val
            35                  40                  45
Cys Met Val Glu Val Glu Gly Lys Gly Phe Arg Ala Ala Cys Val Ala
        50                  55                  60
Lys Val Glu Asp Gly Met Val Ile Asn Thr Glu Ser Asp Glu Val Lys
65                  70                  75                  80
Glu Arg Ile Lys Lys Arg Val Ser Met Leu Leu Asp Lys His Glu Phe
                85                  90                  95
Lys Cys Gly Gln Cys Ser Arg Arg Glu Asn Cys Glu Phe Leu Lys Leu
            100                 105                 110
Val Ile Lys Thr Lys Ala Lys Ala Ser Lys Pro Phe Leu Pro Glu Asp
        115                 120                 125
Lys Asp Ala Leu Val Asp Asn Arg Ser Lys Ala Ile Val Ile Asp Arg
130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
            340                 345                 350
```

```
Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
                420                 425                 430

Asp Phe Ala Glu Asn Lys Glu Leu Glu Asn Val Asp Tyr Thr Glu Val
                435                 440                 445

Arg Gly Phe Lys Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gly Gln Pro His Val
                500                 505                 510

Ser Ala Lys Glu Arg Glu Lys Val Asp Val Arg Thr Val Arg Ala Ser
                515                 520                 525

Val Leu Tyr Asn Gln Asp Lys Asn Leu Glu Lys Arg Lys Ser His Lys
            530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 181
<211> LENGTH: 574
<212> TYPE: PRT
<213> ORGANISM: Chlamydomonas reinhardtii

<400> SEQUENCE: 181

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65              70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Cys Lys Gln His
145                 150                 155                 160
```

```
Thr Ser Thr Cys Ser Ile Gln Phe Ile Lys Lys Asp Gly Gln Arg Ala
            165                 170                 175

Val Gly Thr Val Asp Asp Val Cys Leu Asp Asp Ser Thr Cys Leu Leu
        180                 185                 190

Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
        210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
            245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
            290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
            325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
            370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
            405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
            530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Tyr Asn Lys
            565                 570

<210> SEQ ID NO 182
```

```
<211> LENGTH: 574
<212> TYPE: PRT
<213> ORGANISM: Chlamydomonas reinhardtii

<400> SEQUENCE: 182
```

| | | | | | | | | | | | | | | |
|---|---|---|---|---|---|---|---|---|---|---|---|---|---|---|
| Met | Ala | Lys | Thr | Ile | Ile | Leu | Asn | Gly | Asn | Glu | Val | His | Thr | Asp | Lys |
| 1 | | | | 5 | | | | | 10 | | | | | 15 | |
| Asp | Ile | Thr | Ile | Leu | Glu | Leu | Ala | Arg | Glu | Asn | Asn | Val | Asp | Ile | Pro |
| | | | 20 | | | | | 25 | | | | | 30 | | |
| Thr | Leu | Cys | Phe | Leu | Lys | Asp | Cys | Gly | Asn | Phe | Gly | Lys | Cys | Gly | Val |
| | | 35 | | | | | 40 | | | | | 45 | | | |
| Cys | Met | Val | Glu | Val | Glu | Gly | Lys | Gly | Phe | Arg | Ala | Ala | Cys | Val | Ala |
| | 50 | | | | | 55 | | | | | 60 | | | | |
| Lys | Val | Glu | Asp | Gly | Met | Val | Ile | Asn | Thr | Glu | Ser | Asp | Glu | Val | Lys |
| 65 | | | | | 70 | | | | | 75 | | | | | 80 |
| Glu | Arg | Ile | Lys | Lys | Arg | Val | Ser | Met | Leu | Leu | Asp | Lys | His | Glu | Phe |
| | | | | 85 | | | | | 90 | | | | | 95 | |
| Lys | Cys | Gly | Gln | Cys | Ser | Arg | Arg | Glu | Asn | Cys | Glu | Phe | Leu | Lys | Leu |
| | | | 100 | | | | | 105 | | | | | 110 | | |
| Val | Ile | Lys | Thr | Lys | Ala | Lys | Ala | Ser | Lys | Pro | Phe | Leu | Pro | Glu | Asp |
| | | | 115 | | | | | 120 | | | | | 125 | | |
| Lys | Asp | Ala | Leu | Val | Asp | Asn | Arg | Ser | Lys | Ala | Ile | Val | Ile | Asp | Arg |
| | 130 | | | | | 135 | | | | | 140 | | | | |
| Ser | Lys | Cys | Val | Leu | Cys | Gly | Arg | Cys | Val | Ala | Ala | Cys | Lys | Gln | His |
| 145 | | | | | 150 | | | | | 155 | | | | | 160 |
| Thr | Ser | Thr | Cys | Ser | Ile | Gln | Phe | Ile | Lys | Lys | Asp | Gly | Gln | Arg | Ala |
| | | | | 165 | | | | | 170 | | | | | 175 | |
| Val | Gly | Thr | Val | Asp | Asp | Val | Cys | Leu | Asp | Asp | Ser | Thr | Cys | Leu | Leu |
| | | | 180 | | | | | 185 | | | | | 190 | | |
| Cys | Gly | Gln | Cys | Val | Ile | Ala | Cys | Pro | Val | Ala | Leu | Lys | Glu | Lys |
| | | | 195 | | | | | 200 | | | | | 205 | | |
| Ser | His | Ile | Glu | Lys | Val | Gln | Glu | Ala | Leu | Asn | Asp | Pro | Lys | Lys | His |
| | 210 | | | | | 215 | | | | | 220 | | | | |
| Val | Ile | Val | Ala | Met | Ala | Pro | Ser | Val | Arg | Thr | Ala | Met | Gly | Glu | Leu |
| 225 | | | | | 230 | | | | | 235 | | | | | 240 |
| Phe | Lys | Met | Gly | Tyr | Gly | Lys | Asp | Val | Thr | Gly | Lys | Leu | Tyr | Thr | Ala |
| | | | | 245 | | | | | 250 | | | | | 255 | |
| Leu | Arg | Met | Leu | Gly | Phe | Asp | Lys | Val | Phe | Asp | Ile | Asn | Phe | Gly | Ala |
| | | | 260 | | | | | 265 | | | | | 270 | | |
| Asp | Met | Thr | Ile | Met | Glu | Glu | Ala | Thr | Glu | Leu | Leu | Gly | Arg | Val | Lys |
| | | | 275 | | | | | 280 | | | | | 285 | | |
| Asn | Asn | Gly | Pro | Phe | Pro | Met | Phe | Thr | Ser | Cys | Cys | Pro | Ala | Trp | Val |
| | 290 | | | | | 295 | | | | | 300 | | | | |
| Arg | Leu | Ala | Gln | Asn | Tyr | His | Pro | Glu | Leu | Leu | Asp | Asn | Leu | Ser | Ser |
| 305 | | | | | 310 | | | | | 315 | | | | | 320 |
| Ala | Lys | Ser | Pro | Gln | Gln | Ile | Phe | Gly | Thr | Ala | Ser | Lys | Thr | Tyr | Tyr |
| | | | | 325 | | | | | 330 | | | | | 335 | |
| Pro | Ser | Ile | Ser | Gly | Ile | Ala | Pro | Glu | Asp | Val | Tyr | Thr | Val | Thr | Ile |
| | | | 340 | | | | | 345 | | | | | 350 | | |
| Met | Pro | Cys | Asn | Asp | Lys | Lys | Tyr | Glu | Ala | Asp | Ile | Pro | Phe | Met | Glu |
| | | | 355 | | | | | 360 | | | | | 365 | | |
| Thr | Asn | Ser | Leu | Arg | Asp | Ile | Asp | Ala | Ser | Leu | Thr | Thr | Arg | Glu | Leu |
| | 370 | | | | | 375 | | | | | 380 | | | | |
| Ala | Lys | Met | Ile | Lys | Asp | Ala | Lys | Ile | Lys | Phe | Ala | Asp | Leu | Glu | Asp |
| 385 | | | | | 390 | | | | | 395 | | | | | 400 |

```
Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 183
<211> LENGTH: 583
<212> TYPE: PRT
<213> ORGANISM: Chlamydomonas reinhardtii

<400> SEQUENCE: 183

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205
```

```
Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
        435                 440                 445

Arg Gly Phe Lys Gly Ile Lys Glu Ala Glu Val Glu Ile Ala Gly Asn
    450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
                485                 490                 495

Met Ala Cys Pro Gly Gly Cys Ile Asn Gly Gly Gln Pro His Val
            500                 505                 510

Asn Ala Leu Asp Arg Glu Asn Val Asp Tyr Arg Lys Leu Arg Ala Ser
        515                 520                 525

Val Leu Tyr Asn Gln Asp Lys Asn Val Leu Ser Lys Arg Lys Ser His
    530                 535                 540

Asp Asn Pro Ala Ile Ile Lys Met Tyr Asp Ser Tyr Phe Gly Lys Pro
545                 550                 555                 560

Gly Glu Gly Leu Ala His Lys Leu Leu His Val Lys Tyr Thr Lys Asp
                565                 570                 575

Lys Asn Val Ser Lys His Glu
            580

<210> SEQ ID NO 184
<211> LENGTH: 583
<212> TYPE: PRT
<213> ORGANISM: Chlamydomonas reinhardtii

<400> SEQUENCE: 184
```

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
        100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
        275                 280                 285

Asn Asn Gly Pro Phe Pro Met Phe Thr Ser Cys Cys Pro Ala Trp Val
    290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
        355                 360                 365

Thr Asn Ser Leu Arg Asp Ile Asp Ala Ser Leu Thr Thr Arg Glu Leu
    370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
                405                 410                 415

Phe Gly Ala Thr Gly Gly Val Met Glu Ala Ala Ile Arg Ser Ala Lys
```

```
                420             425             430
Asp Phe Ala Glu Asn Lys Glu Leu Glu Asn Val Asp Tyr Thr Glu Val
            435                 440                 445
Arg Gly Phe Lys Gly Ile Lys Glu Ala Thr Val Glu Ile Gly Gly Glu
        450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
                485                 490                 495
Met Ala Cys Pro Gly Gly Cys Val Asn Gly Gly Gln Pro His Val
            500                 505                 510
Asn Ala Leu Asp Arg Glu Asn Val Asp Tyr Arg Lys Leu Arg Ala Ser
            515                 520                 525
Val Leu Tyr Asn Gln Asp Lys Asn Val Leu Ser Lys Arg Lys Ser His
        530                 535                 540
Asp Asn Pro Ala Ile Ile Lys Met Tyr Asp Ser Tyr Phe Gly Lys Pro
545                 550                 555                 560
Gly Glu Gly Leu Ala His Lys Leu Leu His Val Lys Tyr Thr Lys Asp
                565                 570                 575
Lys Asn Val Ser Lys His Glu
            580

<210> SEQ ID NO 185
<211> LENGTH: 574
<212> TYPE: PRT
<213> ORGANISM: Chlamydomonas reinhardtii

<400> SEQUENCE: 185

Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
            20                  25                  30
Thr Leu Cys Phe Leu Lys Asp Cys Gly Asn Phe Gly Lys Cys Gly Val
        35                  40                  45
Cys Met Val Glu Val Glu Gly Lys Gly Phe Arg Ala Ala Cys Val Ala
    50                  55                  60
Lys Val Glu Asp Gly Met Val Ile Asn Thr Glu Ser Asp Glu Val Lys
65                  70                  75                  80
Glu Arg Ile Lys Lys Arg Val Ser Met Leu Leu Asp Lys His Glu Phe
                85                  90                  95
Lys Cys Gly Gln Cys Ser Arg Arg Glu Asn Cys Glu Phe Leu Lys Leu
            100                 105                 110
Val Ile Lys Thr Lys Ala Lys Ala Ser Lys Pro Phe Leu Pro Glu Asp
        115                 120                 125
Lys Asp Ala Leu Val Asp Asn Arg Ser Lys Ala Ile Val Ile Asp Arg
    130                 135                 140
Ser Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
```

```
                210                 215                 220
Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
            245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
            275                 280                 285

Asn Asn Gly Pro Phe Pro Met Phe Thr Ser Cys Cys Pro Ala Trp Val
290                 295                 300

Arg Leu Ala Gln Asn Tyr His Pro Glu Leu Leu Asp Asn Leu Ser Ser
305                 310                 315                 320

Ala Lys Ser Pro Gln Gln Ile Phe Gly Thr Ala Ser Lys Thr Tyr Tyr
            325                 330                 335

Pro Ser Ile Ser Gly Ile Ala Pro Glu Asp Val Tyr Thr Val Thr Ile
            340                 345                 350

Met Pro Cys Asn Asp Lys Lys Tyr Glu Ala Asp Ile Pro Phe Met Glu
            355                 360                 365

Thr Asn Ser Leu Arg Asp Ile Asp Ala Ser Leu Thr Thr Arg Glu Leu
370                 375                 380

Ala Lys Met Ile Lys Asp Ala Lys Ile Lys Phe Ala Asp Leu Glu Asp
385                 390                 395                 400

Gly Glu Val Asp Pro Ala Met Gly Thr Tyr Ser Gly Ala Gly Ala Ile
            405                 410                 415

Phe Gly Ala Thr Gly Gly Val Met Glu Ala Ala Ile Arg Ser Ala Lys
            420                 425                 430

Asp Phe Ala Glu Asn Lys Glu Leu Glu Asn Val Asp Tyr Thr Glu Val
            435                 440                 445

Arg Gly Phe Lys Gly Ile Lys Glu Ala Glu Val Glu Ile Ala Gly Asn
            450                 455                 460

Lys Leu Asn Val Ala Val Ile Asn Gly Ala Ser Asn Phe Phe Glu Phe
465                 470                 475                 480

Met Lys Ser Gly Lys Met Asn Glu Lys Gln Tyr His Phe Ile Glu Val
            485                 490                 495

Met Ala Cys Pro Gly Gly Cys Ile Asn Gly Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 186
<211> LENGTH: 574
<212> TYPE: PRT
<213> ORGANISM: Chlamydomonas reinhardtii

<400> SEQUENCE: 186

Ala Ile Asn Ile Val Ile Asp Glu Lys Thr Ile Gln Val Gln Glu Asn
1               5                   10                  15

Thr Thr Val Ile Gln Ala Ala Leu Ala Asn Gly Ile Asp Ile Pro Ser
```

```
                   20                  25                  30
Leu Cys Tyr Leu Asn Glu Cys Gly Asn Val Gly Lys Cys Gly Val Cys
                35                  40                  45
Ala Val Glu Ile Glu Gly Lys Asn Asn Leu Ala Leu Ala Cys Ile Thr
                50                  55                  60
Lys Val Glu Glu Gly Met Val Val Lys Thr Asn Ser Glu Lys Val Gln
65                  70                  75                  80
Glu Arg Val Lys Met Arg Val Ala Thr Leu Leu Asp Lys His Glu Phe
                85                  90                  95
Lys Cys Gly Pro Cys Pro Arg Arg Glu Asn Cys Glu Phe Leu Lys Leu
                100                 105                 110
Val Ile Lys Thr Lys Ala Lys Ala Asn Lys Pro Phe Val Val Glu Asp
                115                 120                 125
Lys Ser Gln Tyr Ile Asp Ile Arg Ser Lys Ser Ile Val Ile Asp Arg
                130                 135                 140
Thr Lys Cys Val Leu Cys Gly Arg Cys Glu Ala Ala Cys Lys Thr Lys
145                 150                 155                 160
Thr Gly Thr Gly Ala Ile Ser Ile Cys Lys Ser Glu Ser Gly Arg Ile
                165                 170                 175
Val Gln Ala Thr Gly Gly Lys Cys Phe Asp Asp Thr Asn Cys Leu Leu
                180                 185                 190
Cys Gly Gln Cys Val Ala Ala Cys Pro Val Gly Ala Leu Thr Glu Lys
                195                 200                 205
Thr His Val Asp Arg Val Lys Glu Ala Leu Glu Asp Pro Asn Lys His
                210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
                260                 265                 270
Asp Met Thr Ile Met Glu Glu Ala Thr Glu Leu Leu Gly Arg Val Lys
                275                 280                 285
Asn Asn Gly Pro Phe Pro Met Phe Thr Ser Cys Cys Pro Ala Trp Val
290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
                340                 345                 350
Met Pro Cys Thr Ala Lys Lys Phe Glu Ala Asp Arg Glu Glu Met Tyr
                355                 360                 365
Asn Glu Gly Ile Lys Asn Ile Asp Ala Val Leu Thr Thr Arg Glu Leu
                370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
                420                 425                 430
Asp Phe Val Glu Asp Lys Asp Leu Thr Asp Ile Glu Tyr Thr Gln Ile
                435                 440                 445
```

```
Arg Gly Leu Gln Gly Ile Lys Glu Ala Thr Val Glu Ile Gly Gly Glu
        450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
        530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 187
<211> LENGTH: 575
<212> TYPE: PRT
<213> ORGANISM: Chlamydomonas reinhardtii

<400> SEQUENCE: 187

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255
```

```
Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
            325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
            370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 188
<211> LENGTH: 575
<212> TYPE: PRT
<213> ORGANISM: Chlamydomonas reinhardtii

<400> SEQUENCE: 188

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60
```

-continued

Thr Lys Val Glu Glu Gly Met Val Ile Asn Thr Glu Ser Asp Glu Val
 65                  70                  75                  80

Lys Glu Arg Ile Lys Arg Val Ser Met Leu Leu Asp Lys His Glu
             85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
    130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

```
Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
            515                 520                 525

Ser Val Leu Tyr Asn Gln Asp Lys Asn Leu Glu Lys Arg Lys Ser His
            530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 189
<211> LENGTH: 574
<212> TYPE: PRT
<213> ORGANISM: Chlamydomonas reinhardtii

<400> SEQUENCE: 189

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Arg Glu Asn Cys Glu Phe Leu Lys Leu
            100                 105                 110

Val Ile Lys Thr Lys Ala Lys Ala Asn Lys Pro Phe Val Val Glu Asp
            115                 120                 125

Lys Ser Gln Tyr Ile Asp Ile Arg Ser Lys Ser Ile Val Ile Asp Arg
        130                 135                 140

Thr Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
    290                 295                 300
```

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
                340                 345                 350

Met Pro Cys Thr Ala Lys Lys Phe Glu Ala Asp Arg Glu Glu Met Tyr
                355                 360                 365

Asn Glu Gly Ile Lys Asn Ile Asp Ala Val Leu Thr Thr Arg Glu Leu
                370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
                420                 425                 430

Asp Phe Val Glu Asp Lys Asp Leu Thr Asp Ile Glu Tyr Thr Gln Ile
                435                 440                 445

Arg Gly Leu Gln Gly Ile Lys Glu Ala Thr Val Glu Ile Gly Gly Glu
                450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gln Pro His Val
                500                 505                 510

Ser Ala Lys Glu Arg Glu Lys Val Asp Val Arg Thr Val Arg Ala Ser
                515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 190
<211> LENGTH: 575
<212> TYPE: PRT
<213> ORGANISM: Chlamydomonas reinhardtii

<400> SEQUENCE: 190

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
                50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
                100                 105                 110

```
Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
        130                 135                 140

Arg Thr Lys Cys Val Leu Cys Gly Arg Cys Val Ala Ala Cys Lys Gln
145                 150                 155                 160

His Thr Ser Thr Cys Ser Ile Gln Phe Ile Lys Lys Asp Gly Gln Arg
                165                 170                 175

Ala Val Gly Thr Val Asp Asp Val Cys Leu Asp Asp Ser Thr Cys Leu
            180                 185                 190

Leu Cys Gly Gln Cys Val Ile Ala Cys Pro Val Ala Ala Leu Lys Glu
        195                 200                 205

Lys Ser His Ile Glu Lys Val Gln Glu Ala Leu Asn Asp Pro Lys Lys
    210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
```

```
                  530                 535                 540
Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575
```

<210> SEQ ID NO 191
<211> LENGTH: 575
<212> TYPE: PRT
<213> ORGANISM: Chlamydomonas reinhardtii

<400> SEQUENCE: 191

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
                85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
        115                 120                 125

Asp Lys Asp Ala Leu Val Asp Asn Arg Ser Lys Ala Ile Val Ile Asp
130                 135                 140

Arg Ser Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
```

```
                340              345              350
Ile Met Pro Cys Thr Ala Lys Lys Phe Glu Ala Asp Arg Glu Glu Met
            355              360              365
Tyr Asn Glu Gly Ile Lys Asn Ile Asp Ala Val Leu Thr Thr Arg Glu
    370              375              380
Leu Ala Lys Met Ile Lys Asp Ala Lys Ile Asn Phe Ala Asn Leu Glu
385              390              395              400
Asp Glu Gln Ala Asp Pro Ala Met Gly Tyr Thr Gly Ala Gly Val
                405              410              415
Ile Phe Gly Ala Thr Gly Gly Val Met Glu Ala Ala Leu Arg Thr Ala
            420              425              430
Lys Asp Phe Val Glu Asp Lys Asp Leu Thr Asp Ile Glu Tyr Thr Gln
            435              440              445
Ile Arg Gly Leu Gln Gly Ile Lys Glu Ala Thr Val Glu Ile Gly Gly
        450              455              460
Glu Asn Tyr Asn Val Ala Val Ile Asn Gly Ala Ala Asn Leu Ala Glu
465              470              475              480
Phe Met Asn Ser Gly Lys Ile Leu Glu Lys Asn Tyr His Phe Ile Glu
                485              490              495
Val Met Ala Cys Pro Gly Gly Cys Val Asn Gly Gly Gln Pro His
            500              505              510
Val Ser Ala Lys Glu Arg Glu Lys Val Asp Val Arg Thr Val Arg Ala
            515              520              525
Ser Val Leu Tyr Asn Gln Asp Lys Asn Leu Glu Lys Arg Lys Ser His
        530              535              540
Lys Asn Thr Ala Leu Leu Asn Met Tyr Tyr Asp Tyr Met Gly Ala Pro
545              550              555              560
Gly Gln Gly Lys Ala His Glu Leu Leu His Leu Lys Tyr Asn Lys
                565              570              575

<210> SEQ ID NO 192
<211> LENGTH: 574
<212> TYPE: PRT
<213> ORGANISM: Chlamydomonas reinhardtii

<400> SEQUENCE: 192

Met Ala Lys Thr Ile Ile Leu Asn Gly Asn Glu Val His Thr Asp Lys
1               5                   10                  15
Asp Ile Thr Ile Leu Glu Leu Ala Arg Glu Asn Asn Val Asp Ile Pro
            20                  25                  30
Thr Leu Cys Phe Leu Lys Asp Cys Gly Asn Phe Gly Lys Cys Gly Val
        35                  40                  45
Cys Met Val Glu Val Glu Gly Lys Gly Phe Arg Ala Ala Cys Val Ala
    50                  55                  60
Lys Val Glu Asp Gly Met Val Val Lys Thr Asn Ser Glu Lys Val Gln
65                  70                  75                  80
Glu Arg Val Lys Met Arg Val Ala Thr Leu Leu Asp Lys His Glu Phe
                85                  90                  95
Lys Cys Gly Pro Cys Pro Arg Arg Glu Asn Cys Glu Phe Leu Lys Leu
            100                 105                 110
Val Ile Lys Thr Lys Ala Lys Ala Asn Lys Pro Phe Val Glu Asp
        115                 120                 125
Lys Ser Gln Tyr Ile Asp Ile Arg Ser Lys Ser Ile Val Ile Asp Arg
    130                 135                 140
Thr Lys Cys Val Leu Cys Gly Arg Cys Glu Ala Ala Cys Lys Thr Lys
```

```
                145                 150                 155                 160
Thr Gly Thr Gly Ala Ile Ser Ile Cys Lys Ser Glu Ser Gly Arg Ile
                    165                 170                 175
Val Gln Ala Thr Gly Lys Cys Phe Asp Asp Thr Asn Cys Leu Leu
            180                 185                 190
Cys Gly Gln Cys Val Ala Ala Cys Pro Val Gly Ala Leu Thr Glu Lys
        195                 200                 205
Thr His Val Asp Arg Val Lys Glu Ala Leu Glu Asp Pro Asn Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
                260                 265                 270
Asp Met Thr Ile Met Glu Glu Ala Thr Glu Leu Leu Gly Arg Val Lys
            275                 280                 285
Asn Asn Gly Pro Phe Pro Met Phe Thr Ser Cys Cys Pro Ala Trp Val
        290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
                340                 345                 350
Met Pro Cys Thr Ala Lys Lys Phe Glu Ala Asp Arg Glu Glu Met Tyr
            355                 360                 365
Asn Glu Gly Ile Lys Asn Ile Asp Ala Val Leu Thr Thr Arg Glu Leu
        370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
                420                 425                 430
Asp Phe Val Glu Asp Lys Asp Leu Thr Asp Ile Glu Tyr Thr Gln Ile
            435                 440                 445
Arg Gly Leu Gln Gly Ile Lys Glu Ala Thr Val Glu Ile Gly Gly Glu
        450                 455                 460
Asn Tyr Asn Val Ala Val Ile Asn Gly Ala Ala Asn Leu Ala Glu Phe
465                 470                 475                 480
Met Asn Ser Gly Lys Ile Leu Glu Lys Asn Tyr His Phe Ile Glu Val
                485                 490                 495
Met Ala Cys Pro Gly Gly Cys Val Asn Gly Gly Gln Pro His Val
            500                 505                 510
Ser Ala Lys Glu Arg Glu Lys Val Asp Val Arg Thr Val Arg Ala Ser
        515                 520                 525
Val Leu Tyr Asn Gln Asp Lys Asn Leu Glu Lys Arg Lys Ser His Lys
    530                 535                 540
Asn Thr Ala Leu Leu Asn Met Tyr Tyr Asp Tyr Met Gly Ala Pro Gly
545                 550                 555                 560
Gln Gly Lys Ala His Glu Leu Leu His Leu Lys Tyr Asn Lys
                565                 570
```

<210> SEQ ID NO 193
<211> LENGTH: 575
<212> TYPE: PRT
<213> ORGANISM: Chlamydomonas reinhardtii

<400> SEQUENCE: 193

```
Met Ala Ile Asn Ile Val Ile Asp Glu Lys Thr Ile Gln Val Gln Glu
 1               5                  10                  15
Asn Thr Thr Val Ile Gln Ala Ala Leu Ala Asn Gly Ile Asp Ile Pro
            20                  25                  30
Ser Leu Cys Tyr Leu Asn Glu Cys Gly Asn Val Gly Lys Cys Gly Val
        35                  40                  45
Cys Ala Val Glu Ile Glu Gly Lys Asn Asn Leu Ala Leu Ala Cys Ile
    50                  55                  60
Thr Lys Val Glu Glu Gly Met Val Ile Asn Thr Ser Asp Glu Val
 65                  70                  75                  80
Lys Glu Arg Ile Lys Lys Arg Val Ser Met Leu Leu Asp Lys His Glu
                 85                  90                  95
Phe Lys Cys Gly Gln Cys Ser Arg Arg Glu Asn Cys Glu Phe Leu Lys
            100                 105                 110
Leu Val Ile Lys Thr Lys Ala Lys Ala Ser Lys Pro Phe Leu Pro Glu
        115                 120                 125
Asp Lys Asp Ala Leu Val Asp Asn Arg Ser Lys Ala Ile Val Ile Asp
    130                 135                 140
Arg Ser Lys Cys Val Leu Cys Gly Arg Cys Val Ala Ala Cys Lys Gln
145                 150                 155                 160
His Thr Ser Thr Cys Ser Ile Gln Phe Ile Lys Lys Asp Gly Gln Arg
                165                 170                 175
Ala Val Gly Thr Val Asp Asp Val Cys Leu Asp Asp Ser Thr Cys Leu
            180                 185                 190
Leu Cys Gly Gln Cys Val Ile Ala Cys Pro Val Ala Ala Leu Lys Glu
        195                 200                 205
Lys Ser His Ile Glu Lys Val Gln Glu Ala Leu Asn Asp Pro Lys Lys
    210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
        275                 280                 285
Lys Asn Asn Gly Pro Phe Pro Met Phe Thr Ser Cys Cys Pro Ala Trp
    290                 295                 300
Val Arg Gln Val Glu Asn Tyr Tyr Pro Glu Phe Leu Glu Asn Leu Ser
305                 310                 315                 320
Ser Ala Lys Ser Pro Gln Gln Ile Phe Gly Ala Ala Ser Lys Thr Tyr
                325                 330                 335
Tyr Pro Gln Ile Ser Gly Ile Ser Ala Lys Asp Val Phe Thr Val Thr
            340                 345                 350
Ile Met Pro Cys Thr Ala Lys Lys Phe Glu Ala Asp Arg Glu Glu Met
        355                 360                 365
Tyr Asn Glu Gly Ile Lys Asn Ile Asp Ala Val Leu Thr Thr Arg Glu
    370                 375                 380
```

```
Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
    530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 194
<211> LENGTH: 574
<212> TYPE: PRT
<213> ORGANISM: Chlamydomonas reinhardtii

<400> SEQUENCE: 194

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
        50                  55                  60

Lys Val Glu Asp Gly Met Val Val Lys Thr Asn Ser Glu Lys Val Gln
65                  70                  75                  80

Glu Arg Val Lys Met Arg Val Ala Thr Leu Leu Asp Lys His Glu Phe
                85                  90                  95

Lys Cys Gly Pro Cys Pro Arg Arg Glu Asn Cys Glu Phe Leu Lys Leu
            100                 105                 110

Val Ile Lys Thr Lys Ala Lys Ala Asn Lys Pro Phe Val Val Glu Asp
        115                 120                 125

Lys Ser Gln Tyr Ile Asp Ile Arg Ser Lys Ser Ile Val Ile Asp Arg
    130                 135                 140

Thr Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190
```

```
Cys Gly Gln Cys Val Ile Ala Cys Pro Val Ala Ala Leu Lys Glu Lys
            195                 200                 205

Ser His Ile Glu Lys Val Gln Glu Ala Leu Asn Asp Pro Lys Lys His
210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
            245                 250                 255

Met Arg Ala Leu Gly Phe Asp Lys Val Phe Asp Ile Asn Phe Gly Ala
            260                 265                 270

Asp Met Thr Ile Met Glu Ala Thr Glu Phe Ile Glu Arg Val Lys
            275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
            325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
            355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
            405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
            435                 440                 445

Arg Gly Leu Gln Gly Ile Lys Glu Ala Thr Val Glu Ile Gly Gly Glu
450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 195
<211> LENGTH: 574
<212> TYPE: PRT
<213> ORGANISM: Chlamydomonas reinhardtii

<400> SEQUENCE: 195
```

-continued

```
Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
            35                  40                  45

Cys Met Val Glu Val Glu Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430
```

Asp Phe Val Glu Asp Lys Asp Leu Thr Asp Ile Glu Tyr Thr Gln Ile
            435                 440                 445

Arg Gly Leu Gln Gly Ile Lys Glu Ala Thr Val Glu Ile Gly Gly Glu
            450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
            485                 490                 495

Met Ala Cys Pro Gly Cys Val Asn Gly Gly Gln Pro His Val
            500                 505                 510

Ser Ala Lys Glu Arg Glu Lys Val Asp Val Arg Thr Val Arg Ala Ser
            515                 520                 525

Val Leu Tyr Asn Gln Asp Lys Asn Leu Glu Lys Arg Lys Ser His Lys
            530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
            565                 570

<210> SEQ ID NO 196
<211> LENGTH: 575
<212> TYPE: PRT
<213> ORGANISM: Chlamydomonas reinhardtii

<400> SEQUENCE: 196

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Ile Asn Thr Glu Ser Asp Glu Val
65                  70                  75                  80

Lys Glu Arg Ile Lys Lys Arg Val Ser Met Leu Leu Asp Lys His Glu
            85                  90                  95

Phe Lys Cys Gly Gln Cys Ser Arg Arg Glu Asn Cys Glu Phe Leu Lys
            100                 105                 110

Leu Val Ile Lys Thr Lys Ala Lys Ala Ser Lys Pro Phe Leu Pro Glu
            115                 120                 125

Asp Lys Asp Ala Leu Val Asp Asn Arg Ser Lys Ala Ile Val Ile Asp
130                 135                 140

Arg Ser Lys Cys Val Leu Cys Gly Arg Cys Val Ala Cys Lys Gln
145                 150                 155                 160

His Thr Ser Thr Cys Ser Ile Gln Phe Ile Lys Lys Asp Gly Gln Arg
            165                 170                 175

Ala Val Gly Thr Val Asp Asp Val Cys Leu Asp Ser Thr Cys Leu
            180                 185                 190

Leu Cys Gly Gln Cys Val Ile Ala Cys Pro Val Ala Ala Leu Lys Glu
            195                 200                 205

Lys Ser His Ile Glu Lys Val Gln Glu Ala Leu Asn Asp Pro Lys Lys
            210                 215                 220

His Val Ile Val Ala Met Ala Pro Ser Val Arg Thr Ala Met Gly Glu
225                 230                 235                 240

Leu Phe Lys Met Gly Tyr Gly Lys Asp Val Thr Gly Lys Leu Tyr Thr
                245                 250                 255

Ala Leu Arg Met Leu Gly Phe Asp Lys Val Phe Asp Ile Asn Phe Gly
            260                 265                 270

Ala Asp Met Thr Ile Met Glu Glu Ala Thr Glu Leu Leu Gly Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ser Lys Thr Tyr
                325                 330                 335

Tyr Pro Gln Ile Ser Gly Ile Ser Ala Lys Asp Val Phe Thr Val Thr
                340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
        370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
        435                 440                 445

Ile Arg Gly Leu Gln Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
    530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 197
<211> LENGTH: 574
<212> TYPE: PRT
<213> ORGANISM: Chlamydomonas reinhardtii

<400> SEQUENCE: 197

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

```
Cys Met Val Glu Val Glu Gly Lys Gly Phe Arg Ala Ala Cys Val Ala
    50                  55                  60
Lys Val Glu Asp Gly Met Val Val Lys Thr Asn Ser Glu Lys Val Gln
65                  70                  75                  80
Glu Arg Val Lys Met Arg Val Ala Thr Leu Leu Asp Lys His Glu Phe
                85                  90                  95
Lys Cys Gly Pro Cys Pro Arg Arg Glu Asn Cys Glu Phe Leu Lys Leu
            100                 105                 110
Val Ile Lys Thr Lys Ala Lys Ala Asn Lys Pro Phe Val Val Glu Asp
        115                 120                 125
Lys Ser Gln Tyr Ile Asp Ile Arg Ser Lys Ser Ile Val Ile Asp Arg
    130                 135                 140
Thr Lys Cys Val Leu Cys Gly Arg Cys Val Ala Ala Cys Lys Gln His
145                 150                 155                 160
Thr Ser Thr Cys Ser Ile Gln Phe Ile Lys Lys Asp Gly Gln Arg Ala
                165                 170                 175
Val Gly Thr Val Asp Asp Val Cys Leu Asp Asp Ser Thr Cys Leu Leu
            180                 185                 190
Cys Gly Gln Cys Val Ile Ala Cys Pro Val Ala Ala Leu Lys Glu Lys
        195                 200                 205
Ser His Ile Glu Lys Val Gln Glu Ala Leu Asn Asp Pro Lys Lys His
    210                 215                 220
Val Ile Val Ala Met Ala Pro Ser Val Arg Thr Ala Met Gly Glu Leu
225                 230                 235                 240
Phe Lys Met Gly Tyr Gly Lys Asp Val Thr Gly Lys Leu Tyr Thr Ala
                245                 250                 255
Leu Arg Met Leu Gly Phe Asp Lys Val Phe Asp Ile Asn Phe Gly Ala
            260                 265                 270
Asp Met Thr Ile Met Glu Glu Ala Thr Glu Leu Leu Gly Arg Val Lys
        275                 280                 285
Asn Asn Gly Pro Phe Pro Met Phe Thr Ser Cys Cys Pro Ala Trp Val
    290                 295                 300
Arg Gln Val Glu Asn Tyr Tyr Pro Glu Phe Leu Glu Asn Leu Ser Ser
305                 310                 315                 320
Ala Lys Ser Pro Gln Gln Ile Phe Gly Ala Ala Ser Lys Thr Tyr Tyr
                325                 330                 335
Pro Gln Ile Ser Gly Ile Ser Ala Lys Asp Val Phe Thr Val Thr Ile
            340                 345                 350
Met Pro Cys Thr Ala Lys Lys Phe Glu Ala Asp Arg Glu Glu Met Tyr
        355                 360                 365
Asn Glu Gly Ile Lys Asn Ile Asp Ala Val Leu Thr Thr Arg Glu Leu
    370                 375                 380
Ala Lys Met Ile Lys Asp Ala Lys Ile Asn Phe Ala Asn Leu Glu Asp
385                 390                 395                 400
Glu Gln Ala Asp Pro Ala Met Gly Glu Tyr Thr Gly Ala Gly Val Ile
                405                 410                 415
Phe Gly Ala Thr Gly Gly Val Met Glu Ala Ala Leu Arg Thr Ala Lys
            420                 425                 430
Asp Phe Val Glu Asp Lys Asp Leu Thr Asp Ile Glu Tyr Thr Gln Ile
        435                 440                 445
Arg Gly Leu Gln Gly Ile Lys Glu Ala Thr Val Glu Ile Gly Gly Glu
    450                 455                 460
Asn Tyr Asn Val Ala Val Ile Asn Gly Ala Ala Asn Leu Ala Glu Phe
```

```
                465                 470                 475                 480
Met Asn Ser Gly Lys Ile Leu Glu Lys Asn Tyr His Phe Ile Glu Val
                    485                 490                 495

Met Ala Cys Pro Gly Gly Cys Val Asn Gly Gly Gln Pro His Val
                    500                 505                 510

Ser Ala Lys Glu Arg Glu Lys Val Asp Val Arg Thr Val Arg Ala Ser
                    515                 520                 525

Val Leu Tyr Asn Gln Asp Lys Asn Leu Glu Lys Arg Lys Ser His Lys
                530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                    565                 570

<210> SEQ ID NO 198
<211> LENGTH: 574
<212> TYPE: PRT
<213> ORGANISM: Chlamydomonas reinhardtii

<400> SEQUENCE: 198

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
                20                  25                  30

Thr Leu Cys Phe Leu Lys Asp Cys Gly Asn Phe Gly Lys Cys Gly Val
                35                  40                  45

Cys Met Val Glu Val Glu Gly Lys Gly Phe Arg Ala Ala Cys Val Ala
        50                  55                  60

Lys Val Glu Asp Gly Met Val Ile Asn Thr Ser Asp Glu Val Lys
65                  70                  75                  80

Glu Arg Ile Lys Lys Arg Val Ser Met Leu Leu Asp Lys His Glu Phe
                85                  90                  95

Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
            115                 120                 125

Lys Asp Ala Leu Val Asp Asn Arg Ser Lys Ala Ile Val Ile Asp Arg
        130                 135                 140

Ser Lys Cys Val Leu Cys Gly Arg Cys Glu Ala Ala Cys Lys Thr Lys
145                 150                 155                 160

Thr Gly Thr Gly Ala Ile Ser Ile Cys Lys Ser Glu Ser Gly Arg Ile
                165                 170                 175

Val Gln Ala Thr Gly Gly Lys Cys Phe Asp Asp Thr Asn Cys Leu Leu
            180                 185                 190

Cys Gly Gln Cys Val Ala Ala Cys Pro Val Gly Ala Leu Thr Glu Lys
        195                 200                 205

Thr His Val Asp Arg Val Lys Glu Ala Leu Glu Asp Pro Asn Lys His
    210                 215                 220

Val Ile Val Ala Met Ala Pro Ser Val Arg Thr Ala Met Gly Glu Leu
225                 230                 235                 240

Phe Lys Met Gly Tyr Gly Lys Asp Val Thr Gly Lys Leu Tyr Thr Ala
                245                 250                 255

Leu Arg Met Leu Gly Phe Asp Lys Val Phe Asp Ile Asn Phe Gly Ala
            260                 265                 270

Asp Met Thr Ile Met Glu Glu Ala Thr Glu Leu Leu Gly Arg Val Lys
```

```
                    275                 280                 285
Asn Asn Gly Pro Phe Pro Met Phe Thr Ser Cys Cys Pro Ala Trp Val
            290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
        450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gln Pro His Val
            500                 505                 510

Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 199
<211> LENGTH: 574
<212> TYPE: PRT
<213> ORGANISM: Chlamydomonas reinhardtii

<400> SEQUENCE: 199

Met Ala Lys Thr Ile Ile Leu Asn Gly Asn Glu Val His Thr Asp Lys
1               5                   10                  15

Asp Ile Thr Ile Leu Glu Leu Ala Arg Glu Asn Asn Val Asp Ile Pro
            20                  25                  30

Thr Leu Cys Phe Leu Lys Asp Cys Gly Asn Phe Gly Lys Cys Gly Val
        35                  40                  45

Cys Met Val Glu Val Gly Lys Gly Phe Arg Ala Ala Cys Val Ala
    50                  55                  60

Lys Val Glu Asp Gly Met Val Ile Asn Thr Glu Ser Asp Glu Val Lys
65                  70                  75                  80

Glu Arg Ile Lys Lys Arg Val Ser Met Leu Leu Asp Lys His Glu Phe
```

-continued

```
                85                  90                  95
Lys Cys Gly Gln Cys Ser Arg Arg Glu Asn Cys Glu Phe Leu Lys Leu
            100                 105                 110

Val Ile Lys Thr Lys Ala Lys Ala Ser Lys Pro Phe Leu Pro Glu Asp
        115                 120                 125

Lys Asp Ala Leu Val Asp Asn Arg Ser Lys Ala Ile Val Ile Asp Arg
    130                 135                 140

Ser Lys Cys Val Leu Cys Gly Arg Cys Val Ala Ala Cys Lys Gln His
145                 150                 155                 160

Thr Ser Thr Cys Ser Ile Gln Phe Ile Lys Lys Asp Gly Gln Arg Ala
                165                 170                 175

Val Gly Thr Val Asp Asp Val Cys Leu Asp Asp Ser Thr Cys Leu Leu
            180                 185                 190

Cys Gly Gln Cys Val Ile Ala Cys Pro Val Ala Ala Leu Lys Glu Lys
        195                 200                 205

Ser His Ile Glu Lys Val Gln Glu Ala Leu Asn Asp Pro Lys Lys His
    210                 215                 220

Val Ile Val Ala Met Ala Pro Ser Ile Arg Thr Ser Met Gly Glu Leu
225                 230                 235                 240

Phe Lys Leu Gly Tyr Gly Val Asp Val Thr Gly Lys Leu Tyr Ala Ser
                245                 250                 255

Met Arg Ala Leu Gly Phe Asp Lys Val Phe Asp Ile Asn Phe Gly Ala
            260                 265                 270

Asp Met Thr Ile Met Glu Glu Ala Thr Glu Phe Ile Glu Arg Val Lys
        275                 280                 285

Asn Asn Gly Pro Phe Pro Met Phe Thr Ser Cys Cys Pro Ala Trp Val
    290                 295                 300

Arg Gln Val Glu Asn Tyr Tyr Pro Glu Phe Leu Glu Asn Leu Ser Ser
305                 310                 315                 320

Ala Lys Ser Pro Gln Gln Ile Phe Gly Ala Ala Ser Lys Thr Tyr Tyr
                325                 330                 335

Pro Gln Ile Ser Gly Ile Ser Ala Lys Asp Val Phe Thr Val Thr Ile
            340                 345                 350

Met Pro Cys Thr Ala Lys Lys Phe Glu Ala Asp Arg Glu Glu Met Tyr
        355                 360                 365

Asn Glu Gly Ile Lys Asn Ile Asp Ala Val Leu Thr Thr Arg Glu Leu
    370                 375                 380

Ala Lys Met Ile Lys Asp Ala Lys Ile Asn Phe Ala Asn Leu Glu Asp
385                 390                 395                 400

Glu Gln Ala Asp Pro Ala Met Gly Glu Tyr Thr Gly Ala Gly Val Ile
                405                 410                 415

Phe Gly Ala Thr Gly Gly Val Met Glu Ala Ala Leu Arg Thr Ala Lys
            420                 425                 430

Asp Phe Val Glu Asp Lys Asp Leu Thr Asp Ile Glu Tyr Thr Gln Ile
        435                 440                 445

Arg Gly Leu Gln Gly Ile Lys Glu Ala Thr Val Glu Ile Gly Gly Glu
    450                 455                 460

Asn Tyr Asn Val Ala Val Ile Asn Gly Ala Ala Asn Leu Ala Glu Phe
465                 470                 475                 480

Met Asn Ser Gly Lys Ile Leu Glu Lys Asn Tyr His Phe Ile Glu Val
                485                 490                 495

Met Ala Cys Pro Gly Gly Cys Val Asn Gly Gly Gly Gln Pro His Val
            500                 505                 510
```

```
Ser Ala Lys Glu Arg Glu Lys Val Asp Val Arg Thr Val Arg Ala Ser
        515                 520                 525

Val Leu Tyr Asn Gln Asp Lys Asn Leu Glu Lys Arg Lys Ser His Lys
    530                 535                 540

Asn Thr Ala Leu Leu Asn Met Tyr Tyr Asp Tyr Met Gly Ala Pro Gly
545                 550                 555                 560

Gln Gly Lys Ala His Glu Leu Leu His Leu Lys Tyr Asn Lys
                565                 570

<210> SEQ ID NO 200
<211> LENGTH: 584
<212> TYPE: PRT
<213> ORGANISM: Chlamydomonas reinhardtii

<400> SEQUENCE: 200

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320
```

```
Ser Ala Lys Ser Pro Gln Gln Ile Phe Gly Ala Ala Ser Lys Thr Tyr
            325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
            370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
            405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
            485                 490                 495

Val Met Ala Cys Pro Gly Gly Cys Val Asn Gly Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 201
<211> LENGTH: 575
<212> TYPE: PRT
<213> ORGANISM: Chlamydomonas reinhardtii

<400> SEQUENCE: 201

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65              70                  75                  80

Gln Glu Arg Val Lys Met Arg Val Ala Thr Leu Leu Asp Lys His Glu
            85                  90                  95

Phe Lys Cys Gly Pro Cys Pro Arg Glu Asn Cys Gly Phe Leu Lys
            100                 105                 110
```

```
Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
        130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Thr Val Glu Ile Gly Gly
450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
530                 535                 540
```

```
Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 202
<211> LENGTH: 575
<212> TYPE: PRT
<213> ORGANISM: Chlamydomonas reinhardtii

<400> SEQUENCE: 202

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350
```

Ile Met Pro Cys Asn Asp Lys Lys Tyr Glu Ala Asp Ile Pro Phe Met
              355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
            420                 425                 430

Lys Asp Phe Val Glu Asp Lys Asp Leu Thr Asp Ile Glu Tyr Thr Gln
            435                 440                 445

Ile Arg Gly Leu Gln Gly Ile Lys Glu Ala Thr Val Glu Ile Gly Gly
        450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Ser Ala Lys Glu Arg Glu Lys Val Asp Val Arg Thr Val Arg Ala
        515                 520                 525

Ser Val Leu Tyr Asn Gln Asp Lys Asn Leu Glu Lys Arg Lys Ser His
    530                 535                 540

Lys Asn Thr Ala Leu Leu Asn Met Tyr Tyr Asp Tyr Met Gly Ala Pro
545                 550                 555                 560

Gly Gln Gly Lys Ala His Glu Leu Leu His Leu Lys Tyr Asn Lys
                565                 570                 575

<210> SEQ ID NO 203
<211> LENGTH: 584
<212> TYPE: PRT
<213> ORGANISM: Chlamydomonas reinhardtii

<400> SEQUENCE: 203

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

```
Lys Thr Gly Thr Gly Ala Ile Ser Ile Cys Lys Ser Glu Ser Gly Arg
                165                 170                 175

Ile Val Gln Ala Thr Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Gln Val Glu Asn Tyr Tyr Pro Glu Phe Leu Glu Asn Leu Ser
305                 310                 315                 320

Ser Ala Lys Ser Pro Gln Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
        355                 360                 365

Tyr Asn Glu Gly Ile Lys Asn Ile Asp Ala Val Leu Thr Thr Arg Glu
    370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
        435                 440                 445

Val Arg Gly Phe Lys Gly Ile Lys Glu Ala Thr Val Glu Ile Gly Gly
    450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
            500                 505                 510

Val Asn Ala Leu Asp Arg Glu Asn Val Asp Tyr Arg Lys Leu Arg Ala
        515                 520                 525

Ser Val Leu Tyr Asn Gln Asp Lys Asn Val Leu Ser Lys Arg Lys Ser
    530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
```

<210> SEQ ID NO 204
<211> LENGTH: 584
<212> TYPE: PRT
<213> ORGANISM: Chlamydomonas reinhardtii

<400> SEQUENCE: 204

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
```

```
                    370                 375                 380
Leu Ala Lys Met Ile Lys Asp Ala Lys Ile Asn Phe Ala Asn Leu Glu
385                 390                 395                 400

Asp Glu Gln Ala Asp Pro Ala Met Gly Glu Tyr Thr Gly Ala Gly Val
                405                 410                 415

Ile Phe Gly Ala Thr Gly Gly Val Met Glu Ala Ala Leu Arg Thr Ala
                420                 425                 430

Lys Asp Phe Val Glu Asp Lys Asp Leu Thr Asp Ile Glu Tyr Thr Gln
                435                 440                 445

Ile Arg Gly Leu Gln Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
                485                 490                 495

Val Met Ala Cys Pro Gly Gly Cys Val Asn Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu His Val Lys Tyr Thr Lys
                565                 570                 575

Asp Lys Asn Val Ser Lys His Glu
                580

<210> SEQ ID NO 205
<211> LENGTH: 575
<212> TYPE: PRT
<213> ORGANISM: Chlamydomonas reinhardtii

<400> SEQUENCE: 205

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
            35                  40                  45

Cys Ala Val Glu Ile Glu Gly Lys Asn Asn Leu Ala Leu Ala Cys Ile
50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
        130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
```

```
              165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
            195                 200                 205
Lys Thr His Val Asp Arg Val Lys Glu Ala Leu Glu Asp Pro Asn Lys
            210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
                245                 250                 255
Ser Met Arg Ala Leu Gly Phe Asp Lys Val Phe Asp Ile Asn Phe Gly
            260                 265                 270
Ala Asp Met Thr Ile Met Glu Glu Ala Thr Glu Phe Ile Glu Arg Val
            275                 280                 285
Lys Asn Asn Gly Pro Phe Pro Met Phe Thr Ser Cys Cys Pro Ala Trp
            290                 295                 300
Val Arg Gln Val Glu Asn Tyr Tyr Pro Glu Phe Leu Glu Asn Leu Ser
305                 310                 315                 320
Ser Ala Lys Ser Pro Gln Gln Ile Phe Gly Ala Ala Ser Lys Thr Tyr
                325                 330                 335
Tyr Pro Gln Ile Ser Gly Ile Ser Ala Lys Asp Val Phe Thr Val Thr
            340                 345                 350
Ile Met Pro Cys Thr Ala Lys Lys Phe Glu Ala Asp Arg Glu Glu Met
            355                 360                 365
Tyr Asn Glu Gly Ile Lys Asn Ile Asp Ala Val Leu Thr Thr Arg Glu
            370                 375                 380
Leu Ala Lys Met Ile Lys Asp Ala Lys Ile Lys Phe Ala Asp Leu Glu
385                 390                 395                 400
Asp Gly Glu Val Asp Pro Ala Met Gly Thr Tyr Ser Gly Ala Gly Ala
                405                 410                 415
Ile Phe Gly Ala Thr Gly Gly Val Met Glu Ala Ala Ile Arg Ser Ala
            420                 425                 430
Lys Asp Phe Ala Glu Asn Lys Glu Leu Glu Asn Val Asp Tyr Thr Glu
            435                 440                 445
Val Arg Gly Phe Lys Gly Ile Lys Glu Ala Glu Val Glu Ile Ala Gly
            450                 455                 460
Asn Lys Leu Asn Val Ala Val Ile Asn Gly Ala Ser Asn Phe Phe Glu
465                 470                 475                 480
Phe Met Lys Ser Gly Lys Met Asn Glu Lys Gln Tyr His Phe Ile Glu
                485                 490                 495
Val Met Ala Cys Pro Gly Gly Cys Ile Asn Gly Gly Gly Gln Pro His
            500                 505                 510
Val Ser Ala Lys Glu Arg Glu Lys Val Asp Val Arg Thr Val Arg Ala
            515                 520                 525
Ser Val Leu Tyr Asn Gln Asp Lys Asn Leu Glu Lys Arg Lys Ser His
            530                 535                 540
Lys Asn Thr Ala Leu Leu Asn Met Tyr Tyr Asp Tyr Met Gly Ala Pro
545                 550                 555                 560
Gly Gln Gly Lys Ala His Glu Leu Leu His Leu Lys Tyr Asn Lys
                565                 570                 575

<210> SEQ ID NO 206
<211> LENGTH: 575
```

<212> TYPE: PRT
<213> ORGANISM: Chlamydomonas reinhardtii

<400> SEQUENCE: 206

```
Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
            20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
    50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
        115                 120                 125

Asp Lys Ser Gln Tyr Ile Asp Ile Arg Ser Lys Ser Ile Val Ile Asp
    130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
        195                 200                 205

Lys Thr His Val Asp Arg Val Lys Glu Ala Leu Glu Asp Pro Asn Lys
    210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
        275                 280                 285

Lys Asn Asn Gly Pro Phe Pro Met Phe Thr Ser Cys Cys Pro Ala Trp
    290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
                325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
        355                 360                 365

Glu Thr Asn Ser Leu Arg Asp Ile Asp Ala Ser Leu Thr Thr Arg Glu
    370                 375                 380

Leu Ala Lys Met Ile Lys Asp Ala Lys Ile Asn Phe Ala Asn Leu Glu
385                 390                 395                 400
```

```
Asp Glu Gln Ala Asp Pro Ala Met Gly Glu Tyr Thr Gly Ala Gly Val
                405                 410                 415
Ile Phe Gly Ala Thr Gly Gly Val Met Glu Ala Ala Leu Arg Thr Ala
            420                 425                 430
Lys Asp Phe Val Glu Asp Lys Asp Leu Thr Asp Ile Glu Tyr Thr Gln
        435                 440                 445
Ile Arg Gly Leu Gln Gly Ile Lys Glu Ala Glu Val Glu Ile Ala Gly
    450                 455                 460
Asn Lys Leu Asn Val Ala Val Ile Asn Gly Ala Ser Asn Phe Phe Glu
465                 470                 475                 480
Phe Met Lys Ser Gly Lys Met Asn Glu Lys Gln Tyr His Phe Ile Glu
                485                 490                 495
Val Met Ala Cys Pro Gly Gly Cys Ile Asn Gly Gly Gly Gln Pro His
            500                 505                 510
Val Ser Ala Lys Glu Arg Glu Lys Val Asp Val Arg Thr Val Arg Ala
        515                 520                 525
Ser Val Leu Tyr Asn Gln Asp Lys Asn Leu Glu Lys Arg Lys Ser His
    530                 535                 540
Lys Asn Thr Ala Leu Leu Asn Met Tyr Tyr Asp Tyr Met Gly Ala Pro
545                 550                 555                 560
Gly Gln Gly Lys Ala His Glu Leu Leu His Leu Lys Tyr Asn Lys
                565                 570                 575

<210> SEQ ID NO 207
<211> LENGTH: 575
<212> TYPE: PRT
<213> ORGANISM: Chlamydomonas reinhardtii

<400> SEQUENCE: 207

Met Ala Ile Asn Ile Val Ile Asp Glu Lys Thr Ile Gln Val Gln Glu
1               5                   10                  15
Asn Thr Thr Val Ile Gln Ala Ala Leu Ala Asn Gly Ile Asp Ile Pro
                20                  25                  30
Ser Leu Cys Tyr Leu Asn Glu Cys Gly Asn Val Gly Lys Cys Gly Val
            35                  40                  45
Cys Ala Val Glu Ile Glu Gly Lys Asn Asn Leu Ala Leu Ala Cys Ile
        50                  55                  60
Thr Lys Val Glu Glu Gly Met Val Val Lys Thr Asn Ser Glu Lys Val
65                  70                  75                  80
Gln Glu Arg Val Lys Met Arg Val Ala Thr Leu Leu Asp Lys His Glu
                85                  90                  95
Phe Lys Cys Gly Pro Cys Pro Arg Arg Glu Asn Cys Glu Phe Leu Lys
            100                 105                 110
Leu Val Ile Lys Thr Lys Ala Lys Ala Asn Lys Pro Phe Val Val Glu
        115                 120                 125
Asp Lys Ser Gln Tyr Ile Asp Ile Arg Ser Lys Ser Ile Val Ile Asp
    130                 135                 140
Arg Thr Lys Cys Val Leu Cys Gly Arg Cys Glu Ala Ala Cys Lys Thr
145                 150                 155                 160
Lys Thr Gly Thr Gly Ala Ile Ser Ile Cys Lys Ser Glu Ser Gly Arg
                165                 170                 175
Ile Val Gln Ala Thr Gly Gly Lys Cys Phe Asp Asp Thr Asn Cys Leu
            180                 185                 190
Leu Cys Gly Gln Cys Val Ala Ala Cys Pro Val Gly Ala Leu Thr Glu
        195                 200                 205
```

-continued

```
Lys Thr His Val Asp Arg Val Lys Glu Ala Leu Glu Asp Pro Asn Lys
    210                 215                 220
His Val Ile Val Ala Met Ala Pro Ser Ile Arg Thr Ser Met Gly Glu
225                 230                 235                 240
Leu Phe Lys Leu Gly Tyr Gly Val Asp Val Thr Gly Lys Leu Tyr Ala
            245                 250                 255
Ser Met Arg Ala Leu Gly Phe Asp Lys Val Phe Asp Ile Asn Phe Gly
        260                 265                 270
Ala Asp Met Thr Ile Met Glu Glu Ala Thr Glu Phe Ile Glu Arg Val
    275                 280                 285
Lys Asn Asn Gly Pro Phe Pro Met Phe Thr Ser Cys Cys Pro Ala Trp
290                 295                 300
Val Arg Leu Ala Gln Asn Tyr His Pro Glu Leu Leu Asp Asn Leu Ser
305                 310                 315                 320
Ser Ala Lys Ser Pro Gln Gln Ile Phe Gly Thr Ala Ser Lys Thr Tyr
            325                 330                 335
Tyr Pro Ser Ile Ser Gly Ile Ala Pro Glu Asp Val Tyr Thr Val Thr
        340                 345                 350
Ile Met Pro Cys Asn Asp Lys Lys Tyr Glu Ala Asp Ile Pro Phe Met
    355                 360                 365
Glu Thr Asn Ser Leu Arg Asp Ile Asp Ala Ser Leu Thr Thr Arg Glu
370                 375                 380
Leu Ala Lys Met Ile Lys Asp Ala Lys Ile Lys Phe Ala Asp Leu Glu
385                 390                 395                 400
Asp Gly Glu Val Asp Pro Ala Met Gly Thr Tyr Ser Gly Ala Gly Ala
            405                 410                 415
Ile Phe Gly Ala Thr Gly Gly Val Met Glu Ala Ala Ile Arg Ser Ala
        420                 425                 430
Lys Asp Phe Ala Glu Asn Lys Glu Leu Glu Asn Val Asp Tyr Thr Glu
    435                 440                 445
Val Arg Gly Phe Lys Gly Ile Lys Glu Ala Thr Val Glu Ile Gly Gly
450                 455                 460
Glu Asn Tyr Asn Val Ala Val Ile Asn Gly Ala Ala Asn Leu Ala Glu
465                 470                 475                 480
Phe Met Asn Ser Gly Lys Ile Leu Glu Lys Asn Tyr His Phe Ile Glu
            485                 490                 495
Val Met Ala Cys Pro Gly Gly Cys Val Asn Gly Gly Gly Gln Pro His
        500                 505                 510
Val Ser Ala Lys Glu Arg Glu Lys Val Asp Val Arg Thr Val Arg Ala
    515                 520                 525
Ser Val Leu Tyr Asn Gln Asp Lys Asn Leu Glu Lys Arg Lys Ser His
530                 535                 540
Lys Asn Thr Ala Leu Leu Asn Met Tyr Tyr Asp Tyr Met Gly Ala Pro
545                 550                 555                 560
Gly Gln Gly Lys Ala His Glu Leu Leu His Leu Lys Tyr Asn Lys
            565                 570                 575

<210> SEQ ID NO 208
<211> LENGTH: 584
<212> TYPE: PRT
<213> ORGANISM: Chlamydomonas reinhardtii

<400> SEQUENCE: 208

Met Ala Ile Asn Ile Val Ile Asp Glu Lys Thr Ile Gln Val Gln Glu
1               5                   10                  15
```

```
Asn Thr Thr Val Ile Gln Ala Leu Ala Asn Gly Ile Asp Ile Pro
                20                  25                  30

Ser Leu Cys Tyr Leu Asn Glu Cys Gly Asn Val Gly Lys Cys Gly Val
        35                  40                  45

Cys Ala Val Glu Ile Glu Gly Lys Asn Asn Leu Ala Leu Ala Cys Ile
50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
            100                 105                 110

Leu Val Ile Lys Thr Lys Ala Lys Ala Asn Lys Pro Phe Val Val Glu
            115                 120                 125

Asp Lys Ser Gln Tyr Ile Asp Ile Arg Ser Lys Ser Ile Val Ile Asp
130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
            180                 185                 190

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
                245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
290                 295                 300

Val Arg Gln Val Glu Asn Tyr Tyr Pro Glu Phe Leu Glu Asn Leu Ser
305                 310                 315                 320

Ser Ala Lys Ser Pro Gln Ile Phe Gly Ala Ala Ser Lys Thr Tyr
                325                 330                 335

Tyr Pro Gln Ile Ser Gly Ile Ser Ala Lys Asp Val Phe Thr Val Thr
            340                 345                 350

Ile Met Pro Cys Thr Ala Lys Lys Phe Glu Ala Asp Arg Glu Glu Met
            355                 360                 365

Tyr Asn Glu Gly Ile Lys Asn Ile Asp Ala Val Leu Thr Thr Arg Glu
370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
                405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445
```

Val Arg Gly Phe Lys Gly Ile Lys Glu Ala Glu Val Glu Ile Ala Gly
    450                 455                 460

Asn Lys Leu Asn Val Ala Val Ile Asn Gly Ala Ser Asn Phe Phe Glu
465                 470                 475                 480

Phe Met Lys Ser Gly Lys Met Asn Glu Lys Gln Tyr His Phe Ile Glu
                485                 490                 495

Val Met Ala Cys Pro Gly Gly Cys Ile Asn Gly Gly Gly Gln Pro His
                500                 505                 510

Val Asn Ala Leu Asp Arg Glu Asn Val Asp Tyr Arg Lys Leu Arg Ala
                515                 520                 525

Ser Val Leu Tyr Asn Gln Asp Lys Asn Val Leu Ser Lys Arg Lys Ser
                530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
                565                 570                 575

Asp Lys Asn Val Ser Lys His Glu
                580

<210> SEQ ID NO 209
<211> LENGTH: 584
<212> TYPE: PRT
<213> ORGANISM: Chlamydomonas reinhardtii

<400> SEQUENCE: 209

Met Ala Ile Asn Ile Val Ile Asp Glu Lys Thr Ile Gln Val Gln Glu
1               5                   10                  15

Asn Thr Thr Val Ile Gln Ala Ala Leu Ala Asn Gly Ile Asp Ile Pro
                20                  25                  30

Ser Leu Cys Tyr Leu Asn Glu Cys Gly Asn Val Gly Lys Cys Gly Val
                35                  40                  45

Cys Ala Val Glu Ile Glu Gly Lys Asn Asn Leu Ala Leu Ala Cys Ile
        50                  55                  60

Thr Lys Val Glu Glu Gly Met Val Val Lys Thr Asn Ser Glu Lys Val
65                  70                  75                  80

Gln Glu Arg Val Lys Met Arg Val Ala Thr Leu Leu Asp Lys His Glu
                85                  90                  95

Phe Lys Cys Gly Pro Cys Pro Arg Arg Glu Asn Cys Glu Phe Leu Lys
                100                 105                 110

Leu Val Ile Lys Thr Lys Ala Lys Ala Asn Lys Pro Phe Val Val Glu
                115                 120                 125

Asp Lys Ser Gln Tyr Ile Asp Ile Arg Ser Lys Ser Ile Val Ile Asp
            130                 135                 140

Arg Thr Lys Cys Val Leu Cys Gly Arg Cys Glu Ala Ala Cys Lys Thr
145                 150                 155                 160

Lys Thr Gly Thr Gly Ala Ile Ser Ile Cys Lys Ser Glu Ser Gly Arg
                165                 170                 175

Ile Val Gln Ala Thr Gly Gly Lys Cys Phe Asp Asp Thr Asn Cys Leu
                180                 185                 190

Leu Cys Gly Gln Cys Val Ala Ala Cys Pro Val Gly Ala Leu Thr Glu
            195                 200                 205

Lys Thr His Val Asp Arg Val Lys Glu Ala Leu Glu Asp Pro Asn Lys
        210                 215                 220

His Val Ile Val Ala Met Ala Pro Ser Ile Arg Thr Ser Met Gly Glu
225                 230                 235                 240

Leu Phe Lys Leu Gly Tyr Gly Val Asp Val Thr Gly Lys Leu Tyr Ala
            245                 250                 255

Ser Met Arg Ala Leu Gly Phe Asp Lys Val Phe Asp Ile Asn Phe Gly
            260                 265                 270

Ala Asp Met Thr Ile Met Glu Glu Ala Thr Glu Phe Ile Glu Arg Val
            275                 280                 285

Lys Asn Asn Gly Pro Phe Pro Met Phe Thr Ser Cys Cys Pro Ala Trp
            290                 295                 300

Val Arg Leu Ala Gln Asn Tyr His Pro Glu Leu Leu Asp Asn Leu Ser
305                 310                 315                 320

Ser Ala Lys Ser Pro Gln Gln Ile Phe Gly Thr Ala Ser Lys Thr Tyr
            325                 330                 335

Tyr Pro Ser Ile Ser Gly Ile Ala Pro Glu Asp Val Tyr Thr Val Thr
            340                 345                 350

Ile Met Pro Cys Asn Asp Lys Lys Tyr Glu Ala Asp Ile Pro Phe Met
            355                 360                 365

Glu Thr Asn Ser Leu Arg Asp Ile Asp Ala Ser Leu Thr Thr Arg Glu
            370                 375                 380

Leu Ala Lys Met Ile Lys Asp Ala Lys Ile Lys Phe Ala Asp Leu Glu
385                 390                 395                 400

Asp Gly Glu Val Asp Pro Ala Met Gly Thr Tyr Ser Gly Ala Gly Ala
            405                 410                 415

Ile Phe Gly Ala Thr Gly Gly Val Met Glu Ala Ala Ile Arg Ser Ala
            420                 425                 430

Lys Asp Phe Ala Glu Asn Lys Glu Leu Glu Asn Val Asp Tyr Thr Glu
            435                 440                 445

Val Arg Gly Phe Lys Gly Ile Lys Glu Ala Thr Val Glu Ile Gly Gly
            450                 455                 460

Glu Asn Tyr Asn Val Ala Val Ile Asn Gly Ala Ala Asn Leu Ala Glu
465                 470                 475                 480

Phe Met Asn Ser Gly Lys Ile Leu Glu Lys Asn Tyr His Phe Ile Glu
            485                 490                 495

Val Met Ala Cys Pro Gly Gly Cys Val Asn Gly Gly Gly Gln Pro His
            500                 505                 510

Val Asn Ala Leu Asp Arg Glu Asn Val Asp Tyr Arg Lys Leu Arg Ala
            515                 520                 525

Ser Val Leu Tyr Asn Gln Asp Lys Asn Val Leu Ser Lys Arg Lys Ser
530                 535                 540

His Asp Asn Pro Ala Ile Ile Lys Met Tyr Asp Ser Tyr Phe Gly Lys
545                 550                 555                 560

Pro Gly Glu Gly Leu Ala His Lys Leu Leu His Val Lys Tyr Thr Lys
            565                 570                 575

Asp Lys Asn Val Ser Lys His Glu
            580

<210> SEQ ID NO 210
<211> LENGTH: 36
<212> TYPE: DNA
<213> ORGANISM: Chlamydomonas reinhardtii

<400> SEQUENCE: 210
gcatcgcata tgacaaacat gacaaatatg ataaat                              36

<210> SEQ ID NO 211
<211> LENGTH: 40

```
<212> TYPE: DNA
<213> ORGANISM: Chlamydomonas reinhardtii

<400> SEQUENCE: 211
gcatcgagat cttaatttgg cttttttgcag tcgcctcttg                           40

<210> SEQ ID NO 212
<211> LENGTH: 40
<212> TYPE: DNA
<213> ORGANISM: Chlamydomonas reinhardtii

<400> SEQUENCE: 212
gcatcgccat gggattgaat gaaacaccat ctgcaaaccg                            40

<210> SEQ ID NO 213
<211> LENGTH: 43
<212> TYPE: DNA
<213> ORGANISM: Chlamydomonas reinhardtii

<400> SEQUENCE: 213
gcatcgggat ccctaaagaa tttctgcaag tatgtccggg aag                        43

<210> SEQ ID NO 214
<211> LENGTH: 37
<212> TYPE: DNA
<213> ORGANISM: Chlamydomonas reinhardtii

<400> SEQUENCE: 214
gcatcgcata tggttgaaaa agttgatttt ataaaag                               37

<210> SEQ ID NO 215
<211> LENGTH: 42
<212> TYPE: DNA
<213> ORGANISM: Chlamydomonas reinhardtii

<400> SEQUENCE: 215
gcatcgagat ctttaaaaat aaatatctct ctttcctttt tc                         42

<210> SEQ ID NO 216
<211> LENGTH: 46
<212> TYPE: DNA
<213> ORGANISM: Chlamydomonas reinhardtii

<400> SEQUENCE: 216
gcgaattgca aagactggca aaggatctga atgtaaaaga tatcag                     46

<210> SEQ ID NO 217
<211> LENGTH: 46
<212> TYPE: DNA
<213> ORGANISM: Chlamydomonas reinhardtii

<400> SEQUENCE: 217
cgcttaacgt ttctgaccgt ttcctagact tacattttct atagtc                     46

<210> SEQ ID NO 218
<211> LENGTH: 34
<212> TYPE: DNA
<213> ORGANISM: Chlamydomonas reinhardtii

<400> SEQUENCE: 218
caatacggga taataccgcg ccacatagca gaac                                  34

<210> SEQ ID NO 219
<211> LENGTH: 34
```

```
<212> TYPE: DNA
<213> ORGANISM: Chlamydomonas reinhardtii

<400> SEQUENCE: 219
gttatgccct attatggcgc ggtgtatcgt cttg                              34

<210> SEQ ID NO 220
<211> LENGTH: 47
<212> TYPE: DNA
<213> ORGANISM: Chlamydomonas reinhardtii

<400> SEQUENCE: 220
gggcattaaa gccttttcca tacgctgata gaatatttaa tcaatcg                47

<210> SEQ ID NO 221
<211> LENGTH: 47
<212> TYPE: DNA
<213> ORGANISM: Chlamydomonas reinhardtii

<400> SEQUENCE: 221
cccgtaattt cggaaaaggt atgcgactat cttataaatt agttagc                47

<210> SEQ ID NO 222
<211> LENGTH: 31
<212> TYPE: DNA
<213> ORGANISM: Chlamydomonas reinhardtii

<400> SEQUENCE: 222
ccgacaggac ttaaagatcc ccaccgtttc c                                 31

<210> SEQ ID NO 223
<211> LENGTH: 31
<212> TYPE: DNA
<213> ORGANISM: Chlamydomonas reinhardtii

<400> SEQUENCE: 223
ggctgtcctg aatttctagg ggtggcaaag g                                 31
```